(12) United States Patent
Prayaga et al.

(10) Patent No.: US 6,600,019 B2
(45) Date of Patent: Jul. 29, 2003

(54) POLYPEPTIDES AND NUCLEIC ACIDS ENCODING SAME

(75) Inventors: Sudhirdas K. Prayaga, O'Fallon, MO (US); Kumud Majumder, Stamford, CT (US); Bruce Taillon, Middletown, CT (US); Steven Kurt Spaderna, Berlin, CT (US); Kimberly Spytek, New Haven, CT (US); John MacDougall, New Haven, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/755,665

(22) Filed: Jan. 4, 2001

(65) Prior Publication Data

US 2002/0107186 A1 Aug. 8, 2002

Related U.S. Application Data

(60) Provisional application No. 60/223,524, filed on Aug. 7, 2000, provisional application No. 60/175,819, filed on Jan. 13, 2000, provisional application No. 60/175,743, filed on Jan. 12, 2000, provisional application No. 60/175,696, filed on Jan. 12, 2000, provisional application No. 60/175,488, filed on Jan. 11, 2000, provisional application No. 60/175,434, filed on Jan. 11, 2000, and provisional application No. 60/174,724, filed on Jan. 6, 2000.

(51) Int. Cl.$^7$ ........................ C07K 14/47; G01N 33/53; A61K 38/17

(52) U.S. Cl. ..................... 530/350; 435/975; 514/8; 514/12; 530/395; 530/397; 530/398

(58) Field of Search ................................ 530/350, 395, 530/397, 398; 514/8, 12; 435/975

(56) References Cited

FOREIGN PATENT DOCUMENTS

| EP | 0440321 A | 8/1991 |
|---|---|---|
| WO | WO 95/11305 | 4/1995 |

OTHER PUBLICATIONS

Rudinger. In *Peptide Hormones*, ed. J. A. Parsons, University Park Press, Baltimore, pp. 1–6, 1976.*
Osterhoff et al., Molecular cloning and characterization of a novle human sperm antigen (HE2) specifically expressed in the proximal epididymis, Biology of Reproduction, 50:516–25, 1994.
Kirchhoff et al., "A major mRNA of the human epidydimal principal cells, HE5, encodes the leucocyte differentiation CDw52 antigen peptide backbone", MOl. Repro. Dev., 34:8–15, 1993.
Kirchhoff et al., "Cloning and analysis od mRNAs expressed specifically in the human epididymus", Intl. J. Andrology, 13:155–67, 1990.
Kirchhoff et al., "Molecular aspects of epididymal function and sperm maturation" Cur. Adv Androl, Proc. Int. Cong. Androl 6$^{th}$, pp. 253–259, 1997.

Grasser, et al., 1996 "Maize chromosomal HMGc. Two closely related structure–specific DNA–binding proteins specify a second type of plant high mobility group box protein."*J. Biol. Chem.* 271:32900–32906. GenBank Accession No.: P93631.

Kaul, et al., 1999 Large–scale Mapping and Sequencing of Human Chromosome 7. Unpublished GenBank Accession No.: AC018639.

Kirchhoff, et al, 1994 "Major human epididymis–specific gene product, HE3, is the first representative of a novel gene family." *Mol. Reprod. Dev.* 37 (2), 130–137. GenBank Accession No.: X76386.

Kirchhoff, et al, 1994 "Major human epididymis–specific gene product, HE3, is the first representative of a novel family." *Mol. Reprod. Dev.* 37 (2), 130–137. GenBank Accession No.: NM_022360.

Kirchhoff, et al, 1994 "Major human epididymis–specific gene product, HE3, is the first representative of a novel family." *Mol. Reprod. Dev.* 37 (2), 130–137. GenBank Accession No.: Q14507.

NCBI Annotation Project. 2001 Direct Submission to National Center of Biotechenology. GenBank Accession No.: XP_003504.

NCBI Annotation Project. 2001 Direct Submission. GenBank Accession No.: XP_003501.

Tekamp–Olson, et al., 1990 "Cloning and characterization of cDNAs for murine macrophage inflammatory protein 2 and its human homologues." *J. Exp. Med.* 172 (3), 911–919. GenBank Accession No.: NP_002080.

Wilson, R.K., 1995 Direct Submission. GenBank Accession No.: R05767.

Wilson, R.K., 1996 Direct Submission. GenBank Accession No.: W32867.

Wilson, R.K., 1996 Direct Submission. GenBank Accession No.: W32868.

Yan, et al., 1993 "Neutrophil–activating intercrine secreted by porcine platelets is active without proteolytic processing." *Am. J. Physiol.* 265 (5 Pt 1), C1396–C1404. GenBank Accession No.: AAB28903.

(List continued on next page.)

*Primary Examiner*—Gary Kunz
*Assistant Examiner*—Stephen Gucker
(74) *Attorney, Agent, or Firm*—Mintz Levin; Ivor R. Elrifi; Naomi S. Biswas, Esq.

(57) ABSTRACT

The present invention provides novel isolated NOVX polynucleotides and polypeptides encoded by the NOVX polynucleotides. Also provided are the antibodies that immunospecifically bind to a NOVX polypeptide or any derivative, variant, mutant or fragment of the NOVX polypeptide, polynucleotide or antibody. The invention additionally provides methods in which the NOVX polypeptide, polynucleotide and antibody are utilized in the detection and treatment of a broad range of pathological states, as well as to other uses.

3 Claims, 1 Drawing Sheet

OTHER PUBLICATIONS

Zheng, et al., 1993 "Cloning and characterization and distinct human extracellular signal–regulated kinase activator kinases, MEK1 and MEK2." *J. Biol. Chem.* 268, 11435–11439. GenBank Accession No.: L11285.

Zheng, et al., 1993 "Cloning and characterization and distinct human extracellular signal–regulated kinase activator kinases, MEK1 and MEK2." *J. Biol. Chem.* 268, 11435–11439. GenBank Accession No.: P36507.

* cited by examiner

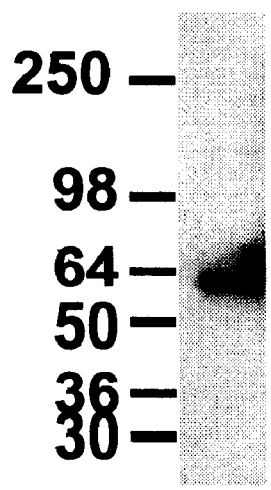
Fig. 1. NOV7 (AL132990) protein secreted by 293 cells.

POLYPEPTIDES AND NUCLEIC ACIDS ENCODING SAME

RELATED APPLICATIONS

This application claims priority to U.S. Ser. Nos. 60/174,724, filed Jan. 6, 2000, 60/175,434, filed Jan. 11, 2000, 60/175,488, filed Jan. 11, 2000, 60/175,696, filed Jan. 12, 2000, 60/175,743, filed Jan. 12, 2000, 60/175,819, filed Jan. 13, 2000, and 60/223,524, filed Aug. 7, 2000 which are incorporated herein by reference in their entirety.

BACKGROUND OF THE INVENTION

The invention generally relates to nucleic acids and polypeptides encoded therefrom. More specifically, the invention relates to nucleic acids encoding cytoplasmic, nuclear, membrane bound and secreted polypeptides, as well as vectors, host cells, antibodies, and recombinant methods for producing these nucleic acids and polypeptides.

SUMMARY OF THE INVENTION

The invention is based, in part, upon the discovery of novel polynucleotide sequences encoding novel polypeptides.

Accordingly, in one aspect, the invention provides an isolated nucleic acid molecule that includes the sequence of SEQ ID NO: 1, 3, 5, 7, 9, 11, 13 or 15 or a fragment, homolog, analog or derivative thereof. The nucleic acid can include, e.g., a nucleic acid sequence encoding a polypeptide at least 85% identical to a polypeptide that includes the amino acid sequences of SEQ ID NO: 2, 4, 6, 8, 10, 12, 14 or 16. The nucleic acid can be, e.g., a genomic DNA fragment, or a cDNA molecule.

Also included in the invention is a vector containing one or more of the nucleic acids described herein, and a cell containing the vectors or nucleic acids described herein.

The invention is also directed to host cells transformed with a vector comprising any of the nucleic acid molecules described above.

In another aspect, the invention includes a pharmaceutical composition that includes an NOVX nucleic acid and a pharmaceutically acceptable carrier or diluent.

In a further aspect, the invention includes a substantially purified NOVX polypeptide, e.g., any of the NOVX polypeptides encoded by an NOVX nucleic acid, and fragments, homologs, analogs, and derivatives thereof. The invention also includes a pharmaceutical composition that includes an NOVX polypeptide and a pharmaceutically acceptable carrier or diluent.

In still a further aspect, the invention provides an antibody that binds specifically to an NOVX polypeptide. The antibody can be, e.g., a monoclonal or polyclonal antibody, and fragments, homologs, analogs, and derivatives thereof. The invention also includes a pharmaceutical composition including NOVX antibody and a pharmaceutically acceptable carrier or diluent. The invention is also directed to isolated antibodies that bind to an epitope on a polypeptide encoded by any of the nucleic acid molecules described above.

The invention also includes kits comprising any of the pharmaceutical compositions described above.

The invention further provides a method for producing an NOVX polypeptide by providing a cell containing an NOVX nucleic acid, e.g., a vector that includes an NOVX nucleic acid, and culturing the cell under conditions sufficient to express the NOVX polypeptide encoded by the nucleic acid. The expressed NOVX polypeptide is then recovered from the cell. Preferably, the cell produces little or no endogenous NOVX polypeptide. The cell can be, e.g., a prokaryotic cell or eukaryotic cell.

The invention is also directed to methods of identifying an NOVX polypeptide or nucleic acid in a sample by contacting the sample with a compound that specifically binds to the polypeptide or nucleic acid, and detecting complex formation, if present.

The invention further provides methods of identifying a compound that modulates the activity of an NOVX polypeptide by contacting an NOVX polypeptide with a compound and determining whether the NOVX polypeptide activity is modified.

The invention is also directed to compounds that modulate NOVX polypeptide activity identified by contacting an NOVX polypeptide with the compound and determining whether the compound modifies activity of the NOVX polypeptide, binds to the NOVX polypeptide, or binds to a nucleic acid molecule encoding an NOVX polypeptide.

In another aspect, the invention provides a method of determining the presence of or predisposition of an NOVX-associated disorder in a subject. The method includes providing a sample from the subject and measuring the amount of NOVX polypeptide in the subject sample. The amount of NOVX polypeptide in the subject sample is then compared to the amount of NOVX polypeptide in a control sample. An alteration in the amount of NOVX polypeptide in the subject protein sample relative to the amount of NOVX polypeptide in the control protein sample indicates the subject has a tissue proliferation-associated condition. A control sample is preferably taken from a matched individual, i.e., an individual of similar age, sex, or other general condition but who is not suspected of having a tissue proliferation-associated condition. Alternatively, the control sample may be taken from the subject at a time when the subject is not suspected of having a tissue proliferation-associated disorder. In some embodiments, the NOVX is detected using an NOVX antibody.

In a further aspect, the invention provides a method of determining the presence of or predisposition of an NOVX-associated disorder in a subject. The method includes providing a nucleic acid sample, e.g., RNA or DNA, or both, from the subject and measuring the amount of the NOVX nucleic acid in the subject nucleic acid sample. The amount of NOVX nucleic acid sample in the subject nucleic acid is then compared to the amount of an NOVX nucleic acid in a control sample. An alteration in the amount of NOVX nucleic acid in the sample relative to the amount of NOVX in the control sample indicates the subject has a NOVX-associated disorder.

In a still further aspect, the invention provides a method of treating or preventing or delaying an NOVX-associated disorder. The method includes administering to a subject in which such treatment or prevention or delay is desired an NOVX nucleic acid, an NOVX polypeptide, or an NOVX antibody in an amount sufficient to treat, prevent, or delay a NOVX-associated disorder in the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a representation of a Western Blot analysis showing expression of NOV7 (AL132990) protein secreted by 293 cells.

DETAILED DESCRIPTION OF THE INVENTION

The present invention provides novel nucleotides and polypeptides encoded thereby. Included in the invention are the novel nucleic acid sequences and their polypeptides. The sequences are collectively referred to as "NOVX nucleic acids" or "NOVX polynucleotides" and the corresponding encoded polypeptides are referred to as "NOVX polypeptides" or "NOVX proteins." Unless indicated otherwise, "NOVX" is meant to refer to any of the novel sequences disclosed herein. Table 1 provides a summary of the NOVX nucleic acids and their encoded polypeptides.

TABLE 1

Sequences and Corresponding SEQ ID Numbers

| NOVX Assign- ment | Internal Identification | SEQ ID NO (nucleic acid) | SEQ ID NO (poly- peptide) | Tissue Expression | Homo- logy |
|---|---|---|---|---|---|
| 1 | AL133371 A | 1 | 2 | | HE3 Alpha and Beta |
| 2 | AL133371 da1 | 3 | 4 | Prostate, kidney and breast cancer | HE3 Alpha and Beta |
| 3 | AL133371 da2 | 5 | 6 | Testis, ovarian cancer, adipose | HE3 Alpha and Beta |
| 4 | AC011005 A | 7 | 8 | Skeletal muscle | Map Kinase Kinase 2 |
| 5 | 78782486 | 9 | 10 | | ELRCXX Chemokines |
| 6 | 78847267 | 11 | 12 | | CXC Chemokines |
| 7 | AL132990 B | 13 | 14 | Liver cirrhosis | Protease Inhibitors |
| 8 | AC018639 A | 15 | 16 | Prostate, kidney and lung cancer | Map Kinase Kinase 2 |

NOVX nucleic acids and their encoded polypeptides are useful in a variety of applications and contexts. The various NOVX nucleic acids and polypeptides according to the invention are useful as novel members of the protein families according to the presence of domains and sequence relatedness to previously described proteins. Additionally, NOVX nucleic acids and polypeptides can also be used to identify proteins that are members of the family to which the NOVX polypeptides belong.

For example, NOV1, 2 and 3 are homologous to members of the human epididymis specific-3 (HE3) family of proteins. Thus, the NOV1, 2, and 3 nucleic acids and polypeptides, antibodies and related compounds according to the invention will be useful in therapeutic and diagnostic applications in disorders of fertility, e.g., spermatogenesis.

NOV4 and NOV8 are homologous to members of the MAP kinase family of proteins. Thus, the NOV4 and NOV8 nucleic acids and polypeptides, antibodies and related compounds according to the invention will be useful in therapeutic and diagnostic applications in cell proliferative disorders, e.g., cancer.

NOV5 is homologous to members of the ELRCXX Chemokine family of proteins. Thus, the NOV5 nucleic acids and polypeptides, antibodies and related compounds according to the invention will be useful in therapeutic and diagnostic applications in various hematopoietic, immunological, inflammatory, and tumor-related disorders and/or pathologies.

NOV6 is homologous to members of the CXC Chemokine family of proteins. Thus, the NOV6 nucleic acids and polypeptides, antibodies and related compounds according to the invention will be useful in therapeutic and diagnostic applications in various hematopoietic, immunological, inflammatory, and tumor-related disorders and/or pathologies.

NOV7 is homologous to members of the Protease Inhibitor family of proteins. Thus, the NOV7 nucleic acids and polypeptides, antibodies and related compounds according to the invention will be useful in therapeutic and diagnostic applications in cell proliferative disorders, e.g., cancer, pulmonary disorders, e.g., emphysema, and hepatic disorders, e.g., cirrhosis.

The NOVX nucleic acids and polypeptides can also be used to screen for molecules, which inhibit or enhance NOVX activity or function. Specifically, the nucleic acids and polypeptides according to the invention may be used as targets for the identification of small molecules that modulate or inhibit, e.g., cell differentiation, cell motility, cell proliferation, angiogenesis, inflammation, and wound healing.

Additional utilities for NOVX nucleic acids and polypeptides according to the invention are disclosed herein.

NOV1

A NOV1 sequence according to the invention is a nucleic acid sequence encoding a polypeptide related to the human epididymis specific gene family of proteins. A NOV1 nucleic acid and its encoded polypeptide includes the sequences shown in Table 2. The disclosed nucleic acid (SEQ ID NO:1) is 559 nucleotides in length and contains an open reading frame (ORF) that begins with an ATG initiation codon at nucleotides 43–45 and ends with a TAG stop codon at nucleotides 448–450. The representative ORF encodes a 135 amino acid polypeptide (SEQ ID NO:2). Putative untranslated regions upstream and downstream of the coding sequence are underlined in SEQ ID NO: 1.

TABLE 2

TTTCTCTTCTCTGTGGACACGCAGGCGGCCCCGGTGACTGAGATGGCATCGTCTCTA    (SEQ ID NO:1)

AAGATCTGGGGCACACTCTTGGCCCTACTTTGCATCCTATGCACACTGCTTGTACAG

AGCAAAGAAGTTTCTTGGAGAGAATTCATGAAACAGCACTACTTAAGTCCAAGTCG

AGAATTCAGAGAGTACAAATGTGATGTCCTCATGAGAGAAAATGAAGCTCTGAAAG

ACAAGAGCTCTCACATGTTTATCTATATCTCATGGTACAAAATCGAGCATATATGCA

CTAGTGACAACTGGATGGATCGCTTCCGAAATGCATATGTATGGGTCCAGATCCTCT

CAAAGTACTCAAGTGTCACCAGGAGAATTCCAAAAATAGCTACACAGAGAGCAGGA

GCTTCAACTACATTGAATTCCATTGTAGCATGGACGGGTATGTTGATAGCATAGAAG

ACCTAAAGATGGTAGAACCTATCGGCAACTAGAAAGTCTATGCACATCCTCAGGTAT

TGGTAGAGTATTCAGTGCTTTCTAAGTAGCAGCCCCTGCCTCCATCAAT

MASSLKIWGTLLALLCILCTLLVQSKEVSWREFMKQHYLSPSREFREYKCDVLMRENEA    (SEQ ID NO:2)

LKDKSSHMFIYISWYKIEHICTSDNWMDRFRNAYVWVQILSKYSSVTRRIPKIATQRAGA

STTLNSIVAWTGMLIA

The NOV1 nucleic acid sequence has a high degree of homology (approximately 99% identity) to human epididymis-specific protein 3 beta (GenBank Accession No: X76386) as shown in Table 3. Furthermore, the NOV1 nucleic acid has a high degree of homology (approximately 87% identity) to human epididymis-specific protein 3 alpha (GenBank Accession No: XM007494) as shown in Table 4.

TABLE 3

```
NOV1:      24 ggcggccccggtgactgagatggcatcgtctctaaagatctggggcacactcttggccct  83  (SEQ ID NO 17)
              ||||||||||||||||||||||||||| ||||||||||||||||||||||||||||||||
HE3 Beta:  42 ggcggccccggtgactgagatggcatcatctctaaagatctggggcacactcttggccct 101 (SEQ ID NO 18)

NOV1:      84 actttgcatcctatgcacactgcttgtacagagcaaagaagtttcttggagagaattcat 143
              ||||||||||||||||||||||||||||||||||||||||||||||||||||||||||||
HE3 Beta: 102 actttgcatcctatgcacactgcttgtacagagcaaagaagtttcttggagagaattcat 161

NOV1:     144 gaaacagcactacttaagtccaagtcgagaattcagagagtacaaatgtgatgtcctcat 203
              ||||||||||||||||||||||||||||||||||||||||||||||||||||||||||||
HE3 Beta: 162 gaaacagcactacttaagtccaagtcgagaattcagagagtacaaatgtgatgtcctcat 221

NOV1:     204 gagagaaaatgaagctctgaaagacaagagctctcacatgtttatctatatctcatggta 263
              ||||||||||||||||||||||||||||||||||||||||||||||||||||||||||||
HE3 Beta: 222 gagagaaaatgaagctctgaaagacaagagctctcacatgtttatctatatctcatggta 281

NOV1:     264 caaaatcgagcatatatgcactagtgacaactggatggatcgcttccgaaatgcatatgt 323
              ||||||||||||||||||||||||||||||||||||||||||||||||||||||||||||
HE3 Beta: 282 caaaatcgagcatatatgcactagtgacaactggatggatcgcttccgaaatgcatatgt 341

NOV1:     324 atgggtccag-atcctctcaaagtactcaagtgtcaccaggagaattccaaaaatagcta 382
              |||||||||| |||||||||||||||||||||||||||||||||||||||||||||||||
HE3 Beta: 342 atgggtccagaatcctctcaaagtactcaagtgtcaccaggagaattccaaaaatagcta 401

NOV1:     383 cacagagagcaggagcttcaactacattgaattccattgtagcatggacgggtatgttga 442
              ||||||||||||||||||||||||||||||||||||||||||||||||||||||||||||
HE3 Beta: 402 cacagagagcaggagcttcaactacattgaattccattgtagcatggacgggtatgttga 461

NOV1:     443 tagcatagaagacctaaagatggtagaacctatcggcaactagaaagtctatgcacatcc 502
              ||||||||||||||||||||||||||||||||||||||||||||||||||||||||||||
HE3 Beta: 462 tagcatagaagacctaaagatggtagaacctatcggcaactagaaagtctatgcacatcc 521

NOV1:     503 tcaggtattggtagagtattcagtgctttctaagtagcagcccctgcctccatcaat     559
              ||||||||||||||||||||||||||| ||||||||||||||||||||||||||||||
HE3 Beta: 522 tcaggtattggtagagtattcagtgctctctaagtagcagcccctgcctccatcaat     578
```

TABLE 4

```
NOV1:      311 gaaatgcatatgtatgggtcc-agatcctctcaaagtactcaagtgtcaccaggagaatt 369 (SEQ ID NO:19)
               ||||||||||||||||| || || | | ||||||||||||| |||||||| |||||| |
HE3alpha:  348 gaaatgcatatgtatgggccccaggtgccctcaaagtactcgagtgtcactgggagaagt 407 (SEQ ID NO:20)

NOV1:      370 ccaaaaatagctacacagagagcaggagcttcaactacattgaattccattgtagcatgg 429
               ||| |||||| ||||||||||||| ||||||| ||||||||||||||||||||| || | |
HE3alpha:  408 acaacaataggtacacagagagcagaagcttcagctacattgaattccattgtggcgtag 467

NOV1:      430 acgggtatgttgatagcatagaagacctaaagatggtagaacctatcggcaactagaaag 489
               | ||| ||||||||||| ||||||||||||| | ||| ||||||||||| |||||||||||
HE3alpha:  468 atggatatgttgataacatagaagacctgaggattatagaacctatcagcaactagaaag 527

NOV1:      490 tctatgcacatcctcaggtattggtagagtattcagtgctttctaagtagcagcccctgc 549
               |||||||||||||||||| |||||||||||||||||||||| | |||| | | ||||||
HE3alpha:  528 tctatgcacatcctcagatattggtagagtattcagtgcttccaaagtggtgggccctgc 587

NOV1:      550 ctccatcaat                                                   559
               ||||||||||
HE3alpha:  588 ctccatcaat                                                   597
```

The HE (human epididymis-specific) family is a group of related proteins specifically expressed in the epididymis and may be involved in spermatogenesis. Accordingly the NOV1 nucleic acid, polypeptide, antibodies and other compositions of the present invention can be used to detect epididymal tissue. A NOV1 nucleic acid was identified in a human epididymis cDNA library.

Based on its relatedness to the known members of the HE3 family, HE3 alpha and HE3 beta, the NOV1 protein is a novel member of the HE3 protein family. The discovery of molecules related to HE3 satisfies a need in the art by providing new diagnostic or therapeutic compositions useful in the treatment of disorders associated with alterations in the expression of members of HE3-like proteins. Nucleic acids, polypeptides, antibodies, and other compositions of the present invention are useful in a variety of diseases and pathologies, including by way of nonlimiting example, those involving spermatogenesis, reproductive abnormalities, cancer and endocrinological defects.

NOV2

A NOV2 sequence according to the invention is a nucleic acid sequence encoding a polypeptide related to the human epididymis specific gene family of proteins. A NOV2 nucleic acid and its encoded polypeptide includes the sequences shown in Table 5. The disclosed nucleic acid (SEQ ID NO:3) is 425 nucleotides in length and contains an open reading frame (ORF) that begins with an ATG initiation codon at nucleotides 16–18 and ends with a TAG stop codon at nucleotides 415–417. The representative ORF includes a 133 amino acid polypeptide (SEQ ID NO:4). Putative untranslated regions upstream and downstream of the coding sequence are underlined in SEQ ID NO: 3.

TABLE 5

<u>GCCCCGGTGACTGAG</u>ATGGCATCCTCTCTGAAGATCTGGGGCAGTCCCTTGGCCCTG   (SEQ ID NO:3)

CTTTGCATTCTTTGCAGGCTACTTGTACACAGCAAGGACGTTTCCTGGAGAGAATTC

ATGACCCTGCACTATTTAGATCCAAGCCAAGATTTTGAAGAGTACAAATGTGATGTC

CTCATGAGAGAAAAAGAAGCTCTGAAACGCAAGAGCTCTCATATGTCCATCTATAG

CTTATGGCACAAAATGGAGTGTATATGCATTATTGAAATGGGAATAACCGATATAGA

TATGCCTATGTATGGGCCCAGGGTGCCCTCAAAGTACTCGAGTGTCAGTGGCAGAAG

TACTGCAATAGCTACACAGAGATCTTCAACTACATTGAATTCCACTGTGGCAAGGAT

GGGTATGTTGATAGCATAG<u>AAGACCTA</u>

MASSLKIWGSPLALLCILCRLLVHSKDVSWREFMTLHYLDPSQDFEEYKCDVLMREKEA   (SEQ ID NO:4)

LKRKSSHMSIYSLWHKMECICIIEMGITDIDMPMYGPRVPSKYSSVSGRSTAIATQRSSTT

LNSTVARMGMLIA

The NOV 2 nucleic acid has homology (approximately 83% identity) to human epididymis-specific protein 3 alpha (GenBank Accession No: XM007494) as shown in Table 6 and to human epididymis-specific protein 3 beta (approximately 84% identity; GenBank Accession No: NM_022360) as shown in Table 7. The NOV2 polypeptide as shown in Table 8 is also 64% identical and 73% similar to the human epididymis-specific protein 3 alpha (Swiss Prot. Acc No.: Q14507).

TABLE 6

```
NOV2:         6 ggtgactgagatggcatcctctctgaagatctggggcagtcccttggccctgctttgcat  65 (SEQ ID NO:21)
                ||||||||||||||| |||||||||||| ||||  ||||||| | ||||||||||||||
HE3alpha:    70 ggtgactgagatgacatcctctctaaagatttggggcatactcttggccctgctttgcat 129 (SEQ ID NO:22)

NOV2:        66 tctttgcaggctacttgtacacagcaaggacgtttcctggagagaattcatgaccctgca 125
                ||||||||||||| |||  |||| ||  || ||| ||||||||||||||||| ||  ||
HE3alpha:   130 cctttgcaggctgtgtgtatacagtaacaacatttactggagagaattcataaaacttca 189

NOV2:       126 ctatttagatccaagccaagattttgaagagtacaaatgtgatgtcctcatgagagaaaa 185
                || ||| |||||  || ||| |||| |||||||||||||||||||||||||||||||||
HE3alpha:   190 ttacttaagtccaagtcgagaattcaaagagtacaaatgtgatgtcctcatgagagaaaa 249

NOV2:       186 agaagctctgaaacgcaagagctctcatatgtccatctatagcttatggcacaaaatgga 245
                ||| |||||||| | ||||||||| ||||||| ||||||||||||||||  |||||| |
HE3alpha:   250 agaggctctgaaaggcaagagcttccatatgttcatctatagcttatggttcaaaattca 309

NOV2:       246 gtgtatatgcattattga-aatgggaataaccgatatagatatgcctatgtatgggccca 304
                | ||  |||||| || |||||||| |||| ||||||||||| |||||||||||||||||
HE3alpha:   310 gcgtgcatgcatcaatgagaagggggagcgaccgatatagaaatgcatatgtatgggcccc 369

NOV2:       305 gggtgccctcaaagtactcgagtgtcagtggcagaagtactgcaatagctacacagag-- 362
                ||||||||||||||||||||||||||| ||| |||||||||| ||| |||||||||||
HE3alpha:   370 aggtgccctcaaagtactcgagtgtcactgggagaagtacaacaataggtacacagagag 429

NOV2:       363 ----atcttcaactacattgaattccactgtggcaaggatgggtatgttgatagcataga 418
                    | |||| |||||||||||||||| ||||||| ||| |||||||||||| ||||||
HE3alpha:   430 cagaagcttcagctacattgaattccattgtggcgtagatggatatgttgataacataga 489

NOV2:       419 agacct 424
                ||||||
HE3alpha:   490 agacct 495
```

TABLE 7

```
NOV2:         1 gccccggtgactgagatggcatcctctctgaagatctggggcagtcccttggccctgctt  60 (SEQ ID NO:23)
                |||||||||||||||||||||||| ||||| ||||||||||| |||| |||||||| ||
HE3beta:     46 gccccggtgactgagatggcatcatctctaaagatctggggcacactcttggccctactt 105 (SEQ ID NO:24)

NOV2:        61 tgcattctttgcaggctacttgtacacagcaaggacgtttcctggagagaattcatgacc 120
                ||||| || |||||||  |||||||| ||||| || ||| ||||||||||||||||| |
HE3beta:    106 tgcatcctatgcacactgcttgtacagagcaaagaagtttcttggagagaattcatgaaa 165

NOV2:       121 ctgcactatttagatccaagccaagattttgaagagtacaaatgtgatgtcctcatgaga 180
                | ||||| || ||||| ||| ||||||| || ||||||||||||||||||||||||||| 
HE3beta:    166 cagcactacttaagtccaagtcgagaattcagagagtacaaatgtgatgtcctcatgaga 225

NOV2:       181 gaaaagaagctctgaaacgcaagagctctcatatgtccatctatagcttatggcacaaa 240
                ||||| |||||||||||| ||||||||||| ||||| ||||||| ||||||| ||||| 
HE3beta:    226 gaaaatgaagctctgaaagacaagagctctcacatgtttatctatctcatggtacaaa 285

NOV2:       241 atggagtgtatatgca 256
                || ||| ||||||||
HE3beta:    286 atcgagcatatatgca 301

NOV2:       365 cttcaactacattgaattccactgtggcaaggatgggtatgttgatagcatagaagacct 424 (SEQ ID NO:25)
                ||||||||||||||||||||| |||| ||  |||| |||||||||||||||||||||||
HE3beta:    417 cttcaactacattgaattccattgtagcatggacgggtatgttgatagcatagaagacct 476 (SEQ ID NO:26)

NOV2:       425 a 425
                |
HE3beta:    477 a 477
```

TABLE 8

```
NOV2:         1 MASSLKIWGSPLALLCILCRLLVHSKDVSWREFMTLHYLDPSQDFEEYKCDVLMREKEAL  60
                 * ******* *********+* ++ ****+ ****  **++*+****************
HE3alpha:     1 MTSSLKIWGILLALLCILCRLCVYSNNIYWREFIKLHYLSPSREFKEYKCDVLMREKEAL  60

NOV2:        61 KRKSSHMSIYSLWHKMECICIIEMGITDIDMPMYGPRVPSKYSSVSGRSTAIATQRS--S 118
                 * **  *****  +++ ** *         *+*** ****+**** * ***+    *
HE3alpha:    61 KGKSFHTFIYSLWFKIQRACINEKGSDRYRNAYVWPQVPSNYSSVTGRSTTIGTQRAEAS 120

NOV2:       119 TTLNSTVA                                                     126 (SEQ ID NO:27)
                 **** **
HE3alpha:   121 ATLNSIVA                                                     128 (SEQ ID NO:28)
```

Where * indicates identity and + indicates similarity.

Based on its relatedness to the known members of the HE3 family, HE3 alpha and HE3 beta, the NOV2 protein is a novel member of the HE3 protein family. The discovery of molecules related to HE3 satisfies a need in the art by providing new diagnostic or therapeutic compositions useful in the treatment of disorders associated with alterations in the expression of members of HE3-like proteins. Nucleic acids, polypeptides, antibodies, and other compositions of the present invention are useful in a variety of diseases and pathologies, including by way of nonlimiting example, those involving spermatogenesis, reproductive abnormalities, cancer and endocrinological defects.

A NOV2 nucleic acid is also useful for detecting specific cell types. For example, expression analysis has demonstrated that a NOV2 nucleic acid is expressed in higher levels in prostate cancer, breast cancer, liver cancer and bladder cancer as compared to normal tissues, and a NOV2 nucleic acid is expressed in lower levels in kidney cancer versus normal tissue and lung cancer versus normal tissue (Example 1, Table 30). Accordingly the NOV2 nucleic acids, polypeptides, antibodies and related compounds according to the invention will have diagnostic and therapeutic applications in the detection of prostate cancer, breast cancer, kidney cancer, bladder cancer, lung cancer and liver cancer.

NOV3

A NOV3 sequence according to the invention is a nucleic acid sequence encoding a polypeptide related to the human epididymis specific gene family of proteins. A NOV3 nucleic acid and its encoded polypeptide includes the sequences shown in Table 9. The disclosed nucleic acid (SEQ ID NO:5) is 554 nucleotides in length and contains an open reading frame (ORF) that begins with an ATG initiation codon at nucleotides 44–46 and ends with a TAG stop codon at nucleotides 485–487. The representative ORF includes a 147 amino acid polypeptide (SEQ ID NO:6). Putative untranslated regions upstream and downstream of the coding sequence are underlined in SEQ ID NO: 5. SIGNALP predicted a secretory signal sequence from residues 1–25.

TABLE 9

TTTTCTCTTCTCTGTGGACACGCAGGCGGCCCCGGTGACTGAGATGGCATCATCTCT (SEQ ID NO:5)

AAAGATCTGGGGCACACTCTTGGCCCTACTTTGCATCCTATGCACACTGCTTGTACA

GAGCAAAGAAGTTTCTTGGAGAGAATTCATGAAACAGCACTACTTAAGTCCAAGTC

GAGAATTCAGAGAGTACAAATGTGATGTCCTCATGAGAGAAAATGAAGCTCTGAAA

GACAAGAGCTCTCACATGTTTATCTATATCTCATGGTACAAAATCGAGCATATATGC

ACTAGTGACAACTGGATGGATCGCTTCCGAAATGCATATGTATGGGTCCAGAATCCT

CTCAAAGTACTCAAGTGTCACCAGGAGAATTCCAAAAATAGCTACACAGAGAGCAG

GAGCTTCAACTACATTGAATTCCATTGTAGCATGGACGGGTATGTTGATAGCATAGA

AGACCTAAAGATGGTAGAACCTATCGGCAACTAGAAAGTCTATGCACATCCTCAGG

TATTGGTAGAGTATTCAGTGCTTTCTAAGTAGCAGCCCAAGGGCG

MASSLKIWGTLLALLCILCTLLVQSKEVSWREFMKQHYLSPSREFREYKCDVLMRENEA (SEQ ID NO:6)

LKDKSSHMFIYISWYKIEHICTSDNWMDRFRNAYVWVQNPLKVLKCHQENSKNSYTES

RSFNYIEFHCSMDGYVDSIEDLKMVEPIGN

The polypeptide has a high degree of homology (approximately 91% identity) to human epididymis-specific protein 3 beta (GenBank Accession No: 071755) as shown in Table 10 and has homology (approximately 61% identity and 71% similarity) to human epididymis-specific protein 3 alpha (GenBank Accession No: 006674) as shown in Table 11.

TABLE 10

```
NOV3:      1 MASSLKIWGXXXXXXXXXXXXXXXVQSKEVSWREFMKQHYLSPSREFREYKCDVLMRENEAL    60 (SEQ ID NO:29)
             ********                ************************************
HE3beta:   1 MASSLKIWGTLLALLCILCTLLVQSKEVSWREFMKQHYLSPSREFREYKCDVLMRENEAL    60 (SEQ ID NO:30)

NOV3:     61 KDKSSHMFIYISWYKIEHICTSDNWMDRFRNAYVWVQNPLKVLKCHQENSKNSYTESRSF   120
             ************************************************************
HE3beta:  61 KDKSSHMFIYISWYKIEHICTSDNWMDRFRNAYVWVQNPLKVLKCHQENSKNSYTESRSF   120

NOV3:    121 NYIEFHCSMDGYVDSIEDLKMVEPIGN                                    147
             **************************
HE3beta: 121 NYIEFHCSMDGYVDSIEDLKMVEPIGN                                    147
```

Where * indicates identity and + indicates similarity.

TABLE 11

```
NOV3:      1 MASSLKIWGXXXXXXXXXXXXXXXVQSKEVSWREFMKQHYLSPSREFREYKCDVLMRENEAL    60
             * *******                * *  + ****+* *********+********** ***
HE3alpha:  1 MTSSLKIWGILLALLCILCRLCVYSNNIYWREFIKLHYLSPSREFKEYKCDVLMREKEAL    60

NOV3:     61 KDKSSHMFIYISWYKIEHICTSDNWMDRFRNAYVWVQNPLKVLKCHQENSKNSYTESRSF   120
             * ** *****  *+**+  * ++   **+*******    ****+** *   * *******
HE3alpha: 61 KGKSFHMFIYSLWFKIQRACINEKGSDRYRNAYVWAPGALKVLECHWEKYNNRYTESRSF   120

N0V3:    121 NYIEFHCSMDGYVDSIEDLKMVEPIGN                                    147 (SEQ ID NO:31)
             +****** +*****+****+++*** *
HE3alpha:121 SYIEFHCGVDGYVDNIEDLRIIEPISN                                    147 (SEQ ID NO:32)
```

Where * indicates identity and + indicates similarity.

Based on its relatedness to the known members of the HE3 family, HE3 alpha and HE3 beta, the NOV3 protein is a novel member of the HE3 protein family. The discovery of molecules related to HE3 satisfies a need in the art by providing new diagnostic or therapeutic compositions useful in the treatment of disorders associated with alterations in the expression of members of HE3-like proteins. Accordingly the NOV3 nucleic acids, polypeptides, antibodies and related compounds according to the invention will have diagnostic and therapeutic applications in the detection of breast cancer, kidney cancer, bladder cancer, lung cancer and liver cancer.

A NOV3 nucleic acid is useful for detecting specific cell types. For example, expression analysis has demonstrated that a NOV3 nucleic acid is expressed in higher levels in ovarian cancer versus normal tissue, testis, and adipose tissue (Example 1, Table 32). Accordingly the NOV3 nucleic acids, polypeptides, antibodies and related compounds according to the invention will have diagnostic and therapeutic applications in the detection of, e.g. ovarian cancer. In addition the NOV3 nucleic acids, polypeptides, antibodies and related compounds according to the invention can be used to detect testis and adipose cells and tissue.

The NOV1, NOV2 and NOV3 polypeptides have homology with one another, particularly in the N-terminal aspect of the polypeptides (Table 43). The NOV1–3 polypeptides form a sub-family within the HE3 family of epididymis specific proteins.

TABLE 43

| | |
|---|---|
| MASSLKIWGTLLALLCILCTLLVQSKEVSWREFMKQHYLSPSREFREYKCDVLMRENEA | (SEQ ID NO.: 2) |
| MASSLKIWGSPLALLCILCRLLVHSKDVSWREFMTLHYLDPSQDFEEYKCDVLMREKEA | |
| MASSLKIWGTLLALLCILCTLLVQSKEVSWREFMKQHYLSPSREFREYKCDVLMRENEA | |
| LKDKSSHMFIYISWYKIEHICTSDNWMDRFRNAYVWVQILSKYSSVTRRIPKIATQRAGA | |
| LKRKSSHMSIYSLWHKMECICIIEMGITDIDMPMYGPRVPSKYSSVSGRSTAIATQRSST | |
| LKDKSSHMFIYISWYKIEHICTSDNWMDRFRNAYVWVQNPLKVLKCHQENSKNSYTESRS | |
| STTLNSIVAWTGMLIA | |
|   TLNSTVARMGMLIA | (SEQ ID NO.: 4) |
| FNYIEFHCSMDGYVDSIEDLKMVEPIGN | (SEQ ID NO.: 6) |

NOV4

A NOV4 sequence according to the invention is a nucleic acid sequence encoding a polypeptide related to the MAP kinase family of proteins. A NOV4 nucleic acid and its encoded polypeptide includes the sequences shown in Table 12. The disclosed nucleic acid (SEQ ID NO: 7) is 1300 nucleotides in length and contains an open reading frame (ORF) that begins with an ATG initiation codon at nucleotides 59–61 and ends with a TAG stop codon at nucleotides 1199–1201. The representative ORF includes a 380 amino acid polypeptide (SEQ ID NO:8). Putative untranslated regions upstream and downstream of the coding sequence are underlined in SEQ ID NO: 7.

The NOV4 polypeptide has a high degree of homology (approximately 90% identity and 92% similarity) to human mitogen-activated protein kinase kinase 2 (MAP kinase kinase 2, MKK2, ERK activator kinase 2, MEK2) (GenBank Acc No: Y41652), as shown in Table 13. The polypeptide also has homology (approximately 75% identity and 83% similarity) to human mitogen-activated protein kinase kinase 1a (MAP kinase kinase 1a, MKK1a, MEK1a) (GenBank Acc No: W32867), as shown in Table 14. The polypeptide also has homology to human mitogen-activated protein kinase kinase 1b (MAP kinase kinase 1b, MKK1b, MEK1b) (approximately 73% identity and 82% similarity; GenBank Acc No: W32868), as shown in Table 15. Pfam domain mapping of the NOV4 polypeptide demonstrates homology to a number of MAP kinase kinase family members (Table 44).

TABLE 12

GCCCGCCCACTACGGGCCCAGGCTAGAGGCGCCGCCGCCACCGGCCCGCGGAGCCCGGATGCTGGCCCGGAGGAAGCC  (SEQ ID NO. 7)

GATGCTGCCGGCGCTCACCATCAACCCTACCATCGCCGAGGGCCCGTCCCCAACCAGCGAGGGCGCCTCCGAGGCAAA

CCTGGTGGACCTGCAGAAGAAGCTGGAGGAGCTGGAACTTGACGAGCAGCAGAAGCGGCTGGAAGCCTTTCTCACCCA

GAAAGCCAAGGTCGGCGAACTCAAAGACGATGACTTCGAAAGGACCTCAGAGCTGGACGCGGGCAACGGCGGGGTGGT

CACCAAAGTCCAGCACAGACCCTCGGGCCTCATCATGGCCAGGAAGCTGATCCACCTTGAGATCAAGCCGGCCATCCG

GAACCAGATCATCCGCGAGCACCAGGTCCTGCACGAGTGCAACTCACCGTACATCGTGGGCTTCTACGGGCCTTCTA

CTGTGACAGGGAGATCAGCATCTGCATGGAGCACATGGATGGCGGCTCCCTGGACCAGGGGCTGAAAGAGGCCAAGAG

GATTCCCGAGGACATCCTGGGGAAAGTCAGCATTGCGGTTCTCCGGGGCTTGGCGTACCTCCGAGAGAAGCACCAGAT

CATGCACCGAAATGTGAAGCCCTCCAACATCCTCGTGAACTCTAGAGGGGAGATCAAGCTGTGTGACTTCGGGGTGAG

CGGCCAGCTCATCGACTCCATGGCCAACTCCTTCGTGGGCACGCGCTCCTACATGGCTCCGGAGCGGTTGCAGGGCAC

ACATTACTCGGTGCAGTCGGTCATCTGGAGCATGGACCTGTCCCTGGTGGAGCTGGCCATCGAAAGGTACCCCATCCC

CCCGCCCGACGCCAAGGAGCTGGAGGCCATCTTTGGCCAGCCCGTGGTCGACAGGGAAGAAGGAGAGCCTCACAGCAT

CTCCTCTTGGCCAGGGTCCCCCGGGCGCCCCAACAGCGGTTACGGGATGGACAGCCTGCCCGCCATGGCCATCTTCGA

ACTGCTGGACTATATTGTGAAAGAGCCGCCTCCTAAGCTGCCCAACGGTGTGTTCACCCCCGAGTTCCAGGAGTTTGT

CAATAAATGCCTCATCAAAAACCCAACGGAGCGGGCGGACCTAAAGATGCTCACAAACCACGCCTTCATCAAGCGGTC

CGAGGTGAAAGAAGCGGATTTTGCCTGCTAGTTGTGTAAAACCCTGGNGGCTGAACCAAGCCCGGCACACCCACGCGC

ACCGCCGTGTACAGTGGCAGGCTCCCCGCGTCCGCTGGTGACTGCCCACGCA

MLARRKPMLPALTINPTIAEGPSPTSEGASEANLVDLQKKLEELELDEQQKRLEAFLTQKAKVGELKDDDFERTSELD  (SEQ ID NO. 8)

AGNGGVVTKVQHRPSGLIMARKLIHLEIKPAIRNQIIREHQVLHECNSPYIVGFYGAFYCDREISICMEHMDGGSLDQ

GLKEAKRIPEDILGKVSIAVLRGLAYLREKHQIMHRNVKPSNILVNSRGEIKLCDFGVSGQLIDSMANSFVGTRSYMA

PERLQGTHYSVQSVIWSMDLSLVELAIERYPIPPPDAKELEAIFGQPVVDREEGEPHSISSWPGSPGRPNSGYGMDSL

PAMAIFELLDYIVKEPPPKLPNGVFTPEFQEFVNKCLIKNPTERADLKMLTNHAFIKRSEVKEADFAC

TABLE 13

```
NOV4:    59 MLARRKPMLPALTINPTIAEGPSPTSEGASEANLVDLQKKLEELELDEQQK-RLEAFLTQ  235  (SEQ ID NO.: 33)
            ******+********************************************** *******
MKK2:     1 MLARRKPVLPALTINPTIAEGPSPTSEGASEANLVDLQKKLEELELDEQQKKRLEAFLTQ   60

NOV4:   236 KAKVGELKDDDFERTSELDAGNGGVVTKVQHRPSGLIMARKLIHLEIKPAIRNQIIREHQ  415
            *************+***.**************************************** *
MKK2:    61 KAKVGELKDDDFERISELGAGNGGVVTKVQHRPSGLIMARKLIHLEIKPAIRNQIIRELQ  120

NOV4:   416 VLHECNSPYIVGFYGAFYCDREISICMEHMDGGSLDQGLKEAKRIPEDILGKVSIAVLRG  595
            **************** ***************** *********+*************
MKK2:   121 VLHECNSPYIVGFYGAFYSDGEISICMEHMDGGSLDQVLKEAKRIPEEILGKVSIAVLRG  180

NOV4:   596 LAYLREKHQIMHRNVKPSNILVNSRGEIKLCDFGVSGQLIDSMANSFVGTRSYMAPERLQ  775
            ******+*****************************************************
MKK2:   181 LAYLREKHQIMHRDVKPSNILVNSRGEIKLCDFGVSGQLIDSMANSFVGTRSYMAPERLQ  240

NOV4:   776 GTHYSVQSVIWSMDLSLVELAIERYPIPPPDAKELEAIFGQPVVDREEGEPHSISSWPGS  955
            ******** **** *******+**********************+**** ******** *
MKK2:   241 GTHYSVQSDIWSMGLSLVELAVGRYPIPPPDAKELEAIFGRPVVDGEEGEPHSISPRPRP  300

NOV4:   956 FGRPNSGYGMDSLPAMAIFELLDYIVKEPPFKLPNGVFTPEFQEFVNKCLIKNPTERADL  1135
            **** **+**** ************* ***************+*******+***** *****
MKK2:   301 PGRPVSGHGMDSRPAMAIFELLDYIVNEPPPKLPNGVFTPDFQEFVNKCLIKNPAERADL  360

NOV4:  1136 KMLTNHAFIKRSEVKEADFAC*LCKTLXAEPSPAHP                         1243
            ****** *******+* *** *****       *   *
MKK2:   361 KMLTNHTFIKRSEVEEVDFAGWLCKTLRLN-QPGTP                          395  (SEQ ID NO.: 34)
```

Where * indicates identity and + indicates similarity.

TABLE 14

```
NOV4:    62 LARRKPMLPALTINPTIAEGPSPTSEGASEANLVDLQKKLEELELDEQQ-KRLEAFLTQK  238  (SEQ ID NO.: 35)
            + ++**  * + +**   +*  +       ++* ** ************* ***********
NKK1a:    1 MPKKKPT-P-IQLNPA-PDGSAVNGTSSAETNLEALQKKLEELELDEQQRKRLEAFLTQK   57

NOV4:   239 AKVGELKDDDFERTSELDAGNGGVVTKVQHRPSGLIMARKLIHLEIKPAIRNQIIRENQV  418
            **********+*** ******* ** *+****+*********************** **
MKK1a:   58 QKVGELKDDDFEKISELGAGNGGVVFKVSHKPSGLVMARKLIHLEIKFAIRNQIIRELQV  117

NOV4:   419 LHECNSPYIVGFYGAFYCDREISICMEHMDGGSLDQGLKEAKRIPEDILGKVSIAVLRGL
            **************** **************** ***+ **** *********++**
MKK1a:  118 LHECNSPYIVGFYGAFYSDGEISICMEHMDGGSLDQVLKKAGRIPEQILGKVSIAVIKGL  177

NOV4:   599 AYLREKHQIMHRNVKPSNILVNSRGEIKLCDFGVSGQLIDSMANSFVGTRSYMAPERLQG  778
            ******+*****.****************************************+******
MKK1a:  178 TYLREKHKIMHRDVKPSNILVNSRGEIKLCDFGVSCQLIDSMANSFVGTRSYMSPERLQG  237

NOV4:   779 THYSVQSVIWSMDLSLVELAIERYPIPPPDAKELEAIFGQPVVDREEGEPHSISSWPGSP  958
            ******** **** *****+*+********** +**  *       **+   * +*
MKK1a:  238 THYSVQSDIWSMGLSLVEMAVGRYPIPPPDAKELELMFGCQV----EGDAAETPPRPRTP  293

NOV4:   959 GRPNSGYGMDSLPAMAIFELLDYIVKEPPPKLPNGVFTPEFQEFVNKCLIKNPTERADLK  1138
            *** * ***** ************ ****+***+*********** ******
MKK1a:  294 GRPLSSYGMDSRPPMAIFELLDYIVNEPPPKLPSGVFSLEFQDFVNKCLIKNPAERADLK  353

NOV4:  1139 MLTNHAFIKRSEVKEADFAC*LCKTLXA-EPS-PAH                         1240
            *  *******+ +* *** **  *+  +***  *
MKK1a:  354 QLMVHAFIKRSDAEEVDFAGWLCSTIGLNQPSTPTH                          389  (SEQ ID NO.: 36)
```

Where * indicates identity and + indicates similarity.

TABLE 15

```
NOV4:   566 GKVSIA----VLRGLAYLREKHQINHRNVKPSNILVNSRGEIKLCDFGVSGQLIDSMANS  733  (SEQ ID NO.: 37)
            *++**     *++*  ***** *+***+****************************
MKK1b:  137 GEISICMEHMVIKGLTYLREKHKIMHRDVKPSNILVNSRGEIKLCDFGVSGQLIDSMANS  196

NOV4:   734 FVGTRSYMAPERLQGTHYSVQSVIWSMDLSLVELAIERYPIPPPDAKELEAIFGQPVVDR  913
            ********+******** ******* **** ****** +*  ************ +** *
MKK1b:  197 FVGTRSYMSPERLQGTHYSVQSDIWSMGLSLVEMAVGRYPIPPPDAKELELMFGCQV---  253

NOV4:   914 EEGEPHSISSWPGS-PGRPNSGYGMDSLPAMAIFELLDYIVKEPPPKLPNGVFTPEFQEF  1090
            **+    * + **** *  **** ***** *******++ ***+  ***+**+
MKK1b:  254 -EGDAAETPPRPRTTPGRPLSSYGMDSRPPMAIFQLLDYIVNEPPPKLPSGVFSLEFDF   312
```

TABLE 15-continued

```
NOV4:  1091 VNKCLIKNPTERADLKMLTNHAFIKRSEVKEADFAC*LCKTLXA-EPS-PAH        1240
            ********* ****** * ********+ +* *** ** *+   +** * *
MKK1b:  313 VNKCLIKNPAERADLKQLMVHAFIKRSDAEEVDFAGWLCSTIGLNQPSTPTH        364 (SEQ ID NO.: 38)
```

Where * indicates identity and + indicates similarity.

TABLE 44

| | | | |
|---|---|---|---|
| NOV4 | 5–71 | RKPMLP--ALTINPTIAEGPSPTSEGASEANLVDLQKKLEELELDEQQK-RLEAFLTQKAKVGELKLDD | (SEQ ID NO.: 83) |
| MPK1 CRIGR/21467 | ..PKKKPT--PIQLNPTP-DGSAVNGTSSAETNLEALQKKWEELELEEQQRNRLEAFLTQKQKVGELKDDD | | (SEQ ID NO.: 84) |
| MPK1 HUMAN/1–66 | ..PKKKPT--PIQLNPAP-DGSAVNGTSSAETNLEALQKKLEELELDEQQRKRLEAFLTQKQKVGELKDDD | | (SEQ ID NO.: 85) |
| MPK1 MOUSE/1–66 | ..PKKKPT--PIQLNPAP-DGSAVNGTSSAETNLEALQKKLEELELDEQQRKRLEAFLTQKQKVGELKDDD | | (SEQ ID NO.: 86) |
| MPK1 RARIT/1–66 | ..PKKKPT--PIQLNPAP-DGSAVNGTSSAETNLEALQKKLEELELDEQQRKRLEAFLTQKQKVGELKLDD | | (SEQ ID NO.: 87) |
| MPK1 RAT/1–66 | . .PKKKPT--PIQLNPAP-DGSAVNGTSSAETNLEALQKKLEELELDEQQRKRLEAFLTQKQKVGELKDDD | | (SEQ ID NO.: 88) |
| MPK1 XENLA/1–66 | ..PKKKPT--PIQLNPNP-EGTAVNGTPTAETNLEALQKKLEELELDEQQRKRLEAFLTQKQEVGELKDDD | | (SEQ ID NO.: 89) |
| MPK2 CYPCA/3–68 | ..PKRRPV--PLIIAPTG-EGQSTNIDAASEANLEALQRKLGELDLDEQQRKRLEAFLTQKAQVGELKDED | | (SEQ ID NO.: 90) |
| MPK2 CHICK/1–69 | MPAKRKPVLPALTITPSPAEGPGPG--GSAEANLVDLQKKLEELELDEQQKKRLEAFLTQKAKVGELKLDD | | (SEQ ID NO.: 91) |
| MPK2 HUMAN/5–71 | ....RKPVLPALTINPTIAEGPSPTSEGASEANLVDLQKKLEELDLDEQQKKRLEAFLTQKAKVGELKDDD | | (SEQ ID NO.: 92) |
| MPK2 MOUSE/5–71 | ....RKPVLPALTINPTIAEGPSPTSEGASEANLVDLQKKLEELDLDEQQRERLEAFLTQKAKVGELKDDD | | (SEQ ID NO.: 93) |
| MPK2 RAT/5–71 | ....  RKPVLPALTINPTIAEGPSPTSEGASEAHLVDLQKKLEELDLDEQQRKRLEAFLTQKAKVGELKDDD | | (SEQ ID NO.: 94) |

Based on its relatedness to the known members of the MAP kinase family the NOV4 protein is a novel member of the MAP kinase protein family. The discovery of molecules related to MAP kinase satisfies a need in the art by providing new diagnostic or therapeutic compositions useful in the treatment of disorders associated with alterations in the expression of members of MAP kinase-like proteins. Nucleic acids, polypeptides, antibodies, and other compositions of the present invention are useful in a variety of diseases and pathologies, including by way of nonlimiting example, those involving cancer and neurological disorders.

A NOV4 nucleic acid is useful for detecting specific cell types. For example, tissue expression analyses have demonstrated that a NOV4 nucleic acid is expressed in higher levels in skeletal muscle (see Example 1, Tables 34 and 36).

NOV 5

A NOV5 sequence according to the invention is a nucleic acid sequence encoding a polypeptide related to the ELRCXX Chemokine family of proteins and a DNA-binding protein. A NOV5 nucleic acid and its encoded polypeptide includes the sequences shown in Table 16. The disclosed nucleic acid (SEQ ID NO: 9) is 324 nucleotides in length and contains an open reading frame (ORF) that begins with an ATG initiation codon at nucleotides 1–3 and ends with a TAA stop codon at nucleotides 322–324. The representative ORF includes a 107 amino acid polypeptide (SEQ ID NO: 10). The NOV5 nucleic acid sequence is derived from a genomic DNA sequence (SEQ ID NO.: 39) 2,096 nucleotides in length.

TABLE 16

| | |
|---|---|
| ATGCCACCCTGCAGCTGTGCCAGATCACTTTGTGCCCTGCAGGTGCTGCTGTTGACTGTTCTGGGTTCCTCCACCAATGGACAAAC | (SEQ ID NO.: 9) |
| TAAGAGAAACATAGGGAAAAGTGTAGACAGTGACTTGTACACTGAACTGCGCTGCGTGTATGTGAAGTCAACCTTTGTACTTCATC | |
| CCAGAAACATCCACAATTTGGAGTTGGTCTCAGCAGGACCCCATTGCAGCAAAGACGAAGAAAAAATCTGCCTGGACCCAGATGCT | |
| CCCAGAATCAATAAAATTGTACAGAAAATGTTGAAAGTTGATGAATTCATCTGGTTAATTTGTTAA | |

NOV5 Genomic DNA

| | |
|---|---|
| GAAGGTGCCACTATATTAAAAGGATAAAGAAAATTCAGATAAAATACGAGCAGGAAGCATATGATAATGG | (SEQ ID NO.: 39) |
| CTCTTATATATCCATACAGTCCCAAAGAACATCTGCTGTCTTTGGCGCAGGGCCATATATTTGTGGTTTC | |
| AGGTGCCCCTAAAGTGTCTATAGGAGCCTATAAACAAAGCCTATAAACTGTGTTGTAGGAAAGACAGCAC | |
| ATATTGTTACAGGCTCATACAAAGAAAATATATGTAGTGTTTCAGTCTAGTTCTTACCTTCCTAAGTAGA | |
| GTCCTTACACATGTGTAAGGGAGATAGGTATTGAGAAAGGGAGAGTGGGAATGTGAAGTGATGCATAACA | |
| TGCAACTTAGTAGGAATTTTGACCTGTGTTGGGCACAGCTTGACAAGCTTGTGTGTGTGTATCACCACAT | |
| ACCCTCACTTCCCCCTTCCCTACCTCTTTCTCCTTACTGACTTCAAGGGAGAGCATATAAATGACATCAA | |

TABLE 16-continued

```
GGGGTATGAAAAGCCACTTAACTGCAGACTTGTAGGCAGCAACTCACCCTCAAGAGGAAGTCTTCAGGCT

CTAGAAACATCTTTAACTTCGGCTTCTGCACCATAAGCCTCAGACTCAATGCCACCCTGCAGCTGTGCCA

GATCACTTTGTQCCCTGCAGGTGCTCCTGTTGACTGTTCTGGGTTCCTCCACCAATGGACAAACTAACAG

AAACATAGGGAAAAGGAAATGTAGAGATCTGTTCCTTGCACCTQTTGCTGCTTCTGCTATACCTGTATCT

GGGAGAAAGACTGGCTTGGTGCTCCTGGGGCTGGAGAGTGCCATTATAACAACAAATCCAAATGGAGGGG

TCACAGAGAGGGGGCACTTCACATTTGCTGGGCATTCTGCTGGGCACTTTAATAAAGCTTTACAGATCAT

ATTCACAATGGCTTTATGAGAGAGGTACAATTACCTTCAATTTACAATTGAGAGAACTGAGAAAAATATT

CACGACCACTAATAGATCACTTTTTACCCCAGCTGTAAGTGTAGACAGTGACTTGTACACTGAACTGCGC

TGCGTGTATGTGAAGTCAACCTTTGTACTTCATCCCAGAAACATCCACAATTTGGAGTTGGTCTCAGCAG

GACCCCATTGCAGCAAAGACGAAGTAATGTAAGCCACTGCTTCTGTGCTATCGCCTCATCAGGGAAGCCC

TCTACCTCCATCCCCATCTGCATTCATTTCCTCCAGTCTCACAGATCCTTTCTGATATTCAGGCCAGGAC

ACCCACAGATAATTCTATTCTCTCTTGCAGAGCCACTCTGTAAGATGGGAGAAAAAATCTGCCTGGACCC

AGATGCTCCCAGAATCAATAAAATTGTACAGAAAATGTTGAAAGTTGATGAATTCATCTGGTTAATTTGT

TAACTTTCTGCTAACGCTTTTCACTGGAAGGGGAGGATTTTGAAGTCTTGACTTTCTCAGATTCTTATTT

ATCCAGGATACTTATTCTTACTGTATTAAAATTTTGATCTAAGTTCTATTCTGTTTCAAAAATCTCATTT

TATTCTGAGAATGCTGGATAAAAGATAACAGAAAGAAGGTGAAAATAAGCAAGCCATGCTTCAATATATA

ATATATGTTTTACCCCCAATCCTTGGCTAAACATTGTAGTGCACTTTCCCTTTATTTATTTGAAAATTTC

TATTGAAACACATCTTTGTTGATTTTTCCAACCCCACTCTACTGTAAGACTAGACATGCTGATGATAATA

AACAGATTTAATAATGGTTAATGATATTAGGAATCACACAGAGCCCAGCGCAAAATACTTGCTCAATAAA

TTTTTGTTAGTATGTTCAGGAACTTAATAGGGTCTTTTAGTGTCTTAGTGCTATTATGTCTTGCTTAAAA

CATCTTCTGAAAGTTTCTTCTGATGTTTGTTTTAGCCTTCAAACCCTAAAAATAATAAAGTTGTAGAATG

TAAGTCTTGTGAACTCTGCTTTTTTACTTTAAAGTGTATATATTTACCCCTGGTAGAATAAAAAATAGAT

GATGGAAATGAATTAATGTATCCCATTAAAAAACCTGTGATATTTTTTGAAACAAGAAAGAAAGAA

MPPCSCARSLCALQVLLLTVLGSSTNGQTKRNIGKSVDSDLYTELRCVYVKSTFVLHPRNIHNLELVSAGPHCSKDEE           (SEQ ID NO.: 10)

KICLDPDAPRINKIVQKMLKVDEFIWLIC
```

The NOV5 nucleic acid was identified by exon-intron scanning bioinformatic analysis of subgenomic library sequences. These sequences were generated by polymerase chain reaction (PCR) screening of bacterial artificial chromosome (BAC) clones containing human genomic DNA with oligonucleotides specific to the Gro2 chemokine gene, which is one of several chemokine genes, e.g. Gro1, ScyB5 and IL-8, contained on human chromosome 4q21. The NOV5 polypeptide has a high degree of homology (56% identity, 66% similarity) with the chemokine human platelet basic protein precursor (PBP, leukocyte-derived growth factor, beta-thromboglobulin precursor)(GenBank Accession No: R05767), as seen in Table 17.

TABLE 17

```
NOV5:     4 PPCSCARSLCALQVLLL-----TVLGSSTNGQTKRNIGK----          156 (SEQ ID NO.: 40)
            SVDSDLYTELRCVYVKS
            * *+ ** * *******     * * *** ******+ *      *+***** ****+
            +*+
PBP:      9 PSCNSARPLHALQVLLLLSLLLTA-                              68
            LASSTKGQTKRNLAKGKEESLDSDLYAELRCMCIKT

NOV5:   157 TFVLHPRNIHNLELVSAGPHCS--------KDEEKICLDPDAPRINKIVQKMLKVDE   303
            *  +**+** +**++  * **+        ** ********** ***** *   **
PBP:     69 TSGIHPKNIQSLEVIGKGTHCNQVEVIATLKDGRKICLDPDAPRIKKIVQKKLAGDE   125 (SEQ ID NO.: 41)
```

Where * indicates identity and + indicates similarity.

Protein alignment of the NOV5 protein with known chemokines, e.g. GRO1 (GenBank Accession No. XP003504), GRO2 (GenBank Accession No. NP002080), and neutrophil-activating peptide (NAP2) (GenBank Accession No. AAB28903) demonstrates homology in the ELRCXX domain, as shown in bold in Table 18.

TABLE 18

```
Nov5:  35 KSVDSDLYTELRCVYVKSTFVLHPRNIHNLELVSAGPHCSKDE--------EKICLDPDA    86  (SEQ ID NO.: 42)

GRO2:  57 RAAGASVATELRCQCLQTLQGIHPKNIQSVNVKSPGPHCAQTEVIATLKNGRFACLNPAS  116  (SEQ ID NO.: 43)

GRO2:  31 RAAGAPLATELRCQCLQTLQGIHLKNIQSVKVKSPGPHCAQTEVIATLKNGQKACLNPAS   90  (SEQ ID NO.: 44)

NAP2:  10 .......HVELRCLCLNTVSGIHPSNIQSLEVIPAGAHCAKVEVIATLKNDDKICLDPEA   63  (SEQ ID NO.: 45)
```

The ELRCXX motif is specific to chemokines and represents a new family of chemokines. Based on its relatedness to the known members of the ELRCXX chemokine family the NOV5 protein is a novel member of the ELRCXX chemokine family. The discovery of molecules related to ELRCXX chemokines satisfies a need in the art by providing new diagnostic or therapeutic compositions useful in the treatment of disorders associated with alterations in the expression of members of ELRCXX chemokine-like proteins. Nucleic acids, polypeptides, antibodies, and other compositions of the present invention are useful in a variety of diseases and pathologies, including by way of nonlimiting example, those involving inflammation and wound healing. Human chromosome 4q21 is known to contain several chemokines including Gro1, Gro2, ScyB5 and IL-8. A NOV5 nucleic acid was discovered using polymerase chain reaction primers specific to the Gro2 gene and is a marker for chromosome 4q21.

NOV6

A NOV6 sequence according to the invention is a nucleic acid sequence encoding a polypeptide related to the CXC Chemokine family of proteins. A NOV6 nucleic acid and its encoded polypeptide includes the sequences shown in Table 19. The disclosed nucleic acid (SEQ ID NO: 11) is 300 nucleotides in length and contains an open reading frame (ORF) that begins with an ATG initiation codon at nucleotides 1–3 and ends with a TAG stop codon at nucleotides 298–300. The representative ORF includes a 99 amino acid polypeptide (SEQ ID NO: 12). The NOV6 nucleic acid sequence is derived from a genomic DNA sequence (SEQ ID NO.: 46) 41,100 nucleotides in length.

TABLE 19

```
ATGACTTCTAAGCTGGCTGTTGCTCTACTGCTTCTTGGCAGTTGCATGCTTTCTGTAGCACTGTGTGAAGTGCCAAGTATTAGTAC    (SEQ ID NO.: 11)

AGTACCACAATGCCAGTGCATGAGGACACATTTTATACCTTTGCATCCCAAATTTATTAAAGAACTCAGAATTATTCAGGTACTTT

CAAAAGTTCTTAGTTATTTTGCTTCTGTACATGTAGACTGTTTAGGTGCTGAGAGTACAATCGTAAACAGAACAGCAAAAAAAAAA

AATTCTGTCTTTACAAATAACTTGGTACTGACATCTGGTTAG

TAAGGGTTGTCGTTCTCCTTCCTGATGATAAGGGAGGAGAGACGCAGGGAGACATCTACTTCCCAAGTAA                    (SEQ ID NO.: 46)

ATCCTATAGTATGGGACACTGAGGTTTCAGGCAAAGTGTTAAATGTTCTCCTGATTTGTATCCAACTTAA

ACCTGATGTCCTGTAGCCCTGGAAGAGACAATACCCCTTAAAGCTAGAGGCACAAAGAGGGATCCAACCA

TTAATAGCTAAGTTTTTGCAATTCGGGTTGTTAAACCTCTGTGAGTCTCGTTGTAATACACCAATCGTAC

CAOTTAAAAAACCAAATGGACACCATAGATTTGGTCAAGAACTTCAAGCTTTCAATGAGGCTGTCATTCC

CATACATCCTATAGTGCCCAATCCCTACGTGCTGTTAGCCTGGGTCCCATCCCTGGOGATGCCAATTTGT

TTACAGAGTTAGATCTTAAAGATGTCTTTTTGTTTTTTTTTTTTTGTTTTTTGTTTTTTTTGGCATTGC

AGTACTCCCTGATTCACAATTCATCTTGGCTTTTGAATGGATTGATCCTGACAGTCATTTGGTTTATCAA

TGAACTTGGACAGTTCTTCCCCAGGTATTTAGGGGCAGCCCTTATCTGTTTGGAAATGCATTGGCTAGAG

AATTAAGGATGTTACACTTAAATAGGGGCATTATTATCCAATATGTGGATGATGTGTTGGTTGCTAGCCC

AACCAAAAGAAACTTGGACGAAAATACCTTTAAGTTGCTAAATTTTCTGGGAGCTAATGTGTATAGGGTC

TCACAGCAGAGGGCCCAGATTTCAACTCAAGAGGCTAAATACTTAGGATATGTCCTAACCCCTGGCACCC

AGGCAATAGTACCAGAACAAAAGGAAGCTATCTTGGGCATTCCAAAACCCCAAACTAGAAAGCAGCTGCG

AGCTTTTCTAGCAGTGTCAGGATTGGGGCATATGGTCAAGCCTTTATATGATGCCCTGAAAGGAGCGAAT

GTAGATTCTTTAGAATGGAATAGCAATTGTAAACAAGCTTTTAATGCTTTCAAGGAAAAATTGGGATCAG

CTCCAGTCCTACGGATCCCTAATTTTGATAAGCCATTTTTCTCTTATGTGGCTAAGAAACAAGGAACCAC

GCTGGGTGTCCTTATCCAGAAACTAGGAGATATCCCCGAACCAGTGATATATTTTTTTAAACAATTAGA

CCATGTCACTTCAGGATGACCTGAATGCCTCAGGGCAGTTGCAGCAACTGCTCTTTTAGGAGATGAAGTC

AATAAAATGGCTTTAGGACAACATCTGGAAGTTTTAACCCCACATCAAGTACAAGGAGTCCTAGAAGCTA
```

TABLE 19-continued

```
AAGGACACCAGTAGATGACAGGAGGTACTTATTGAAATATCAGGCTTTGTTGCTAAACATTCCTCATGCA
ACCCTTAAGATACGCCAGACTTTAAATCCAGCTACCTATCTGCCTGAACCCACTGGCACCCTGTATCATT
CTCGTATACAAGTAATGCACCAAGTTTATTCCAGCTGGCTGGATTTAAATGATGAGCCTCTAGATAATCC
TGAAGTAGAATGTTTTATAGATAGAAGTAGCTTTGTGCGCCAGGGACACAGAAAAGCTGGGTATGCTGTT
GTCAGTCAACACAAGGTAATTAAGTCTCAGGCCTCACCAACTTCTACCTCAGCTCAAAAGGCAGAATGAA
TAGCTCTTGCTAATAGCCCTGCAATTATTAATAGCTCATATTAATAGCCCTGCAATTGGGAAATGACTTA
GTAATTAACATTTGTACTGATTCTATGTATGCCATTCTGGTGCTTCATGCTCATGGAAGGAATGGGGAGA
ATGAGGACTCCTAATTGCTGAGGGTTCCCCTGTGAAACATCACTTAAACATTTTAAATCTATTACATGCT
GTTTTGCTGACCAAGGAAGTAGCTATAATCCATTGCAGAGGGCATCCAAAAGGAGACTCTAGTGTGGCTA
AGGGAAACTCCTTTGCAGATGCAGGAGCTAAGGCAGCTGCATTAAAGCAGCCAGTTGGACTTGTAGGCAT
GTTAGTGCCCTCTGCCCTGGTAATGACAGAACCAAGATATAChAAGAGGAATAAGAATGGGCTAAAGGT
CAGGGTTTAATTCAAGATCCTTCTGGCTGACTTATCAATGACAACAAATTATTGATACCAGGTGCTAATC
AGTGGAAAATAGTTAAGCATTTGCATGACTCTACTCATTTGGGAAGAGATTCCTTCTTTCAATTAATGTC
TCTCTCTCTCTTTTTTTTTATTTTTGAGACAGAGTTTCACTCTTGTTGCCCAGGCTGTAGTGCAATGGCA
CAATCTCAGCTCACCACAACCTCCACCTCCTGTGTTCAAGTGATTCTCCTGCCTCAGCCTCCTGAGTAGC
TGGGATTACAGGCATGCGCCACCACGTCTGGCTAATTTTGTATTTTTAGTAGAGACAGGGTTTCTCTGTG
TTGGTCAGGCTGGTCTCAAACTCCTCACCTCAGGTGATCCATGCGCCTCAGCCTCCCAAAGTGCTAGGAT
TACAGGCATGAACCACCGCTCCCAGCCAATGTCTCGTCTTTTTATAGGAAAAGGCTTACTTACTTAGAAC
AGTAAAGCAGGTAACTCAGTCCTGTGAACTCTGTGCCCAGAATAACCCAAATAACCAACCTTTTCCTTCT
CCTTTAGTAAGGCCTGTTCAGCATAGTGGAATGTATGCCAGTGAAGATTGACTAGTAGATTATGCTCAGA
TGTCCCCATGTAAAGGATTTAAATATTTATTAGTATTCATCAATCCTTTACTGGTTGGACTGAGGCTTTT
CCTACCTGGTCTGAAAAGACAAGGTTTCTAACCTCCTATGAAAGGCAATAATTCCTAGATTTAGGCTGTC
TAATAGCTTGCAAAACAATAATGGCCCATCTTTCACAGTGACAATTAGCCAAAACATAACTTCGGCCCTA
GGAATTAAGTACCTCCTTCATTTAGTATGGATGCCACCATCTTCAGAAAAAGTGGAAAGAGCTAATCAAA
CTAAAAAGTACTATGCCAGGAAACACCAGAAACCGGACTATCTATATTGCCTGTAGCCTTGTTATGGGTT
TAAGCTGTTCCCAAGAGAAATCTATAGTGCAACACTTTAGAAATGATGTATGGAAGGCCTTTCTTAACTA
CAGACTTCCTGATTGACATAGATACTTTCAAGTACAAAATTATGTAATCAACTTAGGACAAATGCAAAAG
GTGCTCCTTGAATATGGAAATCAAAGACTCCCTTCCCCTACTAAGGAAGAGAATATTGTTACAACCCAGC
CAGGAGACCGGGTCCTATTAAAAATTGGAAGGAAGGATCCCCAGCAGATCAACTTTCACCCAAAATGAAA
GGGATCCTATCAAGTTCTCCTTAGTACCCCAACTGCAGTTAAATTTCTAGGAATAAACAGCTGGGTTCAC
TTATCTCGAATGAAACCTGTCTCTTATAAAGTCCCACAGGCCAACAAAACACAAAAGACTGATCCCACTT
ATTCCTGTGGGCCAACCCATGACCTCCAGCTCCTGTTCAAAAGAAACAAAAGGAATGGGTAACATAAAGA
TATGGATTGGCATTCTATTTTTGGGTATAAGCTGGAATCACACAAAGAGTAACTTATTTGCTAAGTGGGC
AGACTGTAGCCTCTCTACATAATCCAACAGTTTGTTGGACTATGTAGAGAATTGCCATTTTCCTTCACTT
CCAGGTTGCCCTGGCATATTCAACCAGCAAACCTAAGTTTATGGGGATTTTATTATGATTGGGAAACTGA
GCATTATAAATATAGTCCCTCTTTTCTCATGTACCATAGCCACACAGGCCTTAGGCCCTTCCTCACTTAT
GGAGAGACAAGAAGGCACCTTTTTCATCTAATTAGGAAACAGCTAAATGGCACCTCGACTTTAGGTTACA
CTGTACACAATAGCTTGGGTGGATGACAGTTGTTCAAGCACAGGTATCAGGCAAAACACCTCTATGTTT
TGAAAGATGCATTAATAGTCACCACCAGACTGAAACCCGCAATATGGGATGGTTGCCACCTCAACAATGT
```

TABLE 19-continued

```
AATCAGACCCTTCTTTTAACAGACCAAATGTGGGTAGGATGGCAACACAATTTGCAAAAAATAGATGCCC
ACCCTTCCCCTTGGGGATGGTTATGGGCTTGTGGAACTCATGGCTGGTTGTATTTACTTTATAGTTGGAC
TTGAAAGTTGTCCTTATCTCCTGGGACTTACCCTCAACAAATTGGACTCTCTCCTGTCTAACTGGGATAC
TGTAAAGGCTCGCCATAGGGCAACAAAAACAGGCTTCTTGGTGGTTCTATCTGATGCTGTATTTTCCCCA
CAGGCAGCCATAATAAATATCAAGTTACAAGTTAAAGCCTTAGCCAAGCACATGGCTGCAGCTTTCAATA
ATACACGCCATGCCCTTACCCTCCTAACTGAGGAAACTTCTCAGATTAGGCAGGTGGCCTTACAAAACCA
TGTGACTTTGAACATTTTAATAGCAGTCCAAGGGGGAACCTGTGCTTTGATCAAAACTGAATGTTGGGCT
AGGCGCAGTGGCTCAGGCCTGTAATCCCAGCACTTTGGGAGGCCATGGTAGGCGGATCACCTGAGGTTGG
ACTTTGAGGCCAGCCTGACCAACATAGAGAAACCCCATCTCTACTAAAAACACAAAATTAGCCAGGCGTG
ATGGTGCATGCTTGTAATCCCAGCTACTCGGGAGGCTGAGGCAGGAGAATCGCTTGAACCCAGGAGGCGG
AGTTTGTGGTGAGCCGAGATCACACCATTGCATTACAGCCTGGGCAATAAGAGTGAAACTCCGTCTCAAA
CAAACAAATGAACAAACAAAACACAAGTGTTGTGTGTATGCTCCAGACTATTCCCATAATATTACCCGGG
CTATGAAAGCTCTAGATACTCATATCTTTGCCACTGATGCACTGCCAGTTGACCCTATATCAACTTGGTT
CCAACCACTACCCAGTTCTTGGAAAGCCTTCCTTTTTAGTTTACTTAGGATGATTTTACTTATTTTGCTT
TGCTGTTGTGGATATATACAATTGTACTCTTTATGTGGGAACGCAAGACAAGCTTACTCAATACTTTCTT
TAAGTTGGATACATTAATTTTCCAGATTTCGCCTTTTGCTGGGACTAATTTATGAACAACCCTCACCATA
CCGAGGCTTTCTGACTGAGTTCCTCTCTACCTTGAATAAAAGAGACTCTAATAATTAGGCAGGAATATCA
TCGCCCCTGTTCAGCCTAAGGAAGTTACAAAAGACTGATCTTTGTCTATCTGCCACCCTTAGGATTAAGG
GTCCTCTTATAAAGGAAGTGGGGAAATATGTCAGAGGTATTCAAACTAGAGTAACTCCACCTTAAGTGAA
GGGTTAAGAAAACATAAGGCTGGGACTTGCTGGGCTGCATTCCCAGAAAGTTAGGTATTCCTAGCCTCTA
GAAGTTTACAGTTAAGGGAACAGATTGATAACATGTACTAAACAGACCCAGACTTAGGAGTTTCCTGGTA
TCCCAATATCTAGAGAACAGAAGCATTCCTAATTTTGCTTTAAAGATACTAATATCAATTCTTGCAAAAT
ATAGTAATTAAGAAAATTAAACCTTCCTCGCAAACTCTTGTAGCAGAGCGTATCTCCCCTTGATCTATTT
TTGTCTTATACATAAACAAGCATTGTACCTAGGGTGAACACGTTCCTCCTCTTACTTTCAGGAACGTCCT
ACTCTGTCTATGGAGTAGCTGTTCTTTCACCACTTTACTCTCTTAACAAACTTACTTTCGCTTTGCATTG
TTGACCCACCCTGAATTCTTTCTGTTGAGATCCAAGAACCCTCATTTAGGGTCTAAATTGGGGCACCCTT
CTGGTAACATTTTTCTGGTGACCATGAAGGGAAAATACTGAGGAGACCCCCAACCCAAAGGAAATAGACT
GCAGTACCAACTAGCTGATTGGGTAAGTGGTTGGGTACCTGGGTAAAGGATGGGATTGGGTTAGAGGCCC
AACTTAGGGGAGTTAGAGTCCCCCAACAGAGAGAGTTAAAGACCCCTCTTGTAAAAGGCAAGGACACTT
GACTGAACCTGGGTTCCAGGCCCAACTTTGGAAGGTTAGAGTCCTTCCTAAGATTTATGGGATTAGAGGA
CCCTTTCAGTAAAGTTCCTCTTGGCTAAGAATAGGTTTGGCACCAGGGGATGTTAACTGCTATGCTGTTT
GCATTTATCTGCCTTGTCCTCTTTGCTGCATGCATCAATTTTTTGGTCGCTATCTCTGCTTCACTGTCAT
TTTCAGGAGATTTCATTTAATTGGTCTTAGAGATTTTAACTTTCTGTTCCCCTGTGTGTCTCCTGATTTA
CATCCATTTGCTTGTGAAACATCGGGAAGAAAAACATTGAAGCTTCCATCTCTAAAATTGCTGATGGAGA
TTTAGCATTTAAGCAATAAGATTACGTGGATGTGACTATGTTTTGTTTCTTAATAAACTTGCTTTTGCTT
TGCATTGTGGACGTGCTCTGAACTCTTTCTTGTGTGAGATCCGAAAACCCTCTCTTGGGTCTGGATCCAG
ACTTTTTTCCGGTAACATTGGTCAGGAAACTGCAGTCACTGTGGTCATTGCTGTTTCCTGCTGATGGCCT
CTCAAAACTGTGATGTATCATGTAGCATTCTTCCCCTACTTCCTTCACCCTGTGACCACCACCTCAAATA
GGCTTGTGTCCCACTTCCTGCCATAACACGTTCTATAGGAGACTGCGTGGTACTTGCAACTTCTTGGCAA
TTTGGTGTGAAAAGCACAATTTTCACATCTACTTGATCTAAGATGGAGACCCAGACAATGTCCATGGAGT
```

TABLE 19-continued

```
TGGCCTGAGGACCAATGACAAGGACCATGTTTCCAAAGCCTCCATAACATTTAATCCCTGCAACACTTCA

GAAGGCTCCTTCTGTTATTATCTTCATCTATAGAAGGGGAAATGAGGTTGAGTGAACTAAAGAAACTTGC

CCAAGATCACAGTGACAGAGCTGGAATTTACTCCAATGTCAGTGTGATCCTTTGAAACCTGTCTTTAACC

ACCATGTGAATAAAATCATCTCTTTTATTCTTTTTACATTCCCTGTTCCATATTAGCAAGAGTTAAGTAG

CCAGTACAGCAAGCTCCAATGTTATAGGATGAGGACTTTGTCTTAGGTTTATGGCTTGGTTTTATTGAAC

CCTTGGGTGCCACTTGTAAACATTTTCCAGTGTCCTCTAACTTGGGGTTAGGGAGTGAAGACTACCATTT

ATGGAGCTTCTCGAATAGGTTGCATTTTTTTTTCTTTTTTGAGACGGAGTCTCACTCTGTCACCCAGG

CTGGAGTGCAGTGGCACGATCTCGGCTCACTGCAAGCTCTGTCTCCCAGGTTCACACCATTCTCCTGCCT

CAGCCTCGCTAGTAGCTGGGACTACAGGGGCCCACCACCACGCCAGCTAATTTTTTTGTATTTTTAGTA

GAGACGGGGTTTCACCATGTTAGCCAGGATGGTCTTGATCTCCTGACCTCGTGATCCACCCACCTCGGCC

TCCCAAAGTGCTGAGATTACAGGTGTGAGCCACCACACCCGGCTGCATTTATTTACTTATCTATAGTTTA

CAAATATTCTTCTTTCTCATCTCATTTATAATTAACTAATAACCTTGGAATTATTAAGAGATTGTTGTTT

TTAACCTATTTACCTGTGAGAAAGGCTCACAGAGGTTGTTTCTTGCTACTTAAAGGTTGTTCCCTTATTT

ACCCAGCTACTTGGGACAATCCAGAACTTGATCTCAAGTACTGGGGCTGCCAGCCTCACCTTCTTGCCTG

TGCTAGAGGCAGTTACCCAAGGTTCAGAATTCCTGAATGAGTCCTGAATCAGAGACAAGTAGATACCTCA

TGCATGCACCATTGTCCTTCCTTTTCAGGTTTGGAGTGTGGTTTCTTTTAGATTATTGAGGTCTTTCTTC

CTTTGACATGACAATTGTGTTTCTGTCCTGAAAACCTGGTGTGCTGCTGTCATCCTGGGGCAGCACTGAA

TACAAAGTTCCCCAGAGGGCAAACGCTATATGAGGTCCCATCAAAATTCCACTAGGAAGGATGCAAACTA

ATGCAGTCAAATCTTAGAAGCATTGTGTTTGGTATATTGCTATAAAGGATTGAAACAACATTAAACTTAG

TGCTAGTTACTTATATTTGAAGGTTAGAACATTGGGTCCAAATTTCAATCAGAAGTTTCCACAAGTGAAG

TATTCAGCCACTCACTTTTTATGGTTCTGTTATGACACAAACTACTTGAGTTTTGAAAAACAAAATATTT

TAGCCACCATTTTATTGACAGCTTCATTAAATTGTCAACAATTATATGAAAAATTATTTAGCAAAAGCAA

ACAAATGCGATCCCTTGTTAAGATAACTACAAGAATTTAATTTTTTTAAATGAAAACAAGTTTATTAAG

AAAGTAAAGCAATAAAGAGTGGCTATTCCATAGGCAAAGCAGCAGCCTGAGCTGCTGGTTGGCCATTTTT

ATGGTTATTTCTTGATTATATGCTAAACAAGGGGTGGACTATTCATGAGTTTTCTAGGAAAGGGGTGGGC

AATTTCCTAGAACTGAGGGTTCCTCTCTTTTTAGACCATACAGGGTAACTTCCTGATGTTGCCATGACA

CTTGTAAACTGTCATGGGCTGGTAAGAGTGTCTTTTAGCATGCTAATATATTATAATTAGTGTATAATG

ACGAGTGAGAACGACAGAGGTCACTCTCGTCTCCATCTTGGCTTTGGTGGGTTTTAGCTGGCTTCTTTAC

TGTAACCTGTTTTATCAGCAAGGTCTTTATGACCTGTATCTTGTGCCAATCTCCTATCTCATCCTGTGAC

TTCGAATGCCTAACCTACTGGGAATGCAGCCCAGCCCAGTAAACCTCAGCCCCATTTTGCCTAGCCCCTA

TTCAAGATGGAGTTGCTCTGGTTAAAACGTCTCTGCCATATTTCCCCCCTCCATATTTTTAAGGAGGTAA

ATTTGAGTAGCAAGGTAGTAAGGAACTTCTTGTAAAAATGGCAATATGTATCAGTGATTCTCCCATCAGG

GGCAAGACCATAGTTTGGTAAGGCACATTCTTTACTAGGTGAGAGCCAAGGGGAGTGACAGCAATCACCA

CATGAAATTAGGCATAATTCATAGTTTATCTGTATAGCAGATTGAAAACCCAGAAAAAAATTGAGAAATA

AATATTGATGTAAATCATCAGATTTTTCAGCAAATATAGTCCTTGTTTCCCCCAAAATAAAACAAACATT

TTATATTTTAAATATTTTATTTTCCTGTTCTTTGTGAAAACATCAATAAATATCGAAACCTCTCTGCTC

TAACACAGAGGGAAACACTGCATAATTAACATTAAACAAGGCAGTATGCCTTACAAGAAAGACATAAAAT

GTCCAAGGGATATTTAGAACATTTTAGTTCTTAAAGCTTCAACATGAGAAATGTTGACCACAAACTGTGA

AATCATTTCAATAAATAACAACTGACATTCATCTTTACAGTTACAAAATAGACACACATACATTTCCCTG
```

TABLE 19-continued

```
CCGTCACATTGATCTCACTCGCCATTTTCTTGGATTCCTCAGCCTCTATCACAGTGGCTGACATGTGATA
TGTCATCACGAAGAAATATTAACAAATGACTAGAGAATATCTGCAAACCTTCTATCTTCAAATTAAATAT
GAATCAGGATTGAACTAACTTGGGTTTGACCTAAAATAAACAATAAATATAATGGGAGAGTGTGCAAGTA
GATTCAATCATAACCTTATTTTACACATAAAATATTAACATAGAATCTTCTAAAACAAACAAATAAATAA
ATAAATAAATAAATAGAAGACTTCTCCTAAGTGATGCTCAAACACATTAGGCGCAATCCAGGTGGCCTCT
GCAGCTGTGTCTCTCTTTCCTCTTCTGTTCCTGTAAGGGCAGGGCCTCCTTCAGCAACAGCCACCAATAA
GCTTCCTCCTTCCTTCTGGTCAGTTGGATTTGCCACTGTAATGAGAAAATGGGTGCCCTGAGTAGGTGCT
CAGGAAAGCTGACTGCACAACAGTCTTCTCCTGTCCTGTTTCCCCAGGCTCTAGAGTTTTCTGAATGCAG
TTTCCCCAGCCTGGCACCCAAGTGGGTACTGCCTGTGACAGCTGTGCTGTGTGGCAAGGACCTCTAGGCT
TGGGATGCTCTTTTAGGAATGGGGGTGACGTGGGGTGGAGGAGTGGCAGTCTACACTGTTTTACTGGCTA
AAACAGCCAGAGCCTATTGCTCTTTGTCATACTGGGCCTCACTTGAGCCTCAAAGCAACCTCATGATGTA
GCTACCATTATTTTCCCTGTTTTGCTGAGTCTCAGATAAACTAAATAATATTGTCTCTGAGTGACATGGC
TAATAGGTGGTGGCAACCAGTTATATACCCAGTGCAATATTATTGTGAAATCTCTGCACTTCAACCCTAA
ACTTTTACAAAAAACCAGGGGGTCTGCTTTTCAGGTCTGAAAGTCAGTAGGAACTAGGGGAAATGAAGCT
TGTGTTTTTTAACAGGTGGAAAACACTTCAGCACAACTGGCAAACTCCAATGAGACCTTACATGAAAGCA
GTTTTACCTACATTCACTGGCAGGAGGGAAGAACCTGGGTGGTGACCCCTGGGCACTGGGAATATCCTCT
GGCACCAGAACAGATTAATAACCTTAATGGCAACTTTAATTGTGAAAATAATAATTTTTTCAGTCCTGCA
GCTAACCCTGGGTTTTCCTGATTTACTTTTTAGGGGCAGACGCCAGTATTTCTGACCAACAGCTCCAGT
CGCCTGTGTACATGGAAATTACAACTCACTTTTTCAGCATCTTTTCGATGATTTTCTTAACCCATGGGCG
ATGCGGGGTTGAGACAAGCTTTCTGCCCATTCTTGAGTGTGGCTCTGCACACAGAAGGGAATCTCGTGAG
ACAGGAGGTCGGGCTGAGGACAGGGTTTGGGGCAGCGGGAGAGTCGGGGACCCCAGCAGTGGCAGCGGCA
GCGATGGGCGAGACTTACATGACTTCGGTTTGGGCGCAGTGGGGTCCGGGGGACTTCACCTTCACACTTT
GGATGTTCTTGAGGTGAATTCCCTGCAGGGTCTGCAAGCACTGGCAGCGCAGTTCAGTGGCCAGGGGCGC
TCCTAGGGAAGAAGAGACTCGCTGATTGAGCGGGGCTGTCGGCGCGGGGCGCCCACCCCAGCCGCGTCCG
GCCCGGGGACCCCAGGGCGCCGGCACCCACCTGCTGCGCGCCGGCTGGCGGCCACCAGGAGCAGGAGCAG
CAGCGCCACCCGCAGGAGCCGGGGATTGCTGGGGCGGCGGAGAGCGTGGCGCGGGCCATGGGGCTCAGC
AGGCGGTTCCACCGGCTGTGCGAGGAGGAGAGCTGGCAAGGAGCTGCCTGTGGCCCGGGCTCTGTGGCTC
TCCGAGAACGGCGAACCCCTTTTATGCATGGTTGGGGCTGGAAAGCCCGGAGTCCCGGGCCAGGGAAATT
CCCGGAGCTCCAGATCGATCCCGAGTTCGGAAGGAAGGCGATGGCCCCGCCTCTGGGGTGGAGGGGGTC
GGGGCACTCACGAGTGACGTCCGGGTCTGACTGTCTTGCGTAACTCCCGCCAACTGTGGGATGTTCTCTT
TCTGCCCCGAATCCCTGGAGCGGGAGCGAGAGCCCGCCGCTCTCAGAGATACCGAGATAACCGCCTGCGA
GGAGGCGCTTCGTGAACCCAGTGcAGTGCGTCGTGGGTCAGATCCCTTAGACCCACGTAGGGACCGCGCT
ACATCCTTACCGGGGGAGTTACTTCTCTGGAAGACATTTCAGTTGTTGGGATTGAAAGTTAGGGCAAGA
ACTGCAGCATGTCTTATCTATCCTCTCTCTTTAGTTTGGGTTCTGCAAATTTCATTAATGTTTGAAATAA
ACGCACGCTTTAACAGTACATGTGTCATCTCAGATGACGCATAAGAGCTTTTGTCTCCTTCCTGGTGTTT
TATGATCTTAAAAGCAAATATCACGTGTGTGTGTGTGTGTCTGTGTGTGTGTGTGTGTGTGT
GTGTGTTTCAACGTAGTGGAGCCAGGTGTTGGGTGCGGGAACAGACCATTGCCCAAGGGTCAATTCAGTG
TTTATTTTAGTTAACAGTGTTGCAATCCCCCATCCTTTCTCTCTTTGAAATCTTGGAACATCTCGAACTC
TAGTAATTCCAGTAGCATCAATTTTTTGTTCTATGGAAGTCTGTGTTTTGATCCATGGAACTCACTGGGA
GCTGCGAGGGGCCTGTTGGGCTCAGGAGGTCTGCCTTTTCTAGTGCTGTCCCTGGGCAGAAAAGGCCATA
```

TABLE 19-continued

```
GACACCACCAGAAAAGGAGCAGGGAATGAGACTCCGCTTGTTTACTACTCTAAGCACAAGCAGACATGTC

TGATATATACATACTAGATTGCTAACATAATTGCATTTCCATGCCATATGTATTTACCAGCATCCTGGGA

TTGGTTCCCTCTAGAGAAACAGCTATCGAGGAAATTTTAGTTCTAGAGGAATGTCAATAAAGCATTTCCA

AGCCTGTTTAGCTGATGCCTTCTCACTGGATTACTGACTTTTCATCATCAATTTCAATGACCCCCTCTCT

TTAAAAATTAAGCTGTAGGCCTACAATACTCTGTCTTAATTCTTCCTGGTGGATGCAGACTTCAGGGATA

TGGAGATATTCTGCCACTGCTATGAGAAGGGCTGGGAGTGGCACGAGGATGAAGAAGTGGGACTACCTTA

GGAATAGAGTGTTCCCTGGATGCTGCAGCTGTAGAGATCACTTGATAAGGATGTCAGGGCTGAAGTTTCA

GCCATACCACTAACTTGCTTCATGACCCTTGGTAATTTATGCTTTATTTGCTCATGTTTCTCCCCTGTAG

AAGAGCTTATAATAGTGCCTGCCTCACGGGGTTGTTAGAAGTATTGATTGTTAATATGTGTAAACCATCA

GTGCATGTAAAGTGTTATGTAAATATTTGTTAAATAACAAAATAGAAGTGGTGTTTCACAACCTTACTGA

TATAGGCTGGATGTTTGTGTCTCTTTCAAATTCAGATGATGAAGCCCTGACTCCCTTATGTGCTAATATT

AGAAGACAGGACCATGGGAAGTAATTAGGTTTAGGTGAGGTTATGAAGGTATGGCCCCCATGATGGGATA

AGTGCCATTACAGCAAGAGATCAGTGAGCTTTCGATCTCTGGCTCTCTCTCCCTTTCTGCATTGTGAGGA

CACAGCAAGAAGGCCACCATCTGCAAACTGAGAAGAGGGCCCTCACCAAGCATGAAATCTGCCAGGATCT

TAATCTTGGACTCCCCAGCCTCCAGAACTGTGAAATAATTGTTGTTTAAGCCCCCTAGCCTATGGCATTC

TGTTATAGCAGCTCAAACTGACTAAGACACTTAACTAAACAGAAGCACTCTGATAAAGCCTTATGAACAC

ACACACGCACAAAGAAAGAAATATTTTCAAAGAAACATCTTCTAATTTACCTTTAAAATTTTTCAGCATC

AGAAATTTTAAAGGAGGGTGCATTTCTATCCTTATGGGATCTTACAATAATTTTTTGATCCATTGTTTGT

TTGAAATTTTAGTTTCAATCACTTTCCACATAAAATGAGAATAAGAGTAAAATTCTACCCTATCCATTTA

TTAGAAAAGATTTATGAAATGACTCTGCCTTGGGCATTAACAGCTAGCTGCCCAAACTTCTTTATTTTGT

GCTAAAGAACTAAAGAACAATAGAAAACATCAGCTTATAATGATTGCCAGACTCATCCCAAAGTATTGAT

GTGAGTAAATAGAAAGAGTAAAATTTCTATTATCTACAGTAACAGTCCCTCAAAAAGATGAGAAATTTCA

AGAATCAGCCCATCATTTGTAAAATTATGTACGTTATTCCTAGAATTTGTTTACTAAAAATTATTTGCTT

TAGGAAGGGAAGTAGAATTCCTTTTTCTTTTCTTAATATACCACTTTCCATGATTTAACTTATGACAGCC

CCAGACCAAGCTTCTGAAGTTTTTAAGGGTACCAGTGTTATGAAACTTACCATAATAAATTCCTTCTTGT

CTTAATATGAGTTGAGTGCCACTGTTACAGGCACAAGTTGTAAACCCATGCAATTACTAACTCAAAGATG

CTATCTCTAAAATGGAAGTACAGTTTCCTAAAATTCCATTCTCCCCTTTAATTTTTATTGTATTTTTCAGA

TTTGACTAGTACAATCTAATATACCTGCAAAATGTAGGCTTGCTGCTCCATGCCGACCACTGACATTCTT

GTTACTTGGGCAGCAAAATGAGTGGTGTGGCTCTGCTTTACCGTGAATTGCCTTGAAGACTTTGCTGATA

TAACCTCCAACATATAGCTTGCTCCTCTAGAGGAACAGACTAGAAAATAAATAAAGAAGTACAACTGATT

TTAGAGATAGATCTGATGGAGGTTGAGATATGGGCTCTGGAATTACAGAATAGAAGACAGATAACATGG

TTCATGATAAGACTTGTTAGTCCTCACACTGTTTATGCTTAGTGACTCCTTTGCTTTCAGGTTTTGCTGC

CACGCATACAAAGTGGACAGTGGTACAACCCCTTTGTTGTGTCTGACTGCATGAAGAAATACATAATTGA

CTTAGTTACATACTATGTGTATTTCTTGTTATTTTTTCACTAAAGAATTAAGGCAGTCTCTCAATGACC

AGAGCCTAGGAATACTTCCTAGTATTATAAACATTGCAATTGACATGTTCTGTGGGCTTTTGTGATTTT

TTGAAAACTGTGGTTTATATTCATTGTGCTAAAGTTTTCCTTACTGGCTCTGGCACCCCGGCTTTGGGTT

GTGGTCCTGCGGAAGAAACATTCTTCCTTGTCTGTGGTTCTTTAGTGGATTGCTTGTTAGCTCAGGGATT

GTGGCCACCACTCATCGAAACATGTGCTCTGGAGATAAAGCGCCAAAGGAAAAGAAGGGAAGTAATATTT

ATTTATTAGATTCCAATTCTTGATTAGATGCAGTGCCTGAGTTTTTCAGTGTACTGTCATTTTAATAATT
```

TABLE 19-continued

```
TCAAGAATGCTGGGAGGCTGGTATCATGAGTCTTATTTTATAGGTAAGGAAACTGGAGTACAAGGTCTTA
GAAGTGGAATTAAATTCAAACCCAAGACTGTCTGACTCAGAAGCTCATAGCCAGTCTTTCTCTAGACAAG
AAAGGAAGTGACAGGAGAAGAAGAGGACATGTAAAAGAATCTTAATTAAGTCTATGGAGGATATTTTATT
ATTTTTCAACCCTACCAGAAAACAATGCATTTATTAAAATATTTAATACAGTTTTGATTAGGAACCAAAC
AGACATGTAGAAGTGATGACAACTAGTAGCCTCCAGAGTCCCAGCAGCCCAGAGAATCTCCTGCTTATTG
TGCCGTCAGCCCCCAAATTCATTCCATGAAGTTCCCAGCAACTCCCAACACCATATCAGAATCTGATATT
ATGATTGAAGGCAGGCTGGGAGTGGTGTCTCACACCTGTAATTCCAGCACTCTGGGAAGCCAAGACAGTA
GGATCACTTGAGGCCAGGAGTTCAAAACCAGCCTGAGCAAGATAGTGAGACCCTGTCTTTATGGAAAAAA
AAAAATTGAAGGCAGATGGTAGCGTAGGTAAAGGATCTAGCTAAGCATCTTACCTCTAGCAGCTCTTAAA
GTATCTTAGAAGGCACTAATAAGAAGGTAGATACCACTATAAACTGTTAAAGGTTGGTCTGTCATCAAGA
GACTAGAGCAATATTTCAATATGTATAAACTACAAGTCATGATCCACTGGAGGGTCATAAAGTCAGTTTT
GTGGGTTGTAACCAGTATTTAAAAATATAAAGGGGCAGTGGCTCATGCCTGTAATCCCAGAACTTTGGGA
GGCCAAGGCGGGCAGATCAGGAGACCAAGAGATTGAGACCATCCTGGCCAACATGGTAAAACCCTGTCTC
TACTAAAAATACAAAAAAAAAATTAGCCGGGCATAGTGGCAGGTGCCTGTAGTCCCAGCTACTTGGGAG
GCTGAGGCAGGAGAATAGCTTGAACCTGGGAGGAAGAGGTTGCAGTGAGCTGAGATTGCACCTCTGCACT
CCAGCCTGGCAACAGAGCGAGACTCCACCTAAAAAAAATATAATTGTATATATACATACACATATATATA
TGAATAAAATAGGATAGAATTTTAAAATGCATGTGCCATAATGCATCACATATTGTTAGTTTAACTGTTA
TTTTATGACACTTTTGTGTCTTATATAGATAGGTAACTGTGTAAAACTAAACATTTGATGCACAAGATGC
AAAAACAGAACTCCCAGGAGTGAAAATATCCCTTCAGAGACGTTATTATATTGATCAAGGCTGTGACTAT
ATAATAAGTTCCCAGTTTGTAGACATTATCTCCTGAGAATTTCCAATCAGGAAAAAAAAGTTGAAGCATA
TTCCATTTTAATGTCATCACTCCCTAAAAGTTTGCACAACAGGGAGTTCCAGTAAATTGCTGAGCTTTTC
CCAGCAGGAATGCCAGGTTCGGATGTTCCTGCTGATAAGGGTGGCCACTTGGCAGTGTTCTCAGCAGAGT
TGAAAGATTAACATAGTACCAGTATTGGTTCGCTTAGCAGAATTTGTTTCAGTCCCTTGGTCATTTGGGC
CACACCGACGAATTATTATATCCAGCTATGAATGTTGCTTGTGGCAGGTACAAAAGGGAAATAAAGAAAA
TATTAAACCTTAATACTTTACCATTGTCACCCTACTTCCTGGTGTGTTAATTTTTCAAAAAAAATCAGTG
GAAGTACCTGTTCAATTTTAACATTCTTTGTTTATTTTTGCCAAAATCTTTGTCTTTTCTAAGTGTCTAA
CTCAACCTACCAAATTATCTATGACAGTACACAAATAACAATATACTAATATGAAAATTATAATTATGAA
TAATAACTAATAATAACAAAAATGCTCTTTTGTACTTTTTATATCTGGAAGAGGGCTGAGATTTTGCATG
CATGTGCATATGTGTGTGCATGTGTGTGTGTGTATGTGTATAATATCTCCTTACATGTAGACACAAAC
TCAAGAGATAGATACTCAAAATATGCCCATTTTTCACATTATGAAACCAAGGTATCTGCCATACTAACAA
AATTGGAACTCAAAATATGGGTGAAAGAGAAACTTTGAATGTTTATACGTATGTGAGTGACATGGTTGTA
TTTGTATTTTAGCAAAATAACTTTTGTGGCATTGAAGGTAAAATGCAGGGGAAATATTTAGGTTACCTGG
GATCATTTTGATATTTTCCAAAATTGTTTCTAAGATTTATTATTGTGGGTCCACAATACCCCTTAGTTTT
GGATTAATTTGACCCACAGAAGGTATTGAGGCAATACCTTTCTGAAAACTCCATATTTGAGCCTGAAGCA
TGCTTTGACTTTTTCAAGACCAATATGAATTTTATATGCTAACAATGTAACCACATTCTTTGTTTCTATT
ATAGAATTTTATTGAATTTAATACATATATTATTAATTTATAATACATAAATTATTTGTTGGATACAAAT
TGAAAGTCTTTGGACTACAGAGGAGTTTCTGTAATAATATATTTATCTGGGATGTAATCCTTTTCTGTTA
CATCTTTACTGTCATTTTTTTCTCTACTTTGCGTGCATATCCATGATAAAAATAGGTAGAAAATACAGTT
TTGTGAGATAAAACATTGTTAGCTCTCTTGTATACCTGCAACAATTACACTTGGAACAAAACAATAACGG
TGGCTATATTTTAAATTTTAAGGTCCCAACAGTCCCGTATAAAAGTCTAATCTCTACGGTCCTTAAACTC
```

TABLE 19-continued

```
ATTTCCTTTAAATCAGATTAAATTTGACTATATGCCTTCATTCCACCAAGGAGAAAACTATTCAATCTCA

GTCATTATTGTAGCTCCCAGACCACACTGAAAGTAGAAAAGGTCCCAAGGGATTTATCCAAGCAAAATAT

TCAGGGCTGTCCATCTGTACTTTGACTTATACTTGTTTTCCATAAAAGGACAAACATTGATATGGTCATT

TTAAGTGCAGCACTGTCCAGCTCTTATCCATTCTGTAGCACAGAAATCTTTGCTAAGGTTGGTAATAACA

GTGCTTGGTAATCTCTTAAGTACAAAGTACAGTCTTTCTTCCAGAGTCCTGCCACCTCCCTGGAAGGAGA

GAGCAGCAAGGAGAAACAAAACTGTTAATTTTGGCAGTGTGTGAAACACTGTGATGCCCCTTTTCCCTT

CCCACTCCTCCCTCCCTGTGGCACACAGCCAGGAAGCAGATGAAGGATAGTTCGTGAGTTCAAAAAGAAG

GGGAGATTTGAGAGTGGTAAGAAAAATAAAATAATGAATGATTCTCAAGAGAGGGAAAAGAGAGGCACAT

CCAAGGGATTTGAGGTTACTTAGCTAACTTTGAAAGTTTTGCCAACTGGTAGTCCAAGATTCAGGAATGA

GGATTTTGAAATGAGAAATAAAGTTAAAGTAGCTGAAAAGGTGGAATGGAGACTAGGAGCTACTTCTGTG

CTCCAGTGCCCTTCTGGTTCTATATTTTCTTCTTGCCTTATTCAGATGTTTGCCAAACTAACATTCAGGC

CATGTAGGACATTGACTACACTGTCTCTCCTCTTCCTCAGTGCAGTTCTAAGGCTACACATATACTCAAC

CACTGGACTTATTTATTAAACAGCAACCATATTTCCAGGATTGAGGGAGCCACTGAGATCCAGAAATCAA

AGTGTCTATTCCTTCCCTCACAAGAGCCACACTCTGGTTGAGCAGACAGGGATGTCAACAGGTGGTAATA

ACCCAGTGTTTATGCTAGGCATTGTGTATGATTACATATGTAAGGAACTGGGGATAAAAAGAAGGGCAAA

ATACTGAATTTGTCCTTAAAGTGCTTAAATTCTAAAATGTAGAATAAACAATTTTTTTAAAAAAATGTAT

TATGTTATGGTCAGTTCCATATGGGGTCCATTACTGCTCTTAGACTCAGGAAAGAAGGTCCCCCTGTCCT

GAGCCTAAGCTTCAGAAGATCTCACTAGCACAACCTTGCAAAAAAACCACAAATGTATTAGAGAACCCCG

GGGGCACTTCTGCCACCTGAGGAACCAGAGCCTAGAGTGGGCGCCAAATGACCCTTAACCTCCTAAACT

TCCTTAACACTAGATACTTACTTTCTTGATTAACGAAGTTCAAGCCCAAGGCTGAGATCCCAGAGGGACA

CAGTGGGGAGCCTAAAGAATAATGATCATGGTGGTTGAGCTCCCTTCTGTTCTCTTTGGCTCTGGAATGA

CTATGAGGAGCTCAAAGCATATTTACAAACCAAAATTTTCACAGGGAACTTGGCCGAAGAAGCTTGGAAA

AAGTCAAGAGGACCATGTATCCTTACTGCCGACTATTTCCACATTTTCCACATCTTTTTCTGAGATCAGT

TAATAAGCATAACCCTAAGGAATCAGTCCACCAGATGCTTTTTAATTTATTCTGAAAGCTAGTGTCTAG

GTAACTTACCACAGCTGACATATTACAATGTGTGAATATAGCATCAAATGTATGCTTTGTTTCTGCATCC

AAGTAGTGCTTTAGGAATCTTATTGTCATTGCATTAGAAGAGTAAAATGTCTCCAAATTTAAATTAATTA

TAAATAAATGTAAGAAATGATTGAAGCATCATCTAAAATGGCACTATTGTCTATAGAACAAAAATTATGT

GACCATTTCAATTATAAAAATGTAATTACTAATTTTGCTGAAGTGAAGAAAAATAAATTTTATATAATAA

ATATAGAATAATAGAATAAATCTTAAATTATGCATGATTTTATTTTGTATGCATCCAGACATTGCCTACA

CAATAACAGAATACCCAGATATGGAATTACAAATTCACTTTTCTCTGATATTTTGCTGATTCTCATCATA

CAAATTCCATAACTTTATATATTTTTAAAATGTTATTAATATATGGTCATGTGTCACATGAAGATCAGAA

CGCATTCTGCAAAATCTGGCATTAGGCTGTTTCCTCCTTGTGTGAACATCTTAGAGTCCACTTATGCAAA

CCCAGATGGTGTAGCCTACTCCACACCTATGCTATATGCTCTATTCTATTCTCCCAGGCTACAAGGCTGT

ACATCATGTTGCTGTACTGAATACTTAGGCAATTGTAACACAACAGTATTTGTGTATCTAAACACACAAA

GGATACAGTAAATATATATATTAATAGTACTGTAATCCTATGTCCTCACCATTGTGTATTCCAACTGTAG

TTGTCCAAAATGTCATTATGTAGTGCATGACTGTATATCTGTGAAGACAGGAAGATCCTCAGACTCATTT

TATTTAACATTTTGTTAGCTAGTTAAGAAAACCGTAAATATTTAGACAGAGAATCATGGGCTTCTCTGAA

CTCTCTCTCAAGACCCCACAATTGTTAGATATGGCCTCATGAAGCATTGAAGAGTGCATATGGAGGAAAA

TTATGAAAAATTATCCTAGAACAGATGACTGAAAAGATGAATTTTGGAAAAAATCTAGGTTATTATAACA
```

TABLE 19-continued

```
TATTTTAATTTGTACTAATTTTGACACCCCCTCAGAGGAATTTTTATGTTTTTGAAACAAGAATTATTTC
TGTTTTTATCTACACACAGAGTTCATTTTATAAGTGCTTGGAACCCAACAGAGCTTAATGAATTGAATAG
GATGTTCTTGGGAAAGAGAGTATAGATAATACGCTTCAATAGTTAAGACATCAGGTGAGAAAGCCATTAA
TTTTAGTTAAAATTACCATTTTAATTAGTCATTTTATGATAACATAGACAATGGAAGATGATTAAGAAAA
ATGAAGAATCAGCATTTCTTGATTCTTCAATAGACACTTGAAAAACTACAACACAAGGAAAACCCACTGT
TTGATGGTCTAAGATCCTATCCCACTATGCTGACATTTGTCAAAACACTTAAATTGTTTGGTTTAAAGAA
ACTCCTTTTTATCCCTGCTACTAATACAAAGAATATACTTGTGTTTGTTCATTGAAGAGTTTCTAAGTAT
TAGAATTTCAGCAACAGGAAATTCATTTCTCAACTTGTATTCTTCACACAAAAGGCATCAAATTGCTCAT
GAGTTAATAGGTTGACAGCTATTGTCATTTCCTGGTGGGAAACTTTCATAGTTAGAGGAAAAGAAGGCTG
AACACCAGATGCTGTTCATCATGTATTTTGGGATATGTTCTTGAAGGTCTGAGATTTACACTGAATTTAT
AAAGCAATGCCATTGAGTCAAGTAGAGAAGAATCTAGATTATAGAACAAGGCTGTGAAGTCAGATGGTTG
TGCCAACAGTGTCTGCTGTGCAGAACCTTTAGCTCCCACTTCTCTCTCACATGCACTGAGTCAGAAAATG
CTATTTTGTAGGCTGTAGCTACTTGTCAGGTTTATGACTCAACAAACTGAAATATTAGCCAAATGAAATA
TTGTTGTGCAATTCAGGGTGCTCACTCATAGCACATACAGTGTTGAATATAATCATCTATAGCTTCAAAT
GTGCTGGTCATGAGTCCACTAAGAAATGCAGAAAAGAAGCAAGAGGAGAAACAGTCTGACCTTAGCTGCA
AAGGGCACCAGGATGCCAGCATGCTAGAGTCATGCTGGTTTCCCCCTTCATGGAAGTGACAGGCCCATGA
CAAATTTACGCAAATATGACATGGAAAATAATTTCTTGAAGAAAACTTCTTTTGCCATATGTTTCCTGGT
TTTCTTCTGGTTTGGCCTGTGAATGGTATCAGTTTATTTTCGAGTCTAGTATCCAATATTCCTGGAAGCT
AGGGCTGAGGAATGTTCATTTCACAGGATGGCCAAGGTCTGATATGCAAGGCTGGGATTGAGTGAGGCCC
CAGGGCAGGCTGAGAACAGGAAGCGGTTTCACTGACATTCCATTCCTTTCTCTCCCTGACCACTCCCATC
TCAGAGTGGCCAAGGATCACTGAAGAAATAGTAATTGTCATCTAAACCTCATAACAGGGGTGTCTGGCAC
TTGAGAGTTGACCCACTTCAATTTATTCAAGCTCCCACTCAAAAAAACTCTCCTTGACTTACAGGATATG
AATACCAATTCCCTAAAGCAAAGCATAGTGAGAATTTCAGTAAAAGAAAAGAAACGAAAACCCCAGAAAA
AGTATTCAGTAATTGAAGAGTCACCATCCCGAGGGTCCTATAGGAGCTCACCCTTGGTCGGTGAGAACTA
CTCAGTCAGCCTCACTTACCTCATTGCTCTGGCCAGCTCATACAGGCTTACAAGAGCAGGTTATTAAATG
GTCAGGAATTTTGATAGCCAGTTATTCATTGTTGGAAGCATAAATTTGACCACAGTGGGAGTGTTTATGG
AAATCAGCAAATGCTACAAATCTGATTTTTTTTAAATTTGAAAGCTGTTTTACCAACACACCGCGGCTT
ATAGCTCTGCATAAACATAATCTGTATCAACTTTATCCTCTTTTTCCTCCCCTTACTATAGCCTCTGTCC
TCTGCCCTCATTATCCTCTGCTGGGATCTCTTGAATATTTTTTCCCCTTTAGCTGGTTTTCTCTTTCACT
CATTGATTTGTCCTGGGTTTCATCATCTAGGCAACTCTCACGCACAGAAAATTCTTGGGAGTTGTTCTCA
CTAGACTGATAGCAATACCACTTTTATTTATTATTATTATTATTATTATTTTGAAACAAGCAAAGGC
TCTAGGAATGAAATACTAGAAGATGAAGGATTTTTTTCTTCTGGATCATAAATCTGGGCATCCCATGCCT
ACATGTTCTGGGACTCATGAGGCATTCTATTGATCCCCAAATTGCTATTAATAGATACCAAGTGAAAATT
TGGTATCTCTTCCCATCAGCCCTAATCTCAGAATGCATTATCTTTTCTAAGCAACAACTGAAGCCTGTGT
GCACTAGCAGTTAAATGTGTATCTGCAGGAGGTTTAAATATTCCTAAGTGAATGTGGGAAGTGGTAGTGT
ATTTGGAATTCAAGGGATCTTAGAAATAATGTAGTCTAATTTGCTCATTAGTCTGGTGAGTAAACAGAG
TTTCAGACAGATTAGCAGTTAGTGGTAGAATCAGTACTAGAATTCAGATCCCTGGCTTCCTCTTCTGGGC
ATTTTCAAATCTGCAACAATGTCTATCTTAATTAACATTATAATTAGGACCAAGATAATCTTCATTCAAC
TCAACAAATATTTTTTGACTACCAGATATATTTCTATGTGCACTTATTTTATACTAGGTACTGTTCCAGG
AGTTGAGACTACCAAGAAGTTCTCTACTTTTTAGAGCATTCTTTTGAGAACTAACATTATTTGTATTAGT
```

TABLE 19-continued

```
ATGACTTAACTCTTTGTTCCAGGAAATTCTTACATAGAAAATAAAACTAAGCTCATGGAGAACTTTGCCA
TTTGCTTGAGGAAATTCTTCTAAGTCAGTTTATTCAGGACATCAGTTTGCACATCTGAGCCAGCAGATCA
CTCCTCAGACAAGTTCGCTTTTTCTAGCAAGACCCTCACCTGTTTTGTCCACTAACTCTATTATGTCAAC
AACTGTGCCCAATTCCAGTCCATTCCCTACCTTGTCAGATCAGTTTTAAACATTTTGAGTCCAATTCTCT
GAACATCCTCCTTCTGAGACACTAAAATGCTGTCAGAGCATTGTTCCTCCTGTTGAGTAATTCTAATAAA
TTTAACGTTTCCTGATTGAAGCGGTTTTTTGTTGTTGTTGGTAGTATTTCTGATGAATTGGCACTTG
ATATGTTCTATTGGAGACTAGAACATAAGAATGGGGAAGGTGATACTTATAATAATCTATCTGGGTATAG
TTAGGATCTTCACATGCCACACTATGTAGTGACATAATTTGACCTGGAAATAGCTGGTCACATTGGCTAT
ATTGATAGCAACAGGAGATAGACAAATTCTTAGGCAGACAGGGGATGCGTCCCTGGTAAAACCTGATCTC
CAAGCCAAAGACAGCCTGAAGACTGAAAACTGAGCTGCCAGTTCGGGTAGAGCCCATGACCAGAGTGAG
AATTTCCTCGATGCCTTTTAGCCAATATAATGATGCTTTTTCCAGGCCCACCCATGGACCAATCAGCATA
CACTCCCCCATTCTGAACCCATAAAAACCCCAAACTCAGCCTTACAGACAGCCACCTGCTTTTGGGCCTC
CTCTCACACAGAGGACCATCCACTTCAAGTCCCCTCTTGTGTTGAGAGCTTTTCTGCCACTCAGGAAAAT
TCTTCTCTGCTTTGCTCACTCTCCGGTGTCTGTGTACGTCATTCTTCTTGGTCACAGGACAAGAACCCGG
AACATGCCAAAAGGGTGTAACACATACTCCTGCTCACTGAGTTACAGGAGTGAAAAAAACCACTGGGTGC
CGCATGCCCCTATTTAGCAGGTACAAATGAGCTGTAACACAACACACCCCCATCCTCCAAGCTGCAGGCA
GCAGGGAGAGCTGTAACATGCCTCCATCCTCCGAGCTGCAGGCTCAAAGAAGTGAACCAGTTAGGCACTA
TTCCCTCCTGGCCAGCTTGCTGAACTACAAAAGCTGCAACATTTCTTGGGAGCTTAGACCTCAGGATTCC
CCAGGCGAGAGCTGTAACATCACCTGGGGCTCCACAGTTGCTGGCATCTCTGAGTTTTCAGGTGCCACTG
CATTCCCCTCATCTAGACTCCGGCTCCCAATGCAAAAGCTGCCTGTGGCATGCCAAGTTTAGCCACAGGC
AAAACACAGACTCCCTGTTCAGATGTGGGATCCAAGCAGGTAGCACAAGCTGAGTACAGCCCATCAGGCT
GAGTGGGAAGAGTGAGCCCAGCAGGCCTTGGCAAGACTACAGGCAGAGGTCACAGCAGCCACAGAGATTT
CCAGCTGGTGAAGCAGCACTGAAGGAGTCCTGTAACAGTATGTTAGTCTACAAACTTGGTAAATTCTCAT
TCTCTGTTTTCTGTGACATTTTGATTTTAAAAATTTTATTCTCCAATACATCGCAAGGACTGGATATCCT
GCCCTCTATTTTGAAAGTATGGTGTCCAAATTCATAGGAGAAGGCAAGGCTAGGTGACTCACAAGCCACA
CACACAAAAAAGAGTCATTGGAGGAACAACCCAGGAAGCCATAGAAGAATGTTATCCCAAACTAGATGGA
AAAGTTTTGTTTTTATGTAATTTAGAAAAACATTCTTATTATTTATTTGCTTAAAGTTTGTCACCATTTT
TTCAAATTTTTTTTATAGAATGCCATCCTATTTAAACTACTATCCACAACATGAAATATAGTTACCACAA
ACATAAAAATAGCCAAGTGGTGGAATGGGGAGGAGGGACCCTGAACTGTTGACCAGGAGGTGGCCTCTGG
TAAGCCTCACCATACCTTGATGAAAGAGCCCTCAAAACTCTCCATCTCCTTTGACTTTAATTCTGTACAA
TCTTCTAATTTAGATACTGATATAGTTTGGATGTTTGTCCACTCCAAATCTCATGTGGAAATGTGATTCC
CAATGTTGGAGGTGGGGTCTGGTGGGAGGGGAATGGATCTTGGGACAGATTCCTTATGAATCGCTTAGC
ACCATTCCCCTTGGTCATAAGTGAGTTCTTGCTCAGTTAGCTCATGTCAGATCTGGTTGTAGAGTCTGGG
ACCTTCCCTCTTCTCTCTTTTGATCTCTCTCTCACCATGTGACAATCACTGCTCTCCCTTTTCTTTTGC
CGTGATTGTAAGTTTCCTGAGGCCCTCACCAGAAGCAGTTGCTGAAGTCATGCTTGCATAGCCTGCAGAA
CCATGAGCCAATTAAACCTCTTTCCTTTATAAGTTACCCAGTCATGGTTATTCCTTTATAGTGCTTTATA
GTCCTTTATAGTGACTCATAAATGGCCCAATACAGGTACTTAGCCTTTTGGTTAAAAGATACCAACACAT
AGGTGACTAGATTGCAGATCATTGGCATTTTGAATTGTTTTTTAAGTACCCATATTACTGTGGTTTACGC
CAAATTGAATCTATTATGTAGAAATATGCCTATAAAACTACTTTCAAATTTGTACAAATATCAGTTTCTC
```

TABLE 19-continued

```
AAAGCGTATATATATATATATGCATGCATGTGTATGTGTCTGTTTAAAATACACCTGCTGGGGATTAG
CATTGAGCTGAAAGACAAGGTCCTGCCCTTGCCCTAGAAGAGTTTGCAGTGTAGATGGAGACCACCTGAC
ACCTCACCTGATCCCTGATAGCAATTCCAGGCCAACTTTCCTAAGCACTATGGGAATTCAGACTAAGGGC
CAGATCACCGTTGCCTGAGATTCCATTGTGATGTTAGAATTCACATTCTCATTCTTATTCAATAGAACTG
ACTCGTTCACCAGAGCACCTACTATGTTCCAGGTGGTATCATAAGAACTTGGGAGACATCACTAAACAAA
ATAGAAAATCCCTGCCCTTATGGAGCTGACATTCTAGTGGGGCTTGGTTTTTTCCTTGGGTACTGGG
TTTGTTTTTCCATGATGAGCATATCCTATGATGCACTATAGCACTCAAGCAAGATGCCTGAAGCAAAGGA
GGTGAGTCACCATCACTGGATAAAAAAACAGGTCAGAGAAGTAGAAGTTATTTTCTCTTATAATTTTAA
ATTTTGCCTTAAGCTCTTCTTTTGAAATGTTCTAGGCCAAAGTAATGATTCATGGATTCAGCACACTTTC
CTTTGTTGAAAAGCACTGCTTGTTCCCCCTCAAAGCTATGTGAGAGGCTGTGTAGGAGAGAGTGGAGAGC
AGGTAGCCTACCGGACCTACAGTTCACCATTTCAGCCCTGTAATTGACCAGCTGTGGGACCTCAGGTAAG
CTGGCTAACCTCTCTCTTACCAATGGTAGATGACTATGAAAGCTCCAAACTCTCTCACAAACATAGGAGA
TTATTAGCATACAAATTAATGTCTAGGTTTGTGGGTCTTGAGGCTTCAGTGGAGGTCATGGGCAAAGCTG
CAAAGAGCATGGGAATTAAAATACATGCTCCAGGATAGGCAGTGTGCTGGCTTTTTCTATGGATTAATTC
ATTTGATTCTCACACCAACCTCAAAAAGAAGGATTATTAGCCCTTGATAGATGAGGTAACTGGGACTCAG
AGAAGTTGTGGAGCCAGGATTCTAGATCAAAGCATTAAGTCTTTGCTTCTGTGCTCTTTCACCTTGGCCA
GGCAGCTGCCCTTGCCCAGTAAATGGTACATCACAGTAAGTGTTTTATTAAAATGCCATTTCCCTGAAAC
AAAGAAATGATGGTATTAGGGGGAGGGCAAGGGAGACATTTTGACAATATTTAAGTATATATGATCACTA
TTTCTTCTTCAAATATCTATCTGGTATAAAACTACTATTCTGTTACTCTAATTATTTTTTGACCATAGGA
GAGACTGCGACAGAAATTCCATTAGTGGATTTGAGATTGAGTTTAGAATATTTATTTAAGTAGAGCTAAG
TGTGGCAATATCTGTCATATCTATTAGTTTGCAGAAATGAAGAAGCTTTTTTAGTTATACATCCAGACAC
CAATGCTAATACCAAATACTACAGCCAGTGTTCTTCTGTCGCCATAGTTGTTACAAGTATGACAGCCTCC
CAAGTCATTTATTGATTCAACTCCCTTTTTGTTTAATGTTGACACACTAGTTTGTATGAACAATGAGCA
CACTAGCTCAGAAGAGGACAACAAGAATTAGCGCGGATGGTTCTTCCCCTTGAGGGGTGCTCTGTCAGT
ATGAACATGCCTTCATGGGCAGAAATTAGGAGCCCACTAGCTGTTAATGAAGAGTGCTTTGCTTTCCTTT
CAGACAGCAGTTTCCAAAGTTCCTCTTCTCCTTTAATGGCATTGCCCTTTAGTGTGTGTTAACCTGTGGT
TTGAAAGAAATACTCGTGTATATTAGCAATGTAAATATAAGTGATTAAATTAAATTACATTTATCAATAA
AAATAGCTATTATCGATAGCTGAATGCATAAAGTATGCAGCATCACATACGGATGAACTCACCGTTTGTC
GTGCTACTACAGGTACATGCTCTACAAACACAGAAATTCTGATATTCTATGAAACATTATTAAATTCCAA
TTGAACATGATCATTCCAATCAAATAAGGGGAAAAAATATAAAGTATTTGTAATCAAAGACCCTGTATTG
TTGAGTATATTCCTGAAGGGGAGGGGTTTGTTTTGTCTAGGATTGATATAAAGTGAATTATCTGCTTATG
ATTTTTCACTCTGATTATTCGAATAATATTCTCCACACTAGCTCCTGGATCTGTGCATTTCAACCTTGTC
TCTTCCATACCTGCATCATTTTGGTATTGTGTATATTAGGACACATTCTGATTTCTGCATCAGAACGCTG
AGTGAGTGTGCACAGTAAGCAAAGGAGTATACCTGGGAGCCAGTCTCACACCAGGATGGCTAGTAAAAAC
AGAACCATTCATAACATAACTGTCAACCAATAAAATACATATCACTAAAGCTAAACTAAATTCGAGTACC
CTCAACTCAACTTCCCCCAGCCACATCTCAAAAACATGACTAGCTACTCCAACATCACCCAATATAAGGA
GAACTGTAAAGAAATAAAGTCAGAGTGAGAGAAAAAAAAGCAGTCCTAATCAACTTGATTAAATATATGA
CTTCACAGCAAATTGCATAAAACTATATGACCACATGAGCACATTCCTAGGCCCTCCCAAGGCCCTGAAA
AAAGCCTGAACTAGGGAGGGGCTCTAATTAGCTTAATGATACACTTACCTATGATTGTGGTTATGTCTTG
ATTTATCTGATTGGCATTGTTTTTTAAATTATCTAAAAGTGTTCATCCTTATTTTTAGGTTAGCAACTGT
```

TABLE 19-continued

```
GACCCTAGTGACTAGTAACAGTAACAAATGAAAGAAGATGCTCTTGTATGGCCAAAACGATGAAACAGAC
CTACATGATTTTATGAAAAGTTTTCCTTGGCTTTGGTTCAAAGAGATTTTTCTTTCCTTGACACTAAAGT
GGTAGTTTGCACTAGGCATATAGATACCGTTCTATCTTTCTGGTTCTCCACTTAAATGACACTCATGTCT
GCTACATTAAAATTAGCTTGTTAGGTTTTATTTCACCAAGTTTATAAAGTAAACCACATATCGTTTTCTC
TTTTGTAGATGCTGAAAGCAAAGTTCATGTGGGAAATGTTTGGCAATAGCTGATTTATCCTCAGGGTAAC
AATATTCTATAACTCCTTTGATCTTGAGGCCTCTGTGATGGAAATGCTTGGAGAAAGGGATTTTAAAGGG
AGATTCTGAAGTCCTTGGGAAAGTCCACAAGTGGACGGGGCTTCATAGCCATGACAACAAATGACATTGT
CTAGGAAACAGTGAGTCATGGCATGCTGAGCTTAGAATGGAGCCAACAGAAGGAACCTGGCCTCGGACAC
AGAATCTTTTGGCTGCTGACCCAGAATGACTGTGAAAGACTAACACTGTTTAGCAGATTTTTCTTGAGTG
TTTACTATGTGTGAGGTTCCTGGGATTCAGATTCAGCTACTATTGTTAAGAGGAAATCAACCAGGAAGTC
AGTTAAGAAAAGGTACAGTGGGTTTTCAGGCTGCAGGGTACAGAAATGTTCCCAGGCCTGGAGAACAAAC
CTTCAGATCTTAATCTGTACAGGGAGGTGGAGGGTGAAAGAATGATCTTTCAGGAAGCGTTCAAGTAGGG
CTGCTGCTTGGATTGAATTTTAAAGAATGCATAGGTTATATGCAGGATCTATATATAGATCAATAGCTTC
CCTGAGCACATGTTCAAAGGTTCAAACATTTGGGGTCATTTCTTTGCAAGAAGAGTCACTCAGTGGCCTG
AAAGTCCATGCAGCAACTTCCCTCATGAGAGCTGCTTCCGCAGCAGGCCCAGGGTTTCTAAAGGAGAGAG
CACACAGATGTAAACACTCTGTGGTTCTGAGGACTGTCACCTCTTCTTTTCACCCATCACTTTTGTCTTA
AGAACTCTATGCTCAACCCTAATTCTCAGTCTCTATATCAATTCCCACCAAACAGATGCAAAGTCCTGTC
ATTTGCTTCCATGAACTCTGTACTTATCGATGATATAATACTCTGCTGACTACATTTTACTTGCCACTT
CATATCCTCACTAGACTGAAAGACCTATAAGGGAAGAGATATCTTATTTATATATCTTTCTTATATATCT
TTCCCATATATCCTATTTACTGTTGTACTTACAACTCCTACAACCGTGCTTGGTACATAGGGTGTTGAAA
AAGTATTTATGAAATTATGAATAACACTGATTCTATTAAATAACATTATTAAGTTAATGAACAAATAATT
AAGCTTAGTAAAATATCAAAAGTTAAAGATATCAAAAACTAAACACTTATAGAATAAAAGTTTGCTTTTC
TTGTCTAGTGAGCACATTAATACAGATTTTAACCCTCTTTTGTCCTCTCCTGATTCACACGAAAAAATAC
ATAGGCCTCAGCTGTTCATTGGTGCCAGATAAAAATAAAGTACTTTTTAATTGTAATTACTGCAAAGGCT
CTTCAACAGTGCACAGTATACCAGGAACTGAAACTTTTCTTATAAAACAAATAAATATCAGTAGAAAACA
GAGCAAAGGCATTTCATTAAGTATTATGGACTGAATTGCATTCCCTGTAAATGTGTTAAAGTCTGAACTC
TCAGTACACCTCAGAATATAACTGTATTTAGAAATAGGGCCTTTAAAGAGGTAGTTAAGATTAAATGAGA
TCATGTGGATTGGTCTTAATCTAAGATGACTGGTGTCATTATAACAAGAGGAGAAGACACCAGAGATGCA
ACCGCACAGAGAAAAGGTCATGTGAGCAGGGATCCCCAAACCCTGAGCCAAGAACTGACAGTGGTCCATG
GCTTGTTAGGAACCATGCCACACAGCAGGAGGTGAGCCAAAGGCAAGGGAGCAAAGCTTCATCTGTATTT
ATAGCCGCTCCCCATTGCTCACATTACCTCCTGAGCTCTGCCTCCTGTCGGATCAGTGGTGGCATTAGAT
TCTCATAGGAGTGCACACCCTATTGTGAACTGCGCATGAGAGGGATCTAGATTGCATGCTCCTTATAAAG
TCTAATGCCTGATGATCTGAGGTGGAGCTGAGGTGGTGATGCTAGCTCTGAGGAGTGGTTGCAAACACAG
ATTAACATTAGCAGAGAGGTTTGACTGCCCAGAGACCATAATAAATCAGTTGCCTGCAGACGCATATCAA
AACCCTGTCAGTGAGTGGCAGGTGATAATTCAGCTGCATCTGGTGGCTGGCTTTATAGTGGCAAGTGCGT
TGATGTACTTCAACTGTACAGCTGCATCTGGTTGCTGGCTTTATAGTGGCAAGTGAGTTGATGTACTTCA
ACTGTACAGCTGCATCTGGTGGCAGGCTTTAAGTCAGAATCTGACACTTATTTTAGTCCATGTGTGTCCT
GCCCATTATTTTATTTGTCACTTCCATCCGCACCTCTTTCCTGCACTGCACACTTGTCTCAATCAGTTTT
GGTAAGCCCACAAGCTAACCCTAGCCAAAATGAATAAAAACAATCATCACTGGAGAGTTTCTTTGAAAAG
```

TABLE 19-continued

```
TGGGAAAGAACCAATGATGAGACAGCAGAAGACTCTAAGACTGCCAACAAAAAGAAAGCTGCATTTAAAA
GAAAATACTGGCCGGGCGCGGTGGCTCATGCCTGTAATCCCAGGACTTTGGGAGGCCGAGGCGGGCGGAT
CACGAGGTCAGGAGATTGAGACCATCCTGGCTAACAAGGTGAAACCCCGTCTCTACTAAAAATACAAAAA
ATTAGCCGGGCATGGTGGCGGGTGTCTGTAGTCCCAGCTACTCAGGAGCCTGAAGCAGGAGAATGGCGTG
AACCTGAGAGGCAGAGCTTCCAGTGAGCCGAGATCGTGCCACTGCACTCCAGCCTGGGTGACAGAGCGAG
ACTCCATCTCAAAAAAAAACAAAAAAAACAAAATACCATGAGTCCTACTTAAATTACAGGGTCATTGCAC
CAGTAATTCACATTCTCCAAGCCCTCTTTTTATAATATGTGGTGGTTGGCTATGCAATGAAGCCATGAA
ACCTTCAGAACTGCTTCACTGCATGGAAACCAAGCACCCTGTGTTAAACAAGACTTTGGAGTTTTTCAAA
AGAAAAAAAAAGATGAACAAGAAGAACAGAAGCAATTATTGAAGGCCACCATTTTATCAAATGTGTCTG
TACTGACAGCATCATATCATTCGTAGTGGCTAACCACATTGCTAAAGTTAAGAAGCCCTTTGCTATTGGT
GAAGAGTTGATTTTGCCTGCTGCTAAGGGTATATGTCATGAACTTTCAGGAGAGGCTGCAGTTCAAAAGG
TGGCATGTGTTTCTCATTTGGCTAGCACATAACTAAATGATTAGATGAAATAGCAGAGAATGTTGAGGTA
CAATTGTTACAGAGAGTTAATGAGCCACCGCAGTACATGATTCAGGTTGATGAGTCTACCAATGTTGGTA
AGGCAACAATGCTTACTTTTGTGCAATATATTTTTCAGAAGATGTGCATGAGGATATGTTATGTGCACTT
TTGTTGCCAACTAATACCATAGCTGCAGAACTATTCAAGTCTTTGAATGATTGCATATCAGGAAAACTCA
ATTGGTCATTTTGTGTCAGTATATGCATGGACGGACCGACTGCCATGACTGGACAGCTTTCTGGTTTCAC
TACTTGGGTCAATGAGGTCACTTCTGAATGTAACTCTTCACACTGTGTCATCCGTAGAGAAATGTCGGCT
AGCCAAAAAATGTCACCTAAATTTAACAATGTTTTGCAAGGTGTGATTAAAATTATTAACCACATTAAAG
TGCATGCCCTTAACTCATATCTGTTCACACAGCTCTGCAAGGAGATGGACACAGAGCACACAGTCTTCTC
TTATATACATAAGTGAGATGGCTTTCTAAAGGTAGATCACTGGCCAGAGTGTTTGAGTTATGAGAGCCAC
TCCAGAGACTTCTTTTAGAAAAACAGACACCACTGGCAGCACATTTCAGTGACACAGAATGGGTTAAAAA
ACTTGCTTACTTGTGTGACATATTCAACCTGTTCAGGGAATTCAATCTTTCACTTCAGAGGAAAATGACA
GCTGTGTTCAAGTTCGCAGATAGAGGGCTGCATTCAAAGCCAAAGTGGAATTATGGGGCAACAAGTGA
ACAGTGAGATTTTTGACATGTTCCAAAATTAGCAAAGATTTTGAAAAAGACTGAGCCATGGCCTTCTTTC
TCCCAGCTAGTGCATGATCACCTGTCTCAGCTTTCAAAAGAGTTTAAGCATTATTTTCTAACTACAAAAG
ACCCTAGAACTGGGAAGGAATGAATCTGTGACCCATTTGTGAATAAGCCAAGTGAACTGACTTTGTCCAT
CCTAGAAGAGGATCAACTGCTTGAGATGGCAAATGACAATGCCCTTAAAAGTATGTTTGAGACAACTTCA
AATCTCCATACATTCTGGATTAAAGTCAAGGTGGAATATCCTGAGATTGCCACAAAAGTACTGAAAATCC
TGCTTCCATTTCCAATATCCTATCTTTGTGAAGTAGGGTTTTCTGCAGCGACAGCAACCACAATGAGATT
ATGGAGTAGACTGGACATAAGCAATATACTGCAGGTGTCACTGCCTCCCATCACCTGCACATGGGACTAT
CTAGTTGCAGGAAAACAAGCTTAGGGCTCTCACTGATTCTACATTATGGTGAGTTGTATAATTATTTAAT
TATATATAATTAATTATTTAATTATATATAATTAATTATTTAATTATACATATATAATTATATATAATTA
AATATATATTTAATTATATAATATATAAAAATATATAATTATTTAATTATATATATGGCGAGTTGTATAA
TTATATATTATAAATGTAATAATAATAGAAATAAAGTATACAATAAATGTAAATGCACTTGAATTATCCC
TAAAGCATCCCCTTATCCCAATCCACAGAAAAATAGTCTTCTATGAAATTGGTCCCTGGTGCCAAAAAGG
TTGGGGGCCATTGCATGTGAGGACACAATGAGAAGGCAACTATCTTCAAGCCAAGGAGAGAGTCCTCAGA
AAAATATCAAACCTGTTGAAACCTTGATCTTGGACTTCCAGCCTCTAGAACTGTGAGAAAATAAATTCCT
GTTGTGTAAGCCACCCAGTCTGTGGCATTTTGTTACAGCAGCCCTAGCAAACTAATATATTCAGCAATTC
TTTTTTTTTTCTAGGACATAAACATATTTTAATGTCCTACTTCCTGGGGAGAAATCCTTTTAATTATTTT
TGTGTATTTGGAAATAGGGGTTGTATTCCAAATTGTAGTCTACCATAAAGAACTACCTGAGGCTGGGTAA
```

TABLE 19-continued

```
TTTATAAGGAAAAGAGGTTTAATTGACTCACAATTCTGCAGGCTGTACAGGAAGCATGGCTGGAAAGCCA
CAGGAAACTTATAATCATGGTAGAAGGTGAAGGGGAAACAAGCACATCTTCACATGGTGACAGGAGAGAG
AGAGAGTGAATGGGGAAGTGCCACACACTTTTACACCACCAGATCTCATGATAATTCACTGTCATGAGAA
GAGCAAGGGGGAAATCCATCCCCATGACTTAATCACCTCACACCAGGTACCTCCCCCAACACTGGGAATT
ACAATTCAACTTGGGATTTGGGTGGGGACACAGAGCCAACCATAACAGGGATATATTATAATAAAACGTA
CTGAGAGGTACACAACAGCACCCTGGAATATTGCTGCCAAAAATGGACCTAATCATAAGGAAACATCAGA
TAAATTCAAATTGAGGAATTGTTCCAGAATAAACAAGACTAAAGCAACATGACAACTAAATGCAATACTT
GAATCTGCATTGGATCCTGAAACAGTTTTATCTATCTATCCATCCATTTATCCACCCATAACGGTAAAGG
ATATTATTGGGATAATTGTCATAATTTGAATAAAATCTATAGATTAGGTATTAGCATTACATCACCATTA
ATTTCCTAGTTTTGATAGTTGTATTCTGCTTTTATAAGAGAATTTTCTTGTTCTTAGGAAATACTGGATA
ATCTGGGCAAAAAAATTCTGGAATTCTTTAGACTCTTCTTTCAACTTTTCCATATAAGTTTTAAGTTTAT
TTCAAAGTATGAATGCTATAAAATTAGGAATTCAAACAAAAATAATCAAATTGAGAGGTGTGTACATTTA
ACAAAACAGTTATATTAAATCAGGTTAAATTTTAAGCATGCTGAAAATTTGCTGAGACCTGGGAGTGTTT
GTTTCTGCCAGTGTTAGTTTCAAAGTCCATAGTGGCATATTGAATTTTGTGTAATTTCCAGTAACATAGT
GCAAGGATGAGTAGCCACACACATTTAGTGTTGCAATAATATAAAAAGCCTCAGGAGCACTCCAGCCAGC
ACAACAAGTCCCCAGGGACAGCTAAGCACTCCAGTGTCTAGGGACTGTGGGAACTGGAAAGAAACA[]TC
CAGTGTAAATATGACTTCTAAGCTGGCTGTTGCTCTACTGCTTTCTTGGCAGTTGCATGCTTTCTGTAGC
ACTGTGTGAAGGTAGGCTCATCTTTCTAATCAATAGAGTTTTCTTTTGTCTAAATATGATTCTCCGAAAG
CAAGGCTATCCAAAATGCTTTGAGATTTGCTTATTAAAACAAAAAAAAATCCCCATTTGCATTCATTTGA
TGTTGTCATGAGTACAAAATAACTTTTGTGGGCCTTAGACATTTTACCTTTGTGGGACTCTTCAGCCAT
CATAATATCAATACTTAAAATTTTTTTATGTAACTTAGAATGCTTCAACATTTTTTCTGTTTTAGGTAAA
ATTTAGGGGATTTTATGGGCCCTAAAAATTTCTTTATTTCTGTTGTGAGAAAAAAATAACACTTTCTTA
GATTCTAAAACTTCATGTTTTTCTTCCGACTTTAAAGGCAATTAAAACAATTTCATGGGCTTCTAAAATT
ATTGTGGGCCCTAGGCACTATGCCTACTGGCCCTAATGCATAAGTTACCCCTAATTTGCATTAAATTTGG
AATTATTTAGGTTCTATCTCTATACCTCTCAGAAAAGTGTAATATTTGCATTGATGTAGACATTTAGTTG
CTAAAATTCACAACTTGTCCTATAACACATATATCACTATATATACTTATATTCATTTATAATTTATATT
ATATTCCATTGGGGGGCACAGTTGGTTAATATTGCCTGTTAAAATTGAACTAGGTAACCACGTATTTTTA
CTCAGTGTTCTGCTGACAAAGGCTTAGACAGTAATCATTTTCTGCCTGCTTTGAAGAGTTTTGATGGGCC
CTAGACCATCTTAAGATCCTGCTATATAACAAATAGTGTGTTTTTAGCATGCGTTTTCTGTATTTGCTTT
TTCGTTTTATCAGCATTAAAAGTTTTTTTTAAAAAAAATACAAGTCATCTCTGTAAAATAGTCATGTTT
CTGTTTATTCTTTCTGAAGGTGATATATCTGTTGATAAGATCATTGTTTATCTCCTATAAATAACATTAT
AGCATCATGAAGAATACTGCAAAATCAAATAGAAGAATGGCCATATGGATATAAAATATTAATTTTAATA
AATTTATAGTTTTATGTATTTATATATTTATATATTAGTTTTTATATTGACATTCAAAATAGTCAGTGAG
AATCATTTTGAAAGAAAGGAAATTAATTTCAAGGGTTGGTCTAAAACTAGTCTTTCTATTTGTAGCAACC
TGTTTCGTTAAGACATTTCTCATGGTCCTAAAAATCATCATATTCAAATTTAAAGGGTATCTAGCAGAGT
TGTGCCCTTTGATGAAAGCAGTCCTTACTTCCTTGCTATGTTCACTGCTTCCATTGTGCCAAGTATTAGT
ACAGTACCACAATGCCAGTGCATGAGGACACATTTTATACCTTTGCATCCCAAATTTATTAAAGAACTCA
GAATTATTCAGAGTGGATTATATTATAAAAATTAAGAAATCATGTAAGTACTTTCAAAAGTTCTTAGTTA
TTTTGCTTCTGTACATGTAGACTGTTTAGGTGCTGAGAGTACAATGGTAAACAGAACAGCAAAAAAAAAA
```

TABLE 19-continued

```
AATTCTGTCTTTACAAATAACTTGGTACTGACATCTGGTTAGTTTTAGCTATTGTGTCTCCCTTGCTTCT
GAATTCCAGAGCAATACTTTCATTTTTTGATATAAGCAAATTCTAAAACACATTGTGGGAGGTAGATAA
TCTGACATTTTGCAGAGTTAAAGTAATTAGAGAAGCACAAGAAAGTTTCGAAAATGATAATTAAATTTGA
AATAGGAATTAGCATGAGTGAAGCAACTCCAGGTACATGGTGATTAACCCAAGTAATATGACTCCAGGTA
TCCTGGGAATTCCTTTCACTGTGAAAGCTGCAATCAGTGGCCTTTGGAAAAGTAAGTGGGGTTCCTGCAG
CTCCCAGAAAATTGTGAAAAAATCCTGTTGGGATCATTTCCATTTACCACTGAGCCAAATGACCATGATT
TCCAACTGCAAAGGGATATCTAAAACCAGATAAGTAATTTACCTAAGTAGTCTTTTTCACTCTTTAGTGT
GAAGCTTATTCATGAAGAGACCTCTGCCTGAACATACAGCAAATTTAAGAAGGTTGTGCAGATAGTCTGA
AGGAGGTGAGTTAGTTTTTCCCACTTTCTCAAATTTCTCAAATTTCATTTGTCATGAAACTAATAGGAAA
GATTCACAAATGTCAGTTTAAGAGTTTTACCTAATGGAATCTCACTTTTATTTATTTTTTGCTTCTATT
TAAAAGCTTTTTTTTCAATGATAGAAAAAATGCTAGCGATAGTAATTTGCTTTTTTAATAATGGAAAATG
TAGAGCAATATAGCAAACCTCAAAGAGTATTGATTTCTCAAAACAAAAGCATAACAAAATTTGTTTATTC
TCTTTTAATTTATGGTTTTAAAAATTTTACTTGTATTTAGAAATAAGGAAAAATGAATAAGAAAAAATTA
AAGAGCATTCTTCCATGGTTTCCAAGAATTTCTTATTAAATATGTTAACAAAACTCGAAGTGAATAAAAG
TTAGAGCTATAGCCTATGCTATTGGATACCCACCCATATCATCTGATCTGCACCACTTCAATGCTCACTG
TTTTGTCTTCCAAGGGCTTTCTCTGGTTACCAGCGTCCACTATACTAGCAAGGCCCAGGTTGGAAATATT
GGAAAATTAATGGCCTTGGGCGCAGTCTTTAACTAATGACCCACTAAAGCAGTGTACTGTAAGTCCTCAC
TTAACCTCATCAATAAATTCTTGGAAACTGTGACTTTAAATGAAATGAATAGCAAAACAGATTTTATTAT
AACTTATTTGATAGAAATAATAGTTAAGTTTCTAAGGCATATTTCTAGTCACAAAACATCATCAAACTGC
CAAATAAAGATCAAAATAATTCTAATATTAAACACTGAAATATATGTGAACTATATATACATTTCGGAAA
GATTAATAAAAAGAAGATAATTACTCAATTTTTGGTGAATCTGTGAGTGACAAAGGTCATAGTAGTGGTG
GGTGATGTGGGGAGGGATGTTTACTCCTTATCCTAGTGAGGAGTAAACATGAGTCTTCCAATATCCACAC
CTTGCTGTCCATCATCAAATCTCTTAAAATATCTAGTTTTGTTTCTAATGTCACACTTTTTCTCTGGTGT
GTGTGTGTGTGGCCATAGACGTAAGAAGAGGTGGATAGTGCAACTTTAAAGTTTATTACAACAAAGTTAA
GTCAGGGAATGAATATGTAAGAAGCACCCCCTACCAGTATATAATTCAAAAACAAACATAAAAAATATGG
TGCCCTCCCTGAGCTCATACGATATCTTTTATTGTCATGTACTTGTATGATTATTGTATACTTTATATTT
TTTTATTTTTTCATTAATACATAATAGATGTACATATTTTGGGGATACTTGTGATAATCTGATACATTAA
TGATATGGTTTGGCTGTTTCCCCATCCAAATCTCATCTTGAATTTCAGTTCCCATAATCCCCATGTGTCG
AGGAAGGGACCCGGTGGGAGGTAATTGAATCATGGGGCGATTTCCCCCATGTCGTTCTCCTGATAGTGA
ATGAGTTATCATGAGGTCTGATGGTTTTACAAGAGGCTTCCCCTTTGACTTGGCACTCATTCTCTGTCCT
GCCGCTCCGTGAAGAGGTGCATTCTGCCATGATTGTAAGTTTCCTGAGGCCTCCCCGGCCCTGCCGAACT
GTGAGTCAATTATGCCTCTTTTCTTTATAAATTGCCCAGTTTGGGGGCAGTTTTTTATAGCAGTGTGAGA
CTGAATTAATACAATCAAATCAGGGTAATTGGGATGTACATCACCTTAAATACTTTTCTTTGTGCCAGGA
ACATTTGAATTATTCTCTTCTAGCTATTTGAAATGTACAATAGATTGACTTACCCTACTGAACTATGGA
ACACAATGTCTTATTTCTTTCAATTAACTGTATAGTTGTCCTCACTATTCAATCTCTGTTCTTCCTCCTC
ACTTCCAACAATTCTTGGCCTTGGTAACCATCAATCTACTCTCTATCTTCATGATATCTACTTTTGTGTC
TCCCACATATGAGTGAGAATAGGCCATATTTGTCTCTCTGTGCTTGGCTTATTTCACTTAACATAATGAC
CTCCAGTTCCATCTATGTTGCTGCAAATGACAGGATTGCATTAGTTGTTGTGGCTGAAAAATATTCAATT
ATGTATATATACCACAGTTTCTTTATACACTCATCCATTGATGGACACTTAGGTTGATTACATATTTTGT
CTATTGTGAATAGTGCTGCAATAAATATGGGATTGCAGATACCTCTTTGATATACCGATTTTCTTTCTTT
```

TABLE 19-continued

```
TGGATATATACCCAGTAGTTAATTGCTGGGTCATGTGTAGTTCTATTTTCAGTTTTTGGAGGAACCTCCA

TACCGTTTTTCATAGTGGTCATTTTAATTTACTTTCCCACCAACATGTATGAGGGTTTCCCTTTCTCTCC

ATCCTCGCCAGCATCTGTTATTACCTGTCATTTTGATAAAGGCCATTGTAAGTGGGGTTAGATGATATCT

CATTGTGGTTTGGATTTGCATTTTTCTGGTGACTAGTGATGTTGAGTATTTTTTTCATATAACTGTTGGC

CATTTGTATGCCTTCATTTGAGAAATGTCTGTTCAGATCTGTTGTCCGTTTTAAAATCAGATTATTTTGT

TTTGCGCTATTGAATTGTTGGAGCTCCTTATATATTCTTGTTACTAATACTTGTGAAATGGATAGTTTAT

AAAAATTTTCTCCCATTCTGTCTCTTTACTTTGGTGATTGTTTTTCTTGCTGTGCAGAAGCTTTTTAGCT

TTATGTAATCTCAATTGTCAATTTTTGTTCTTATTGCCTGTGCTTTGCCCAGCCCAATGTCCTAGAATGT

TTCCCCAATGTTTTCTTCTAGTAGCTTCATAGTTTCAGGTCTTAGATTTAAGTCTTTAATTCATTTTGAT

TACATTTTTGTATAGCCTGAGACATAGGGGTCTAATTTCACTCTATGCATATGGTTATCCAGTTTTCCCA

GCACCATTTATGAAAGAGACTGCCCTTCCCCCATTGTCTATTCTTGGTGTCTTTGTAAAAAATGACTTCG

CTATAAATGTGTTTATTGATATCTGGGTTCTCTATTCTATTCCATTAGTGTACATGTCTGTTTTTCTACC

AACCATGCTAATTTGGTTACCATACCTTTGTAGTATGTTTTAAAGTTGGATAGTGTGATGCTTCCAGCTT

TGTGTTTTTTACTCAGGATTGCTTTGGCTATTCAGGGAATTTTTTAGTGTGTGGTTCTATGTAAATTTGA

GAATTTTTTTCTATTTATGGGAAGAAAGTCAGAATTTTGACAGGGATTGCATTGAATCTCTAAATTGCTT

GTCATTCTTG
```

MTSKLAVALLLLGSCMLSVALCEVPSISTVPQCQCMRTHFIFLHPKFIKELRIIQVLSKVLSYFASVHVDCLGAESTM   (SEQ ID NO.: 12)

VNRTAKKKNSVFTNNLVLTSG

A NOV6 nucleic acid was identified by exon-intron scanning bioinformatic analysis of subgenomic library sequences. These sequences were generated by polymerase chain reaction (PCR) screening of bacterial artificial chromosome (BAC) clones containing human genomic DNA with oligonucleotides specific to the Gro2 chemokine gene, which is one of several chemokine genes, e.g. Gro1, ScyB5 and IL-8, contained on human chromosome 4q21. The NOV6 polypeptide has homology (39% identity, 59% similarity) with human neutrophil chemotactic factor (GenBank Accession No. P93631), as seen in Table 20. The polypeptide also has a high degree of homology (38% identity, 57% similarity) with human interleukin 8 (GenBank Accession No.: XP 003501), as seen in Table 21.

TABLE 20

```
NOV6:    1 MTSKLAVALLLLGSCMLSVALCE---VPSISTVPQCQCMRTHFIPLHPKFIKELRIIQ--    165 (SEQ ID NO.: 47)
           **********   + ++* ****   +*  +   +***++*+  * *********+*+
NCF:     1 MTSKLAVALL--AAFLISAALCEGAVLPRSAKELRCQCIKTYSKPFEPKFIKELRVIESG    58

NOV6:  166 ---VLSKVLSYFASVHVDCLGAESTMVNRTAKK                              255
              ++++    +     ** +    * *  +*
NCF:    59 PHCANTEIIVKLSDGRELCLDPKENWVQRVVEK                              91 (SEQ ID NO.: 48)
```

Where * indicates identity and + indicates similarity.

TABLE 21

```
NOV6:    1 MTSKLAVALLLLGSCMLSVALCE---VPSISTVPQCQCMRTHFIPLHPKFIKELRIIQ--    55 (SEQ ID NO.: 49)
           **********   + ++* ****   +*  +   +***++*+  * *********+*+
IL-8:   25 MTSKLAVALL--AAFLISAALCEGAVLPRSAKELRCQCIKTYSKPFHPKFIKELRVIESG   82

NOV6:   56 ---VLSKVLSYFASVHVDCLGAESTMVNRTAKK                              85
              ++++    +     ** +    * *  +*
IL-8:   83 PHCANTEIIVKLSDGRELCLDPKENWVQRVVEK                              115 (SEQ ID NO.: 50)
```

Where * indicates identity and + indicates similarity.

Protein alignment of the NOV6 protein with known CXC chemokines, e.g. IL-8 (GenBank Accession No. XP 003501), alveolar macrophage chemotactic factor-I (AMCF-1) (GenBank Accession No. A44253) and human neutrophil chemotactic factor (NCF) (GenBank Accession No: P93631) demonstrates homology in the CXC domain, shown bold in Table 22.

TABLE 22

```
NOV6:    1 MTSKLAVALLLLGSCNLSVALCE---VPSISTVPQCQCMRTHFIPLHPKFIKELRIIQ-- 55  (SEQ ID NO.: 51)

IL-8:   25 MTSKLAVALL--AAFLISAALCEGAVLPRSAKELRCQCIKTYSKPFHPKFIKELRVIESG 82  (SEQ ID NO.: 52)

AMCF-    1 MTSKLAVAFLAV--FLLSAALCEADVLARVSAELRCQCINTHSTPFHPKFIKELRVIE   56  (SEQ ID NO.: 53)
1:

NCF:     1 MTSKLAVALL--AAFLISAALCEGAVLPRSAKELRCQCIKTYSKPFEPKFIKELRVIESG 58  (SEQ ID NO.: 54)
```

Based on its relatedness to the known members of the CXC chemokine family the NOV6 protein is a novel member of the CXC chemokine family. The discovery of molecules related to CXC chemokines satisfies a need in the art by providing new diagnostic or therapeutic compositions useful in the treatment of disorders associated with alterations in the expression of members of CXC chemokine-like proteins. Nucleic acids, polypeptides, antibodies, and other compositions of the present invention are useful in a variety of diseases and pathologies, including by way of nonlimiting example, those involving inflammation, angiogenesis and wound healing.

NOV7

A NOV7 sequence according to the invention is a nucleic acid sequence encoding a polypeptide related to the serpin Protease Inhibitor family of proteins. A NOV7 nucleic acid and its encoded polypeptide includes the sequences shown in Table 23. The disclosed nucleic acid (SEQ ID NO:13) is 1245 nucleotides in length and contains an open reading frame (ORF) that begins with an ATG initiation codon at nucleotides 1–3 and ends with a TAA stop codon at nucleotides 1243–1245. The representative ORF includes a 414 amino acid polypeptide (SEQ ID NO:14). SIGNALP predicts a secretory signal sequence from residues 1–19. The molecular cloning of NOV7 is shown in Example 2.

TABLE 23

```
ATGAACCCCACACTAGGCCTGGCCATTTTTCTGGCTGTTCTCCTCACGGTGAAAGGTCTTCTAAAGCCGAGCTTCTCACCAAGGAA    (SEQ ID NO.: 13)

TTATAAAGCTTTGAGCGAGGTCCAAGGATGGAAGCAAAGGATGGCAGCCAAGGAGCTTGCAAGGCAGAACATGGACTTAGGCTTTA

AGCTGCTCAAGAAGCTGGCCTTTTACAACCCTGGCAGGAACATCTTCCTATCCCCCTTGAGCATCTCTACAGCTTTCTCCATGCTG

TGCCTGGGTGCCCAGGACAGCACCCTGGACGAGATCAAGCAGGGGTTCAACTTCAGAAAGATGCCAGAAAAAGATCTTCATGAGGG

CTTCCATTACATCATCCACGAGCTGACCCAGAAGACCCAGGACCTCAAACTGAGCATTGGGAACACGCTGTTCATTGACCAGAGGC

TGCAGCCACAGCGTAAGTTTTTGGAAGATGCCAAGAACTTTTACAGTGCCGAAACCATCCTTACCAACTTTCAGAATTTGGAAATG

GCTCAGAAGCAGATCAATGACTTTATCAGTCAAAAAACCCATGGGAAAATTAACAACCTGATCGAGAATATAGACCCCGGCACTGT

GATGCTTCTTGCAAATTATATTTTCTTTCGAGCCAGGTGGAAACATGAGTTTGATCCAAATGTAACTAAAGAGGAAGATTTCTTTC

TGGAGAAAAACAGTTCAGTCAAGGTGCCCATGATGTTCCGTAGTGGCATATACCAAGTTGGCTATGACGATAAGCTCTCTTGCACC

ATCCTGGAAATACCCTACCAGAAAAATATCACAGCCATCTTCATCCTTCCTGATGAGGGCAAGCTGAAGCACTTGGAGAAGGGATT

GCAGGTGGACACTTTCTCCAGATGGAAAACATTACTGTCACGCAGGGTCGTAGACGTGTCTGTACCCAGACTCCACATGACGGGCA

CCTTCGACCTGAAGAAGACTCTCTCCTACATAGGTGTCTCCAAAATCTTTGAGGAACATGGTGATCTCACCAAGATCGCCCCTCAT

CGCAGCCTGAAAGTGGGCGAGGCTGTGCACAAGGCTGAGCTGAAGATGGATGAGAGGGGTACGGAAGGGGCCGCTGGCACCGGAGC

ACAGACTCTGCCCATGGAGACACCACTCGTCGTCAAGATAGACAAACCCTATCTGCTGCTGATTTACAGCGAGAAAATACCTTCCG

TGCTCTTCCTGGGAAAGATTGTTAACCCTATTGGAAAATAA

MNPTLGLAIFLAVLLTVKGLLKPSFSPRNYKALSEVQGWKQRMAAKELARQNNDLGFKLLKKLAFYNPGRNIFLSPLSISTAFSML    (SEQ ID NO.: 14)

CLGAQDSTLDEIKQGFNFRKMPEKDLHEGFHYIIHELTQKTQDLKLSIGNTLFIDQRLQPQRKFLEDAKNFYSAETILTNFQNLEM

AQKQINDFISQKTHGKINNLIENIDPGTVNLLANYIFFRARWKHEFDPNVTKEEDFFLEKNSSVKVPMMFRSGIYQVGYDDKLSCT

ILEIPYQKNITAIFILPDEGKLKHLEKGLQVDTFSRWKTLLSRRVVDVSVFRLHMTGTFDLKKTLSYIGVSKIFEEEGDLTKIAPH

RSLKVGEAVEKAELKMDERGTEGAAGTGAQTLPMETPLVVKIDKPYLLLIYSEKIPSVLFLGKIVNPIGK
```

The NOV7 polypeptide has a high degree of homology (100% identity) with an uncharacterized human secreted protein HWHGUS54, as seen in Table 24. Also, the NOV7 polypeptide has homology (40% identity, 62% similarity) with the serpin protease family member human alpha1 anti-trypsin (A1AT) (GenBank Accession No. 1313184B), as seen in Table 25.

TABLE 24

```
NOV7:     1 MNPTLGLAIFLAVLLTVKGLLKPSFSPRNYKALSEVQGWKQRMAAKELARQNMDLGFKLL  180   (SEQ ID NO.: 55)
            ************************************************************
HWHG:     1 MNPTLGLAIFLAVLLTVKGLLKPSFSPRNYKALSEVQGWKQRMAAKELARQNMDLGFKLL   60

NOV7:   181 KKLAFYNPGRNIFLSPLSISTAFSMLCLGAQDSTLDEIKQGFNFRKMPEKDLHEGFEYII  360
            ***********************************************************
HWHG:    61 KKLAFYNPGRNIFLSPLSISTAFSMLCLGAQDSTLDEIKQGFNFRKMPEKDLHEGFHYII  120

NOV7:   361 HELTQKTQDLKLSIGNTLFIDQRLQPQRKFLEDAKNFYSAETILTNFQNLEMAQKQINDF  540
            ***********************************************************
HWHG:   121 HELTQKTQDLKLSIGNTLFIDQRLQPQRKFLEDAKNFYSAETILTNFQNLEMAQKQINDF  180

NOV7:   541 ISQKTHGKINNLIENIDPGTVMLLANYIFFRARWKEEFDPNVTKEEDFFLEKNSSVKVPM  720
            ***********************************************************
HWHG:   181 ISQKTHGKINNLIENIDPGTVMLLANYIFFRARWKHEFDPNVTKEEDFFLEKNSSVKVPM  240

NOV7:   721 MFRSGIYQVGYDDKLSCTILEIPYQKNITAIFILPDEGKLKHLEKGLQVDTFSRWKTLLS  900
            ***********************************************************
HWHG:   241 MFRSGIYQVGYDDKLSCTILEIPYQKNITAIFILPDEGKLKHLEKGLQVDTFSRWKTLLS  300

NOV7:   901 RRVVDVSVPRLHMTGTFDLKKTLSYIGVSKIFEEHGDLTKIAPHRSLKVGEAVHKAELKM 1080
            ***********************************************************
HWHG:   301 RRVVDVSVFRLHMTGTFDLKKTLSYIGVSKIFEEHGDLTKIAPHRSLKVGEAVHKAELKM  360

NOV7:  1081 DERGTEGAAGTGAQTLPMETPLVVKIDKPYLLLIYSEKIPSVLFLGKIVNPIGK       1242
            ******************************************************
HWHG:   361 DERGTEGAAGTGAQTLPMETPLVVKIDKPYLLLIYSEKIPSVLFLGKIVNPIGK        414   (SEQ ID NO.: 56)
```

Where * indicates identity and + indicates similarity.

TABLE 25

```
NOV7:    54 DLGFKLLKKLAFYNPGRNIFLSPLSISTAFSMLCLGAQDSTLDEIKQGFNFR--KMPEKD  111  (SEQ ID NO.: 57)
            + *  * ++**  +   *** **+**+***+**  **  +   ** +*  **    ++*+
A1AT:    47 EFAFSLYRQLAHQSNSTNIFFSPVSIATAFAMLSLGTKADTQSEILEGLNFNLTEIPQAQ  106

NOV7:   112 LHEGFHYIIHELTQKTQDLKLSIGNTLFIDQRLQPQRKFLEDAKNFYSAETILTNFQNLE  171
            +****  ++   *  +     *+*+** **+++*+   *****  ** + +   ***+ *
A1AT:   107 VHEGFQELLRTLNKPDSQLQLTTGNGLFLNKSLKVVDKFLEDVKNLYHSEAPSVNFQDTE  166

NOV7:   172 MAQKQINDFISQKTHGKINNLIENIDPGTVMLLANYIFFRARWKHEFDPNVTKEEDFFLE  231
            *+****++++  *  **+  +*++  +*      **   * *****+ +**+   *+     ++
A1AT:   167 EAKKQINNYVEKGTQGKVVDLVKELDRDTVFALVNYIFFKGKWERPFEVEATEEEDFHVD  226

NOV7:   232 KNSSVKVPMMFRSGIYQVGYDDKLSCTILEIPYQKNITAIFILPDEGKLKHLEKGLQVDT  291
            +  ++******  *  *++ + + +***    +*   + *  *  **** +***+***   *   *
A1AT:   227 QATTVKVPMMRRLGMFNIYHCEKLSSWVLLMKYLGNATAIFFLPDQGKLQHLENELTHDI  286

NOV7:   292 FSRWKTLLSRRVVDVSVPRLHMTGTFDLKKTLSYIGVSKIFEEHGDLTKIAPHRSLKVGE  351
            +++      +**  ++ +*+*  +***+***  *  ++*+*+*       ***  +        **+  +
A1AT:   287 ITKFLENENRRSANLHLPKLAITGTYDLKTVLGHLGITKVFSNGADLSGVTEDAPLKLSK  346

NOV7:   352 AVHKAELKMDERXXXXXXXXXXXXLPMETPLVVKIDKPYLLLIYSEKIPSVLFLGKIVNP  411
            ***** * +**+                +** *   ** +**++*+  +    *  **+**+***
A1AT:   347 AVHKAVLTIDEKGTEAAGANFLEAIPMSIPPEVKFNKPFVFLMIEQNTKSPLFIGKVVNP  406

NOV7:   412 IGK                                                          414
            *
A1AT:   407 TQK                                                          409  (SEQ ID NO.: 58)
```

Where * indicates identity and + indicates similarity.

Based on its relatedness to the known members of the serpin protease inhibitor family the NOV7 protein is a novel member of the serpin protease inhibitor protein family. The discovery of molecules related to serpin protease inhibitors satisfies a need in the art by providing new diagnostic or therapeutic compositions useful in the treatment of disorders associated with alterations in the expression of members of serpin protease inhibitor-like proteins. Nucleic acids, polypeptides, antibodies, and other compositions of the present invention are useful in a variety of diseases and pathologies, including by way of nonlimiting example, those involving liver disease, e.g. cirrhosis and lung disease, e.g. emphysema.

A NOV7 nucleic acid is useful for detecting specific cell types. For example, expression analysis has demonstrated that a NOV7 nucleic acid is expressed in high levels in liver cirrhosis and stimulated smooth muscle cells (Example 1, Table 38). The results shown in Example 1 for NOV7 indicate that NOV7 will be useful in treating liver cirrhosis and inflammatory conditions, including the results shown for CD45RA CD4 lymphocyte anti-CD28/anti-CD3 conkinase family of proteins. A NOV8 nucleic acid and its encoded polypeptide includes the sequences shown in Table 26. The disclosed nucleic acid (SEQ ID NO:15) is 1,123 nucleotides in length and contains an open reading frame (ORF) that begins with an ATG initiation codon at nucleotides 9–11 and ends with a TGA stop codon at nucleotides 1116–1118. The representative ORF includes a 369 amino acid polypeptide (SEQ ID NO:16). Putative untranslated regions upstream and downstream of the coding sequence are underlined in SEQ ID NO: 15.

TABLE 26

AGCCTCGGATGCTGGCCCGGAGGAAGCCGATGCTGCCGGCGCTCACCATCAACCCTACCATCGCCGAGGGCCCGTCCC (SEQ ID NO.: 15)

CAACCAGCGAGGGCGCCTCCGAGGCAAACCTGGTGGACCTGCAGAAGAAGCTGGAGGAGCTGGAACTTGACGAGCAGC

AGAAGCGGCTGGAAGCCTTTCTCACCCAGAAAGCCAAGGTCGGCGAACTCAAAGACGATGACTTCGAAAGGACCTCAG

AGCTGGACGCGGGCAACGGCGGGGTGGTCACCAAAGTCCAGCACAGACCCTCGGGCCTCATCATGGCCAGGAAGCTGA

TCCACCTTGAGATCAAGCCGGCCATCCGGAACCAGATCATCCGCGAGCACCAGGTCCTGCACGAGTGCAACTCACCGT

ACATCGTGGGCTTCTACGGGGCCTTCTACTGTGACAGGGAGATCAGCATCTGCATGGAGCACATGGATGGCGGCTCCC

TGGACCAGGGGCTGAAAGAGGCCAAGAGGATTCCCGAGGACATCCTGGGGAAAGTCAGCATTGCGGTTCTCCGGGGCT

TGGCGTACCTCCGAGAGAAGCACCAGATCATGCACCGAAATGTGAAGCCCTCCAACATCCTCGTGAACTCTAGAGGGG

AGATCAAGCTGTGTGACTTCGGGGTGAGCGGCCAGCTCATCGACTCCATGGCCAACTCCTTCGTGGGCACGCGCTCCT

ACATGGCTCCGGAGCGGTTGCAGGGCACACATTACTCGGTGCAGTCGGTCATCTGGAGCATGGACCTGTCCCTGGTGG

AGCTGGCCATCGAAAGGTACCCCATCCCCCCGCCCGACGCCAAGGAGCTGGAGGCCATCTTTGGCCAGCCCGTGGTCG

ACAGGGAAGAAGGAGAGCCTCACAGCATCTCCTCTTGGCCAGGGTCCCCGGGCGCCCCAACAGCGGTTACGGGATGG

ACAGCCTGCCCGCCATGGCCATCTTCGAACTGCTGGACTATATTGTGAAAGAGCCGCCTCCTAAGCTGCCCAACGGTG

TGTTCACCCCCGACTTCCAGGAGTTTGTCAATAAATGCCTCATCAAAAACCCAACGGAGCGGGCGGACCTAAAGATGC

TCAGTGAGGTCATTCCATGTATATGAATATA

MLARRKPMLPALTINPTIAEGPSPTSEGASEANLVDLQKKLEELELDEQQKRLEAFLTQKAKVGELKDDDF (SEQ ID NO.: 16)

ERTSELDAGNGGVVTKVQHRPSGLIMARKLIHLEIKPAIRNQIIREHQVLHECNSPYIVGFYGAFYCDREISIC

MEHMDGGSLDQGLKEAKRIPEDILGKVSIAVLRGLAYLREKHQIMHRNVKPSNILVNSRGEIKLCDFGVSG

QLIDSMANSFVGTRSYMAPERIQGTHYSVQSVIWSMDLSLVELAIERYPIPPPDAKELEAIFGQPVVDEEG

EPHSISSWPGSPGRPNSGYGMDSLPAMAIFELLDYIVKEPPPKLPNGVFTPDFQEFVNKCLIKNPTERADLKM

LSEVIPCI trasted with those for CD45RO CD4 lymphocyte anti-CD28/anti-CD3, and the results obtained with astrocytes stimulated with TNFa and IL1b compared to resting astrocytes. In addition, NOV7 nucleic acids, polypeptides, antibodies and other compositions of the present invention may be useful in treating atherosclerosis or coronary artery inflammation, as seen with the results for coronary Artery SMC treated with TNFa and IL1b in contrast with resting coronary artery SMC.

NOV8

A NOV8 sequence according to the invention is a nucleic acid sequence encoding a polypeptide related to the MAP The NOV8 nucleic acid has a high degree of homology (100% identity) with a region of human chromosome 7 bounded by clone PR11–128A6 (GenBank Accession No: AC018639), as shown in Table 27. Also, the NOV8 nucleic acid has a high degree of homology (95% identity) with human MAP kinase kinase 2 (MEK2) (GenBank Accession No. L11285), as shown in Table 28. Also, the NOV8 polypeptide has homology (87% identity, 88% similarity with human MEK2 (GenBank Accession No. P36507), as shown in Table 29. Pfam domain mapping of the NOV8 polypeptide demonstrates homology to a number of MAP kinase kinase family members (Table 45).

TABLE 27

```
NOV8:         6 cggatgctggcccggaggaagccgatgctgccggcgctcaccatcaaccctaccatcgcc    65  (SEQ ID NO.: 59)
                ||||||||||||||||||||||||||||||||||||||||||||||||||||||||
Chr 7:   142794 cggatgctggcccggaggaagccgat-
                gctgccggcgctcaccatcaaccctaccatcgcc
         142853

NOV8:        66 gagggcccgtccccaaccagcgagggcgcctccgaggcaaacctggtggacctgcagaag   125
                ||||||||||||||||||||||||||||||||||||||||||||||||||||||||
Chr 7:   142854 gagggcccgtccccaaccagc-
                gagggcgcctccgaggcaaacctggtggacctgcagaag
         142913

NOV8:       126 aagctggaggagctggaacttgacgagcagcagaagcggctggaagcctttctcacccag   185
                ||||||||||||||||||||||||||||||||||||||||||||||||||||||||||||
Chr 7:   142914 aagctggaggagctggaacttgacgagcagcagaagcggctggaagcctttctcacccag
         142973

NOV8:       186 aaagccaaggtcggcgaactcaaagacgatgacttcgaaaggacctcagagctggacgcg   245
                ||||||||||||||||||||||||||||||||||||||||||||||||||||||||||||
Chr 7:   142974 aaagccaaggtcggcgaactcaaagacgatgacttcgaaaggacctcagagctggacgcg
         143033

NOV8:       246 ggcaacggcggggtggtcaccaaagtccagcacagaccctcgggcctcatcatggccagg   305
                ||||||||||||||||||||||||||||||||||||||||||||||||||||||||||||
Chr 7:   143034 ggcaacggcggggtggtcaccaaagtccagcacagaccctcgggcctcatcatggccagg
         143093

NOV8:       306 aagctgatccaccttgagatcaagccggccatccggaaccagatcatccgcgagcaccag   365
                ||||||||||||||||||||||||||||||||||||||||||||||||||||||||||||
Chr 7:   143094 aagctgatccaccttgagatcaagccggccatccggaaccagatcatccgcgagcaccag
         143153

NOV8:       366 gtcctgcacgagtgcaactcaccgtacatcgtgggcttctacggggccttctactgtgac   425
                ||||||||||||||||||||||||||||||||||||||||||||||||||||||||||||
Chr 7:   143154 gtcctgcacgagtgcaactcaccgtacatcgtgggcttctacggggccttctactgtgac
         143213

NOV8:       426 agggagatcagcatctgcatggagcacatggatggcggctccctggaccaggggctgaaa   485
                ||||||||||||||||||||||||||||||||||||||||||||||||||||||||||||
Chr 7:   143214 agggagatcagcatctgcatggagcacatggatggcggctccctggaccaggggctgaaa
         143273

NOV8:       486 gaggccaagaggattcccgaggacatcctggggaaagtcagcattgcggttctccgggc    545
                ||||||||||||||||||||||||||||||||||||||||||||||||||||||||||||
Chr 7:   143274 gaggccaagaggattcccgaggacatcctggggaaagtcagcattgcggttctccgggc
         143333

NOV8:       546 ttggcgtacctccgagagaagcaccagatcatgcaccgaaatgtgaagccctccaacatc   605
                ||||||||||||||||||||||||||||||||||||||||||||||||||||||||||||
Chr 7:   143334 ttggcgtacctccgagagaagcaccagatcatgcaccgaaatgtgaagccctccaacatc
         143393

NOV8:       606 ctcgtgaactctagagggagatcaagctgtgtgacttcggggtgagcggccagctcatc   665
                ||||||||||||||||||||||||||||||||||||||||||||||||||||||||||||
Chr 7:   143394 ctcgtgaactctagagggagatcaagctgtgtgacttcggggtgagcggccagctcatc
         143453

NOV8:       666 gactccatggccaactccttcgtgggcacgcgctcctacatggctccggagcggttgcag   725
                ||||||||||||||||||||||||||||||||||||||||||||||||||||||||||||
Chr 7:   143454 gactccatggccaactccttcgtgggcacgcgctcctacatggctccggagcggttgcag
         143513

NOV8:       726 ggcacacattactcggtgcagtcggtcatctggagcatggacctgtccctggtggagctg   785
                ||||||||||||||||||||||||||||||||||||||||||||||||||||||||||||
Chr 7:   143514 ggcacacattactcggtgcagtcggtcatctggagcatggacctgtccctggtggagctg
         143573

NOV8:       786 gccatcgaaaggtaccccatcccccgcccgacgccaaggagctggaggccatctttggc   845
                ||||||||||||||||||||||||||||||||||||||||||||||||||||||||||||
Chr 7:   143574 gccatcgaaaggtaccccatcccccgcccgacgccaaggagctggaggccatctttggc
         143633

NOV8:       846 cagcccgtggtcgacagggaagaaggagagcctcacagcatctcctcttggccagggtcc   905
                ||||||||||||||||||||||||||||||||||||||||||||||||||||||||||||
Chr 7:   143634 cagcccgtggtcgacagggaagaaggagagcctcacagcatctcctcttggccagggtcc
         143693
```

TABLE 27-continued

```
NOV8:     906 cccgggcgccccaacagcggttacgggatggacagcctgcccgccatggccatcttcgaa    965
              ||||||||||||||||||||||||||||||||||||||||||||||||||||||||||||
Chr 7: 143694 cccgggcgccccaacagcggttacgggatggacagcctgcccgccatggccatcttcgaa
143753

NOV8:     966 ctgctggactatattgtgaaagagccgcctcctaagctgcccaacggtgtgttcaccccc   1025
              ||||||||||||||||||||||||||||||||||||||||||||||||||||||||||||
Chr 7: 143754 ctgctggactatattgtgaaagagccgcctcctaagctgcccaacggtgtgttcaccccc
143813

NOV8:    1026 gacttccaggagtttgtcaataaatgcctcatcaaaaacccaacggagcgggcggaccta   1085
              ||||||||||||||||||||||||||||||||||||||||||||||||||||||||||||
Chr 7: 143814 gacttccaggagtttgtcaataaatgcctcatcaaaaacccaacggagcgggcggaccta
143873

NOV8:    1086 aagatgctca   1095
              ||||||||||
Chr 7: 143874 aagatgctca   143883 (SEQ ID NO.: 60)
```

TABLE 28

```
NOV8:       8 gatgctggcccggaggaagccgatgctgccggcgctcaccatcaaccctaccatcgccga    67 (SEQ ID NO.: 61)
              |||||||||||||||||||||| |||||||||||||||||||||||||||||||||||||
MEK2:      84 gatgctggcccggaggaagccggtgctgccggcgctcaccatcaaccctaccatcgccga   143

NOV8:      68 gggcccgtccccaaccagcgagggcgcctccgaggcaaacctggtggacctgcagaagaa   127
              ||||||| |||||||||||||||||||||||||||||||||||||||||||||||||||
MEK2:     144 gggcccatcccctaccagcgagggcgcctccgaggcaaacctggtggacctgcagaagaa   203

NOV8:     128 gctggaggagctggaacttgacgagcagc---agaagcggctggaagcctttctcaccca   184
              |||||||||||||||||||||||||||||   ||||||||||||||||||||||||||||
MEK2:     204 gctggaggagctggaacttgacgagcagcagaagaagcggctggaagcctttctcaccca   263

NOV8:     185 gaaagccaaggtcggcgaactcaaagacgatgacttcgaaaggacctcagagctggacgc   244
              |||||||||||| ||||||||||||||||||||||||||||||| ||||||||||| ||
MEK2:     264 gaaagccaaggttggcgaactcaaagacgatgacttcgaaaggatctcagagctgggcgc   323

NOV8:     245 gggcaacggcggggtggtcaccaaagtccagcacagaccctcgggcctcatcatggccag   304
              ||||||||||||||||||||||||||||||||||||||||||||||||||||||||||||
MEK2:     324 gggcaacggcggggtggtcaccaaagtccagcacagaccctcgggcctcatcatggccag   383

NOV8:     305 gaagctgatccaccttgagatcaagccggccatccggaaccagatcatccgcgagcacca   364
              |||||||||||||||||||||||||||||||||||||||||||||||||||||||||| |
MEK2:     384 gaagctgatccaccttgagatcaagccggccatccggaaccagatcatccgcgagcacgca   443

NOV8:     365 ggtcctgcacgagtgcaactcaccgtacatcgtgggcttctacggggccttctactgtga   424
              ||||||||||| | ||||||| |||||||||||||||||||||||||||||||| |||||
MEK2:     444 ggtcctgcacgaatgcaactcgccgtacatcgtgggcttctacggggccttctacagtga   503

NOV8:     425 cagggagatcagcatctgcatggagcacatggatggcggctccctggaccaggggctgaa   484
              | |||||||||||||| |||||||| |||||||| |||||||||||||||||| ||||||
MEK2:     504 cggggagatcagcatttgcatggaacacatggacggcggctccctggaccaggtgctgaa   563

NOV8:     485 agaggccaagaggattcccgaggacatcctggggaaagtcagcattgcggttctccgggg   544
              ||||||||||||||||||||||||| ||||||||||||||||||| |||||||||||||
MEK2:     564 agaggccaagaggattcccgaggagatcctggggaaagtcagcatcgcggttctccgggg   623

NOV8:     545 cttggcgtacctccgagagaagcaccagatcatgcaccgaaatgtgaagccctccaacat   604
              ||||||||||||||||||||||||||||||||||||||||| ||||||||||||||||||
MEK2:     624 cttggcgtacctccgagagaagcaccagatcatgcaccgagatgtgaagccctccaacat   683

NOV8:     605 cctcgtgaactctagaggggagatcaagctgtgtgacttcggggtgagcggccagctcat   664
              ||||||||||||||||||||||||||||||||||||||||||||||||||||||||||||
MEK2:     684 cctcgtgaactctagaggggagatcaagctgtgtgacttcggggtgagcggccagctcat   743

NOV8:     665 cgactccatggccaactccttcgtgggcacgcgctcctacatggctccggagcggttgca   724
              | ||||||||||||||||||||||||||||||||||||||||||||||||||||||||||
MEK2:     744 agactccatggccaactccttcgtgggcacgcgctcctacatggctccggagcggttgca   803

NOV8:     725 gggcacacattactcggtgcagtcggtcatctggagcatggacctgtccctggtggagct   784
              |||||||||||||||||||||||| || |||||||||||| |||||||||||||||||||
MEK2:     804 gggcacacattactcggtgcagtcggacatctggagcatgggcctgtccctggtggagct   863
```

TABLE 28-continued

```
NOV8:   785 ggccatcgaaaggtaccccatcccccgcccgacgccaaggagctggaggccatctttgg  844
            ||||||||||||||||||||||||||||||||||||||||||||||||||||||||||||
MEK2:   864 ggccgtcggaaggtaccccatcccccgccgacgccaaagagctggaggccatctttgg    923

NOV8:   845 ccagcccgtggtcgacagggaagaaggagagcctcacagcatctcctcttggccagggtc  904
            ||||||||||||||||||||||||||||||||||||||||| |||| ||| || ||||
MEK2:   924 ccggcccgtggtcgacggggaagaaggagagcctcacagcatctcgcctccgccgaggcc   983

NOV8:   905 ccccggcgccccaacagcggttacgggatggacagcctgcccgccatggccatcttcga   964
            ||||||||||| ||||||||| |||||||||||| ||||||||||||||||||||||| 
MEK2:   984 ccccggcgccccgtcagcggtcacgggatggatagccggcctgccatggccatcttga   1043

NOV8:   965 actgctggactatattgtgaaagagccgcctcctaagttgcccaacggtgtgttcacccc 1024
            ||| ||||||||||||||||| ||||| ||||||||| ||||||||||||||||||||||
MEK2:  1044 actcctggactatattgtgaacgagccacctcctaagctgcccaacggtgtgttcacccc 1103

NOV8:  1025 cgacttccaggagtttgtcaataaatgcctcatcaaaaacccaacggagcgggcggaccc 1084
            |||||||||||||||||||||||||||||||||||||  |||| |||||||||||||| 
MEK2:  1104 cgacttccaggagtttgtcaataaatgcctcatcaagaacccagcggagcgggcggacct 1163

NOV8:  1085 aaagatgctca                                                  1095
            |||||||||||
MEK2:  1164 gaagatgctca                                                  1174 (SEQ ID NO.: 62)
```

TABLE 29

```
NOV8:    1 MLARRKPMLPALTINPTIAEGPSPTSEGASEANLVXXXXXXXXXXXXXXXXXXXX-AFLTQ  59 (SEQ ID NO.: 63)
           ******+********************                              *****
MEK2:    1 MLARRKPVLPALTINPTIAEGPSPTSEGASEANLVDLQKKLEELELDEQQKKRLEAFLTQ   60

NOV8:   60 KAKVGELKDDDFERTSELDAGNGGVVTKVQHRPSGLIMARKLIHLEIKPAIRNQIIREHQ  119
           ************* *** ****************************************** *
MEK2:   61 KAKVGELKDDDFERISELGAGNGGVVTKVQHRPSGLIMARKLIHLEIKPAIRNQIIRELQ  120

NOV8:  120 VLHECNSPYIVGFYGAFYCDREISICMEHMDGGSLDQGLKEAKRIPEDILGKVSIAVLRG  179
           **************** * *************** *********+************
MEK2:  121 VLHECNSPYIVGFYGAFYSDGEISICMEHMDGGSLDQVLKEAKRIPEEILGKVSIAVLRG  180

NOV8:  180 LAYLREKHQIMHRNVKPSNILVNSREGEIKLCDFGVSGQLIDSMANSFVGTRSYMAPERLQ 239
           ****************+*******************************************
MEK2:  181 LAYLREKHQIMHRDVKPSNILVNSREGEIKLCDFGVSGQLIDSMANSFVGTRSYMAPERLQ 240

NOV8:  240 GTHYSVQSVIWSMDLSLVELAIERYPIPPPDAKELEAIFGQPVVDREEGEPHSISSWPGS  299
           ******** **** ********+*************+**** ********
MEK2:  241 GTHYSVQSDIWSMGLSLVELAVGRYPIPFPDAKELEAIFGRPVVDGEEGEPHSISPRPRP  300

NOV8:  300 PGRPNSGYGMDSLPAMAIFELLDYIVKEPFPKLPNGVFTFDFQEFVNKCLIKNPTERALL  359
           ****  +**** ********************* ********************* ****
MEK2:  301 PGRPVSGHGMDSRPAMAIFELLDYIVEPPPKLPNGVFTPDFQEFVNKCLIKNPAERADL   360

NOV8:  360 KMLS                                                          363
           ***+
MEK2:  361 KNLT                                                          364 (SEQ ID NO.: 64)
```

Where * indicates identity and + indicates similarity.

TABLE 45

```
NOV85-70.
--RKPMLPALTINPTIAEGPSPTSEGA--SEANLVDLQKKLEELELDEQQ--KRLEAFLTQAKVGELKDDD    (SEQ ID NO.:95)

MPK1CRIGR/2-67
.. PKKKPT--PIQLNPTP-DGSAVNGTSSAETNLEALQKKLEELELEEQQRNRLEAFLTQKQKVGELKDDD   (SEQ ID NO.:96)

MPK1HUMAN/1-66
.. PKKKPT--PIQLNPAP-DGSAVNGTSSAETNLEALQKKLEELELDEQQRKRLEAFLTQKQKVGELKDDD   (SEQ ID NO.:97)

MPK1MOUSE/1-66
.. PKKKPT--PIQLNPAP-DGSAVNGTSSAETNLEALQKKLEELELDEQQRKRLEAFLTQKQKVGELKDDD   (SEQ ID NO.:98)

MPK1RABIT/1-66
.. PKKKPT--PIQLNPAP-DGSAVNGTSSAETNLEALQKKLEELELDEQQRKRLEAFLTQKQKVGELKDDD   (SEQ ID NO.:99)
```

TABLE 45-continued

```
MPK1RAT/1-66
.. PKKKPT--PIQLNPAP-DGSAVNGTSSAETNLEALQKKLEELELDEQQRKRLEAFLTQKQKVGELKDDD         (SEQ ID NO.:100)

MPK1XENLA/1-66
.. PKKKPT--PIQLNPNP-EGTAVNGTPTAETNLEALQKKLEELELDEQQRKRLEAFLTQKQKVGELKDDD         (SEQ ID NO.:101)

MPK2CYPCA/3-68
.. PKRRPV--PLIIAPTG-EGQSTNIDAASEANLEALQRKLGELDLDEQQRKRLEAFLTQKAQVGELKDED         (SEQ ID NO.:102)

MPK2CHICK/1-69
AKRKPVLPALTITPSPAEGPGPG--GSAEANLVDLQKKLEELELDEQQKKRLEAFLTQKAKVGELKDDD           (SEQ ID NO.:103)

MPK2HUMAN/5-71
...--RKPVLPALTINPTIAEGPSPTSEGASEANLVDLQKKLEELELDEQQKKRLEAFLTQKAKVGELKDDD        (SEQ ID NO.:104)

MPK2MOUSE/5-71
.. --RKPVLPALTINPTIAEGPSPTSEGASEANLVDLQKKLEELDLDEQQRKRLEAFLTQKAKVGELKDDD        (SEQ ID NO.:105)

MPK2RAT/5-71
...--RKPVLPALTINPTIAEGPSPTSEGASEAHLVDLQKKLEELDLDEQQRKRLEAFLTQKAKVGELKDDD        (SEQ ID NO.:106)
```

Based on its relatedness to the known members of the MAP kinase family the NOV8 protein is a novel member of the MAP kinase protein family. The discovery of molecules related to MAP kinase satisfies a need in the art by providing new diagnostic or therapeutic compositions useful in the treatment of disorders associated with alterations in the expression of members of MAP kinase-like proteins. Nucleic acids, polypeptides, antibodies, and other compositions of the present invention are useful in a variety of diseases and pathologies, including by way of nonlimiting example, those involving cancer and angiogenic disorders. In addition, the NOV8 nucleic acid will be useful in identifying chromosome 7 and specific regions thereof.

A NOV8 nucleic acid is useful for detecting specific cell types. For example, expression analysis has demonstrated that a NOV8 nucleic acid is expressed in higher levels in gastric cancer, kidney cancer and lung cancer than in corresponding normal tissue (Example 1, Table 40 and 41).

NOVX Nucleic Acids

The nucleic acids of the invention include those that encode a NOVX polypeptide or protein. As used herein, the terms polypeptide and protein are interchangeable.

In some embodiments, a NOVX nucleic acid encodes a mature NOVX polypeptide. As used herein, a "mature" form of a polypeptide or protein described herein relates to the product of a naturally occurring polypeptide or precursor form or proprotein. The naturally occurring polypeptide, precursor or proprotein includes, by way of nonlimiting example, the full-length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps that may take place within the cell in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

Among the NOVX nucleic acids is the nucleic acid whose sequence is provided in SEQ ID NO: 1, 3, 5, 7, 9, 11, 13, or 15, or a fragment thereof. Additionally, the invention includes mutant or variant nucleic acids of SEQ ID NO: 1, 3, 5, 7, 9, 11, 13, or 15, or a fragment thereof, any of whose bases may be changed from the corresponding bases shown in SEQ ID NO: 1, 3, 5, 7, 9, 11, 13, or 15, while still encoding a protein that maintains at least one of its NOVX-like activities and physiological functions (i.e., modulating angiogenesis, neuronal development). The invention further includes the complement of the nucleic acid sequence of SEQ ID NO: 1, 3, 5, 7, 9, 11, 13, or 15, including fragments, derivatives, analogs and homologs thereof. The invention additionally includes nucleic acids or nucleic acid fragments, or complements thereto, whose structures include chemical modifications.

One aspect of the invention pertains to isolated nucleic acid molecules that encode NOVX proteins or biologically active portions thereof. Also included are nucleic acid fragments sufficient for use as hybridization probes to identify NOVX-encoding nucleic acids (e.g., NOVX mRNA) and fragments for use as polymerase chain reaction (PCR) primers for the amplification or mutation of NOVX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use.

Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated NOVX nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO: 1, 3, 5, 7, 9, 11, 13, or 15, or a complement of any of this nucleotide sequence, can be isolated using standard molecular biology techniques and the sequence information provided herein. Using all or a portion of the nucleic acid sequence of SEQ ID NO: 1, 3, 5, 7, 9, 11, 13, or 15, as a hybridization probe, NOVX nucleic acid sequences can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to NOVX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO: 1, 3, 5, 7, 9, 11, 13, or 15, or a complement thereof. Oligonucleotides may be chemically synthesized and may be used as probes.

In another embodiment, an isolated nucleic acid molecule of the invention comprises a nucleic acid molecule that is a complement of the nucleotide sequence shown in SEQ ID NO: 1, 3, 5, 7, 9, 11, 13, or 15, or a portion of this nucleotide sequence. A nucleic acid molecule that is complementary to the nucleotide sequence shown in SEQ ID NO: 1, 3, 5, 7, 9, 11, 13, or 15 is one that is sufficiently complementary to the nucleotide sequence shown in SEQ ID NO: 1, 3, 5, 7, 9, 11, 13, or 15 that it can hydrogen bond with little or no mismatches to the nucleotide sequence shown in SEQ ID NO: 1, 3, 5, 7, 9, 11, 13, or 15, thereby forming a stable duplex.

As used herein, the term "complementary" refers to Watson-Crick or Hoogsteen base pairing between nucleotide units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO: 1, 3, 5, 7, 9, 11, 13, or 15, e.g., a fragment that can be used as a probe or primer, or a fragment encoding a biologically active portion of NOVX. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482–489, which is incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a NOVX polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a NOVX polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human NOVX protein. Homologous nucleic acid sequences include those nucleic acid sequences that encode conservative amino acid substitutions (see below) in SEQ ID NO: 2, 4, 6, 8, 10, 12, or 14 as well as a polypeptide having NOVX activity. Biological activities of the NOVX proteins are described below. A homologous amino acid sequence does not encode the amino acid sequence of a human NOVX polypeptide.

The nucleotide sequence determined from the cloning of the human NOVX gene allows for the generation of probes and primers designed for use in identifying and/or cloning NOVX homologues in other cell types, e.g., from other tissues, as well as NOVX homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 or more consecutive sense strand nucleotide sequence of SEQ ID NO: 1, 3, 5, 7, 9, 11, 13, or 15; or an anti-sense strand nucleotide sequence of SEQ ID NO: 1, 3, 5, 7, 9, 11, 13, or 15; or of a naturally occurring mutant of SEQ ID NO: 1, 3, 5, 7, 9, 11, 13, or 15.

Probes based on the human NOVX nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a NOVX protein, such as by measuring a level of a NOVX-encoding nucleic acid in a sample of cells from a subject e.g., detecting NOVX mRNA levels or determining whether a genomic NOVX gene has been mutated or deleted.

A "polypeptide having a biologically active portion of NOVX" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of NOVX" can be prepared by isolating a portion of SEQ ID NO: 1, 3, 5, 7, 9, 11, 13 or 15 that encodes a polypeptide having a NOVX biological activity (biological activities of the NOVX proteins are described below), expressing the encoded portion of NOVX protein (e.g., by recombinant expression in vitro) and assessing the activity of the encoded portion of NOVX. For example, a nucleic acid fragment encoding a biologically active portion of NOVX can optionally include an ATP-binding domain. In another embodiment, a nucleic acid fragment encoding a biologically active portion of NOVX includes one or more regions.

NOVX Variants

The invention further encompasses nucleic acid molecules that differ from the nucleotide sequences shown in SEQ ID NO: 1, 3, 5, 7, 9, 11, 13, or 15 due to the degeneracy of the genetic code. These nucleic acids thus encode the same NOVX protein as that encoded by the nucleotide sequence shown in SEQ ID NO: 1, 3, 5, 7, 9, 11, 13, or 15 e.g., the polypeptide of SEQ ID NO: 2, 4, 6, 8, 10, 12, 14 or 16. In another embodiment, an isolated nucleic acid molecule of the invention has a nucleotide sequence encoding a protein having an amino acid sequence shown in SEQ ID NO: 2

In addition to the human NOVX nucleotide sequence shown in SEQ ID NO: 1, 3, 5, 7, 9, 11, 13, or 15, it will be appreciated by those skilled in the art that DNA sequence polymorphisms that lead to changes in the amino acid sequences of NOVX may exist within a population (e.g., the human population). Such genetic polymorphism in the NOVX gene may exist among individuals within a population due to natural allelic variation. As used herein, the terms "gene" and "recombinant gene" refer to nucleic acid molecules comprising an open reading frame encoding a NOVX protein, preferably a mammalian NOVX protein. Such natural allelic variations can typically result in 1–5% variance in the nucleotide sequence of the NOVX gene. Any and all such nucleotide variations and resulting amino acid polymorphisms in NOVX that are the result of natural allelic variation and that do not alter the functional activity of NOVX are intended to be within the scope of the invention.

Moreover, nucleic acid molecules encoding NOVX proteins from other species, and thus that have a nucleotide sequence that differs from the human sequence of SEQ ID NO: 1, 3, 5, 7, 9, 11, 13, or 15 are intended to be within the scope of the invention. Nucleic acid molecules corresponding to natural allelic variants and homologues of the NOVX cDNAs of the invention can be isolated based on their homology to the human NOVX nucleic acids disclosed herein using the human cDNAs, or a portion thereof, as a hybridization probe according to standard hybridization techniques under stringent hybridization conditions. For example, a soluble human NOVX cDNA can be isolated based on its homology to human membrane-bound NOVX. Likewise, a membrane-bound human NOVX cDNA can be isolated based on its homology to soluble human NOVX.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO: 1, 3, 5, 7, 9, 11, 13, or 15. In another embodiment, the nucleic acid is at least 10, 25, 50, 100, 250, 500 or 750 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding NOVX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO: 1, 3, 5, 7, 9, 11, 13, or 15 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO: 1, 3, 5, 7, 9, 11, 13, or 15, or fragments, analogs or derivatives thereof, under conditions of moderate stringency is provided. A non-limiting example of moderate stringency hybridization conditions are hybridization in 6×SSC, 5× Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NO: 1, 3, 5, 7, 9, 11, 13, or 15, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, *Proc Natl Acad Sci USA* 78: 6789–6792.

Conservative Mutations

In addition to naturally-occurring allelic variants of the NOVX sequence that may exist in the population, the skilled artisan will further appreciate that changes can be introduced by mutation into the nucleotide sequence of SEQ ID NO: 1, 3, 5, 7, 9, 11, 13, or 15, thereby leading to changes in the amino acid sequence of the encoded NOVX protein, without altering the functional ability of the NOVX protein. For example, nucleotide substitutions leading to amino acid substitutions at "non-essential" amino acid residues can be made in the sequence of SEQ ID NO: 1, 3, 5, 7, 9, 11, 13, or 15. A "non-essential" amino acid residue is a residue that can be altered from the wild-type sequence of NOVX without altering the biological activity, whereas an "essential" amino acid residue is required for biological activity. For example, amino acid residues that are conserved among the NOVX proteins of the present invention, are predicted to be particularly unamenable to alteration.

Another aspect of the invention pertains to nucleic acid molecules encoding NOVX proteins that contain changes in amino acid residues that are not essential for activity. Such NOVX proteins differ in amino acid sequence from SEQ ID NO: 2, 4, 6, 8, 10, 12, 14 or 16, yet retain biological activity. In one embodiment, the isolated nucleic acid molecule comprises a nucleotide sequence encoding a protein, wherein the protein comprises an amino acid sequence at least about 75% homologous to the amino acid sequence of SEQ ID NO: 2, 4, 6, or 8. Preferably, the protein encoded by the nucleic acid is at least about 80% homologous to SEQ ID NO: 2, 4, 6, 8, 10, 12, 14 or 16, more preferably at least about 90%, 95%, 98%, and most preferably at least about 99% homologous to SEQ ID NO: 2, 4, 6, 8, 10, 12, 14 or 16.

An isolated nucleic acid molecule encoding a NOVX protein homologous to the protein of can be created by introducing one or more nucleotide substitutions, additions or deletions into the nucleotide sequence of SEQ ID NO: 1, 3, 5, 7, 9, 11, 13, or 15, such that one or more amino acid substitutions, additions or deletions are introduced into the encoded protein.

Mutations can be introduced into the nucleotide sequence of SEQ ID NO: 1, 3, 5, 7, 9, 11, 13, or 15 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in NOVX is replaced with another amino acid residue from the same side chain family. Alternatively, in another embodiment, mutations can be introduced randomly along all or part of a NOVX coding sequence, such as by saturation mutagenesis, and the resultant mutants can be screened for NOVX biological activity to identify mutants that retain activity. Following mutagenesis of SEQ ID NO: 1, 3, 5, 7, 9, 11, 13, or 15 the encoded protein can be expressed by any recombinant technology known in the art and the activity of the protein can be determined.

In one embodiment, a mutant NOVX protein can be assayed for (1) the ability to form protein:protein interactions with other NOVX proteins, other cell-surface proteins, or biologically active portions thereof, (2) complex formation between a mutant NOVX protein and a NOVX receptor; (3) the ability of a mutant NOVX protein to bind to an intracellular target protein or biologically active portion thereof; (e.g., avidin proteins); (4) the ability to bind NOVX protein; or (5) the ability to specifically bind an anti-NOVX protein antibody.

Antisense NOVX Nucleic Acids

Another aspect of the invention pertains to isolated antisense nucleic acid molecules that are hybridizable to or complementary to the nucleic acid molecule comprising the nucleotide sequence of SEQ ID NO: 1, 3, 5 or 7, 9, 11, 13 or 15 fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire NOVX coding strand, or to only a portion thereof. Nucleic acid molecules encoding fragments, homologs, derivatives and analogs of a NOVX protein of SEQ ID NO: 2, 4, 6, 8, 10, 12, 14 or 16 or antisense nucleic acids complementary to a NOVX nucleic acid sequence of SEQ ID NO: 1, 3, 5, 7, 9, 11, 13, or 15 are additionally provided.

In one embodiment, an antisense nucleic acid molecule is antisense to a "coding region" of the coding strand of a nucleotide sequence encoding NOVX. The term "coding region" refers to the region of the nucleotide sequence comprising codons which are translated into amino acid residues (e.g., the protein coding region of human NOVX corresponds to SEQ ID NO: 2, 4, 6, 8, 10, 12, 14 or 16). In another embodiment, the antisense nucleic acid molecule is antisense to a "noncoding region" of the coding strand of a nucleotide sequence encoding NOVX. The term "noncoding region" refers to 5' and 3' sequences which flank the coding region that are not translated into amino acids (i.e., also referred to as 5' and 3' untranslated regions).

Given the coding strand sequences encoding NOVX disclosed herein (e.g., SEQ ID NO: 1, 3, 5, 7, 9, 11, 13, or 15), antisense nucleic acids of the invention can be designed according to the rules of Watson and Crick or Hoogsteen base pairing. The antisense nucleic acid molecule can be complementary to the entire coding region of NOVX mRNA, but more preferably is an oligonucleotide that is antisense to only a portion of the coding or noncoding region of NOVX mRNA. For example, the antisense oligonucleotide can be complementary to the region surrounding the translation start site of NOVX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a NOVX protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625–6641). The antisense nucleic acid molecule can also comprise a 2'-o-methylribonucleotide (Inoue et al. (1987) *Nucleic Acids Res* 15: 6131–6148) or a chimeric RNA-DNA analogue (Inoue et al. (1987) *FEBS Lett* 215: 327–330).

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

NOVX Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as a mRNA, to which they have a complementary region. Thus, ribozymes (e.g., hammerhead ribozymes (described in Haselhoff and Gerlach (1988) *Nature* 334:585–591)) can be used to catalytically cleave NOVX mRNA transcripts to thereby inhibit translation of NOVX mRNA. A ribozyme having specificity for a NOVX-encoding nucleic acid can be designed based upon the nucleotide sequence of a NOVX DNA disclosed herein (i.e., SEQ ID NO: 1, 3, 5, 7, 9, 11, 13, or 15). For example, a derivative of a Tetrahymena L-19 IVS RNA can be constructed in which the nucleotide sequence of the active site is complementary to the nucleotide sequence to be cleaved in a NOVX-encoding mRNA. See, e.g., Cech et al. U.S. Pat. No. 4,987,071; and Cech et al. U.S. Pat. No. 5,116,742. Alternatively, NOVX mRNA can be used to select a catalytic RNA having a specific ribonuclease activity from a pool of RNA molecules. See, e.g., Bartel et al., (1993) *Science* 261:1411–1418.

Alternatively, NOVX gene expression can be inhibited by targeting nucleotide sequences complementary to the regulatory region of the NOVX (e.g., the NOVX promoter and/or enhancers) to form triple helical structures that prevent transcription of the NOVX gene in target cells. See generally, Helene. (1991) *Anticancer Drug Des.* 6: 569–84; Helene. et al. (1992) *Ann. N.Y. Acad. Sci.* 660:27–36; and Maher (1992) *Bioassays* 14: 807–15.

In various embodiments, the nucleic acids of NOVX can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAS" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of NOVX can be used in therapeutic and diagnostic applications. For example, PNAs can be used as antisense or antigene agents for sequence-specific modulation of gene expression by, e.g., inducing transcription or translation arrest or inhibiting replication. PNAs of NOVX can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of NOVX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NOVX can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl) amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. W088/09810) or the blood-brain barrier (see, e.g., PCT Publication No. W089/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

NOVX Polypeptides

A NOVX polypeptide of the invention includes the NOVX-like protein whose sequence is provided in SEQ ID NO: 2, 4, 6, 8, 10, 12, 14 or 16. The invention also includes a mutant or variant protein any of whose residues may be changed from the corresponding residue shown in SEQ ID NO: 2, 4, 6, 8, 10, 12, 14 or 16 while still encoding a protein that maintains its NOVX-like activities and physiological functions, or a functional fragment thereof. In some embodiments, up to 20% or more of the residues may be so changed in the mutant or variant protein. In some embodiments, the NOVX polypeptide according to the invention is a mature polypeptide.

In general, a NOVX-like variant that preserves NOVX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated NOVX proteins, and biologically active portions thereof, or derivatives, fragments, analogs or homologs thereof. Also provided are polypeptide fragments suitable for use as immunogens to raise anti-NOVX antibodies. In one embodiment, native NOVX proteins can be isolated from cells or tissue sources by an appropriate purification scheme using standard protein purification techniques. In another embodiment, NOVX proteins are produced by recombinant DNA techniques. Alternative to recombinant expression, a NOVX protein or polypeptide can be synthesized chemically using standard peptide synthesis techniques.

An "isolated" or "purified" protein or biologically active portion thereof is substantially free of cellular material or other contaminating proteins from the cell or tissue source from which the NOVX protein is derived, or substantially free from chemical precursors or other chemicals when chemically synthesized. The language "substantially free of cellular material" includes preparations of NOVX protein in which the protein is separated from cellular components of the cells from which it is isolated or recombinantly produced. In one embodiment, the language "substantially free of cellular material" includes preparations of NOVX protein having less than about 30% (by dry weight) of non-NOVX protein (also referred to herein as a "contaminating protein"), more preferably less than about 20% of non-NOVX protein, still more preferably less than about 10% of non-NOVX protein, and most preferably less than about 5% non-NOVX protein. When the NOVX protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of NOVX protein in which the protein is separated from chemical precursors or other chemicals that are involved in the synthesis of the protein. In one embodiment, the language "substantially free of chemical precursors or other chemicals" includes preparations of NOVX protein having less than about 30% (by dry weight) of chemical precursors or non-NOVX chemicals, more preferably less than about 20% chemical precursors or non-NOVX chemicals, still more preferably less than about 10% chemical precursors or non-NOVX chemicals, and most preferably less than about 5% chemical precursors or non-NOVX chemicals.

Biologically active portions of a NOVX protein include peptides comprising amino acid sequences sufficiently homologous to or derived from the amino acid sequence of the NOVX protein, e.g., the amino acid sequence shown in SEQ ID NO: 2, 4, 6, 8, 10, 12, 14 or 16 that include fewer amino acids than the full length NOVX proteins, and exhibit at least one activity of a NOVX protein. Typically, biologically active portions comprise a domain or motif with at least one activity of the NOVX protein. A biologically active portion of a NOVX protein can be a polypeptide which is, for example, 10, 25, 50, 100 or more amino acids in length.

A biologically active portion of a NOVX protein of the present invention may contain at least one of the above-identified domains conserved between the NOVX proteins, e.g. TSR modules. Moreover, other biologically active portions, in which other regions of the protein are deleted, can be prepared by recombinant techniques and evaluated for one or more of the functional activities of a native NOVX protein.

In an embodiment, the NOVX protein has an amino acid sequence shown in SEQ ID NO: 2, 4, 6, 8, 10, 12, 14 or 16. In other embodiments, the NOVX protein is substantially homologous to SEQ ID NO: 2, 4, 6, 8, 10, 12, 14 or 16 and retains the functional activity of the protein of SEQ ID NO: 2, 4, 6, 8, 10, 12, 14 or 16 yet differs in amino acid sequence due to natural allelic variation or mutagenesis, as described in detail below. Accordingly, in another embodiment, the NOVX protein is a protein that comprises an amino acid sequence at least about 45% homologous to the amino acid sequence of SEQ ID NO: 2, 4, 6, 8, 10, 12, 14 or 16 and retains the functional activity of the NOVX proteins of SEQ ID NO: 2, 4, 6, 8, 10, 12, 14 or 16.

Determining Homology Between Two or More Sequence

To determine the percent homology of two amino acid sequences or of two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO: 1, 3, 5, 7, 9, 11, 13, or 15.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Chimeric and Fusion Proteins

The invention also provides NOVX chimeric or fusion proteins. As used herein, a NOVX "chimeric protein" or "fusion protein" comprises a NOVX polypeptide operatively linked to a non-NOVX polypeptide. An "NOVX polypeptide" refers to a polypeptide having an amino acid sequence corresponding to NOVX, whereas a "non-NOVX polypeptide" refers to a polypeptide having an amino acid sequence corresponding to a protein that is not substantially homologous to the NOVX protein, e.g., a protein that is different from the NOVX protein and that is derived from the same or a different organism. Within a NOVX fusion protein the NOVX polypeptide can correspond to all or a portion of a NOVX protein. In one embodiment, a NOVX fusion protein comprises at least one biologically active portion of a NOVX protein. In another embodiment, a NOVX fusion protein comprises at least two biologically active portions of a NOVX protein. Within the fusion protein, the term "operatively linked" is intended to indicate that the NOVX polypeptide and the non-NOVX polypeptide are fused in-frame to each other. The non-NOVX polypeptide can be fused to the N-terminus or C-terminus of the NOVX polypeptide.

For example, in one embodiment a NOVX fusion protein comprises a NOVX polypeptide operably linked to the extracellular domain of a second protein. Such fusion proteins can be further utilized in screening assays for compounds that modulate NOVX activity (such assays are described in detail below).

In another embodiment, the fusion protein is a GST-NOVX fusion protein in which the NOVX sequences are fused to the C-terminus of the GST (i.e., glutathione S-transferase) sequences. Such fusion proteins can facilitate the purification of recombinant NOVX.

In another embodiment, the fusion protein is a NOVX-immunoglobulin fusion protein in which the NOVX sequences comprising one or more domains are fused to sequences derived from a member of the immunoglobulin protein family. The NOVX-immunoglobulin fusion proteins of the invention can be incorporated into pharmaceutical compositions and administered to a subject to inhibit an interaction between a NOVX ligand and a NOVX protein on the surface of a cell, to thereby suppress NOVX-mediated signal transduction in vivo. In one nonlimiting example, a contemplated NOVX ligand of the invention is the NOVX receptor. The NOVX-immunoglobulin fusion proteins can be used to affect the bioavailability of a NOVX cognate ligand. Inhibition of the NOVX ligand/NOVX interaction may be useful therapeutically for both the treatment of proliferative and differentiative disorders, e.g., cancer as well as modulating (e.g., promoting or inhibiting) cell survival, as well as acute and chronic inflammatory disorders and hyperplastic wound healing, e.g. hypertrophic scars and keloids. Moreover, the NOVX-immunoglobulin fusion proteins of the invention can be used as immunogens to produce anti-NOVX antibodies in a subject, to purify NOVX ligands, and in screening assays to identify molecules that inhibit the interaction of NOVX with a NOVX ligand.

A NOVX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A NOVX-encoding nucleic acid can be cloned into such an expression vector such that the fusion moiety is linked in-frame to the NOVX protein.

NOVX Agonists and Antagonists

The present invention also pertains to variants of the NOVX proteins that function as either NOVX agonists (mimetics) or as NOVX antagonists. Variants of the NOVX protein can be generated by mutagenesis, e.g., discrete point mutation or truncation of the NOVX protein. An agonist of the NOVX protein can retain substantially the same, or a subset of, the biological activities of the naturally occurring form of the NOVX protein. An antagonist of the NOVX protein can inhibit one or more of the activities of the naturally occurring form of the NOVX protein by, for example, competitively binding to a downstream or upstream member of a cellular signaling cascade which includes the NOVX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the NOVX proteins.

Variants of the NOVX protein that function as either NOVX agonists (mimetics) or as NOVX antagonists can be identified by screening combinatorial libraries of mutants, e.g., truncation mutants, of the NOVX protein for NOVX protein agonist or antagonist activity. In one embodiment, a variegated library of NOVX variants is generated by combinatorial mutagenesis at the nucleic acid level and is encoded by a variegated gene library. A variegated library of NOVX variants can be produced by, for example, enzymatically ligating a mixture of synthetic oligonucleotides into gene sequences such that a degenerate set of potential NOVX sequences is expressible as individual polypeptides, or alternatively, as a set of larger fusion proteins (e.g., for phage display) containing the set of NOVX sequences therein. There are a variety of methods which can be used to produce libraries of potential NOVX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NOVX sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the NOVX protein coding sequence can be used to generate a variegated population of NOVX fragments for screening and subsequent selection of variants of a NOVX protein. In one embodiment, a library of coding sequence fragments can be generated by treating a double stranded PCR fragment of a NOVX coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the NOVX protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NOVX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique that enhances the frequency of functional mutants in the libraries, can be used in combination with the screening assays to identify NOVX variants (Arkin and Yourvan (1992) PNAS 89:7811–7815; Delgrave et al. (1993) Protein Engineering 6:327–331).

NOVX Antibodies

Also included in the invention are antibodies to NOVX proteins, or fragments of NOVX proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated NOVX-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO: 2, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of NOVX-related protein that is located on the surface of the protein, e.g., a hydrophilic region. A hydrophobicity analysis of the human NOVX-related protein sequence will indicate which regions of a NOVX-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and Corynebacterium parvum, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice,* Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications,* Marcel Dekker, Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al, (*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., 1991 EMBO J., 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217–225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (Fc R), such as Fc RI (CD64), Fc RII (CD32) and Fc RIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fc regions and can thereby have enhanced complement lysis and ADCC capabilities. See Stevenson et al., Anti-Cancer Drug Design, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

NOVX Recombinant Expression Vectors and Host Cells

Another aspect of the invention pertains to vectors, preferably expression vectors, containing a nucleic acid encoding a NOVX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NOVX proteins, mutant forms of NOVX proteins, fusion proteins, etc.).

The recombinant expression vectors of the invention can be designed for expression of NOVX proteins in prokaryotic or eukaryotic cells. For example, NOVX proteins can be expressed in bacterial cells such as Escherichia coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in Escherichia coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion E. coli expression vectors include pTrc (Amrann et al., (1988) Gene 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in E. coli is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in E. coli (see, e.g., Wada, et al., 1992. Nucl. Acids Res. 20: 2111–2118). Such alteration of nucleic acid sequences of the invention can be carried out by standard DNA synthesis techniques.

In another embodiment, the NOVX expression vector is a yeast expression vector. Examples of vectors for expression in yeast Saccharomyces cerivisae include pYepSec1 (Baldari, et al., 1987. EMBO J. 6: 229–234), pMFa (Kurjan and Herskowitz, 1982. Cell 30: 933–943), pJRY88 (Schultz et al., 1987. Gene 54: 113–123), pYES2 (Invitrogen Corporation, San Diego, Calif.), and picZ (InVitrogen Corp, San Diego, Calif.).

Alternatively, NOVX can be expressed in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156–2165) and the pVL series (Lucklow and Summers, 1989. Virology 170: 31–39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268–277), lymphoid-specific promoters (Calame and Eaton, 1988. Adv. Immunol. 43: 235–275), in particular promoters of T cell receptors (Winoto and Baltimore, 1989. EMBO J. 8: 729–733) and immunoglobulins (Banerji, et al., 1983. Cell 33: 729–740; Queen and Baltimore, 1983. Cell 33: 741–748), neuron-specific promoters (e.g., the neurofilament promoter; Byrne and Ruddle, 1989. Proc. Natl. Acad. Sci. USA 86: 5473–5477), pancreas-specific promoters (Edlund, et al., 1985. Science 230: 912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374–379) and the α-fetoprotein promoter (Campes and Tilghman, 1989. Genes Dev. 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to NOVX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics,* Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NOVX protein can be expressed in bacterial cells such as *E. coli,* insect cells, yeast or mammalian cells (such as human, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding NOVX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) NOVX protein. Accordingly, the invention further provides methods for producing NOVX protein using the host cells of the invention. In one embodiment, the method comprises culturing the host cell of invention (into which a recombinant expression vector encoding NOVX protein has been introduced) in a suitable medium such that NOVX protein is produced. In another embodiment, the method further comprises isolating NOVX protein from the medium or the host cell.

Transgenic NOVX Animals

The host cells of the invention can also be used to produce non-human transgenic animals. For example, in one embodiment, a host cell of the invention is a fertilized oocyte or an embryonic stem cell into which NOVX protein-coding sequences have been introduced. Such host cells can then be used to create non-human transgenic animals in which exogenous NOVX sequences have been introduced into their genome or homologous recombinant animals in which endogenous NOVX sequences have been altered. Such animals are useful for studying the function and/or activity of NOVX protein and for identifying and/or evaluating modulators of NOVX protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NOVX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NOVX-encoding nucleic acid into the male pronuclei of a fertilized oocyte (e.g., by microinjection, retroviral infection) and allowing the oocyte to develop in a pseudopregnant female foster animal. Sequences including SEQ ID NO: 1, 3, 5, 7, 9, 11, 13, or 15 can be introduced as a transgene into the genome of a non-human animal. Alternatively, a non-human homologue of the human NOVX gene, such as a mouse NOVX gene, can be isolated based on hybridization to the human NOVX cDNA (described further supra) and used as a transgene. Intronic sequences and polyadenylation signals can also be included in the transgene to increase the efficiency of expression of the transgene. A tissue-specific regulatory sequence(s) can be operably-linked to the NOVX transgene to direct expression of NOVX protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the NOVX transgene in its genome and/or expression of NOVX mRNA in tissues or cells of the animals. A transgenic founder animal can then be used to breed additional animals carrying the transgene. Moreover, transgenic animals carrying a transgene-encoding NOVX protein can further be bred to other transgenic animals carrying other transgenes.

To create a homologous recombinant animal, a vector is prepared which contains at least a portion of a NOVX gene into which a deletion, addition or substitution has been introduced to thereby alter, e.g., functionally disrupt, the NOVX gene. The NOVX gene can be a human gene (e.g., the DNA of SEQ ID NO: 1, 3, 5, 7, 9, 11, 13, or 15), but more preferably, is a non-human homologue of a human NOVX gene. For example, a mouse homologue of human NOVX gene of SEQ ID NO: 1, 3, 5, 7, 9, 11, 13, or 15 can be used to construct a homologous recombination vector suitable for altering an endogenous NOVX gene in the mouse genome. In one embodiment, the vector is designed such that, upon homologous recombination, the endogenous NOVX gene is functionally disrupted (i.e., no longer encodes a functional protein; also referred to as a "knock out" vector).

Alternatively, the vector can be designed such that, upon homologous recombination, the endogenous NOVX gene is mutated or otherwise altered but still encodes functional protein (e.g., the upstream regulatory region can be altered to thereby alter the expression of the endogenous NOVX protein). In the homologous recombination vector, the altered portion of the NOVX gene is flanked at its 5'- and 3'-termini by additional nucleic acid of the NOVX gene to allow for homologous recombination to occur between the exogenous NOVX gene carried by the vector and an endogenous NOVX gene in an embryonic stem cell. The additional flanking NOVX nucleic acid is of sufficient length for successful homologous recombination with the endogenous gene. Typically, several kilobases of flanking DNA (both at the 5'- and 3'-termini) are included in the vector. See, e.g., Thomas, et al., 1987. *Cell* 51: 503 for a description of homologous recombination vectors. The vector is ten introduced into an embryonic stem cell line (e.g., by electroporation) and cells in which the introduced NOVX gene has homologously-recombined with the endogenous NOVX gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The NOVX nucleic acid molecules, NOVX proteins, and anti-NOVX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286–288 (1982) via a disulfide-interchange reaction. A chemotherapeutic agent (such as Doxorubicin) is optionally contained within the liposome. See Gabizon et al., J. National Cancer Inst., 81(19): 1484 (1989).

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a NOVX protein or anti-NOVX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., 1993 *Proc. Natl. Acad. Sci. USA*, 90: 7889–7893. The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Screening and Detection Methods

The isolated nucleic acid molecules of the invention can be used to express NOVX protein (e.g., via a recombinant expression vector in a host cell in gene therapy applications), to detect NOVX mRNA (e.g., in a biological sample) or a genetic lesion in a NOVX gene, and to modulate NOVX activity, as described further, below. In addition, the NOVX proteins can be used to screen drugs or compounds that modulate the NOVX protein activity or expression as well as to treat disorders characterized by insufficient or excessive production of NOVX protein or production of NOVX protein forms that have decreased or aberrant activity compared to NOVX wild-type protein. In addition, the anti-NOVX antibodies of the invention can be used to detect and isolate NOVX proteins and modulate NOVX activity. For example, NOVX activity includes growth and differentiation, antibody production, and tumor growth.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to NOVX proteins or have a stimulatory or inhibitory effect on, e.g., NOVX protein expression or NOVX protein activity. The invention also includes compounds identified in the screening assays described herein.

In one embodiment, the invention provides assays for screening candidate or test compounds which bind to or modulate the activity of the membrane-bound form of a NOVX protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. U.S.A.* 87: 6378–6382; Felici, 1991. *J. Mol. Biol.* 222: 301–310; Ladner, U.S. Pat. No. 5,233,409.).

In one embodiment, an assay is a cell-based assay in which a cell which expresses a membrane-bound form of NOVX protein, or a biologically-active portion thereof, on the cell surface is contacted with a test compound and the ability of the test compound to bind to a NOVX protein determined. The cell, for example, can be of mammalian origin or a yeast cell. Determining the ability of the test compound to bind to the NOVX protein can be accomplished, for example, by coupling the test compound with a radioisotope or enzymatic label such that binding of the test compound to the NOVX protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of NOVX protein, or a biologically-active portion thereof, on the cell surface with a known compound which binds NOVX to form an assay mixture, contacting the assay mixture with a test compound, and determining the ability of the test compound to interact with a NOVX protein, wherein determining the ability of the test compound to interact with a NOVX protein comprises determining the ability of the test compound to preferentially bind to NOVX protein or a biologically-active portion thereof as compared to the known compound.

In another embodiment, an assay is a cell-based assay comprising contacting a cell expressing a membrane-bound form of NOVX protein, or a biologically-active portion thereof, on the cell surface with a test compound and determining the ability of the test compound to modulate (e.g., stimulate or inhibit) the activity of the NOVX protein or biologically-active portion thereof. Determining the ability of the test compound to modulate the activity of NOVX or a biologically-active portion thereof can be accomplished, for example, by determining the ability of the NOVX protein to bind to or interact with a NOVX target molecule. As used herein, a "target molecule" is a molecule with which a NOVX protein binds or interacts in nature, for example, a molecule on the surface of a cell which expresses a NOVX interacting protein, a molecule on the surface of a second cell, a molecule in the extracellular milieu, a molecule associated with the internal surface of a cell membrane or a cytoplasmic molecule. A NOVX target molecule can be a non-NOVX molecule or a NOVX protein or polypeptide of the invention In one embodiment, a NOVX target molecule is a component of a signal transduction pathway that facilitates transduction of an extracellular signal (e.g. a signal generated by binding of a compound to a membrane-bound NOVX molecule) through the cell membrane and into the cell. The target, for example, can be a second intercellular protein that has catalytic activity or a protein that facilitates the association of downstream signaling molecules with NOVX.

Determining the ability of the NOVX protein to bind to or interact with a NOVX target molecule can be accomplished by one of the methods described above for determining direct binding. In one embodiment, determining the ability of the NOVX protein to bind to or interact with a NOVX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a NOVX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a NOVX protein or biologically-active portion thereof with a test compound and determining the ability of the test compound to bind to the NOVX protein or biologically-active portion thereof. Binding of the test compound to the NOVX protein can be determined either directly or indirectly as described above. In one such embodiment, the assay comprises contacting the NOVX protein or biologically-active portion thereof with a known compound which binds NOVX to form an assay mixture, contacting the assay mixture with a test compound, and determining the ability of the test compound to interact with a NOVX protein, wherein determining the ability of the test compound to interact with a NOVX protein comprises determining the ability of the test compound to preferentially bind to NOVX or biologically-active portion thereof as compared to the known compound.

In still another embodiment, an assay is a cell-free assay comprising contacting NOVX protein or biologically-active portion thereof with a test compound and determining the ability of the test compound to modulate (e.g. stimulate or inhibit) the activity of the NOVX protein or biologically-active portion thereof. Determining the ability of the test compound to modulate the activity of NOVX can be accomplished, for example, by determining the ability of the NOVX protein to bind to a NOVX target molecule by one of the methods described above for determining direct binding. In an alternative embodiment, determining the ability of the test compound to modulate the activity of NOVX protein can be accomplished by determining the ability of the NOVX protein further modulate a NOVX target molecule. For example, the catalytic/enzymatic activity of the target molecule on an appropriate substrate can be determined as described above.

In yet another embodiment, the cell-free assay comprises contacting the NOVX protein or biologically-active portion thereof with a known compound which binds NOVX protein to form an assay mixture, contacting the assay mixture with a test compound, and determining the ability of the test compound to interact with a NOVX protein, wherein determining the ability of the test compound to interact with a NOVX protein comprises determining the ability of the NOVX protein to preferentially bind to or modulate the activity of a NOVX target molecule.

The cell-free assays of the invention are amenable to use of both the soluble form or the membrane-bound form of NOVX protein. In the case of cell-free assays comprising the membrane-bound form of NOVX protein, it may be desirable to utilize a solubilizing agent such that the membrane-bound form of NOVX protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the invention, it may be desirable to immobilize either NOVX protein or its target molecule to facilitate separation of complexed from uncomplexed forms of one or both of the proteins, as well as to accommodate automation of the assay. Binding of a test compound to NOVX protein, or interaction of NOVX protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-NOVX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or NOVX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of NOVX protein binding or activity determined using standard techniques.

Other techniques for immobilizing proteins on matrices can also be used in the screening assays of the invention. For example, either the NOVX protein or its target molecule can be immobilized utilizing conjugation of biotin and streptavidin. Biotinylated NOVX protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with NOVX protein or target molecules, but which do not interfere with binding of the NOVX protein to its target molecule, can be derivatized to the wells of the plate, and unbound target or NOVX protein trapped in the wells by antibody conjugation. Methods for detecting such complexes, in addition to those described above for the GST-immobilized complexes, include immunodetection of complexes using antibodies reactive with the NOVX protein or target molecule, as well as enzyme-linked assays that rely on detecting an enzymatic activity associated with the NOVX protein or target molecule.

In another embodiment, modulators of NOVX protein expression are identified in a method wherein a cell is contacted with a candidate compound and the expression of NOVX mRNA or protein in the cell is determined. The level of expression of NOVX mRNA or protein in the presence of the candidate compound is compared to the level of expression of NOVX mRNA or protein in the absence of the candidate compound. The candidate compound can then be identified as a modulator of NOVX mRNA or protein expression based upon this comparison. For example, when expression of NOVX mRNA or protein is greater (i.e., statistically significantly greater) in the presence of the candidate compound than in its absence, the candidate compound is identified as a stimulator of NOVX mRNA or protein expression. Alternatively, when expression of NOVX mRNA or protein is less (statistically significantly less) in the presence of the candidate compound than in its absence, the candidate compound is identified as an inhibitor of NOVX mRNA or protein expression. The level of NOVX mRNA or protein expression in the cells can be determined by methods described herein for detecting NOVX mRNA or protein.

In yet another aspect of the invention, the NOVX proteins can be used as "bait proteins" in a two-hybrid assay or three hybrid assay (see, e.g., U.S. Pat. No. 5,283,317; Zervos, et al., 1993. *Cell* 72: 223–232; Madura, et al., 1993. *J. Biol. Chem.* 268: 12046–12054; Bartel, et al., 1993. *Biotechniques* 14: 920–924; Iwabuchi, et al., 1993. *Oncogene* 8: 1693–1696; and Brent WO 94/10300), to identify other proteins that bind to or interact with NOVX ("NOVX-binding proteins" or "NOVX-bp") and modulate NOVX activity. Such NOVX-binding proteins are also likely to be involved in the propagation of signals by the NOVX proteins as, for example, upstream or downstream elements of the NOVX pathway.

The two-hybrid system is based on the modular nature of most transcription factors, which consist of separable DNA-binding and activation domains. Briefly, the assay utilizes two different DNA constructs. In one construct, the gene that codes for NOVX is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a NOVX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with NOVX.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) identify an individual from a minute biological sample (tissue typing); and (ii) aid in forensic identification of a biological sample. Some of these applications are described in the subsections, below.

Tissue Typing

The NOVX sequences of the invention can be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the NOVX sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The NOVX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NO: 1, 3, 5, 7, 9, 11, 13, or 15 are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining NOVX protein and/or nucleic acid expression as well as NOVX activity, in the context of a biological sample (e.g., blood, serum, cells, tissue) to thereby determine whether an individual is afflicted with a disease or disorder, or is at risk of developing a disorder, associated with aberrant NOVX expression or activity. Disorders associated with aberrant NOVX expression of activity include, for example, cell proliferative, angiogenic, pulmonary, hepatic hematopoietic, immunological, inflammatory, and tumor-related disorders and/or pathologies.

The invention also provides for prognostic (or predictive) assays for determining whether an individual is at risk of developing a disorder associated with NOVX protein, nucleic acid expression or activity. For example, mutations in a NOVX gene can be assayed in a biological sample. Such assays can be used for prognostic or predictive purpose to thereby prophylactically treat an individual prior to the onset of a disorder characterized by or associated with NOVX protein, nucleic acid expression, or biological activity.

Another aspect of the invention provides methods for determining NOVX protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of NOVX in clinical trials.

These and other agents are described in further detail in the following sections.

Diagnostic Assays

An exemplary method for detecting the presence or absence of NOVX in a biological sample involves obtaining a biological sample from a test subject and contacting the biological sample with a compound or an agent capable of detecting NOVX protein or nucleic acid (e.g., mRNA, genomic DNA) that encodes NOVX protein such that the presence of NOVX is detected in the biological sample. An agent for detecting NOVX mRNA or genomic DNA is a labeled nucleic acid probe capable of hybridizing to NOVX mRNA or genomic DNA. The nucleic acid probe can be, for example, a full-length NOVX nucleic acid, such as the nucleic acid of SEQ ID NO: 1, 3, 5, 7, 9, 11, 13, or 15, or a portion thereof, such as an oligonucleotide of at least 15, 30, 50, 100, 250 or 500 nucleotides in length and sufficient to specifically hybridize under stringent conditions to NOVX mRNA or genomic DNA. Other suitable probes for use in the diagnostic assays of the invention are described herein.

One agent for detecting NOVX protein is an antibody capable of binding to NOVX protein, preferably an antibody with a detectable label. Antibodies directed against a protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds.

An antibody specific for a protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect NOVX mRNA, protein, or genomic DNA in a biological sample in vitro as well as in vivo. For example, in vitro techniques for detection of NOVX mRNA include Northern hybridizations and in situ hybridizations. In vitro techniques for detection of NOVX protein include enzyme linked immunosorbent assays (ELISAs), Western blots, immunoprecipitations, and immunofluorescence. In vitro techniques for detection of NOVX genomic DNA include Southern hybridizations. Furthermore, in vivo techniques for detection of NOVX protein include introducing into a subject a labeled anti-NOVX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In one embodiment, the methods further involve obtaining a control biological sample from a control subject, contacting the control sample with a compound or agent capable of detecting NOVX protein, mRNA, or genomic DNA, such that the presence of NOVX protein, mRNA or genomic DNA is detected in the biological sample, and comparing the presence of NOVX protein, mRNA or genomic DNA in the control sample with the presence of NOVX protein, mRNA or genomic DNA in the test sample.

The invention also encompasses kits for detecting the presence of NOVX in a biological sample. For example, the kit can comprise: a labeled compound or agent capable of detecting NOVX protein or mRNA in a biological sample; means for determining the amount of NOVX in the sample; and means for comparing the amount of NOVX in the sample with a standard. The compound or agent can be packaged in a suitable container. The kit can further comprise instructions for using the kit to detect NOVX protein or nucleic acid.

Prognostic Assays

The diagnostic methods described herein can furthermore be utilized to identify subjects having or at risk of developing a disease or disorder associated with aberrant NOVX expression or activity. For example, the assays described herein, such as the preceding diagnostic assays or the following assays, can be utilized to identify a subject having or at risk of developing a disorder associated with NOVX protein, nucleic acid expression or activity. Such disorders include for example, pulmonary, neurodegenerative, cell proliferative, angiogenic, hematopoietic, hepatic, immunological, inflammatory, and tumor-related disorders and/or pathologies.

Alternatively, the prognostic assays can be utilized to identify a subject having or at risk for developing a disease or disorder. Thus, the invention provides a method for identifying a disease or disorder associated with aberrant NOVX expression or activity in which a test sample is obtained from a subject and NOVX protein or nucleic acid (e.g., mRNA, genomic DNA) is detected, wherein the presence of NOVX protein or nucleic acid is diagnostic for a subject having or at risk of developing a disease or disorder associated with aberrant NOVX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NOVX expression or activity. For example, such methods can be used to determine whether a subject can be effectively treated with an agent for a disorder. Thus, the invention provides methods for determining whether a subject can be effectively treated with an agent for a disorder associated with aberrant NOVX expression or activity in which a test sample is obtained and NOVX protein or nucleic acid is detected (e.g., wherein the presence of NOVX protein or nucleic acid is diagnostic for a subject that can be administered the agent to treat a disorder associated with aberrant NOVX expression or activity).

The methods of the invention can also be used to detect genetic lesions in a NOVX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding a NOVX-protein, or the misexpression of the NOVX gene. For example, such genetic lesions can be detected by ascertaining the existence of at least one of: (i) a deletion of one or more nucleotides from a NOVX gene; (ii) an addition of one or more nucleotides to a NOVX gene; (iii) a substitution of one or more nucleotides of a NOVX gene, (iv) a chromosomal rearrangement of a NOVX gene; (v) an alteration in the level of a messenger RNA transcript of a NOVX gene, (vi) aberrant modification of a NOVX gene, such as of the methylation pattern of the genomic DNA, (vii) the presence of a non-wild-type splicing pattern of a messenger RNA transcript of a NOVX gene, (viii) a non-wild-type level of a NOVX protein, (ix) allelic loss of a NOVX gene, and (x) inappropriate post-translational modification of a NOVX protein. As described herein, there are a large number of assay techniques known in the art which can be used for detecting lesions in a NOVX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. *Science* 241: 1077–1080; and Nakazawa, et al., 1994. *Proc. Natl. Acad. Sci. USA* 91: 360–364), the latter of which can be particularly useful for detecting point mutations in the NOVX-gene (see, Abravaya, et al., 1995. *Nucl. Acids Res.* 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to a NOVX gene under conditions such that hybridization and amplification of the NOVX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see, Guatelli, et al., 1990. *Proc. Natl. Acad. Sci. USA* 87: 1874–1878), transcriptional amplification system (see, Kwoh, et al., 1989. *Proc. Natl. Acad. Sci. USA* 86: 1173–1177); Qβ Replicase (see, Lizardi, et al, 1988. *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a NOVX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in NOVX can be identified by hybridizing a sample and control nucleic acids, e.g., DNA or RNA, to high-density arrays containing hundreds or thousands of oligonucleotides probes. See, e.g., Cronin, et al., 1996. *Human Mutation* 7: 244–255; Kozal, et al., 1996. *Nat. Med.* 2: 753–759. For example, genetic mutations in NOVX can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NOVX gene and detect mutations by comparing the sequence of the sample NOVX with the corresponding wild-type (control) sequence. Examples of sequencing reactions include those based on techniques developed by Maxim and Gilbert, 1977. *Proc. Natl. Acad. Sci. USA* 74: 560 or Sanger, 1977. *Proc. Natl. Acad. Sci. USA* 74: 5463. It is also contemplated that any of a variety of automated sequencing procedures can be utilized when performing the diagnostic assays (see, e.g., Naeve, et al., 1995. *Biotechniques* 19: 448), including sequencing by mass spectrometry (see, e.g., PCT International Publication No. WO 94/16101; Cohen, et al., 1996. *Adv. Chromatography* 36: 127–162; and Griffin, et al., 1993. *Appl. Biochem. Biotechnol.* 38: 147–159).

Other methods for detecting mutations in the NOVX gene include methods in which protection from cleavage agents is used to detect mismatched bases in RNA/RNA or RNA/DNA heteroduplexes. See, e.g., Myers, et al., 1985. *Science* 230: 1242. In general, the art technique of "mismatch cleavage" starts by providing heteroduplexes of formed by hybridizing (labeled) RNA or DNA containing the wild-type NOVX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. *Proc. Natl. Acad. Sci. USA* 85: 4397; Saleeba, et al., 1992. *Methods Enzymol.* 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NOVX cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. *Carcinogenesis* 15: 1657–1662. According to an exemplary embodiment, a probe based on a NOVX sequence, e.g., a wild-type NOVX sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NOVX genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA:* 86: 2766; Cotton, 1993. *Mutat. Res.* 285: 125–144; Hayashi, 1992. *Genet. Anal. Tech. Appl.* 9: 73–79. Single-stranded DNA fragments of sample and control NOVX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. *Trends Genet.* 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al, 1985. *Nature* 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324: 163; Saiki, et al., 1989. *Proc. Natl. Acad. Sci. USA* 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs, et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it may be desirable to introduce a novel restriction site in the region of the mutation to create cleavage-based detection. See, e.g., Gasparini, et al., 1992. *Mol. Cell Probes* 6: 1. It is anticipated that in certain embodiments amplification may also be performed using Taq ligase for amplification. See, e.g., Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a NOVX gene.

Furthermore, any cell type or tissue, preferably peripheral blood leukocytes, in which NOVX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on NOVX activity (e.g., NOVX gene expression), as identified by a screening assay described herein can be administered to individuals to treat (prophylactically or therapeutically) disorders (e.g., cell proliferative, angiogenic, pulmonary, hepatic, hematopoietic, immunological, inflammatory, and tumor-related disorders and/or pathologies). In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NOVX protein, expression of NOVX nucleic acid, or mutation content of NOVX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. Pharmacol. Physiol.,* 23: 983–985; Linder, 1997. *Clin. Chem.,* 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of NOVX protein, expression of NOVX nucleic acid, or mutation content of NOVX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a NOVX modulator, such as a modulator identified by one of the exemplary screening assays described herein.

Monitoring of Effects During Clinical Trials

Monitoring the influence of agents (e.g., drugs, compounds) on the expression or activity of NOVX (e.g., the ability to modulate aberrant cell proliferation) can be applied not only in basic drug screening, but also in clinical trials. For example, the effectiveness of an agent determined by a screening assay as described herein to increase NOVX gene expression, protein levels, or upregulate NOVX activity, can be monitored in clinical trails of subjects exhibiting decreased NOVX gene expression, protein levels, or downregulated NOVX activity. Alternatively, the effectiveness of an agent determined by a screening assay to decrease NOVX gene expression, protein levels, or downregulate NOVX activity, can be monitored in clinical trails of subjects exhibiting increased NOVX gene expression, protein levels, or upregulated NOVX activity. In such clinical trials, the expression or activity of NOVX and, preferably, other genes that have been implicated in, for example, a cellular proliferation or immune disorder can be used as a "read out" or markers of the immune responsiveness of a particular cell.

By way of example, and not of limitation, genes, including NOVX, that are modulated in cells by treatment with an agent (e.g., compound, drug or small molecule) that modulates NOVX activity (e.g., identified in a screening assay as described herein) can be identified. Thus, to study the effect of agents on cellular proliferation disorders, for example, in a clinical trial, cells can be isolated and RNA prepared and analyzed for the levels of expression of NOVX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NOVX or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a NOVX protein, mRNA, or genomic DNA in the preadministration sample; (iii) obtaining one or more post-administration samples from the subject; (iv) detecting the level of expression or activity of the NOVX protein, mRNA, or genomic DNA in the post-administration samples; (v) comparing the level of expression or activity of the NOVX protein, mRNA, or genomic DNA in the pre-administration sample with the NOVX protein, mRNA, or genomic DNA in the post administration sample or samples; and (vi) altering the administration of the agent to the subject accordingly. For example, increased administration of the agent may be desirable to increase the expression or activity of NOVX to higher levels than detected, i.e., to increase the effectiveness of the agent. Alternatively, decreased administration of the agent may be desirable to decrease expression or activity of NOVX to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant NOVX expression or activity. Disorders associated with aberrant NOVX expression include, for example, hepatic diseases, e.g. cirrhosis, cell proliferative diseases, e.g. cancer and diabetic retinopathy, reproductive disorders, e.g. sterility, immunological diseases, and hyperplastic wound healing, e.g. hypertrophic scars and keloids.

These methods of treatment will be discussed more fully, below.

Disease and Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989. *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant NOVX expression or activity, by administering to the subject an agent that modulates NOVX expression or at least one NOVX activity. Subjects at risk for a disease that is caused or contributed to by aberrant NOVX expression or activity can be identified by, for example, any or a combination of diagnostic or prognostic assays as described herein. Administration of a prophylactic agent can occur prior to the manifestation of symptoms characteristic of the NOVX aberrancy, such that a disease or disorder is prevented or, alternatively, delayed in its progression. Depending upon the type of NOVX aberrancy, for example, a NOVX agonist or NOVX antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating NOVX expression or activity for therapeutic purposes. The modulatory method of the invention involves contacting a cell with an agent that modulates one or more of the activities of NOVX protein activity associated with the cell. An agent that modulates NOVX protein activity can be an agent as described herein, such as a nucleic acid or a protein, a naturally-occurring cognate ligand of a NOVX protein, a peptide, a NOVX peptidomimetic, or other small molecule. In one embodiment, the agent stimulates one or more NOVX protein activity. Examples of such stimulatory agents include active NOVX protein and a nucleic acid molecule encoding NOVX that has been introduced into the cell. In another embodiment, the agent inhibits one or more NOVX protein activity. Examples of such inhibitory agents include antisense NOVX nucleic acid molecules and anti-NOVX antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of a NOVX protein or nucleic acid molecule. In one embodiment, the method involves administering an agent (e.g., an agent identified by a screening assay described herein), or combination of agents that modulates (e.g., up-regulates or down-regulates) NOVX expression or activity. In another embodiment, the method involves administering a NOVX protein or nucleic acid molecule as therapy to compensate for reduced or aberrant NOVX expression or activity.

Stimulation of NOVX activity is desirable in situations in which NOVX is abnormally downregulated and/or in which increased NOVX activity is likely to have a beneficial effect. One example of such a situation is where a subject has a disorder characterized by aberrant cell proliferation and/or differentiation (e.g., cancer or immune associated ). Another example of such a situation is where the subject has an immunodeficiency disease (e.g., AIDS).

Antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand which may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

EXAMPLE 1

Quantitative Expression Analysis of Clones in Various Cells and Tissues

The quantitative expression of various clones was assessed using microtiter plates containing RNA samples from a variety of normal and pathology-derived cells, cell lines and tissues using real time quantitative PCR (RTQ PCR; TAQMAN®). RTQ PCR was performed on a Perkin-Elmer Biosystems ABI PRISM® 7700 Sequence Detection System. Various collections of samples are assembled on the plates, and referred to as Panel 1 (containing cells and cell lines from normal and cancer sources), Panel 2 (containing samples derived from tissues, in particular from surgical samples, from normal and cancer sources), and Panel 4 (containing cells and cell lines from normal cells and cells related to inflammatory conditions).

First, the RNA samples were normalized to constitutively expressed genes such as -actin and GAPDH. RNA (~50 ng total or ~1 ng polyA+) was converted to cDNA using the TAQMAN® Reverse Transcription Reagents Kit (PE Biosystems, Foster City, Calif.; Catalog No. N808-0234) and random hexamers according to the manufacturer's protocol. Reactions were performed in 20 ul and incubated for 30 min. at 48° C. cDNA (5 ul) was then transferred to a separate plate for the TAQMAN® reaction using -actin and GAPDH TAQMAN® Assay Reagents (PE Biosystems; Catalog Nos. 4310881 E and 4310884E, respectively) and TAQMAN® universal PCR Master Mix (PE Biosystems; Catalog No. 4304447) according to the manufacturer's protocol. Reactions were performed in 25 ul using the following parameters: 2 min. at 50° C.; 10 min. at 95° C.; 15 sec. at 95° C./1 min. at 60° C. (40 c as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100. The average CT values obtained for β-actin and GAPDH were used to normalize RNA samples. The RNA sample generating the highest CT value required no further diluting, while all other samples were diluted relative to this sample according to their -actin /GAPDH average CT values.

Normalized RNA (5 ul) was converted to cDNA and analyzed via TAQMAN® using One Step RT-PCR Master Mix Reagents (PE Biosystems; Catalog No. 4309169) and gene-specific primers according to the manufacturer's instructions. Probes and primers were designed for each assay according to Perkin Elmer Biosystem's Primer Express Software package (version I for Apple Computer's Macintosh Power PC) or a similar algorithm using the target sequence as input. Default settings were used for reaction conditions and the following parameters were set before selecting primers: primer concentration=250 nM, primer melting temperature ($T_m$) range=58 °–60° C., primer optimal Tm=59° C., maximum primer difference=2° C., probe does not have 5' G, probe Tm must be 10° C. greater than primer $T_m$, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM.

PCR conditions: Normalized RNA from each tissue and each cell line was spotted in each well of a 96 well PCR plate (Perkin Elmer Biosystems). PCR cocktails including two probes (a probe specific for the target clone and another gene-specific probe multiplexed with the target probe) were set up using 1× TaqMan™ PCR Master Mix for the PE Biosystems 7700, with 5 mM MgCl2, dNTPs (dA, G, C, U at 1:1:1:2 ratios), 0.25 U/ml AmpliTaq Gold™ (PE Biosystems), and 0.4 U/µl RNase inhibitor, and 0.25 U/µl reverse transcriptase. Reverse transcription was performed at 48° C. for 30 minutes followed by amplification/PCR cycles as follows: 95° C. 10 min, then 40 cycles of 95° C. for 15 seconds, 60° C. for 1 minute.

RTQ-PCR Panel 2 Description

This 96 well (2 control wells, 94 test samples) panel and its variants (Panel 2X, etc.) are composed of RNA/cDNA isolated from human tissue procured by surgeons working in close cooperation with the National Cancer Institute's Cooperative Human Tissue Network (CHTN) or the National Disease Research Initiative (NDRI). The tissues procured are derived from human malignancies and in cases where indicated many malignant tissues have "matched margins". The tumor tissue and the "matched margins" are evaluated by two independent pathologists (the surgical pathologists and again by a pathologists at NDRI or CHTN). This analysis provides a gross histopathological assessment of tumor differentiation grade. Moreover, most samples include the original surgical pathology report that provides information regarding the clinical stage of the patient. These matched margins are taken from the tissue surrounding (i.e. immediately proximal) to the zone of surgery (designated "NAT", for normal adjacent tissue, in Tables 30 and 40). In addition, RNA/cDNA was obtained from various human tissues derived from human autopsies performed on deceased elderly people or sudden death victims (accidents, etc.). These tissue were ascertained to be free of disease and were purchased from various high quality commercial sources such as Clontech, Research Genetics, and Invitrogen.

RNA integrity from all samples is controlled for quality by visual assessment of agarose gel electrophoresis using 28s and 18s ribosomal RNA staining intensity ratio as a guide (2:1 to 2.5:1 28s: 1 8s) and the presence of low molecular weight RNAs indicative of degradation products. Samples are quality controlled for genomic DNA contamination by reactions run in the absence of reverse transcriptase using probe and primer sets designed to amplify across the span of a single exon.

RTQ-PCR Panel 4 Description

A 96 well plate (2 control wells, 94 test samples) is composed of RNA (Panel 4r) or cDNA (Panel 4d) isolated from various human cell lines or tissues related to inflammatory conditions. Total RNA from control normal tissues: colon, and lung were purchased from Stratagene (La Jolla, Calif.); thymus and kidney total RNA was obtained from Clontech (Palo Alto, Calif.). Total RNA from liver tissue from Cirrhosis patients and kidney from Lupus patients were obtained from Biochain. Intestinal tissue for RNA preparation from Crohns disease and ulcerative colitis patients was obtained from the National Disease Research Interchange (NDRI) (Philadelphia, Pa.).

Astrocytes, lung fibroblasts, dermal fibroblasts, coronary artery smooth muscle cells, small airway epithelium, bronchial epithelium, microvascular dermal endothelial cells, microvascular lung endothelial cells, human pulmonary aortic endothelial cells, human umbilical vein endothelial cells were all purchased from Clonetics (Walkersville, Md.) and grown in the media supplied for these cell types by Clonetics. These primary cell types were activated with various cytokines or combinations of cytokines for 6 and/or 12–14 hours, as indicated. The following cytokines were used; IL-1 beta at approximately 1–5 ng/ml, TNF alpha at approximately 5–10 ng/ml, IFN gamma at approximately 20–50 ng/ml, IL-4 at approximately 5–10 ng/ml, IL-9 at approximately 5–10 ng/ml, IL-13 at approximately 5–10 ng/ml. Endothelial cells were sometimes starved for various times by culture in the basal media from Clonetics with 0.1% serum.

Mononuclear cells were prepared from blood of employees at CuraGen Corporation, using Ficoll. LAK cells were prepared from these cells by culture in DMEM 5% FCS (Hyclone), 100 µM non essential amino acids (Gibco/Life Technologies, Rockville, Md.), 1 mM sodium pyruvate (Gibco), mercaptoethanol $5.5 \times 10^{-5}$ M (Gibco), and 10 mM Hepes (Gibco) and Interleukin 2 for 4–6 days. Cells were then either activated with 10–20 ng/ml PMA and 1–2 µg/ml ionomycin, IL-12 at 5–10 ng/ml, IFN gamma at 20–50 ng/ml and IL-18 at 5–10 ng/ml for 6 hours. In some cases, mononuclear cells were cultured for 4–5 days in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco) with PHA (phytohemagglutinin) or PWM (pokeweed mitogen) at approximately 5 µg/ml. Samples were taken at 24, 48 and 72 hours for RNA preparation. MLR (mixed lymphocyte reaction) samples were obtained by taking blood from two donors, isolating the mononuclear cells using Ficoll and mixing the isolated mononuclear cells 1:1 at a final concentration of approximately $2 \times 10^6$ cells/ml in DMEM 5% FCS (Hyclone), 100 µM non essential amino acids (Gibco), 1 mM sodium pyruvate (Gibco), mercaptoethanol ($5.5 \times 10^{-5}$ M) (Gibco), and 10 mM Hepes (Gibco). The MLR was cultured and samples taken at various time points ranging from 1–7 days for RNA preparation.

Monocytes were isolated from mononuclear cells using CD14 Miltenyi Beads, +ve VS selection columns and a Vario Magnet according to the manufacturer's instructions. Monocytes were differentiated into dendritic cells by culture in DMEM 5% fetal calf serum (FCS) (Hyclone, Logan, Utah), 100 µM non essential amino acids (Gibco), 1 mM sodium pyruvate (Gibco), mercaptoethanol $5.5 \times 10^{-5}$ M (Gibco), and 10 mM Hepes (Gibco), 50 ng/ml GMCSF and 5 ng/ml IL-4 for 5–7 days. Macrophages were prepared by culture of monocytes for 5–7 days in DMEM 5% FCS (Hyclone), 100 µM non essential amino acids (Gibco), 1 mM sodium pyruvate (Gibco), mercaptoethanol $5.5 \times 10^{-5}$ M (Gibco), 10 mM Hepes (Gibco) and 10% AB Human Serum or MCSF at approximately 50 ng/ml. Monocytes, macrophages and dendritic cells were stimulated for 6 and 12–14 hours with lipopolysaccharide (LPS) at 100 ng/ml. Dendritic cells were also stimulated with anti-CD40 monoclonal antibody (Pharmingen) at 10 µg/ml for 6 and 12–14 hours.

CD4 lymphocytes, CD8 lymphocytes and NK cells were also isolated from mononuclear cells using CD4, CD8 and CD56 Miltenyi beads, positive VS selection columns and a Vario Magnet according to the manufacturer's instructions. CD45RA and CD45RO CD4 lymphocytes were isolated by depleting mononuclear cells of CD8, CD56, CD14 and CD19 cells using CD8, CD56, CD14 and CD19 Miltenyi beads and +ve selection. Then CD45RO beads were used to isolate the CD45RO CD4 lymphocytes with the remaining cells being CD45RA CD4 lymphocytes. CD45RA CD4, CD45RO CD4 and CD8 lymphocytes were placed in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco) and plated at 106 cells/ml onto Falcon 6 well tissue culture plates that had been coated overnight with 0.5 µg/ml anti-CD28 (Pharmingen) and 3 ug/ml anti-CD3 (OKT3, ATCC) in PBS. After 6 and 24 hours, the cells were harvested for RNA preparation. To prepare chronically activated CD8 lymphocytes, we activated the isolated CD8 lymphocytes for 4 days on anti-CD28 and anti-CD3 coated plates and then harvested the cells and expanded them in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco) and IL-2. The expanded CD8 cells were then activated again with plate bound anti-CD3 and anti-CD28 for 4 days and expanded as before. RNA was isolated 6 and 24 hours after the second activation and after 4 days of the second expansion culture. The isolated NK cells were cultured in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco) and IL-2 for 4–6 days before RNA was prepared.

To obtain B cells, tonsils were procured from NDRI. The tonsil was cut up with sterile dissecting scissors and then passed through a sieve. Tonsil cells were then spun down and resupended at $10^6$ cells/ml in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco). To activate the cells, we used PWM at 5 µg/ml or anti-CD40 (Pharmingen) at approximately 10 µg/ml and IL-4 at 5–10 ng/ml. Cells were harvested for RNA preparation at 24, 48 and 72 hours.

To prepare the primary and secondary Th1/Th2 and Tr1 cells, six-well Falcon plates were coated overnight with 10 µg/ml anti-CD28 (Pharmingen) and 2 µg/ml OKT3 (ATCC), and then washed twice with PBS. Umbilical cord blood CD4 lymphocytes (Poietic Systems, German Town, Md.) were cultured at $10^5$–$10^6$ cells/ml in DMEM 5% FCS (Hyclone), 100 µM non essential amino acids (Gibco), 1 mM sodium pyruvate (Gibco), mercaptoethanol $5.5 \times 10^{-5}$ M (Gibco), 10 mM Hepes (Gibco) and IL-2 (4 ng/ml). IL-12 (5 ng/ml) and anti-IL4 (1 µg/ml) were used to direct to Th1, while IL-4 (5 ng/ml) and anti-IFN gamma (1 pg/ml) were used to direct to Th2 and IL-10 at 5 ng/ml was used to direct to Tr1. After 4–5 days, the activated Th1, Th2 and Tr1 lymphocytes were washed once in DMEM and expanded for 4–7 days in DMEM 5% FCS (Hyclone), 100 µM non essential amino acids (Gibco), 1 mM sodium pyruvate (Gibco), mercaptoethanol $5.5 \times 10^{-5}$ M (Gibco), 10 mM Hepes (Gibco) and IL-2 (1 ng/ml). Following this, the activated Th1, Th2 and Tr1 lymphocytes were re-stimulated for 5 days with anti-CD28/OKT3 and cytokines as described above, but with the addition of anti-CD95L (1 µg/ml) to prevent apoptosis. After 4–5 days, the Th1, Th2 and Tr1 lymphocytes were washed and then expanded again with IL-2 for 4–7 days. Activated Th1 and Th2 lymphocytes were maintained in this way for a maximum of three cycles. RNA was prepared from primary and secondary Th1, Th2 and Tr1 after 6 and 24 hours following the second and third activations with plate bound anti-CD3 and anti-CD28 mabs and 4 days into the second and third expansion cultures in Interleukin 2.

The following leukocyte cells lines were obtained from the ATCC: Ramos, EOL-1, KU-812. EOL cells were further differentiated by culture in 0.1 mM dbcAMP at $5 \times 10^5$ cells/ml for 8 days, changing the media every 3 days and adjusting the cell concentration to $5 \times 10^5$ cells/ml. For the culture of these cells, we used DMEM or RPMI (as recommended by the ATCC), with the addition of 5% FCS (Hyclone), 100 µM non essential amino acids (Gibco), 1 mM sodium pyruvate (Gibco), mercaptoethanol $5.5 \times 10^{-5}$ M (Gibco), 10 mM Hepes (Gibco). RNA was either prepared from resting cells or cells activated with PMA at 10 ng/ml and ionomycin at 1 µg/ml for 6 and 14 hours. Keratinocyte line CCD106 and an airway epithelial tumor line NCI-H292 were also obtained from the ATCC. Both were cultured in DMEM 5% FCS (Hyclone), 100 µM non essential amino acids (Gibco), 1 mM sodium pyruvate (Gibco), mercaptoethanol $5.5 \times 10^{-5}$ M (Gibco), and 10 mM Hepes (Gibco). CCD1106 cells were activated for 6 and 14 hours with approximately 5 ng/ml TNF alpha and 1 ng/ml IL-1 beta, while NCI-H292 cells were activated for 6 and 14 hours with the following cytokines: 5 ng/ml IL-4, 5 ng/ml IL-9, 5 ng/ml IL-13 and 25 ng/ml IFN gamma.

For these cell lines and blood cells, RNA was prepared by lysing approximately $10^7$ cells/ml using Trizol (Gibco BRL). Briefly, 1/10 volume of bromochloropropane (Molecular Research Corporation) was added to the RNA sample, vortexed and after 10 minutes at room temperature, the tubes were spun at 14,000 rpm in a Sorvall SS34 rotor. The aqueous phase was removed and placed in a 15 ml Falcon Tube. An equal volume of isopropanol was added and left at −20 degrees C. overnight. The precipitated RNA was spun down at 9,000 rpm for 15 min in a Sorvall SS34 rotor and washed in 70% ethanol. The pellet was redissolved in 300 µl of RNAse-free water and 35 µl buffer (Promega) 5 µl DTT, 7 µl RNAsin and 8 µl DNAse were added. The tube was incubated at 37 degrees C. for 30 minutes to remove contaminating genomic DNA, extracted once with phenol chloroform and re-precipitated with 1/10 volume of 3 M sodium acetate and 2 volumes of 100% ethanol. The RNA was spun down and placed in RNAse free water. RNA was stored at −80 degrees C.

TABLE 30

NOV2 (AL133371_da1) Probe Name: Ag1348 Results Panel 2

| Tissue_Name | Rel. Expr., % |
|---|---|
| 83786 Kidney Ca, Nuclear grade 2 (OD04338) | 4.2 |
| 83219 CC Well to Mod Diff (ODO3866) | 0.4 |
| 83220 CC NAT (ODO3866) | 0.2 |
| 83221 CC Gr.2 rectosigmoid (ODO3868) | 1.1 |
| 83222 CC NAT (ODO3868) | 0.0 |
| 83235 CC Mod Diff (ODO3920) | 3.4 |
| 83236 CC NAT (ODO3920) | 4.1 |
| 83237 CC Gr.2 ascend colon (ODO3921) | 1.4 |
| 83238 CC NAT (ODO3921) | 0.1 |
| 83239 Lung Met to Muscle (ODO4286) | 0.3 |
| 83240 Muscle NAT (ODO4286) | 3.3 |
| 83241 CC from Partial Hepatectomy (ODO4309) | 2.6 |
| 83242 Liver NAT (ODO4309) | 10.3 |
| 83255 Ocular Mel Met to Liver (ODO4310) | 1.4 |
| 83256 Liver NAT (ODO4310) | 11.0 |
| 83787 Kidney NAT (OD04338) | 5.5 |
| 83788 Kidney Ca Nuclear grade 1/2 (OD04339) | 27.2 |
| 83789 Kidney NAT (OD04339) | 11.6 |
| 83790 Kidney Ca, Clear cell type (OD04340) | 6.2 |
| 83791 Kidney NAT (OD04340) | 2.4 |
| 83792 Kidney Ca, Nuclear grade 3 (OD04348) | 1.9 |
| 83793 Kidney NAT (OD04348) | 4.6 |
| 84136 Lung Malignant Cancer (OD03126) | 3.0 |
| 84137 Lung NAT (OD03126) | 0.9 |
| 84138 Lung NAT (OD04321) | 2.9 |

TABLE 30-continued

NOV2 (AL133371_da1) Probe Name: Ag1348 Results Panel 2

| Tissue_Name | Rel. Expr., % |
|---|---|
| 84139 Melanoma Mets to Lung (OD04321) | 3.3 |
| 84140 Prostate Cancer (OD04410) | 9.3 |
| 84141 Prostate NAT (OD04410) | 8.2 |
| 84871 Lung Cancer (OD04404) | 1.3 |
| 84872 Lung NAT (OD04404) | 0.5 |
| 84875 Lung Cancer (OD04565) | 1.5 |
| 84877 Breast Cancer (OD04566) | 0.5 |
| 85950 Lung Cancer (OD04237-01) | 3.7 |
| 85970 Lung NAT (OD04237-02) | 6.7 |
| 85973 Kidney Cancer (OD04450-01) | 0.8 |
| 85974 Kidney NAT (OD04450-03) | 9.5 |
| 85975 Breast Cancer (OD04590-01) | 15.0 |
| 85976 Breast Cancer Mets (OD04590-03) | 27.4 |
| 87070 Breast Cancer Metastasis (OD04655-05) | 15.5 |
| 87071 Bladder Cancer (OD04718-01) | 5.8 |
| 87072 Bladder Normal Adjacent (OD04718-03) | 12.2 |
| 87073 Prostate Cancer (OD04720-01) | 100.0 |
| 87074 Prostate NAT (OD04720-02) | 9.5 |
| 87472 Colon mets to lung (OD04451-01) | 0.3 |
| 87473 Lung NAT (OD04451-02) | 0.0 |
| 87474 Kidney Cancer (OD04622-01) | 5.8 |
| 87475 Kidney NAT (OD04622-03) | 0.1 |
| 87492 Ovary Cancer (OD04768-07) | 22.1 |
| 87493 Ovary NAT (OD04768-08) | 2.9 |
| Bladder Cancer INVITROGEN A302173 | 0.4 |
| Bladder Cancer Research Genetics RNA 1023 | 0.3 |
| Breast Cancer Clontech 9100266 | 0.1 |
| Breast Cancer INVITROGEN A209073 | 0.7 |
| Breast Cancer Res. Gen. 1024 | 2.8 |
| Breast NAT Clontech 9100265 | 0.1 |
| Breast NAT INVITROGEN A2090734 | 1.9 |
| GENPAK Breast Cancer 064006 | 10.6 |
| Gastric Cancer Clontech 9060395 | 0.0 |
| Gastric Cancer Clontech 9060397 | 0.0 |
| Gastric Cancer GENPAK 064005 | 0.3 |
| Kidney Cancer Clontech 8120607 | 0.0 |
| Kidney Cancer Clontech 8120613 | 0.0 |
| Kidney Cancer Clontech 9010320 | 0.1 |
| Kidney NAT Clontech 8120608 | 0.0 |
| Kidney NAT Clontech 8120614 | 0.1 |
| Kidney NAT Clontech 9010321 | 0.0 |
| Liver Cancer GENPAK 064003 | 0.2 |
| Liver Cancer Research Genetics RNA 1025 | 0.2 |
| Liver Cancer Research Genetics RNA 1026 | 0.1 |
| NAT Stomach Clontech 9060359 | 0.1 |
| NAT Stomach Clontech 9060394 | 0.0 |
| NAT Stomach Clontech 9060396 | 0.0 |
| Normal Bladder GENPAK 061001 | 0.3 |
| Normal Breast GENPAK 061019 | 1.8 |
| Normal Colon GENPAK 061003 | 0.1 |
| Normal Kidney GENPAK 061008 | 0.2 |
| Normal Liver GENPAK 061009 | 0.4 |
| Normal Lung GENPAK 061010 | 0.5 |
| Normal Ovary Res. Gen. | 0.0 |
| Normal Prostate Clontech A+ 6546-1 | 0.0 |
| Normal Stomach GENPAK 061017 | 0.0 |
| Normal Thyroid Clontech A+ 6570-1** | 0.0 |
| Normal Uterus GENPAK 061018 | 1.9 |
| Ovarian Cancer GENPAK 064008 | 0.8 |
| Paired Liver Cancer Tissue Research Genetics RNA 6004-T | 0.3 |
| Paired Liver Cancer Tissue Research Genetics RNA 6005-T | 0.1 |
| Paired Liver Tissue Research Genetics RNA 6004-N | 0.3 |
| Paired Liver Tissue Research Genetics RNA 6005-N | 0.0 |
| Thyroid Cancer GENPAK 064010 | 0.0 |
| Thyroid Cancer INVITROGEN A302152 | 8.8 |
| Thyroid NAT INVITROGEN A302153 | 2.2 |
| Uterus Cancer GENPAK 064011 | 12.4 |
| Genomic DNA control | 0.5 |

TABLE 31

NOV2 (AL133371_da1)
Probe Name: Ag1348

| Primers | Sequences | TM °C. | Length | Start Position |
|---|---|---|---|---|
| Forward | 5'-AGATGGCATCCTCTCTGAAGAT-3' (SEQ ID NO.: 68) | 59.3 | 22 | 14 |
| Probe | TET-5'-CCTGCTTTGCATTCTTTGCAGGCT-3'-TAMRA (SEQ ID NO.: 69) | 69.5 | 24 | 54 |
| Reverse | 5'-AACGTCCTTGCTGTGTACAAGT-3' (SEQ ID NO.: 70) | 58.8 | 22 | 78 |

TABLE 32

NOV3 (AL133371_da2) Probe Name: Ag1346 TaqMan Results Panel 1

| Tissue_Name | Rel. Expr., % |
|---|---|
| Endothelial cells | 0.0 |
| Endothelial cells (treated) | 0.4 |
| Pancreas | 0.0 |
| Pancreatic ca. CAPAN 2 | 0.0 |
| Adrenal Gland (new lot*) | 0.0 |
| Thyroid | 0.0 |
| Salivary gland | 0.6 |
| Pituitary gland | 0.0 |
| Brain (fetal) | 0.2 |
| Brain (whole) | 0.3 |
| Brain (amygdala) | 0.3 |
| Brain (cerebellum) | 0.0 |
| Brain (hippocampus) | 1.1 |
| Brain (thalamus) | 1.2 |
| Cerebral Cortex | 0.8 |
| Spinal cord | 0.5 |
| CNS ca. (glio/astro) U87-MG | 0.0 |
| CNS ca. (glio/astro) U-118-MG | 0.0 |
| CNS ca. (astro) SW1783 | 0.0 |
| CNS ca.* (neuro; met) SK-N-AS | 0.0 |
| CNS ca. (astro) SF-539 | 0.3 |
| CNS ca. (astro) SNB-75 | 0.0 |
| CNS ca. (glio) SNB-19 | 0.5 |
| CNS ca. (glio) U251 | 0.0 |
| CNS ca. (glio) SF-295 | 0.0 |
| Heart | 2.2 |
| Skeletal Muscle (new lot*) | 0.2 |
| Bone marrow | 0.1 |
| Thymus | 0.0 |
| Spleen | 0.0 |
| Lymph node | 0.0 |
| Colorectal | 0.2 |
| Stomach | 0.1 |
| Small intestine | 0.3 |
| Colon ca. SW480 | 0.0 |
| Colon ca.* (SW480 met)SW620 | 0.0 |
| Colon ca. HT29 | 0.2 |
| Colon ca. HCT-116 | 0.0 |
| Colon ca. CaCo-2 | 1.0 |
| 83219 CC Well to Mod Diff (ODO3866) | 0.6 |
| Colon ca. HCC-2998 | 0.1 |
| Gastric ca.* (liver met) NCI-N87 | 0.0 |
| Bladder | 1.1 |
| Trachea | 0.2 |
| Kidney | 0.7 |
| Kidney (fetal) | 0.6 |
| Renal ca. 786-0 | 0.0 |
| Renal ca. A498 | 0.0 |
| Renal ca. RXF 393 | 0.0 |
| Renal ca. ACHN | 0.0 |
| Renal ca. UO-31 | 0.3 |
| Renal ca. TK-10 | 0.4 |
| Liver | 0.0 |
| Liver (fetal) | 0.0 |
| Liver ca. (hepatoblast) HepG2 | 0.0 |
| Lung | 0.0 |
| Lung (fetal) | 0.4 |
| Lung ca. (small cell) LX-1 | 0.0 |
| Lung ca. (small cell) NCI-H69 | 2.6 |
| Lung ca. (s.cell var.) SHP-77 | 0.1 |
| Lung ca. (large cell)NCI-H460 | 0.8 |
| Lung ca. (non-sm. Cell) A549 | 0.8 |
| Lung ca. (non-s.cell) NCI-H23 | 0.0 |
| Lung ca (non-s.cell) HOP-62 | 0.0 |
| Lung ca. (non-s.cl) NCI-H522 | 0.0 |
| Lung ca. (squam.) SW 900 | 1.3 |
| Lung ca. (squam.) NCI-H596 | 0.5 |
| Mammary gland | 0.5 |
| Breast ca.* (pl. effusion) MCF-7 | 0.0 |
| Breast ca.* (pl.ef) MDA-MB-231 | 0.0 |
| Breast ca.* (pl. effusion) T47D | 1.3 |
| Breast ca. BT-549 | 0.4 |
| Breast ca. MDA-N | 0.2 |
| Ovary | 0.5 |
| Ovarian ca. OVCAR-3 | 0.2 |
| Ovarian ca. OVCAR-4 | 0.9 |
| Ovarian ca. OVCAR-5 | 8.9 |
| Ovarian ca. OVCAR-8 | 0.3 |
| Ovarian ca. IGROV-1 | 0.3 |
| Ovarian ca.* (ascites) SK-OV-3 | 0.5 |
| Uterus | 0.3 |
| Placenta | 0.3 |
| Prostate | 3.3 |
| Prostate ca.* (bone met)PC-3 | 0.3 |
| Testis | 8.2 |
| Melanoma Hs688(A).T | 0.0 |
| Melanoma* (met) Hs688(B).T | 0.4 |
| Melanoma UACC-62 | 0.0 |
| Melanoma M14 | 0.8 |
| Melanoma LOX IMVI | 0.0 |
| Melanoma* (met) SK-MEL-5 | 0.1 |
| Adipose | 100.0 |

For Panel 1, the following abbreviations are used: ca. = carcinoma, * = established from metastasis, met = metastasis, s cell var = small cell variant, non-s = non-sm = non-small, squam = squamous, pl. eff = pl effusion = pleural effusion, glio = glioma, astro = astrocytoma, and neuro = neuroblastoma.

TABLE 33

NOV3 (AL133371_da2) Probe Name: Ag1346

| Primers | Sequences | Length | Start Position |
|---|---|---|---|
| Forward | 5'-CAGAGCAAAGAAGTTTCTTGGA-3' (SEQ ID NO.: 65) | 22 | 113 |
| Probe | TET-5'-TGAAACAGCACTACTTAAGTCCAAGTCGA-3'-TAMRA (SEQ ID NO.: 66) | 29 | 144 |
| Reverse | 5'-TCTCATGAGGACATCACATTTG-3' (SEQ ID NO.: 67) | 22 | 187 |

TABLE 34

NOV4 (AC011005_A) PROBE NAME: AG356 RESULTS

| Tissue_Name | Rel. Expr., % |
|---|---|
| Adipose | 3.4 |
| Adrenal gland | 15.6 |
| Bladder | 18.8 |
| Bone marrow | 9.0 |
| Endothelial cells | 25.5 |
| Endothelial cells (treated) | 19.1 |
| Liver | 13.6 |
| Liver (fetal) | 11.8 |
| Spleen | 5.5 |
| Thymus | 7.4 |
| Thyroid | 16.6 |
| Trachea | 9.5 |
| Testis | 32.8 |
| Spinal cord | 9.1 |
| Salivary gland | 17.6 |
| Brain (amygdala) | 6.5 |
| Brain (cerebellum) | 34.4 |
| Brain (hippocampus) | 12.8 |
| Brain (substantia nigra) | 20.0 |
| Brain (thalamus) | 17.8 |
| Cerebral Cortex | 27.6 |
| Brain (whole) | 25.2 |
| Brain (fetal) | 13.2 |
| CNS ca. (glio/astro) U-118-MG | 12.2 |
| CNS ca. (astro) SF-539 | 9.0 |
| CNS ca. (astro) SNB-75 | 10.6 |
| CNS ca. (astro) SW1783 | 7.1 |
| CNS ca. (glio) U251 | 7.5 |
| CNS ca. (glio) SF-295 | 18.1 |
| CNS ca. (glio) SNB-19 | 14.5 |
| CNS ca. (glio/astro) U87-MG | 21.0 |
| CNS ca.* (neuro; met) SK-N-AS | 25.0 |
| Small intestine | 18.8 |
| Colorectal | 6.4 |
| Colon ca. HT29 | 9.9 |
| Colon ca. CaCo-2 | 12.8 |
| Colon ca. HCT-15 | 18.1 |
| Colon ca. HCT-116 | 11.8 |
| Colon ca. HCC-2998 | 16.3 |
| Colon ca. SW480 | 9.7 |
| Colon ca.* (SW480 met)SW620 | 13.8 |
| Fetal Skeletal | 10.4 |
| Skeletal muscle | 100.0 |
| Heart | 31.9 |
| Stomach | 15.1 |
| Gastric ca.* (liver met) NCI-N87 | 12.3 |
| Kidney | 25.0 |
| Kidney (fetal) | 11.7 |
| Renal ca. 786-0 | 9.1 |
| Renal ca. A498 | 10.7 |
| Renal ca. ACHN | 14.9 |
| Renal ca. TK-10 | 18.2 |
| Renal ca. UO-31 | 14.8 |
| Renal ca. RXF 393 | 4.2 |
| Pancreas | 27.9 |
| Pancreatic ca. CAPAN 2 | 5.1 |
| Ovary | 11.6 |
| Ovarian ca. IGROV-1 | 15.5 |
| Ovarian ca. OVCAR-3 | 12.8 |
| Ovarian ca. OVCAR-4 | 22.2 |
| Ovarian ca. OVCAR-5 | 20.2 |
| Ovarian ca. OVCAR-8 | 16.6 |
| Ovarian ca.* (ascites) SK-OV-3 | 20.6 |
| Prostate | 16.4 |
| Prostate ca.* (bone met)PC-3 | 34.2 |
| Placenta | 13.1 |
| Pituitary gland | 19.8 |
| Uterus | 6.3 |

TABLE 35

NOV4 (AC011005_A) PROBE NAME: AG356

| Primers | Sequences | Length | Start Position |
|---|---|---|---|
| Forward | 5'-AAAGTCAGCATTGCGGTTCTC-3' (SEQ ID NO.: 71) | 21 | 569 |
| Probe | TET-5'-CTTGGCGTACCTCCGAGAGAAGCACC-3'-TAMRA (SEQ ID NO.: 72) | 26 | 595 |
| Reverse | 5'-GCTTCACATTTCGGTGCATG-3' (SEQ ID NO.: 73) | 20 | 625 |

TABLE 36

NOV4 (AC011005_A) PROBE NAME: AG755 RESULTS PANEL 1

| Tissue_Name | Rel. Expr., % |
|---|---|
| Endothelial cells | 7.7 |
| Endothelial cells (treated) | 6.8 |
| Pancreas | 12.1 |
| Pancreatic ca. CAPAN 2 | 0.5 |
| Adrenal Gland (new lot*) | 7.2 |
| Thyroid | 12.2 |
| Salavary gland | 12.5 |
| Pituitary gland | 12.2 |
| Brain (fetal) | 4.9 |
| Brain (whole) | 6.7 |
| Brain (amygdala) | 4.9 |
| Brain (cerebellum) | 4.3 |
| Brain (hippocampus) | 6.5 |
| Brain (thalamus) | 4.4 |
| Cerebral Cortex | 9.5 |
| Spinal cord | 2.2 |
| CNS ca. (glio/astro) U87-MG | 7.9 |
| CNS ca. (glio/astro) U-118-MG | 4.3 |
| CNS ca. (astro) SW1783 | 2.0 |
| CNS ca.* (neuro; met) SK-N-AS | 8.0 |
| CNS ca. (astro) SF-539 | 2.3 |
| CNS ca. (astro) SNB-75 | 4.8 |
| CNS ca. (glio) SNB-19 | 7.5 |
| CNS ca. (glio) U251 | 3.6 |
| CNS ca. (glio) SF-295 | 4.0 |
| Heart | 15.2 |
| Skeletal Muscle (new lot*) | 100.0 |
| Bone marrow | 3.2 |
| Thymus | 1.4 |
| Spleen | 3.0 |
| Lymph node | 3.5 |
| Colorectal | 0.8 |
| Stomach | 4.7 |
| Small intestine | 10.4 |
| Colon ca. SW480 | 2.3 |
| Colon ca.* (SW480 met)SW620 | 7.6 |
| Colon ca. HT29 | 2.4 |
| Colon ca. HCT-116 | 6.2 |
| Colon ca. CaCo-2 | 7.0 |
| 83219 CC Well to Mod Diff (ODO3866) | 1.1 |
| Colon ca. HCC-2998 | 6.6 |
| Gastric ca.* (liver met) NCI-N87 | 4.3 |
| Bladder | 6.5 |
| Trachea | 1.9 |
| Kidney | 10.7 |
| Kidney (fetal) | 4.9 |
| Renal ca. 786-0 | 2.5 |
| Renal ca. A498 | 3.7 |
| Renal ca. RXF 393 | 0.8 |
| Renal ca. ACHN | 4.1 |
| Renal ca. UO-31 | 1.4 |
| Renal ca. TK-10 | 2.3 |
| Liver | 3.9 |
| Liver (fetal) | 4.0 |
| Liver ca. (hepatoblast) HepG2 | 2.3 |
| Lung | 2.1 |
| Lung (fetal) | 2.9 |
| Lung ca. (small cell) LX-1 | 8.0 |
| Lung ca. (small cell) NCI-H69 | 4.1 |
| Lung ca. (s.cell var.) SHP-77 | 1.1 |
| Lung ca. (large cell)NCI-H460 | 7.3 |
| Lung ca. (non-sm. cell) A549 | 9.0 |
| Lung ca. (non-s.cell) NCI-H23 | 1.9 |
| Lung ca (non-s.cell) HOP-62 | 4.8 |
| Lung ca. (non-s.cl) NCI-H522 | 17.7 |
| Lung ca. (squam.) SW 900 | 2.5 |
| Lung ca. (squam.) NCI-H596 | 5.8 |
| Mammary gland | 5.6 |
| Breast ca.* (pl. effusion) MCF-7 | 8.8 |
| Breast ca.* (pl.ef) MDA-MB-231 | 5.6 |
| Breast ca.* (pl. effusion) T47D | 5.2 |
| Breast ca. BT-549 | 2.9 |
| Breast ca. MDA-N | 5.6 |
| Ovary | 4.0 |
| Ovarian ca. OVCAR-3 | 4.9 |
| Ovarian ca. OVCAR-4 | 6.0 |
| Ovarian ca. OVCAR-5 | 9.0 |
| Ovarian ca. OVCAR-8 | 8.7 |
| Ovarian ca. IGROV-1 | 5.2 |
| Ovarian ca.* (ascites) SK-OV-3 | 8.8 |
| Uterus | 2.1 |
| Plancenta | 4.9 |
| Prostate | 6.7 |
| Prostate ca.* (bone met)PC-3 | 12.9 |
| Testis | 8.1 |
| Melanoma Hs688(A).T | 2.1 |
| Melanoma* (met) Hs688(B).T | 2.2 |
| Melanoma UACC-62 | 14.1 |
| Melanoma M14 | 2.9 |
| Melanoma LOX IMVI | 4.6 |
| Melanoma* (met) SK-MEL-5 | 4.6 |
| Adipose | 0.3 |

For Panel 1, the following abbreviations are used: ca. = carcinoma, * = established from metastasis, met = metastasis, s cell var = small cell variant, non-s = non-sm = non-small, squam = squamous, pl. eff = pl effusion = pleural effusion, glio = glioma, astro = astrocytoma, and neuro = neuroblastoma.

TABLE 37

NOV4 (AC011005_A) PROBE NAME: AG755

| Primers | Sequences | TM ° C. | Length | Start Position |
|---|---|---|---|---|
| Forward | 5'-GCTGGAGGAGCTGGAACTT-3' ((SEQ ID NO.: 74) | 59.5 | 19 | 178 |
| Probe | TET-5'-AAGCCTTTCTCACCCAGAAAGCCAAG-3'-TAMRA (SEQ ID NO.: 75) | 69.4 | 26 | 219 |
| Reverse | 5'-TTTCGAAGTCATCGTCTTTGA-3' (SEQ ID NO.: 76) | 58.5 | 21 | 255 |

TABLE 38

NOV7 (AL132990_B) Ag301 Panel 4 Results

| Tissue_Name | Rel. Expr., % |
|---|---|
| 93768_Secondary Th1_anti-CD28/anti-CD3 | 0.0 |
| 93769_Secondary Th2_anti-CD28/anti-CD3 | 0.0 |
| 93770_Secondary Tr1_anti-CD28/anti-CD3 | 0.0 |
| 93573_Secondary Th1_resting day 4–6 in IL-2 | 0.0 |
| 93572_Secondary Th2_resting day 4–6 in IL-2 | 0.0 |
| 93571_Secondary Tr1_resting day 4–6 in IL-2 | 0.0 |
| 93568_primary Th1_anti-CD28/anti-CD3 | 0.0 |
| 93569_primary Th2_anti-CD28/anti-CD3 | 0.0 |
| 93570_primary Tr1_anti-CD28/anti-CD3 | 0.0 |
| 93565_primary Th1_resting dy 4–6 in IL-2 | 0.0 |
| 93566_primary Th2_resting dy 4–6 in IL-2 | 0.0 |
| 93567_primary Tr1_resting dy 4–6 in IL-2 | 4.3 |
| 93351_CD45RA CD4 lymphocyte_anti-CD28/anti-CD3 | 26.2 |
| 93352_CD45RO CD4 lymphocyte_anti-CD28/anti-CD3 | 0.0 |
| 93251_CD8 Lymphocytes_anti-CD28/anti-CD3 | 0.0 |
| 93353_chronic CD8 Lymphocytes 2ry_resting dy 4–6 in IL-2 | 0.0 |
| 93574_chronic CD8 Lymphocytes 2ry_activated CD3/CD28 | 3.8 |
| 93354_CD4_none | 0.0 |
| 93252_Secondary Th1/Th2/Tr1_anti-CD95 CH11 | 0.0 |
| 93103_LAK cells_resting | 0.0 |
| 93788_LAK cells_IL-2 | 0.0 |
| 93787_LAK cells_IL-2 + IL-12 | 0.0 |
| 93789_LAK cells_IL-2 + IFN gamma | 0.0 |
| 93790_LAK cells_IL-2 + IL-18 | 0.0 |
| 93104_LAK cells_PMA/ionomycin and IL-18 | 0.0 |
| 93578_NK Cells IL-2_resting | 0.0 |
| 93109_Mixed Lymphocyte Reaction_Two Way MLR | 0.0 |
| 93110_Mixed Lymphocyte Reaction_Two Way MLR | 0.0 |
| 93111_Mixed Lymphocyte Reaction_Two Way MLR | 0.0 |
| 93112_Mononuclear Cells (PBMCs)_resting | 0.0 |
| 93113_Mononuclear Cells (PBMCs)_PWM | 0.0 |
| 93114_Mononuclear Cells (PBMCs)_PHA-L | 0.0 |
| 93249_Ramos (B cell)_none | 0.0 |
| 93250_Ramos (B cell)_ionomycin | 0.0 |
| 93349_B lymphocytes_PWM | 0.0 |
| 93350_B lymphoytes_CD40L and IL-4 | 0.0 |
| 92665_EOL-1 (Eosinophil)_dbcAMP differentiated | 0.0 |
| 93248_EOL-1 (Eosinophil)_dbcAMP/PMAionomycin | 0.0 |
| 93356_Dendritic Cells_none | 0.0 |
| 93355_Dendritic Cells_LPS 100 ng/ml | 0.0 |
| 93775_Dendritic Cells_anti-CD40 | 6.0 |
| 93774_Monocytes_resting | 0.0 |
| 93776_Monocytes_LPS 50 ng/ml | 0.0 |
| 93581_Macrophages_resting | 0.0 |
| 93582_Macrophages_LPS 100 ng/ml | 0.0 |
| 93098_HUVEC (Endothelial)_none | 0.0 |
| 93099_HUVEC (Endothelial)_starved | 0.0 |
| 93100_HUVEC (Endothelial)_IL-1b | 0.0 |
| 93779_HUVEC (Endothelial)_IFN gamma | 0.0 |
| 93102_HUVEC (Endothelial)_TNF alpha + IFN gamma | 0.0 |
| 93101_HUVEC (Endothelial)_TNF alpha + IL4 | 0.0 |
| 93781_HUVEC (Endothelial)_IL-11 | 0.0 |
| 93583_Lung Microvascular Endothelial Cells_none | 19.5 |
| 93584_Lung Microvascular Endothelial Cells_TNFa (4 ng/ml) and IL1b (1 ng/ml) | 0.0 |
| 92662_Microvascular Dermal endothelium_none | 0.0 |
| 92663_Microvasular Dermal endothelium_TNFa (4 ng/ml) and IL1b (1 ng/ml) | 0.0 |
| 93773_Bronchial epithelium_TNFa (4 ng/ml) and IL1b (1 ng/ml)** | 0.0 |
| 93347_Small Airway Epithelium_none | 0.0 |
| 93348_Small Airway Epithelium_TNFa (4 ng/ml) and IL1b (1 ng/ml) | 0.0 |
| 92668_Coronary Artery SMC_resting | 3.9 |
| 92669_Coronary Artery SMC_TNFa (4 ng/ml) and IL1b (1 ng/ml) | 23.0 |
| 93107_astrocytes_resting | 0.0 |
| 93108_astrocytes_TNFa (4 ng/ml) and IL1b (1 ng/ml) | 4.6 |
| 92666_KU-812 (Basophil)_resting | 0.0 |
| 92667_KU-812 (Basophil)_PMA/ionoycin | 0.0 |
| 93579_CCD1106 (Keratinocytes)_none | 0.0 |
| 93580_CCD1106 (Keratinocytes)_TNFa and IFNg** | 4.6 |
| 93791_Liver Cirrhosis | 45.1 |
| 93792_Lupus Kidney | 0.0 |
| 93577_NCI-H292 | 4.8 |
| 93358_NCI-H292_IL-4 | 0.0 |
| 93360_NCI-H292_IL-9 | 0.0 |
| 93359_NCI-H292_IL-13 | 0.0 |
| 93357_NCI-H292_IFN gamma | 0.0 |
| 93777_HPAEC_- | 0.0 |
| 93778_HPAEC_IL-1 beta/TNA alpha | 0.0 |
| 93254_Normal Human Lung Fibroblast_none | 0.0 |
| 93253_Normal Human Lung Fibroblast_TNFa (4 ng/ml) and IL-1b (1 ng/ml) | 0.0 |
| 93257_Normal Human Lung Fibroblast_IL-4 | 0.0 |
| 93256_Normal Human Lung Fibroblast_IL-9 | 0.0 |
| 93255_Normal Human Lung Fibroblast_IL-13 | 0.0 |
| 93258_Normal Human Lung Fibroblast_IFN gamma | 4.7 |
| 93106_Dermal Fibroblasts CCD1070_resting | 0.0 |
| 93361_Dermal Fibroblasts CCD1070_TNF alpha 4 ng/ml | 0.0 |
| 93105_Dermal Fibroblasts CCD1070_IL-1 beta 1 ng/ml | 0.0 |
| 93772_dermal fibroblast_IFN gamma | 0.0 |
| 93771_dermal fibroblast_IL-4 | 0.0 |
| 93260_IBD Colitis 2 | 6.6 |
| 93261_IBD Crohns | 0.0 |
| 735010_Colon_normal | 9.7 |
| 735019_Lung_none | 0.0 |
| 64028-1_Thymus_none | 4.3 |
| 64030-1_Kidney_none | 5.7 |
| 93100_HUVEC (Endothelial)_IL-1b | 0.0 |

**GENOMIC CONTAMINATION

TABLE 39

NOV7 (AL132990_B) Ag301 Panel 4D

| Primers | Sequences | Length | Start Position |
|---|---|---|---|
| Forward | 5'-CATGAGGGCTTCCATTACATCA-3' (SEQ ID NO.: 77) | 22 | 337 |
| Probe | TET-5'-AGCTGACCCAGAAGACCCAGGACCTC-3'-TAMRA (SEQ ID NO.: 78) | 26 | 365 |
| Reverse | 5'-GCGTGTTCCCAATGCTCAGT-3' (SEQ ID NO.: 79) | 20 | 393 |

TABLE 40

NOV8 (AC018639_A) PROBE NAME: AG355 PANEL 2 RESULTS

| Tissue_Name | Rel. Expr., % |
|---|---|
| 83786 Kidney Ca, Nuclear grade 2 (OD04338) | 1.5 |
| 83219 CC Well to Mod Diff (ODO3866) | 0.0 |
| 83220 CC NAT (ODO3866) | 1.0 |
| 83221 CC Gr.2 rectosigmoid (ODO3868) | 1.7 |
| 83222 CC NAT (ODO3868) | 0.0 |
| 83235 CC Mod Diff (ODO3920) | 17.1 |
| 83236 CC NAT (ODO3920) | 3.6 |
| 83237 CC Gr.2 ascend colon (ODO3921) | 8.4 |
| 83238 CC NAT (ODO3921) | 0.9 |
| 83239 Lung Met to Muscle (ODO4286) | 0.9 |
| 83240 Muscle NAT (ODO4286) | 14.8 |
| 83241 CC from Partial Hepatectomy (ODO4309) | 6.2 |
| 83242 Liver NAT (ODO4309) | 5.2 |
| 83255 Ocular Mel Met to Liver (ODO4310) | 4.2 |
| 83256 Liver NAT (ODO4310) | 35.9 |
| 83787 Kidney NAT (OD04338) | 6.5 |
| 83788 Kidney Ca Nuclear grade ½ (OD04339) | 88.3 |
| 83789 Kidney NAT (OD04339) | 6.7 |
| 83790 Kidney Ca, Clear cell type (OD04340) | 1.8 |
| 83791 Kidney NAT (OD04340) | 0.9 |
| 83792 Kidney Ca, Nuclear grade 3 (OD04348) | 2.1 |
| 83793 Kidney NAT (OD04348) | 6.3 |
| 84136 Lung Malignant Cancer (OD03126) | 7.0 |
| 84137 Lung NAT (OD03126) | 16.8 |
| 84138 Lung NAT (OD04321) | 4.5 |
| 84139 Melanoma Mets to Lung (OD04321) | 2.7 |
| 84140 Prostate Cancer (OD04410) | 16.2 |
| 84141 Prostate NAT (OD04410) | 6.8 |
| 84871 Lung Cancer (OD04404) | 11.3 |
| 84872 Lung NAT (OD04404) | 2.3 |
| 84875 Lung Cancer (OD04565) | 6.3 |
| 84877 Breast Cancer (OD04566) | 0.3 |
| 85950 Lung Cancer (OD04237-01) | 17.3 |
| 85970 Lung NAT (OD04237-02) | 1.0 |
| 85973 Kidney Cancer (OD04450-01) | 0.5 |
| 85974 Kidney NAT (OD04450-03) | 18.2 |
| 85975 Breast Cancer (OD04590-01) | 7.3 |
| 85976 Breast Cancer Mets (OD04590-03) | 100.0 |
| 87070 Breast Cancer Metastasis (OD04655-05) | 20.6 |
| 87071 Bladder Cancer (OD04718-01) | 11.6 |
| 87072 Bladder Normal Adjacent (OD04718-03) | 5.9 |
| 87073 Prostate Cancer (OD04720-01) | 70.2 |
| 87074 Prostate NAT (OD04720-02) | 2.4 |
| 87472 Colon mets to lung (OD04451-01) | 1.1 |
| 87473 Lung NAT (OD04451-02) | 0.9 |
| 87474 Kidney Cancer (OD04622-01) | 8.5 |
| 87475 Kidney NAT (OD04622-03) | 1.7 |
| 87492 Ovary Cancer (OD04768-07) | 16.3 |
| 87493 Ovary NAT (OD04768-08) | 13.3 |
| Bladder Cancer INVITROGEN A302173 | 2.0 |
| Bladder Cancer Research Genetics RNA 1023 | 1.8 |
| Breast Cancer Clontech 9100266 | 0.2 |
| Breast Cancer INVITROGEN A209073 | 0.0 |
| Breast Cancer Res. Gen. 1024 | 5.3 |
| Breast NAT Clontech 9100265 | 0.6 |
| Breast NAT INVITROGEN A2090734 | 1.7 |
| GENPAK Breast Cancer 064006 | 6.7 |
| Gastric Cancer Clontech 9060395 | 0.0 |
| Gastric Cancer Clontech 9060397 | 1.2 |
| Gastric Cancer GENPAK 064005 | 1.9 |
| Kidney Cancer Clontech 8120607 | 0.0 |
| Kidney Cancer Clontech 8120613 | 1.0 |
| Kidney Cancer Clontech 9010320 | 0.0 |
| Kidney NAT Clontech 8120608 | 0.0 |
| Kidney NAT Clontech 8120614 | 3.4 |
| Kidney NAT Clontech 9010321 | 0.0 |
| Liver Cancer GENPAK 064003 | 0.9 |
| Liver Cancer Research Genetics RNA 1025 | 0.0 |
| Liver Cancer Research Genetics RNA 1026 | 0.0 |
| NAT Stomach Clontech 9060359 | 0.0 |
| NAT Stomach Clontech 9060394 | 2.0 |
| NAT Stomach Clontech 9060396 | 0.0 |
| Normal Bladder GENPAK 061001 | 0.2 |
| Normal Breast GENPAK 061019 | 0.4 |
| Normal Colon GENPAK 061003 | 0.0 |
| Normal Kidney GENPAK 061008 | 0.7 |
| Normal Liver GENPAK 061009 | 3.7 |
| Normal Lung GENPAK 061010 | 0.0 |
| Normal Ovary Res. Gen. | 0.0 |
| Normal Prostate Clontech A+ 6546-1 | 0.0 |
| Normal Stomach GENPAK 061017 | 0.0 |
| Normal Thyroid Clontech A+ 6570-1** | 0.0 |
| Normal Uterus GENPAK 061018 | 0.9 |
| Ovarian Cancer GENPAK 064008 | 0.5 |
| Paired Liver Cancer Tissue Research Genetics RNA 6004-T | 3.1 |
| Paired Liver Cancer Tissue Research Genetics RNA 6005-T | 0.0 |
| Paired Liver Tissue Research Genetics RNA 6004-N | 1.2 |
| Paired Liver Tissue Research Genetics RNA 6005-N | 1.8 |
| Thyroid Cancer GENPAK 064010 | 0.8 |
| Thyroid Cancer INVITROGEN A302152 | 10.4 |
| Thyroid NAT INVITROGEN A302153 | 6.3 |
| Uterus Cancer GENPAK 064011 | 14.6 |
| genomic DNA control | 2.1 |
| 87492 Ovary Cancer (OD04768-07) | 16.3 |

TABLE 41

NOV8 (AC018639_A) PROBE NAME: AG355 PANEL 1 RESULTS

| Tissue_Name | Rel. Expr., % |
|---|---|
| Endothelial cells | 0.0 |
| Endothelial cells (treated) | 1.7 |
| Pancreas | 8.1 |
| Pancreatic ca. CAPAN 2 | 0.0 |
| Adipose | 0.3 |
| Adrenal gland | 2.0 |
| Thyroid | 23.7 |
| Salavary gland | 4.7 |
| Pituitary gland | 1.0 |
| Brain (fetal) | 0.2 |
| Brain (whole) | 5.6 |
| Brain (amygdala) | 0.5 |
| Brain (cerebellum) | 5.5 |
| Brain (hippocampus) | 1.9 |
| Brain (substantia nigra) | 6.3 |
| Brain (thalamus) | 4.8 |
| Brain (hypothalamus) | 27.0 |
| Spinal cord | 6.8 |
| CNS ca. (glio/astro) U87-MG | 24.8 |
| CNS ca. (glio/astro) U-118-MG | 4.5 |
| CNS ca. (astro) SW1783 | 0.9 |
| CNS ca.* (neuro; met) SK-N-AS | 64.6 |
| CNS ca. (astro) SF-539 | 15.9 |
| CNS ca. (astro) SNB-75 | 6.4 |
| CNS ca. (glio) SNB-19 | 1.0 |
| CNS ca. (glio) U251 | 0.6 |
| CNS ca. (glio) SF-295 | 39.5 |
| Heart | 12.9 |
| Skeletal muscle | 100.0 |
| Bone marrow | 3.1 |
| Thymus | 6.1 |
| Spleen | 1.8 |
| Lymph node | 0.0 |
| Colon (ascending) | 0.1 |
| Stomach | 9.0 |
| Small intestine | 7.8 |
| Colon ca. SW480 | 0.0 |
| Colon ca.* (SW480 met) SW620 | 0.4 |
| Colon ca. HT29 | 1.7 |
| Colon ca. HCT-116 | 9.6 |
| Colon ca. CaCo-2 | 6.5 |

TABLE 41-continued

NOV8 (AC018639_A) PROBE NAME: AG355 PANEL 1 RESULTS

| Tissue_Name | Rel. Expr., % |
|---|---|
| Colon ca. HCT-15 | 73.7 |
| Colon ca. HCC-2998 | 1.4 |
| Gastric ca.* (liver met) NCI-N87 | 0.3 |
| Bladder | 0.2 |
| Trachea | 0.3 |
| Kidney | 0.4 |
| Kidney (fetal) | 4.4 |
| Renal ca. 786-0 | 0.8 |
| Renal ca. A498 | 0.8 |
| Renal ca. RXF 393 | 0.0 |
| Renal ca. ACHN | 2.6 |

TABLE 41-continued

NOV8 (AC018639_A) PROBE NAME: AG355 PANEL 1 RESULTS

| Tissue_Name | Rel. Expr., % |
|---|---|
| Melanoma UACC-62 | 41.5 |
| Melanoma M14 | 21.3 |
| Melanoma LOX IMVI | 0.2 |
| Melanoma* (met) SK-MEL-5 | 12.2 |
| Melanoma SK-MEL-28 | 0.0 |

For Panel 1, the following abbreviations are used: ca. = carcinoma, * = established from metastasis, met = metastasis, s cell var = small cell variant, non-s = non-sm = non-small, squam = squamous, pl. eff = pl effusion = pleural effusion, glio = glioma, astro = astrocytoma, and neuro = neuroblastoma.

TABLE 42

NOV8 (AC018639_A) PROBE NAME: AG355

| Primers | Sequences | Length | Start Position |
|---|---|---|---|
| Forward | 5'-GGAAAGTCAGCATTGCGGTT-3' (SEQ ID NO.: 80) | 20 | 517 |
| Probe | TET-5'-CTTGGCGTACCTCCGAGAGAAGCACC-3'-TAMRA (SEQ ID NO.: 81) | 26 | 545 |
| Reverse | 5'-TTCACATTTCGGTGCATGATC-3' (SEQ ID NO.: 82) | 21 | 572 |

TABLE 41-continued

NOV8 (AC018639_A) PROBE NAME: AG355 PANEL 1 RESULTS

| Tissue_Name | Rel. Expr., % |
|---|---|
| Renal ca. UO-31 | 1.8 |
| Renal ca. TK-10 | 2.3 |
| Liver | 2.1 |
| Liver (fetal) | 23.8 |
| Liver ca. (hepatoblast) HepG2 | 21.3 |
| Lung | 0.0 |
| Lung (fetal) | 0.2 |
| Lung ca. (small cell) LX-1 | 0.0 |
| Lung ca. (small cell) NCI-H69 | 15.4 |
| Lung ca. (s. cell var.) SHP-77 | 0.1 |
| Lung ca. (large cell) NCI-H460 | 84.7 |
| Lung ca. (non-sm. cell) A549 | 14.3 |
| Lung ca. (non-s. cell) NCI-H23 | 10.4 |
| Lung ca (non-s. cell) HOP-62 | 4.7 |
| Lung ca. (non-s. cl) NCI-H522 | 16.6 |
| Lung ca. (squam.) SW 900 | 0.4 |
| Lung ca. (squam.) NCI-H596 | 7.7 |
| Mammary gland | 15.4 |
| Breast ca.* (pl. effusion) MCF-7 | 8.9 |
| Breast ca.* (pl. ef) MDA-MB-231 | 10.7 |
| Breast ca.* (pl. effusion) T47D | 0.7 |
| Breast ca. BT-549 | 13.9 |
| Breast ca. MDA-N | 20.9 |
| Ovary | 57.4 |
| Ovarian ca. OVCAR-3 | 0.5 |
| Ovarian ca. OVCAR-4 | 39.8 |
| Ovarian ca. OVCAR-5 | 12.2 |
| Ovarian ca. OVCAR-8 | 100.0 |
| Ovarian ca. IGROV-1 | 11.6 |
| Ovarian ca.* (ascites) SK-OV-3 | 31.2 |
| Uterus | 1.9 |
| Placenta | 1.2 |
| Prostate | 7.3 |
| Prostate ca.* (bone met) PC-3 | 68.3 |
| Testis | 80.7 |
| Melanoma Hs688(A).T | 0.0 |
| Melanoma* (met) Hs688(B).T | 0.0 |

EXAMPLE 2

Molecular Cloning of NOV7 AL132990)

The NOV7 cDNA coding for the predicted mature NOV7 protein between residues 20–414, was targeted for cloning.

The following oligonucleotide primers were designed to PCR amplify the desired cDNA.
GGATCCCTTCTAAAGCCGAGCTTCTCACCAAGG (AL132990 Forward; SEQ ID NO: 107),
CTCGAGTTTTCCAATAGGGTTAACAATCTTTCCCAGG (AL132990 Reverse; SEQ ID NO: 108).

For downstream cloning purposes, the forward primer includes an in-frame BamHII site and the reverse primer contains an in-frame XhoI restriction site. (Restriction site sequences are underlined above.)

A PCR reaction was set up using a total of 5 ng cDNA, combined from equal amounts of human fetal brain, testis, mammary and skeletal muscle, as template. The reaction mixtures contained 1 microM of each of the AL132990 Forward and AL 132990 Reverse primers, 5 micromoles dNTP (Clontech Laboratories, Palo Alto Calif.) and 1 microliter of 50xAdvantage-HF 2 polymerase (Clontech Laboratories, Palo Alto Calif.) in 50 microliter reaction volume. The following reaction conditions were used:

a) 96° C. 3 minutes
b) 96° C. 30 seconds denaturation
c) 60° C. 30 seconds, primer annealing.
d) 72° C. 2 minute extension.
   Repeat steps b–d 35 times
e) 72° C. 5 minutes final extension The expected 1.1 kbp amplified product was detected by agarose gel electrophoresis. The fragment was purified from the agarose gel and ligated to pCR2.1 vector (Invitrogen, Carlsbad, Calif.) following the manufacturer's recommendation. The cloned insert was sequenced, using vector specific M13 Forward and M13 Reverse primers and the following gene-specific primers:
TACATCATCCACGAGCTGACC (AL132990 S1; SEQ ID NO:109),
GGTCAGCTCGTGGATGATC (AL 132990 S2; SEQ ID NO:110),
AGTTCAGTCAAGGTGCCC (AL132990 S3; SEQ ID NO:111),
GGGCACCTTGACTGAACTG (AL132990 S4; SEQ ID NO:112),
CATGGTGATCTCACCAAGATCG (AL132990 S5; SEQ ID NO:113), and
CGATCTTGGTGAGATCACCATG (AL132990 S6; SEQ ID NO:114).

The insert was verified as an open reading frame coding for the predicted AL132990 between residues 20 and 414. The construct is called pCR2.1-AL132990-S447r2. The nucleotide sequence obtained matches the predicted shown in Table 23 (SEQ ID NO:13) beginning at nucleotide 58.

EXAMPLE 3

Preparation of Mammalian Expression Vector pCEP4/Sec

The oligonucleotide primers,
pSec-V5-His Forward
CTCGTCCTCGAGGGTAAGCCTATCCCTAAC (SEQ ID NO:115)
and
pSec-V5-His Reverse
CTCGTCGGGCCCCTGATCAGCGGGTTTAAAC (SEQ ID NO:116),
were designed to amplify a fragment from the pcDNA3.1-V5His (Invitrogen, Carlsbad, Calif.) expression vector that includes V5 and His6. The PCR product was digested with XhoI and ApaI and ligated into the XhoI/ApaI digested pSecTag2 B vector harboring an Ig kappa leader sequence (Invitrogen, Carlsbad Calif.). The correct structure of the resulting vector, pSecV5His, including an in-frame Ig-kappa leader and V5-His6 was verified by DNA sequence analysis. The vector pSecV5His was digested with PmeI and NheI to provide a fragment retaining the above elements in the correct frame. The PmeI-NheI fragment was ligated into the BamHI/Klenow and NheI treated vector pCEP4 (Invitrogen, Carlsbad, Calif.). The resulting vector was named pCEP4/Sec and includes an in-frame Ig kappa leader, a site for insertion of a clone of interest, V5 and His6 under control of the PCMV and/or the PT7 promoter. pCEP4/Sec is an expression vector that allows heterologous protein expression and secretion by fusing any protein to the Ig Kappa chain signal peptide. Detection and purification of the expressed protein are aided by the presence of the V5 epitope tag and 6xHis tag at the C-terminus (Invitrogen, Carlsbad, Calif.).

EXAMPLE 4

Expression of NOV7 (AL132990) in Human Embryonic Kidney 293 Cells

The BamHI-XhoI fragment containing the AL132990 sequence was isolated from pCR2.1-AL132990-S447-r2 and subcloned into the vector pCEP4/Sec to generate expression vector pCEP4/Sec-AL132990. The pCEP4/Sec-AL132990 vector was transfected into 293 cells using the LipofectaminePlus reagent following the manufacturer's instructions (Gibco/BRL/Life Technologies, Rockville, Md.). The cell pellet and supernatant were harvested 72 hours after transfection and examined for AL132990 expression by Western blotting (reducing conditions) with an anti-V5 antibody. FIG. 1 shows that AL132990 is expressed as a polypeptide having an approximate Mr value of 60 kDa that is secreted by 293 cells. The molecular weight marker standard used was SeeBlue Marker manufactured by Invitrogen (Calif., Carlsbad).

EXAMPLE 5

Molecular Cloning of NOV3 (AL133371_da2)

The NOV3 cDNA coding for the mature protein between residues 26–147, was targeted for cloning.

The following oligonucleotide primers were designed to PCR amplify the desired cDNA.
GGATCCAAAGAAGTTTCTTGGAGAGAATTCATG (AL133371_da2 MAT-F; SEQ ID NO:117),
CTCGAGGTTGCCGATAGGTTCTACCATC (AL133371_da2 FL-REV-real; SEQ ID NO:118).

For downstream cloning purposes, the forward primer includes an in-frame BamHI restriction site and the reverse primer contains an in-frame XhoI restriction site. (Restriction site sequences are underlined above.)

A PCR reaction was set up using a total of 5 ng human testis cDNA, as template. The reaction mixtures contained 1 microM of each of the AL133371_da2 MAT-F and AL133371_da2 FL-REV-real primers, 5 micromoles dNTP (Clontech Laboratories, Palo Alto Calif.) and 1 microliter of 50×Advantage-HF 2 polymerase (Clontech Laboratories, Palo Alto Calif.) in 50 microliter reaction volume. The following reaction conditions were used:

a) 96° C. 3 minutes
b) 96° C. 30 seconds denaturation
c) 60° C. 30 seconds, primer annealing.
d) 72° C. 1 minute extension.
   Repeat steps b–d 35 times
e) 72° C. 5 minutes final extension The expected amplified product of about 400 bp was detected by agarose gel electrophoresis. The fragment was purified from agarose gel and ligated to pCR2.1 vector (Invitrogen, Carlsbad, Calif.) following the manufacturer's recommendation. The cloned insert was sequenced, using vector specific, M13 Forward and M13 Reverse primers as well as gene-specific primers.

The insert was verified as an open reading frame coding for the predicted AL133371_da2 between residues 26–147. The polypeptide encoded by this sequence is 100% identical to the corresponding mature portion of the AL133371_da2 protein presented in Table 9. The construct is called pCR2.1-AL133371_da2-A123_1A.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polypeptide comprising SEQ ID NO: 4.
2. A composition comprising the polypeptide of claim 2 and a carrier.
3. A kit comprising in one or more containers, the composition of claim 2.

* * * * *

SEQUENCE LISTING

<160> NUMBER OF SEQ ID NOS: 118

<210> SEQ ID NO 1
<211> LENGTH: 559
<212> TYPE: DNA
<213> ORGANISM: Homo sapiens
<220> FEATURE:
<221> NAME/KEY: CDS
<222> LOCATION: (43)..(450)

<400> SEQUENCE: 1

```
tttctcttct ctgtggacac gcaggcggcc ccggtgactg ag atg gca tcg tct        54
                                              Met Ala Ser Ser
                                                1 cta aag atc tgg ggc aca ctc ttg gcc cta ctt tgc atc cta tgc aca      102
Leu Lys Ile Trp Gly Thr Leu Leu Ala Leu Leu Cys Ile Leu Cys Thr
 5              10                  15                  20 ctg ctt gta cag agc aaa gaa gtt tct tgg aga gaa ttc atg aaa cag      150
Leu Leu Val Gln Ser Lys Glu Val Ser Trp Arg Glu Phe Met Lys Gln
                25                  30                  35 cac tac tta agt cca agt cga gaa ttc aga gag tac aaa tgt gat gtc      198
His Tyr Leu Ser Pro Ser Arg Glu Phe Arg Glu Tyr Lys Cys Asp Val
            40                  45                  50 ctc atg aga gaa aat gaa gct ctg aaa gac aag agc tct cac atg ttt      246
Leu Met Arg Glu Asn Glu Ala Leu Lys Asp Lys Ser Ser His Met Phe
        55                  60                  65 atc tat atc tca tgg tac aaa atc gag cat ata tgc act agt gac aac      294
Ile Tyr Ile Ser Trp Tyr Lys Ile Glu His Ile Cys Thr Ser Asp Asn
    70                  75                  80 tgg atg gat cgc ttc cga aat gca tat gta tgg gtc cag atc ctc tca      342
Trp Met Asp Arg Phe Arg Asn Ala Tyr Val Trp Val Gln Ile Leu Ser
85                  90                  95                 100 aag tac tca agt gtc acc agg aga att cca aaa ata gct aca cag aga      390
Lys Tyr Ser Ser Val Thr Arg Arg Ile Pro Lys Ile Ala Thr Gln Arg
                105                 110                 115 gca gga gct tca act aca ttg aat tcc att gta gca tgg acg ggt atg      438
Ala Gly Ala Ser Thr Thr Leu Asn Ser Ile Val Ala Trp Thr Gly Met
            120                 125                 130 ttg ata gca tag aagacctaaa gatggtagaa cctatcggca actagaaagt          490
Leu Ile Ala
        135 ctatgcacat cctcaggtat tggtagagta ttcagtgctt tctaagtagc agccctgcc     550 tccatcaat                                                            559
```

<210> SEQ ID NO 2
<211> LENGTH: 135
<212> TYPE: PRT
<213> ORGANISM: Homo sapiens

<400> SEQUENCE: 2

```
Met Ala Ser Ser Leu Lys Ile Trp Gly Thr Leu Leu Ala Leu Leu Cys
  1               5                  10                  15

Ile Leu Cys Thr Leu Leu Val Gln Ser Lys Glu Val Ser Trp Arg Glu
             20                  25                  30

Phe Met Lys Gln His Tyr Leu Ser Pro Ser Arg Glu Phe Arg Glu Tyr
         35                  40                  45

Lys Cys Asp Val Leu Met Arg Glu Asn Glu Ala Leu Lys Asp Lys Ser
     50                  55                  60
```

```
Ser His Met Phe Ile Tyr Ile Ser Trp Tyr Lys Ile Glu His Ile Cys
 65                  70                  75                  80

Thr Ser Asp Asn Trp Met Asp Arg Phe Arg Asn Ala Tyr Val Trp Val
                 85                  90                  95

Gln Ile Leu Ser Lys Tyr Ser Ser Val Thr Arg Arg Ile Pro Lys Ile
            100                 105                 110

Ala Thr Gln Arg Ala Gly Ala Ser Thr Thr Leu Asn Ser Ile Val Ala
        115                 120                 125

Trp Thr Gly Met Leu Ile Ala
    130             135

<210> SEQ ID NO 3
<211> LENGTH: 425
<212> TYPE: DNA
<213> ORGANISM: Homo sapiens
<220> FEATURE:
<221> NAME/KEY: CDS
<222> LOCATION: (16)..(417)

<400> SEQUENCE: 3
gccccggtga ctgag atg gca tcc tct ctg aag atc tgg ggc agt ccc ttg        51
                 Met Ala Ser Ser Leu Lys Ile Trp Gly Ser Pro Leu
                  1               5                  10 gcc ctg ctt tgc att ctt tgc agg cta ctt gta cac agc aag gac gtt        99
Ala Leu Leu Cys Ile Leu Cys Arg Leu Leu Val His Ser Lys Asp Val
         15                  20                  25 tcc tgg aga gaa ttc atg acc ctg cac tat tta gat cca agc caa gat       147
Ser Trp Arg Glu Phe Met Thr Leu His Tyr Leu Asp Pro Ser Gln Asp
 30                  35                  40 ttt gaa gag tac aaa tgt gat gtc ctc atg aga gaa aaa gaa gct ctg       195
Phe Glu Glu Tyr Lys Cys Asp Val Leu Met Arg Glu Lys Glu Ala Leu
 45                  50                  55                  60 aaa cgc aag agc tct cat atg tcc atc tat agc tta tgg cac aaa atg       243
Lys Arg Lys Ser Ser His Met Ser Ile Tyr Ser Leu Trp His Lys Met
                 65                  70                  75 gag tgt ata tgc att att gaa atg gga ata acc gat ata gat atg cct       291
Glu Cys Ile Cys Ile Ile Glu Met Gly Ile Thr Asp Ile Asp Met Pro
             80                  85                  90 atg tat ggg ccc agg gtg ccc tca aag tac tcg agt gtc agt ggc aga       339
Met Tyr Gly Pro Arg Val Pro Ser Lys Tyr Ser Ser Val Ser Gly Arg
         95                 100                 105 agt act gca ata gct aca cag aga tct tca act aca ttg aat tcc act       387
Ser Thr Ala Ile Ala Thr Gln Arg Ser Ser Thr Thr Leu Asn Ser Thr
    110                 115                 120 gtg gca agg atg ggt atg ttg ata gca tag aagaccta                      425
Val Ala Arg Met Gly Met Leu Ile Ala
125             130

<210> SEQ ID NO 4
<211> LENGTH: 133
<212> TYPE: PRT
<213> ORGANISM: Homo sapiens

<400> SEQUENCE: 4

Met Ala Ser Ser Leu Lys Ile Trp Gly Ser Pro Leu Ala Leu Leu Cys
 1               5                  10                  15

Ile Leu Cys Arg Leu Leu Val His Ser Lys Asp Val Ser Trp Arg Glu
             20                  25                  30

Phe Met Thr Leu His Tyr Leu Asp Pro Ser Gln Asp Phe Glu Glu Tyr
         35                  40                  45
```

```
Lys Cys Asp Val Leu Met Arg Glu Lys Glu Ala Leu Lys Arg Lys Ser
 50                  55                  60

Ser His Met Ser Ile Tyr Ser Leu Trp His Lys Met Glu Cys Ile Cys
 65                  70                  75                  80

Ile Ile Glu Met Gly Ile Thr Asp Ile Asp Met Pro Met Tyr Gly Pro
                 85                  90                  95

Arg Val Pro Ser Lys Tyr Ser Ser Val Ser Gly Arg Ser Thr Ala Ile
            100                 105                 110

Ala Thr Gln Arg Ser Ser Thr Thr Leu Asn Ser Thr Val Ala Arg Met
        115                 120                 125

Gly Met Leu Ile Ala
        130
```

<210> SEQ ID NO 5
<211> LENGTH: 554
<212> TYPE: DNA
<213> ORGANISM: Homo sapiens
<220> FEATURE:
<221> NAME/KEY: CDS
<222> LOCATION: (44)..(487)

<400> SEQUENCE: 5

```
ttttctcttc tctgtggaca cgcaggcggc cccggtgact gag atg gca tca tct      55
                                             Met Ala Ser Ser
                                              1 cta aag atc tgg ggc aca ctc ttg gcc cta ctt tgc atc cta tgc aca     103
Leu Lys Ile Trp Gly Thr Leu Leu Ala Leu Leu Cys Ile Leu Cys Thr
  5              10                  15                  20 ctg ctt gta cag agc aaa gaa gtt tct tgg aga gaa ttc atg aaa cag     151
Leu Leu Val Gln Ser Lys Glu Val Ser Trp Arg Glu Phe Met Lys Gln
             25                  30                  35 cac tac tta agt cca agt cga gaa ttc aga gag tac aaa tgt gat gtc     199
His Tyr Leu Ser Pro Ser Arg Glu Phe Arg Glu Tyr Lys Cys Asp Val
         40                  45                  50 ctc atg aga gaa aat gaa gct ctg aaa gac aag agc tct cac atg ttt     247
Leu Met Arg Glu Asn Glu Ala Leu Lys Asp Lys Ser Ser His Met Phe
     55                  60                  65 atc tat atc tca tgg tac aaa atc gag cat ata tgc act agt gac aac     295
Ile Tyr Ile Ser Trp Tyr Lys Ile Glu His Ile Cys Thr Ser Asp Asn
 70                  75                  80 tgg atg gat cgc ttc cga aat gca tat gta tgg gtc cag aat cct ctc     343
Trp Met Asp Arg Phe Arg Asn Ala Tyr Val Trp Val Gln Asn Pro Leu
 85                  90                  95                 100 aaa gta ctc aag tgt cac cag gag aat tcc aaa aat agc tac aca gag     391
Lys Val Leu Lys Cys His Gln Glu Asn Ser Lys Asn Ser Tyr Thr Glu
             105                 110                 115 agc agg agc ttc aac tac att gaa ttc cat tgt agc atg gac ggg tat     439
Ser Arg Ser Phe Asn Tyr Ile Glu Phe His Cys Ser Met Asp Gly Tyr
         120                 125                 130 gtt gat agc ata gaa gac cta aag atg gta gaa cct atc ggc aac tag     487
Val Asp Ser Ile Glu Asp Leu Lys Met Val Glu Pro Ile Gly Asn
     135                 140                 145 aaagtctatg cacatcctca ggtattggta gagtattcag tgctttctaa gtagcagccc    547
aagggcg                                                              554
```

<210> SEQ ID NO 6
<211> LENGTH: 147
<212> TYPE: PRT
<213> ORGANISM: Homo sapiens -continued

```
<400> SEQUENCE: 6

Met Ala Ser Ser Leu Lys Ile Trp Gly Thr Leu Leu Ala Leu Leu Cys
  1               5                  10                  15

Ile Leu Cys Thr Leu Leu Val Gln Ser Lys Glu Val Ser Trp Arg Glu
             20                  25                  30

Phe Met Lys Gln His Tyr Leu Ser Pro Ser Arg Glu Phe Arg Glu Tyr
         35                  40                  45

Lys Cys Asp Val Leu Met Arg Glu Asn Glu Ala Leu Lys Asp Lys Ser
     50                  55                  60

Ser His Met Phe Ile Tyr Ile Ser Trp Tyr Lys Ile Glu His Ile Cys
 65                  70                  75                  80

Thr Ser Asp Asn Trp Met Asp Arg Phe Arg Asn Ala Tyr Val Trp Val
                 85                  90                  95

Gln Asn Pro Leu Lys Val Leu Lys Cys His Gln Glu Asn Ser Lys Asn
            100                 105                 110

Ser Tyr Thr Glu Ser Arg Ser Phe Asn Tyr Ile Glu Phe His Cys Ser
        115                 120                 125

Met Asp Gly Tyr Val Asp Ser Ile Glu Asp Leu Lys Met Val Glu Pro
    130                 135                 140

Ile Gly Asn
145

<210> SEQ ID NO 7
<211> LENGTH: 1300
<212> TYPE: DNA
<213> ORGANISM: Homo sapiens
<220> FEATURE:
<221> NAME/KEY: CDS
<222> LOCATION: (59)..(1201)
<221> NAME/KEY: misc_feature
<222> LOCATION: (1218)
<223> OTHER INFORMATION: Wherein n is G or A or T or C

<400> SEQUENCE: 7 gccgcccac tacgggccca ggctagaggc gccgccgcca ccggcccgcg gagcccgg        58 atg ctg gcc cgg agg aag ccg atg ctg ccg gcg ctc acc atc aac cct    106
Met Leu Ala Arg Arg Lys Pro Met Leu Pro Ala Leu Thr Ile Asn Pro
  1               5                  10                  15 acc atc gcc gag ggc ccg tcc cca acc agc gag ggc gcc tcc gag gca    154
Thr Ile Ala Glu Gly Pro Ser Pro Thr Ser Glu Gly Ala Ser Glu Ala
             20                  25                  30 aac ctg gtg gac ctg cag aag aag ctg gag gag ctg gaa ctt gac gag    202
Asn Leu Val Asp Leu Gln Lys Lys Leu Glu Glu Leu Glu Leu Asp Glu
         35                  40                  45 cag cag aag cgg ctg gaa gcc ttt ctc acc cag aaa gcc aag gtc ggc    250
Gln Gln Lys Arg Leu Glu Ala Phe Leu Thr Gln Lys Ala Lys Val Gly
     50                  55                  60 gaa ctc aaa gac gat gac ttc gaa agg acc tca gag ctg gac gcg ggc    298
Glu Leu Lys Asp Asp Asp Phe Glu Arg Thr Ser Glu Leu Asp Ala Gly
 65                  70                  75                  80 aac ggc ggg gtg gtc acc aaa gtc cag cac aga ccc tcg ggc ctc atc    346
Asn Gly Gly Val Val Thr Lys Val Gln His Arg Pro Ser Gly Leu Ile
                 85                  90                  95 atg gcc agg aag ctg atc cac ctt gag atc aag ccg gcc atc cgg aac    394
Met Ala Arg Lys Leu Ile His Leu Glu Ile Lys Pro Ala Ile Arg Asn
            100                 105                 110 cag atc atc cgc gag cac cag gtc ctg cac gag tgc aac tca ccg tac    442
Gln Ile Ile Arg Glu His Gln Val Leu His Glu Cys Asn Ser Pro Tyr
        115                 120                 125
```

```
atc gtg ggc ttc tac ggg gcc ttc tac tgt gac agg gag atc agc atc      490
Ile Val Gly Phe Tyr Gly Ala Phe Tyr Cys Asp Arg Glu Ile Ser Ile
    130                 135                 140 tgc atg gag cac atg gat ggc ggc tcc ctg gac cag ggg ctg aaa gag      538
Cys Met Glu His Met Asp Gly Gly Ser Leu Asp Gln Gly Leu Lys Glu
145                 150                 155                 160 gcc aag agg att ccc gag gac atc ctg ggg aaa gtc agc att gcg gtt      586
Ala Lys Arg Ile Pro Glu Asp Ile Leu Gly Lys Val Ser Ile Ala Val
                165                 170                 175 ctc cgg ggc ttg gcg tac ctc cga gag aag cac cag atc atg cac cga      634
Leu Arg Gly Leu Ala Tyr Leu Arg Glu Lys His Gln Ile Met His Arg
            180                 185                 190 aat gtg aag ccc tcc aac atc ctc gtg aac tct aga ggg gag atc aag      682
Asn Val Lys Pro Ser Asn Ile Leu Val Asn Ser Arg Gly Glu Ile Lys
        195                 200                 205 ctg tgt gac ttc ggg gtg agc ggc cag ctc atc gac tcc atg gcc aac      730
Leu Cys Asp Phe Gly Val Ser Gly Gln Leu Ile Asp Ser Met Ala Asn
    210                 215                 220 tcc ttc gtg ggc acg cgc tcc tac atg gct ccg gag cgg ttg cag ggc      778
Ser Phe Val Gly Thr Arg Ser Tyr Met Ala Pro Glu Arg Leu Gln Gly
225                 230                 235                 240 aca cat tac tcg gtg cag tcg gtc atc tgg agc atg gac ctg tcc ctg      826
Thr His Tyr Ser Val Gln Ser Val Ile Trp Ser Met Asp Leu Ser Leu
                245                 250                 255 gtg gag ctg gcc atc gaa agg tac ccc atc ccc ccg ccc gac gcc aag      874
Val Glu Leu Ala Ile Glu Arg Tyr Pro Ile Pro Pro Pro Asp Ala Lys
            260                 265                 270 gag ctg gag gcc atc ttt ggc cag ccc gtg gtc gac agg gaa gaa gga      922
Glu Leu Glu Ala Ile Phe Gly Gln Pro Val Val Asp Arg Glu Glu Gly
        275                 280                 285 gag cct cac agc atc tcc tct tgg cca ggg tcc ccc ggg cgc ccc aac      970
Glu Pro His Ser Ile Ser Ser Trp Pro Gly Ser Pro Gly Arg Pro Asn
    290                 295                 300 agc ggt tac ggg atg gac agc ctg ccc gcc atg gcc atc ttc gaa ctg     1018
Ser Gly Tyr Gly Met Asp Ser Leu Pro Ala Met Ala Ile Phe Glu Leu
305                 310                 315                 320 ctg gac tat att gtg aaa gag ccg cct cct aag ctg ccc aac ggt gtg     1066
Leu Asp Tyr Ile Val Lys Glu Pro Pro Pro Lys Leu Pro Asn Gly Val
                325                 330                 335 ttc acc ccc gag ttc cag gag ttt gtc aat aaa tgc ctc atc aaa aac     1114
Phe Thr Pro Glu Phe Gln Glu Phe Val Asn Lys Cys Leu Ile Lys Asn
            340                 345                 350 cca acg gag cgg gcg gac cta aag atg ctc aca aac cac gcc ttc atc     1162
Pro Thr Glu Arg Ala Asp Leu Lys Met Leu Thr Asn His Ala Phe Ile
        355                 360                 365 aag cgg tcc gag gtg aaa gaa gcg gat ttt gcc tgc tag ttgtgtaaaa     1211
Lys Arg Ser Glu Val Lys Glu Ala Asp Phe Ala Cys
    370                 375                 380 ccctggnggc tgaaccaagc ccggcacacc cacgcgcacc gccgtgtaca gtggcaggct   1271
ccccgcgtcc gctggtgact gcccacgca                                     1300

<210> SEQ ID NO 8
<211> LENGTH: 380
<212> TYPE: PRT
<213> ORGANISM: Homo sapiens

<400> SEQUENCE: 8

Met Leu Ala Arg Arg Lys Pro Met Leu Pro Ala Leu Thr Ile Asn Pro
1               5                   10                  15
```

```
Thr Ile Ala Glu Gly Pro Ser Pro Thr Ser Glu Gly Ala Ser Glu Ala
                20                  25                  30
Asn Leu Val Asp Leu Gln Lys Lys Leu Glu Glu Leu Glu Leu Asp Glu
            35                  40                  45
Gln Gln Lys Arg Leu Glu Ala Phe Leu Thr Gln Lys Ala Lys Val Gly
        50                  55                  60
Glu Leu Lys Asp Asp Asp Phe Glu Arg Thr Ser Glu Leu Asp Ala Gly
 65                  70                  75                  80
Asn Gly Gly Val Val Thr Lys Val Gln His Arg Pro Ser Gly Leu Ile
                85                  90                  95
Met Ala Arg Lys Leu Ile His Leu Glu Ile Lys Pro Ala Ile Arg Asn
            100                 105                 110
Gln Ile Ile Arg Glu His Gln Val Leu His Glu Cys Asn Ser Pro Tyr
        115                 120                 125
Ile Val Gly Phe Tyr Gly Ala Phe Tyr Cys Asp Arg Glu Ile Ser Ile
        130                 135                 140
Cys Met Glu His Met Asp Gly Ser Leu Asp Gln Gly Leu Lys Glu
145                 150                 155                 160
Ala Lys Arg Ile Pro Glu Asp Ile Leu Gly Lys Val Ser Ile Ala Val
                165                 170                 175
Leu Arg Gly Leu Ala Tyr Leu Arg Glu Lys His Gln Ile Met His Arg
            180                 185                 190
Asn Val Lys Pro Ser Asn Ile Leu Val Asn Ser Arg Gly Glu Ile Lys
        195                 200                 205
Leu Cys Asp Phe Gly Val Ser Gly Gln Leu Ile Asp Ser Met Ala Asn
210                 215                 220
Ser Phe Val Gly Thr Arg Ser Tyr Met Ala Pro Glu Arg Leu Gln Gly
225                 230                 235                 240
Thr His Tyr Ser Val Gln Ser Val Ile Trp Ser Met Asp Leu Ser Leu
                245                 250                 255
Val Glu Leu Ala Ile Glu Arg Tyr Pro Ile Pro Pro Asp Ala Lys
            260                 265                 270
Glu Leu Glu Ala Ile Phe Gly Gln Pro Val Val Asp Arg Glu Glu Gly
        275                 280                 285
Glu Pro His Ser Ile Ser Ser Trp Pro Gly Ser Pro Gly Arg Pro Asn
    290                 295                 300
Ser Gly Tyr Gly Met Asp Ser Leu Pro Ala Met Ala Ile Phe Glu Leu
305                 310                 315                 320
Leu Asp Tyr Ile Val Lys Glu Pro Pro Lys Leu Pro Asn Gly Val
            325                 330                 335
Phe Thr Pro Glu Phe Gln Glu Phe Val Asn Lys Cys Leu Ile Lys Asn
        340                 345                 350
Pro Thr Glu Arg Ala Asp Leu Lys Met Leu Thr Asn His Ala Phe Ile
        355                 360                 365
Lys Arg Ser Glu Val Lys Glu Ala Asp Phe Ala Cys
        370                 375                 380

<210> SEQ ID NO 9
<211> LENGTH: 324
<212> TYPE: DNA
<213> ORGANISM: Homo sapiens
<220> FEATURE:
<221> NAME/KEY: CDS
<222> LOCATION: (1)..(324)
```

-continued

```
<400> SEQUENCE: 9 atg cca ccc tgc agc tgt gcc aga tca ctt tgt gcc ctg cag gtg ctg      48
Met Pro Pro Cys Ser Cys Ala Arg Ser Leu Cys Ala Leu Gln Val Leu
 1               5                  10                  15 ctg ttg act gtt ctg ggt tcc tcc acc aat gga caa act aag aga aac      96
Leu Leu Thr Val Leu Gly Ser Ser Thr Asn Gly Gln Thr Lys Arg Asn
             20                  25                  30 ata ggg aaa agt gta gac agt gac ttg tac act gaa ctg cgc tgc gtg     144
Ile Gly Lys Ser Val Asp Ser Asp Leu Tyr Thr Glu Leu Arg Cys Val
         35                  40                  45 tat gtg aag tca acc ttt gta ctt cat ccc aga aac atc cac aat ttg     192
Tyr Val Lys Ser Thr Phe Val Leu His Pro Arg Asn Ile His Asn Leu
     50                  55                  60 gag ttg gtc tca gca gga ccc cat tgc agc aaa gac gaa gaa aaa atc     240
Glu Leu Val Ser Ala Gly Pro His Cys Ser Lys Asp Glu Glu Lys Ile
 65                  70                  75                  80 tgc ctg gac cca gat gct ccc aga atc aat aaa att gta cag aaa atg     288
Cys Leu Asp Pro Asp Ala Pro Arg Ile Asn Lys Ile Val Gln Lys Met
                 85                  90                  95 ttg aaa gtt gat gaa ttc atc tgg tta att tgt taa                     324
Leu Lys Val Asp Glu Phe Ile Trp Leu Ile Cys
            100                 105

<210> SEQ ID NO 10
<211> LENGTH: 107
<212> TYPE: PRT
<213> ORGANISM: Homo sapiens

<400> SEQUENCE: 10

Met Pro Pro Cys Ser Cys Ala Arg Ser Leu Cys Ala Leu Gln Val Leu
 1               5                  10                  15

Leu Leu Thr Val Leu Gly Ser Ser Thr Asn Gly Gln Thr Lys Arg Asn
             20                  25                  30

Ile Gly Lys Ser Val Asp Ser Asp Leu Tyr Thr Glu Leu Arg Cys Val
         35                  40                  45

Tyr Val Lys Ser Thr Phe Val Leu His Pro Arg Asn Ile His Asn Leu
     50                  55                  60

Glu Leu Val Ser Ala Gly Pro His Cys Ser Lys Asp Glu Glu Lys Ile
 65                  70                  75                  80

Cys Leu Asp Pro Asp Ala Pro Arg Ile Asn Lys Ile Val Gln Lys Met
                 85                  90                  95

Leu Lys Val Asp Glu Phe Ile Trp Leu Ile Cys
            100                 105

<210> SEQ ID NO 11
<211> LENGTH: 300
<212> TYPE: DNA
<213> ORGANISM: Homo sapiens
<220> FEATURE:
<221> NAME/KEY: CDS
<222> LOCATION: (1)..(300)

<400> SEQUENCE: 11 atg act tct aag ctg gct gtt gct cta ctg ctt ctt ggc agt tgc atg      48
Met Thr Ser Lys Leu Ala Val Ala Leu Leu Leu Leu Gly Ser Cys Met
 1               5                  10                  15 ctt tct gta gca ctg tgt gaa gtg cca agt att agt aca gta cca caa      96
Leu Ser Val Ala Leu Cys Glu Val Pro Ser Ile Ser Thr Val Pro Gln
             20                  25                  30 tgc cag tgc atg agg aca cat ttt ata cct ttg cat ccc aaa ttt att     144
```

```
Cys Gln Cys Met Arg Thr His Phe Ile Pro Leu His Pro Lys Phe Ile
         35                  40                  45 aaa gaa ctc aga att att cag gta ctt tca aaa gtt ctt agt tat ttt        192
Lys Glu Leu Arg Ile Ile Gln Val Leu Ser Lys Val Leu Ser Tyr Phe
     50                  55                  60 gct tct gta cat gta gac tgt tta ggt gct gag agt aca atg gta aac        240
Ala Ser Val His Val Asp Cys Leu Gly Ala Glu Ser Thr Met Val Asn
 65                  70                  75                  80 aga aca gca aaa aaa aaa aat tct gtc ttt aca aat aac ttg gta ctg        288
Arg Thr Ala Lys Lys Lys Asn Ser Val Phe Thr Asn Asn Leu Val Leu
                 85                  90                  95 aca tct ggt tag                                                        300
Thr Ser Gly
           100

<210> SEQ ID NO 12
<211> LENGTH: 99
<212> TYPE: PRT
<213> ORGANISM: Homo sapiens

<400> SEQUENCE: 12

Met Thr Ser Lys Leu Ala Val Ala Leu Leu Leu Gly Ser Cys Met
 1               5                  10                  15

Leu Ser Val Ala Leu Cys Glu Val Pro Ser Ile Ser Thr Val Pro Gln
             20                  25                  30

Cys Gln Cys Met Arg Thr His Phe Ile Pro Leu His Pro Lys Phe Ile
         35                  40                  45

Lys Glu Leu Arg Ile Ile Gln Val Leu Ser Lys Val Leu Ser Tyr Phe
     50                  55                  60

Ala Ser Val His Val Asp Cys Leu Gly Ala Glu Ser Thr Met Val Asn
 65                  70                  75                  80

Arg Thr Ala Lys Lys Lys Asn Ser Val Phe Thr Asn Asn Leu Val Leu
                 85                  90                  95

Thr Ser Gly

<210> SEQ ID NO 13
<211> LENGTH: 1245
<212> TYPE: DNA
<213> ORGANISM: Homo sapiens
<220> FEATURE:
<221> NAME/KEY: CDS
<222> LOCATION: (1)..(1245)

<400> SEQUENCE: 13 atg aac ccc aca cta ggc ctg gcc att ttt ctg gct gtt ctc ctc acg        48
Met Asn Pro Thr Leu Gly Leu Ala Ile Phe Leu Ala Val Leu Leu Thr
 1               5                  10                  15 gtg aaa ggt ctt cta aag ccg agc ttc tca cca agg aat tat aaa gct        96
Val Lys Gly Leu Leu Lys Pro Ser Phe Ser Pro Arg Asn Tyr Lys Ala
             20                  25                  30 ttg agc gag gtc caa gga tgg aag caa agg atg gca gcc aag gag ctt        144
Leu Ser Glu Val Gln Gly Trp Lys Gln Arg Met Ala Ala Lys Glu Leu
         35                  40                  45 gca agg cag aac atg gac tta ggc ttt aag ctg ctc aag aag ctg gcc        192
Ala Arg Gln Asn Met Asp Leu Gly Phe Lys Leu Leu Lys Lys Leu Ala
     50                  55                  60 ttt tac aac cct ggc agg aac atc ttc cta tcc ccc ttg agc atc tct        240
Phe Tyr Asn Pro Gly Arg Asn Ile Phe Leu Ser Pro Leu Ser Ile Ser
 65                  70                  75                  80 aca gct ttc tcc atg ctg tgc ctg ggt gcc cag gac agc acc ctg gac        288
```

```
Thr Ala Phe Ser Met Leu Cys Leu Gly Ala Gln Asp Ser Thr Leu Asp
                    85                  90                  95 gag atc aag cag ggg ttc aac ttc aga aag atg cca gaa aaa gat ctt        336
Glu Ile Lys Gln Gly Phe Asn Phe Arg Lys Met Pro Glu Lys Asp Leu
            100                 105                 110 cat gag ggc ttc cat tac atc atc cac gag ctg acc cag aag acc cag        384
His Glu Gly Phe His Tyr Ile Ile His Glu Leu Thr Gln Lys Thr Gln
        115                 120                 125 gac ctc aaa ctg agc att ggg aac acg ctg ttc att gac cag agg ctg        432
Asp Leu Lys Leu Ser Ile Gly Asn Thr Leu Phe Ile Asp Gln Arg Leu
    130                 135                 140 cag cca cag cgt aag ttt ttg gaa gat gcc aag aac ttt tac agt gcc        480
Gln Pro Gln Arg Lys Phe Leu Glu Asp Ala Lys Asn Phe Tyr Ser Ala
145                 150                 155                 160 gaa acc atc ctt acc aac ttt cag aat ttg gaa atg gct cag aag cag        528
Glu Thr Ile Leu Thr Asn Phe Gln Asn Leu Glu Met Ala Gln Lys Gln
                165                 170                 175 atc aat gac ttt atc agt caa aaa acc cat ggg aaa att aac aac ctg        576
Ile Asn Asp Phe Ile Ser Gln Lys Thr His Gly Lys Ile Asn Asn Leu
            180                 185                 190 atc gag aat ata gac ccc ggc act gtg atg ctt ctt gca aat tat att        624
Ile Glu Asn Ile Asp Pro Gly Thr Val Met Leu Leu Ala Asn Tyr Ile
        195                 200                 205 ttc ttt cga gcc agg tgg aaa cat gag ttt gat cca aat gta act aaa        672
Phe Phe Arg Ala Arg Trp Lys His Glu Phe Asp Pro Asn Val Thr Lys
    210                 215                 220 gag gaa gat ttc ttt ctg gag aaa aac agt tca gtc aag gtg ccc atg        720
Glu Glu Asp Phe Phe Leu Glu Lys Asn Ser Ser Val Lys Val Pro Met
225                 230                 235                 240 atg ttc cgt agt ggc ata tac caa gtt ggc tat gac gat aag ctc tct        768
Met Phe Arg Ser Gly Ile Tyr Gln Val Gly Tyr Asp Asp Lys Leu Ser
                245                 250                 255 tgc acc atc ctg gaa ata ccc tac cag aaa aat atc aca gcc atc ttc        816
Cys Thr Ile Leu Glu Ile Pro Tyr Gln Lys Asn Ile Thr Ala Ile Phe
            260                 265                 270 atc ctt cct gat gag ggc aag ctg aag cac ttg gag aag gga ttg cag        864
Ile Leu Pro Asp Glu Gly Lys Leu Lys His Leu Glu Lys Gly Leu Gln
        275                 280                 285 gtg gac act ttc tcc aga tgg aaa aca tta ctg tca cgc agg gtc gta        912
Val Asp Thr Phe Ser Arg Trp Lys Thr Leu Leu Ser Arg Arg Val Val
    290                 295                 300 gac gtg tct gta ccc aga ctc cac atg acg ggc acc ttc gac ctg aag        960
Asp Val Ser Val Pro Arg Leu His Met Thr Gly Thr Phe Asp Leu Lys
305                 310                 315                 320 aag act ctc tcc tac ata ggt gtc tcc aaa atc ttt gag gaa cat ggt       1008
Lys Thr Leu Ser Tyr Ile Gly Val Ser Lys Ile Phe Glu Glu His Gly
                325                 330                 335 gat ctc acc aag atc gcc cct cat cgc agc ctg aaa gtg ggc gag gct       1056
Asp Leu Thr Lys Ile Ala Pro His Arg Ser Leu Lys Val Gly Glu Ala
            340                 345                 350 gtg cac aag gct gag ctg aag atg gat gag agg ggt acg gaa ggg gcc       1104
Val His Lys Ala Glu Leu Lys Met Asp Glu Arg Gly Thr Glu Gly Ala
        355                 360                 365 gct ggc acc gga gca cag act ctg ccc atg gag aca cca ctc gtc gtc       1152
Ala Gly Thr Gly Ala Gln Thr Leu Pro Met Glu Thr Pro Leu Val Val
    370                 375                 380 aag ata gac aaa ccc tat ctg ctg ctg att tac agc gag aaa ata cct       1200
Lys Ile Asp Lys Pro Tyr Leu Leu Leu Ile Tyr Ser Glu Lys Ile Pro
385                 390                 395                 400
```

```
tcc gtg ctc ttc ctg gga aag att gtt aac cct att gga aaa taa        1245
Ser Val Leu Phe Leu Gly Lys Ile Val Asn Pro Ile Gly Lys
                405                 410                 415
```

<210> SEQ ID NO 14
<211> LENGTH: 414
<212> TYPE: PRT
<213> ORGANISM: Homo sapiens

<400> SEQUENCE: 14

```
Met Asn Pro Thr Leu Gly Leu Ala Ile Phe Leu Ala Val Leu Leu Thr
 1               5                  10                  15

Val Lys Gly Leu Leu Lys Pro Ser Phe Ser Pro Arg Asn Tyr Lys Ala
                20                  25                  30

Leu Ser Glu Val Gln Gly Trp Lys Gln Arg Met Ala Ala Lys Glu Leu
            35                  40                  45

Ala Arg Gln Asn Met Asp Leu Gly Phe Lys Leu Lys Lys Leu Ala
        50                  55                  60

Phe Tyr Asn Pro Gly Arg Asn Ile Phe Leu Ser Pro Leu Ser Ile Ser
65                  70                  75                  80

Thr Ala Phe Ser Met Leu Cys Leu Gly Ala Gln Asp Ser Thr Leu Asp
                85                  90                  95

Glu Ile Lys Gln Gly Phe Asn Phe Arg Lys Met Pro Glu Lys Asp Leu
            100                 105                 110

His Glu Gly Phe His Tyr Ile Ile His Glu Leu Thr Gln Lys Thr Gln
        115                 120                 125

Asp Leu Lys Leu Ser Ile Gly Asn Thr Leu Phe Ile Asp Gln Arg Leu
    130                 135                 140

Gln Pro Gln Arg Lys Phe Leu Glu Asp Ala Lys Asn Phe Tyr Ser Ala
145                 150                 155                 160

Glu Thr Ile Leu Thr Asn Phe Gln Asn Leu Glu Met Ala Gln Lys Gln
                165                 170                 175

Ile Asn Asp Phe Ile Ser Gln Lys Thr His Gly Lys Ile Asn Asn Leu
            180                 185                 190

Ile Glu Asn Ile Asp Pro Gly Thr Val Met Leu Leu Ala Asn Tyr Ile
        195                 200                 205

Phe Phe Arg Ala Arg Trp Lys His Glu Phe Asp Pro Asn Val Thr Lys
    210                 215                 220

Glu Glu Asp Phe Phe Leu Glu Lys Asn Ser Ser Val Lys Val Pro Met
225                 230                 235                 240

Met Phe Arg Ser Gly Ile Tyr Gln Val Gly Tyr Asp Asp Lys Leu Ser
                245                 250                 255

Cys Thr Ile Leu Glu Ile Pro Tyr Gln Lys Asn Ile Thr Ala Ile Phe
            260                 265                 270

Ile Leu Pro Asp Glu Gly Lys Leu Lys His Leu Glu Lys Gly Leu Gln
        275                 280                 285

Val Asp Thr Phe Ser Arg Trp Lys Thr Leu Leu Ser Arg Arg Val Val
    290                 295                 300

Asp Val Ser Val Pro Arg Leu His Met Thr Gly Thr Phe Asp Leu Lys
305                 310                 315                 320

Lys Thr Leu Ser Tyr Ile Gly Val Ser Lys Ile Phe Glu Glu His Gly
                325                 330                 335

Asp Leu Thr Lys Ile Ala Pro His Arg Ser Leu Lys Val Gly Glu Ala
            340                 345                 350

Val His Lys Ala Glu Leu Lys Met Asp Glu Arg Gly Thr Glu Gly Ala
```

```
                355                 360                 365
Ala Gly Thr Gly Ala Gln Thr Leu Pro Met Glu Thr Pro Leu Val Val
            370                 375                 380
Lys Ile Asp Lys Pro Tyr Leu Leu Ile Tyr Ser Glu Lys Ile Pro
385                 390                 395                 400
Ser Val Leu Phe Leu Gly Lys Ile Val Asn Pro Ile Gly Lys
                405                 410

<210> SEQ ID NO 15
<211> LENGTH: 1123
<212> TYPE: DNA
<213> ORGANISM: Homo sapiens
<220> FEATURE:
<221> NAME/KEY: CDS
<222> LOCATION: (9)..(1118)

<400> SEQUENCE: 15 agcctcgg atg ctg gcc cgg agg aag ccg atg ctg ccg gcg ctc acc atc      50
         Met Leu Ala Arg Arg Lys Pro Met Leu Pro Ala Leu Thr Ile
           1               5                  10 aac cct acc atc gcc gag ggc ccg tcc cca acc agc gag ggc gcc tcc      98
Asn Pro Thr Ile Ala Glu Gly Pro Ser Pro Thr Ser Glu Gly Ala Ser
 15                  20                  25                  30 gag gca aac ctg gtg gac ctg cag aag aag ctg gag gag ctg gaa ctt     146
Glu Ala Asn Leu Val Asp Leu Gln Lys Lys Leu Glu Glu Leu Glu Leu
                 35                  40                  45 gac gag cag cag aag cgg ctg gaa gcc ttt ctc acc cag aaa gcc aag     194
Asp Glu Gln Gln Lys Arg Leu Glu Ala Phe Leu Thr Gln Lys Ala Lys
             50                  55                  60 gtc ggc gaa ctc aaa gac gat gac ttc gaa agg acc tca gag ctg gac     242
Val Gly Glu Leu Lys Asp Asp Asp Phe Glu Arg Thr Ser Glu Leu Asp
 65                  70                  75 gcg ggc aac ggg ggg gtg gtc acc aaa gtc cag cac aga ccc tcg ggc     290
Ala Gly Asn Gly Gly Val Val Thr Lys Val Gln His Arg Pro Ser Gly
             80                  85                  90 ctc atc atg gcc agg aag ctg atc cac ctt gag atc aag ccg gcc atc     338
Leu Ile Met Ala Arg Lys Leu Ile His Leu Glu Ile Lys Pro Ala Ile
 95                 100                 105                 110 cgg aac cag atc atc cgc gag cac cag gtc ctg cac gag tgc aac tca     386
Arg Asn Gln Ile Ile Arg Glu His Gln Val Leu His Glu Cys Asn Ser
                115                 120                 125 ccg tac atc gtg ggc ttc tac ggg gcc ttc tac tgt gac agg gag atc     434
Pro Tyr Ile Val Gly Phe Tyr Gly Ala Phe Tyr Cys Asp Arg Glu Ile
                130                 135                 140 agc atc tgc atg gag cac atg gat ggc ggc tcc ctg gac cag ggg ctg     482
Ser Ile Cys Met Glu His Met Asp Gly Gly Ser Leu Asp Gln Gly Leu
145                 150                 155 aaa gag gcc aag agg att ccc gag gac atc ctg ggg aaa gtc agc att     530
Lys Glu Ala Lys Arg Ile Pro Glu Asp Ile Leu Gly Lys Val Ser Ile
160                 165                 170 gcg gtt ctc cgg ggc ttg gcg tac ctc cga gag aag cac cag atc atg     578
Ala Val Leu Arg Gly Leu Ala Tyr Leu Arg Glu Lys His Gln Ile Met
175                 180                 185                 190 cac cga aat gtg aag ccc tcc aac atc ctc gtg aac tct aga ggg gag     626
His Arg Asn Val Lys Pro Ser Asn Ile Leu Val Asn Ser Arg Gly Glu
                195                 200                 205 atc aag ctg tgt gac ttc ggg gtg agc ggc cag ctc atc gac tcc atg     674
Ile Lys Leu Cys Asp Phe Gly Val Ser Gly Gln Leu Ile Asp Ser Met
                210                 215                 220 gcc aac tcc ttc gtg ggc acg cgc tcc tac atg gct ccg gag cgg ttg     722
```

```
cag ggc aca cat tac tcg gtg cag tcg gtc atc tgg agc atg gac ctg      770
Gln Gly Thr His Tyr Ser Val Gln Ser Val Ile Trp Ser Met Asp Leu
    240                 245                 250 tcc ctg gtg gag ctg gcc atc gaa agg tac ccc atc ccc ccg ccc gac      818
Ser Leu Val Glu Leu Ala Ile Glu Arg Tyr Pro Ile Pro Pro Pro Asp
255                 260                 265                 270 gcc aag gag ctg gag gcc atc ttt ggc cag ccc gtg gtc gac agg gaa      866
Ala Lys Glu Leu Glu Ala Ile Phe Gly Gln Pro Val Val Asp Arg Glu
                275                 280                 285 gaa gga gag cct cac agc atc tcc tct tgg cca ggg tcc ccc ggg cgc      914
Glu Gly Glu Pro His Ser Ile Ser Ser Trp Pro Gly Ser Pro Gly Arg
            290                 295                 300 ccc aac agc ggt tac ggg atg gac agc ctg ccc gcc atg gcc atc ttc      962
Pro Asn Ser Gly Tyr Gly Met Asp Ser Leu Pro Ala Met Ala Ile Phe
        305                 310                 315 gaa ctg ctg gac tat att gtg aaa gag ccg cct cct aag ctg ccc aac     1010
Glu Leu Leu Asp Tyr Ile Val Lys Glu Pro Pro Pro Lys Leu Pro Asn
    320                 325                 330 ggt gtg ttc acc ccc gac ttc cag gag ttt gtc aat aaa tgc ctc atc     1058
Gly Val Phe Thr Pro Asp Phe Gln Glu Phe Val Asn Lys Cys Leu Ile
335                 340                 345                 350 aaa aac cca acg gag cgg gcg gac cta aag atg ctc agt gag gtc att     1106
Lys Asn Pro Thr Glu Arg Ala Asp Leu Lys Met Leu Ser Glu Val Ile
                355                 360                 365 cca tgt ata tga atata                                               1123
Pro Cys Ile
        370

<210> SEQ ID NO 16
<211> LENGTH: 369
<212> TYPE: PRT
<213> ORGANISM: Homo sapiens

<400> SEQUENCE: 16

Met Leu Ala Arg Arg Lys Pro Met Leu Pro Ala Leu Thr Ile Asn Pro
1               5                   10                  15

Thr Ile Ala Glu Gly Pro Ser Pro Thr Ser Glu Gly Ala Ser Glu Ala
            20                  25                  30

Asn Leu Val Asp Leu Gln Lys Lys Leu Glu Glu Leu Glu Leu Asp Glu
        35                  40                  45

Gln Gln Lys Arg Leu Glu Ala Phe Leu Thr Gln Lys Ala Lys Val Gly
    50                  55                  60

Glu Leu Lys Asp Asp Asp Phe Glu Arg Thr Ser Glu Leu Asp Ala Gly
65                  70                  75                  80

Asn Gly Gly Val Val Thr Lys Val Gln His Arg Pro Ser Gly Leu Ile
                85                  90                  95

Met Ala Arg Lys Leu Ile His Leu Glu Ile Lys Pro Ala Ile Arg Asn
            100                 105                 110

Gln Ile Ile Arg Glu His Gln Val Leu His Glu Cys Asn Ser Pro Tyr
        115                 120                 125

Ile Val Gly Phe Tyr Gly Ala Phe Tyr Cys Asp Arg Glu Ile Ser Ile
    130                 135                 140

Cys Met Glu His Met Asp Gly Gly Ser Leu Asp Gln Gly Leu Lys Glu
145                 150                 155                 160

Ala Lys Arg Ile Pro Glu Asp Ile Leu Gly Lys Val Ser Ile Ala Val
                165                 170                 175
```

Leu Arg Gly Leu Ala Tyr Leu Arg Glu Lys His Gln Ile Met His Arg
            180                 185                 190

Asn Val Lys Pro Ser Asn Ile Leu Val Asn Ser Arg Gly Glu Ile Lys
        195                 200                 205

Leu Cys Asp Phe Gly Val Ser Gly Gln Leu Ile Asp Ser Met Ala Asn
    210                 215                 220

Ser Phe Val Gly Thr Arg Ser Tyr Met Ala Pro Glu Arg Leu Gln Gly
225                 230                 235                 240

Thr His Tyr Ser Val Gln Ser Val Ile Trp Ser Met Asp Leu Ser Leu
            245                 250                 255

Val Glu Leu Ala Ile Glu Arg Tyr Pro Ile Pro Pro Asp Ala Lys
        260                 265                 270

Glu Leu Glu Ala Ile Phe Gly Gln Pro Val Val Asp Arg Glu Glu Gly
    275                 280                 285

Glu Pro His Ser Ile Ser Ser Trp Pro Gly Ser Gly Arg Pro Asn
            290                 295                 300

Ser Gly Tyr Gly Met Asp Ser Leu Pro Ala Met Ala Ile Phe Glu Leu
305                 310                 315                 320

Leu Asp Tyr Ile Val Lys Glu Pro Pro Lys Leu Pro Asn Gly Val
            325                 330                 335

Phe Thr Pro Asp Phe Gln Glu Phe Val Asn Lys Cys Leu Ile Lys Asn
    340                 345                 350

Pro Thr Glu Arg Ala Asp Leu Lys Met Leu Ser Glu Val Ile Pro Cys
        355                 360                 365

Ile

<210> SEQ ID NO 17
<211> LENGTH: 536
<212> TYPE: DNA
<213> ORGANISM: Homo sapiens

<400> SEQUENCE: 17
ggcggccccg gtgactgaga tggcatcgtc tctaaagatc tggggcacac tcttggccct    60
actttgcatc ctatgcacac tgcttgtaca gagcaaagaa gtttcttgga gagaattcat   120
gaaacagcac tacttaagtc caagtcgaga attcagagag tacaaatgtg atgtcctcat   180
gagagaaaat gaagctctga agacaagag ctctcacatg tttatctata tctcatggta   240
caaaatcgag catatatgca ctagtgacaa ctggatggat cgcttccgaa atgcatatgt   300
atgggtccag atcctctcaa gtactcaag tgtcaccagg agaattccaa aaatagctac   360
acagagagca ggagcttcaa ctacattgaa ttccattgta gcatggacgg gtatgttgat   420
agcatagaag acctaaagat ggtagaacct atcggcaact agaaagtcta tgcacatcct   480
caggtattgg tagagtattc agtgctttct aagtagcagc ccctgcctcc atcaat       536

<210> SEQ ID NO 18
<211> LENGTH: 537
<212> TYPE: DNA
<213> ORGANISM: Homo sapiens

<400> SEQUENCE: 18
ggcggccccg gtgactgaga tggcatcatc tctaaagatc tggggcacac tcttggccct    60
actttgcatc ctatgcacac tgcttgtaca gagcaaagaa gtttcttgga gagaattcat   120
gaaacagcac tacttaagtc caagtcgaga attcagagag tacaaatgtg atgtcctcat   180

```
gagagaaaat gaagctctga aagacaagag ctctcacatg tttatctata tctcatggta     240
caaaatcgag catatatgca ctagtgacaa ctggatggat cgcttccgaa atgcatatgt     300
atgggtccag aatcctctca aagtactcaa gtgtcaccag gagaattcca aaatagcta      360 cacagagagc aggagcttca actacattga attccattgt agcatggacg ggtatgttga     420
tagcatagaa gacctaaaga tggtagaacc tatcggcaac tagaaagtct atgcacatcc     480
tcaggtattg gtagagtatt cagtgctctc taagtagcag cccctgcctc catcaat        537

<210> SEQ ID NO 19
<211> LENGTH: 249
<212> TYPE: DNA
<213> ORGANISM: Homo sapiens

<400> SEQUENCE: 19
gaaatgcata tgtatgggtc cagatcctct caaagtactc aagtgtcacc aggagaattc      60
caaaaatagc tacacagaga gcaggagctt caactacatt gaattccatt gtagcatgga     120
cgggtatgtt gatagcatag aagacctaaa gatggtagaa cctatcggca actagaaagt     180
ctatgcacat cctcaggtat tggtagagta ttcagtgctt ctaagtagc agcccctgcc      240 tccatcaat                                                             249

<210> SEQ ID NO 20
<211> LENGTH: 250
<212> TYPE: DNA
<213> ORGANISM: Homo sapiens

<400> SEQUENCE: 20
gaaatgcata tgtatgggcc ccaggtgccc tcaaagtact cgagtgtcac tgggagaagt      60
acaacaatag gtacacagag agcagaagct tcagctacat tgaattccat tgtggcgtag     120
atggatatgt tgataacata gaagacctga ggattataga acctatcagc aactagaaag     180
tctatgcaca tcctcagata ttggtagagt attcagtgct tccaaagtgg tgggccctgc     240
ctccatcaat                                                            250

<210> SEQ ID NO 21
<211> LENGTH: 419
<212> TYPE: DNA
<213> ORGANISM: Homo sapiens

<400> SEQUENCE: 21
ggtgactgag atggcatcct ctctgaagat ctggggcagt cccttggccc tgctttgcat      60
tctttgcagg ctacttgtac acagcaagga cgtttcctgg agagaattca tgaccctgca     120
ctatttagat ccaagccaag attttgaaga gtacaaatgt gatgtcctca tgagagaaaa     180
agaagctctg aaacgcaaga gctctcatat gtccatctat agcttatggc acaaaatgga     240
gtgtatatgc attattgaaa tgggaataac cgatatagat atgcctatgt atgggcccag     300
ggtgccctca aagtactcga gtgtcagtgg cagaagtact gcaatagcta cacagagatc     360
ttcaactaca ttgaattcca ctgtggcaag gatgggtatg ttgatagcat agaagacct      419

<210> SEQ ID NO 22
<211> LENGTH: 426
<212> TYPE: DNA
<213> ORGANISM: Homo sapiens

<400> SEQUENCE: 22
ggtgactgag atgacatcct ctctaaagat ttggggcata ctcttggccc tgctttgcat      60
```

```
ccttttgcagg ctgtgtgtat acagtaacaa catttactgg agagaattca taaaacttca    120
ttacttaagt ccaagtcgag aattcaaaga gtacaaatgt gatgtcctca tgagagaaaa    180
agaggctctg aaaggcaaga gctttcatat gttcatctat agcttatggt tcaaaattca    240
gcgtgcatgc atcaatgaga aggggagcga ccgatataga aatgcatatg tatgggcccc    300
aggtgccctc aaagtactcg agtgtcactg ggagaagtac aacaataggt acacagagag    360
cagaagcttc agctacattg aattccattg tggcgtagat ggatatgttg ataacataga    420
agacct                                                                426

<210> SEQ ID NO 23
<211> LENGTH: 256
<212> TYPE: DNA
<213> ORGANISM: Homo sapiens

<400> SEQUENCE: 23
gccccggtga ctgagatggc atcctctctg aagatctggg gcagtcccct tggccctgctt    60 tgcattcttt gcaggctact tgtacacagc aaggacgttt cctggagaga attcatgacc    120
ctgcactatt tagatccaag ccaagatttt gaagagtaca aatgtgatgt cctcatgaga    180 gaaaagaag ctctgaaacg caagagctct catatgtcca tctatagctt atggcacaaa    240
atggagtgta tatgca                                                     256

<210> SEQ ID NO 24
<211> LENGTH: 256
<212> TYPE: DNA
<213> ORGANISM: Homo sapiens

<400> SEQUENCE: 24
gccccggtga ctgagatggc atcatctcta aagatctggg gcacactctt ggccctactt    60
tgcatcctat gcacactgct tgtacagagc aaagaagttt cttggagaga attcatgaaa    120
cagcactact taagtccaag tcgagaattc agagagtaca aatgtgatgt cctcatgaga    180
gaaaatgaag ctctgaaaga caagagctct cacatgtttta tctatatctc atggtacaaa    240
atcgagcata tatgca                                                     256

<210> SEQ ID NO 25
<211> LENGTH: 61
<212> TYPE: DNA
<213> ORGANISM: Homo sapiens

<400> SEQUENCE: 25
cttcaactac attgaattcc actgtggcaa ggatgggtat gttgatagca tagaagacct    60
a                                                                     61

<210> SEQ ID NO 26
<211> LENGTH: 61
<212> TYPE: DNA
<213> ORGANISM: Homo sapiens

<400> SEQUENCE: 26
cttcaactac attgaattcc attgtagcat ggacgggtat gttgatagca tagaagacct    60
a                                                                     61

<210> SEQ ID NO 27
<211> LENGTH: 126
<212> TYPE: PRT
```

<213> ORGANISM: Homo sapiens

<400> SEQUENCE: 27

```
Met Ala Ser Ser Leu Lys Ile Trp Gly Ser Pro Leu Ala Leu Leu Cys
 1               5                  10                  15
Ile Leu Cys Arg Leu Leu Val His Ser Lys Asp Val Ser Trp Arg Glu
                20                  25                  30
Phe Met Thr Leu His Tyr Leu Asp Pro Ser Gln Asp Phe Glu Glu Tyr
                35                  40                  45
Lys Cys Asp Val Leu Met Arg Glu Lys Glu Ala Leu Lys Arg Lys Ser
            50                  55                  60
Ser His Met Ser Ile Tyr Ser Leu Trp His Lys Met Glu Cys Ile Cys
65                  70                  75                  80
Ile Ile Glu Met Gly Ile Thr Asp Ile Asp Met Pro Met Tyr Gly Pro
                85                  90                  95
Arg Val Pro Ser Lys Tyr Ser Val Ser Gly Arg Ser Thr Ala Ile
                100                 105                 110
Ala Thr Gln Arg Ser Ser Thr Thr Leu Asn Ser Thr Val Ala
            115                 120                 125
```

<210> SEQ ID NO 28
<211> LENGTH: 128
<212> TYPE: PRT
<213> ORGANISM: Homo sapiens

<400> SEQUENCE: 28

```
Met Thr Ser Ser Leu Lys Ile Trp Gly Ile Leu Ala Leu Leu Cys
 1               5                  10                  15
Ile Leu Cys Arg Leu Cys Val Tyr Ser Asn Asn Ile Tyr Trp Arg Glu
                20                  25                  30
Phe Ile Lys Leu His Tyr Leu Ser Pro Ser Arg Glu Phe Lys Glu Tyr
                35                  40                  45
Lys Cys Asp Val Leu Met Arg Glu Lys Glu Ala Leu Lys Gly Lys Ser
            50                  55                  60
Phe His Thr Phe Ile Tyr Ser Leu Trp Phe Lys Ile Gln Arg Ala Cys
65                  70                  75                  80
Ile Asn Glu Lys Gly Ser Asp Arg Tyr Arg Asn Ala Tyr Val Trp Pro
                85                  90                  95
Gln Val Pro Ser Asn Tyr Ser Val Thr Gly Arg Ser Thr Thr Ile
                100                 105                 110
Gly Thr Gln Arg Ala Glu Ala Ser Ala Thr Leu Asn Ser Ile Val Ala
            115                 120                 125
```

<210> SEQ ID NO 29
<211> LENGTH: 147
<212> TYPE: PRT
<213> ORGANISM: Homo sapiens
<220> FEATURE:
<221> NAME/KEY: VARIANT
<222> LOCATION: (1)..(147)
<223> OTHER INFORMATION: Wherein Xaa is any amino acid as defined in the
      specification

<400> SEQUENCE: 29

```
Met Ala Ser Ser Leu Lys Ile Trp Gly Xaa Xaa Xaa Xaa Xaa Xaa
 1               5                  10                  15
Xaa Xaa Xaa Xaa Xaa Xaa Val Gln Ser Lys Glu Val Ser Trp Arg Glu
                20                  25                  30
```

```
Phe Met Lys Gln His Tyr Leu Ser Pro Ser Arg Glu Phe Arg Glu Tyr
        35                  40                  45

Lys Cys Asp Val Leu Met Arg Glu Asn Glu Ala Leu Lys Asp Lys Ser
    50                  55                  60

Ser His Met Phe Ile Tyr Ile Ser Trp Tyr Lys Ile Glu His Ile Cys
65                  70                  75                  80

Thr Ser Asp Asn Trp Met Asp Arg Phe Arg Asn Ala Tyr Val Trp Val
                85                  90                  95

Gln Asn Pro Leu Lys Val Leu Lys Cys His Gln Glu Asn Ser Lys Asn
                100                 105                 110

Ser Tyr Thr Glu Ser Arg Ser Phe Asn Tyr Ile Glu Phe His Cys Ser
        115                 120                 125

Met Asp Gly Tyr Val Asp Ser Ile Glu Asp Leu Lys Met Val Glu Pro
    130                 135                 140

Ile Gly Asn
145

<210> SEQ ID NO 30
<211> LENGTH: 147
<212> TYPE: PRT
<213> ORGANISM: Homo sapiens

<400> SEQUENCE: 30

Met Ala Ser Ser Leu Lys Ile Trp Gly Thr Leu Leu Ala Leu Leu Cys
1               5                   10                  15

Ile Leu Cys Thr Leu Val Gln Ser Lys Glu Val Ser Trp Arg Glu
        20                  25                  30

Phe Met Lys Gln His Tyr Leu Ser Pro Ser Arg Glu Phe Arg Glu Tyr
        35                  40                  45

Lys Cys Asp Val Leu Met Arg Glu Asn Glu Ala Leu Lys Asp Lys Ser
    50                  55                  60

Ser His Met Phe Ile Tyr Ile Ser Trp Tyr Lys Ile Glu His Ile Cys
65                  70                  75                  80

Thr Ser Asp Asn Trp Met Asp Arg Phe Arg Asn Ala Tyr Val Trp Val
                85                  90                  95

Gln Asn Pro Leu Lys Val Leu Lys Cys His Gln Glu Asn Ser Lys Asn
                100                 105                 110

Ser Tyr Thr Glu Ser Arg Ser Phe Asn Tyr Ile Glu Phe His Cys Ser
        115                 120                 125

Met Asp Gly Tyr Val Asp Ser Ile Glu Asp Leu Lys Met Val Glu Pro
    130                 135                 140

Ile Gly Asn
145

<210> SEQ ID NO 31
<211> LENGTH: 147
<212> TYPE: PRT
<213> ORGANISM: Homo sapiens
<220> FEATURE:
<221> NAME/KEY: VARIANT
<222> LOCATION: (1)..(147)
<223> OTHER INFORMATION: Wherein Xaa is any amino acid as defined in the
      specification

<400> SEQUENCE: 31

Met Ala Ser Ser Leu Lys Ile Trp Gly Xaa Xaa Xaa Xaa Xaa Xaa Xaa
1               5                   10                  15

Xaa Xaa Xaa Xaa Xaa Xaa Val Gln Ser Lys Glu Val Ser Trp Arg Glu
```

-continued

```
                        20                  25                  30

Phe Met Lys Gln His Tyr Leu Ser Pro Ser Arg Glu Phe Arg Glu Tyr
            35                  40                  45

Lys Cys Asp Val Leu Met Arg Glu Asn Glu Ala Leu Lys Asp Lys Ser
     50                  55                  60

Ser His Met Phe Ile Tyr Ile Ser Trp Tyr Lys Ile Glu His Ile Cys
 65                  70                  75                  80

Thr Ser Asp Asn Trp Met Asp Arg Phe Arg Asn Ala Tyr Val Trp Val
                 85                  90                  95

Gln Asn Pro Leu Lys Val Leu Lys Cys His Gln Glu Asn Ser Lys Asn
            100                 105                 110

Ser Tyr Thr Glu Ser Arg Ser Phe Asn Tyr Ile Glu Phe His Cys Ser
        115                 120                 125

Met Asp Gly Tyr Val Asp Ser Ile Glu Asp Leu Lys Met Val Glu Pro
    130                 135                 140

Ile Gly Asn
145

<210> SEQ ID NO 32
<211> LENGTH: 147
<212> TYPE: PRT
<213> ORGANISM: Homo sapiens

<400> SEQUENCE: 32

Met Thr Ser Ser Leu Lys Ile Trp Gly Ile Leu Leu Ala Leu Leu Cys
 1               5                  10                  15

Ile Leu Cys Arg Leu Cys Val Tyr Ser Asn Asn Ile Tyr Trp Arg Glu
            20                  25                  30

Phe Ile Lys Leu His Tyr Leu Ser Pro Ser Arg Glu Phe Lys Glu Tyr
        35                  40                  45

Lys Cys Asp Val Leu Met Arg Glu Lys Glu Ala Leu Lys Gly Lys Ser
     50                  55                  60

Phe His Met Phe Ile Tyr Ser Leu Trp Phe Lys Ile Gln Arg Ala Cys
 65                  70                  75                  80

Ile Asn Glu Lys Gly Ser Asp Arg Tyr Arg Asn Ala Tyr Val Trp Ala
                 85                  90                  95

Pro Gly Ala Leu Lys Val Leu Glu Cys His Trp Glu Lys Tyr Asn Asn
            100                 105                 110

Arg Tyr Thr Glu Ser Arg Ser Phe Ser Tyr Ile Glu Phe His Cys Gly
        115                 120                 125

Val Asp Gly Tyr Val Asp Asn Ile Glu Asp Leu Arg Ile Ile Glu Pro
    130                 135                 140

Ile Ser Asn
145

<210> SEQ ID NO 33
<211> LENGTH: 394
<212> TYPE: PRT
<213> ORGANISM: Homo sapiens
<220> FEATURE:
<221> NAME/KEY: VARIANT
<222> LOCATION: (1)..(394)
<223> OTHER INFORMATION: Wherein Xaa is any amino acid as defined in the
      specification

<400> SEQUENCE: 33

Met Leu Ala Arg Arg Lys Pro Met Leu Pro Ala Leu Thr Ile Asn Pro
 1               5                  10                  15
```

```
Thr Ile Ala Glu Gly Pro Ser Pro Thr Ser Glu Gly Ala Ser Glu Ala
             20                  25                  30

Asn Leu Val Asp Leu Gln Lys Lys Leu Glu Glu Leu Glu Leu Asp Glu
         35                  40                  45

Gln Gln Lys Arg Leu Glu Ala Phe Leu Thr Gln Lys Ala Lys Val Gly
     50                  55                  60

Glu Leu Lys Asp Asp Asp Phe Glu Arg Thr Ser Glu Leu Asp Ala Gly
 65                  70                  75                  80

Asn Gly Gly Val Val Thr Lys Val Gln His Arg Pro Ser Gly Leu Ile
                 85                  90                  95

Met Ala Arg Lys Leu Ile His Leu Glu Ile Lys Pro Ala Ile Arg Asn
            100                 105                 110

Gln Ile Ile Arg Glu His Gln Val Leu His Glu Cys Asn Ser Pro Tyr
        115                 120                 125

Ile Val Gly Phe Tyr Gly Ala Phe Tyr Cys Asp Arg Glu Ile Ser Ile
    130                 135                 140

Cys Met Glu His Met Asp Gly Gly Ser Leu Asp Gln Gly Leu Lys Glu
145                 150                 155                 160

Ala Lys Arg Ile Pro Glu Asp Ile Leu Gly Lys Val Ser Ile Ala Val
                165                 170                 175

Leu Arg Gly Leu Ala Tyr Leu Arg Glu Lys His Gln Ile Met His Arg
            180                 185                 190

Asn Val Lys Pro Ser Asn Ile Leu Val Asn Ser Arg Gly Glu Ile Lys
        195                 200                 205

Leu Cys Asp Phe Gly Val Ser Gly Gln Leu Ile Asp Ser Met Ala Asn
    210                 215                 220

Ser Phe Val Gly Thr Arg Ser Tyr Met Ala Pro Glu Arg Leu Gln Gly
225                 230                 235                 240

Thr His Tyr Ser Val Gln Ser Val Ile Trp Ser Met Asp Leu Ser Leu
                245                 250                 255

Val Glu Leu Ala Ile Glu Arg Tyr Pro Ile Pro Pro Asp Ala Lys
            260                 265                 270

Glu Leu Glu Ala Ile Phe Gly Gln Pro Val Val Asp Arg Glu Glu Gly
        275                 280                 285

Glu Pro His Ser Ile Ser Ser Trp Pro Gly Ser Pro Gly Arg Pro Asn
    290                 295                 300

Ser Gly Tyr Gly Met Asp Ser Leu Pro Ala Met Ala Ile Phe Glu Leu
305                 310                 315                 320

Leu Asp Tyr Ile Val Lys Glu Pro Pro Lys Leu Pro Asn Gly Val
                325                 330                 335

Phe Thr Pro Glu Phe Gln Glu Phe Val Asn Lys Cys Leu Ile Lys Asn
            340                 345                 350

Pro Thr Glu Arg Ala Asp Leu Lys Met Leu Thr Asn His Ala Phe Ile
        355                 360                 365

Lys Arg Ser Glu Val Lys Glu Ala Asp Phe Ala Cys Leu Cys Lys Thr
    370                 375                 380

Leu Xaa Ala Glu Pro Ser Pro Ala His Pro
385                 390

<210> SEQ ID NO 34
<211> LENGTH: 395
<212> TYPE: PRT
<213> ORGANISM: Homo sapiens
```

-continued

```
<400> SEQUENCE: 34

Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
            20                  25                  30

Asn Leu Val Asp Leu Gln Lys Lys Leu Glu Glu Leu Glu Leu Asp Glu
            35                  40                  45

Gln Gln Lys Lys Arg Leu Glu Ala Phe Leu Thr Gln Lys Ala Lys Val
        50                  55                  60

Gly Glu Leu Lys Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
            100                 105                 110

Asn Gln Ile Ile Arg Glu Leu Gln Val Leu His Glu Cys Asn Ser Pro
        115                 120                 125

Tyr Ile Val Gly Phe Tyr Gly Ala Phe Tyr Ser Asp Gly Glu Ile Ser
130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
            180                 185                 190

Arg Asp Val Lys Pro Ser Asn Ile Leu Val Asn Ser Arg Gly Glu Ile
        195                 200                 205

Lys Leu Cys Asp Phe Gly Val Ser Gly Gln Leu Ile Asp Ser Met Ala
210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
                245                 250                 255

Leu Val Glu Leu Ala Val Gly Arg Tyr Pro Ile Pro Pro Asp Ala
            260                 265                 270

Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Pro Gly Arg Pro
290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Lys Leu Pro Asn Gly
                325                 330                 335

Val Phe Thr Pro Asp Phe Gln Glu Phe Val Asn Lys Cys Leu Ile Lys
            340                 345                 350

Asn Pro Ala Glu Arg Ala Asp Leu Lys Met Leu Thr Asn His Thr Phe
        355                 360                 365

Ile Lys Arg Ser Glu Val Glu Glu Val Asp Phe Ala Gly Trp Leu Cys
370                 375                 380

Lys Thr Leu Arg Leu Asn Gln Pro Gly Thr Pro
385                 390                 395

<210> SEQ ID NO 35
```

-continued

```
<211> LENGTH: 392
<212> TYPE: PRT
<213> ORGANISM: Homo sapiens
<220> FEATURE:
<221> NAME/KEY: VARIANT
<222> LOCATION: (1)..(392)
<223> OTHER INFORMATION: Wherein Xaa is any amino acid as defined in the
      specification

<400> SEQUENCE: 35

Leu Ala Arg Arg Lys Pro Met Leu Pro Ala Leu Thr Ile Asn Pro Thr
 1               5                  10                  15

Ile Ala Glu Gly Pro Ser Pro Thr Ser Glu Gly Ala Ser Glu Ala Asn
                20                  25                  30

Leu Val Asp Leu Gln Lys Lys Leu Glu Glu Leu Glu Leu Asp Glu Gln
            35                  40                  45

Gln Lys Arg Leu Glu Ala Phe Leu Thr Gln Lys Ala Lys Val Gly Glu
        50                  55                  60

Leu Lys Asp Asp Asp Phe Glu Arg Thr Ser Glu Leu Asp Ala Gly Asn
 65                  70                  75                  80

Gly Gly Val Val Thr Lys Val Gln His Arg Pro Ser Gly Leu Ile Met
                85                  90                  95

Ala Arg Lys Leu Ile His Leu Glu Ile Lys Pro Ala Ile Arg Asn Gln
                100                 105                 110

Ile Ile Arg Glu His Gln Val Leu His Glu Cys Asn Ser Pro Tyr Ile
            115                 120                 125

Val Gly Phe Tyr Gly Ala Phe Tyr Cys Asp Arg Glu Ile Ser Ile Cys
        130                 135                 140

Met Glu His Met Asp Gly Gly Ser Leu Asp Gln Gly Leu Lys Glu Ala
145                 150                 155                 160

Lys Arg Ile Pro Glu Asp Ile Leu Gly Lys Val Ser Ile Ala Val Leu
                165                 170                 175

Arg Gly Leu Ala Tyr Leu Arg Glu Lys His Gln Ile Met His Arg Asn
            180                 185                 190

Val Lys Pro Ser Asn Ile Leu Val Asn Ser Arg Gly Glu Ile Lys Leu
        195                 200                 205

Cys Asp Phe Gly Val Ser Gly Gln Leu Ile Asp Ser Met Ala Asn Ser
210                 215                 220

Phe Val Gly Thr Arg Ser Tyr Met Ala Pro Glu Arg Leu Gln Gly Thr
225                 230                 235                 240

His Tyr Ser Val Gln Ser Val Ile Trp Ser Met Asp Leu Ser Leu Val
                245                 250                 255

Glu Leu Ala Ile Glu Arg Tyr Pro Ile Pro Pro Asp Ala Lys Glu
            260                 265                 270

Leu Glu Ala Ile Phe Gly Gln Pro Val Val Asp Arg Glu Glu Gly Glu
        275                 280                 285

Pro His Ser Ile Ser Ser Trp Pro Gly Ser Pro Gly Arg Pro Asn Ser
290                 295                 300

Gly Tyr Gly Met Asp Ser Leu Pro Ala Met Ala Ile Phe Glu Leu Leu
305                 310                 315                 320

Asp Tyr Ile Val Lys Glu Pro Pro Lys Leu Pro Asn Gly Val Phe
                325                 330                 335

Thr Pro Glu Phe Gln Glu Phe Val Asn Lys Cys Leu Ile Lys Asn Pro
            340                 345                 350

Thr Glu Arg Ala Asp Leu Lys Met Leu Thr Asn His Ala Phe Ile Lys
        355                 360                 365
```

```
Arg Ser Glu Val Lys Glu Ala Asp Phe Ala Cys Leu Cys Lys Thr Leu
    370                 375                 380
Xaa Ala Glu Pro Ser Pro Ala His
385                 390
```

<210> SEQ ID NO 36
<211> LENGTH: 389
<212> TYPE: PRT
<213> ORGANISM: Homo sapiens

<400> SEQUENCE: 36

```
Met Pro Lys Lys Pro Thr Pro Ile Gln Leu Asn Pro Ala Pro Asp
  1               5                  10                  15
Gly Ser Ala Val Asn Gly Thr Ser Ser Ala Glu Thr Asn Leu Glu Ala
                 20                  25                  30
Leu Gln Lys Lys Leu Glu Glu Leu Glu Leu Asp Glu Gln Gln Arg Lys
             35                  40                  45
Arg Leu Glu Ala Phe Leu Thr Gln Lys Gln Lys Val Gly Glu Leu Lys
         50                  55                  60
Asp Asp Asp Phe Glu Lys Ile Ser Glu Leu Gly Ala Gly Asn Gly Gly
 65                  70                  75                  80
Val Val Phe Lys Val Ser His Lys Pro Ser Gly Leu Val Met Ala Arg
                 85                  90                  95
Lys Leu Ile His Leu Glu Ile Lys Pro Ala Ile Arg Asn Gln Ile Ile
                100                 105                 110
Arg Glu Leu Gln Val Leu His Glu Cys Asn Ser Pro Tyr Ile Val Gly
            115                 120                 125
Phe Tyr Gly Ala Phe Tyr Ser Asp Gly Glu Ile Ser Ile Cys Met Glu
        130                 135                 140
His Met Asp Gly Gly Ser Leu Asp Gln Val Leu Lys Lys Ala Gly Arg
145                 150                 155                 160
Ile Pro Glu Gln Ile Leu Gly Lys Val Ser Ile Ala Val Ile Lys Gly
                165                 170                 175
Leu Thr Tyr Leu Arg Glu Lys His Lys Ile Met His Arg Asp Val Lys
                180                 185                 190
Pro Ser Asn Ile Leu Val Asn Ser Arg Gly Glu Ile Lys Leu Cys Asp
            195                 200                 205
Phe Gly Val Ser Gly Gln Leu Ile Asp Ser Met Ala Asn Ser Phe Val
        210                 215                 220
Gly Thr Arg Ser Tyr Met Ser Pro Glu Arg Leu Gln Gly Thr His Tyr
225                 230                 235                 240
Ser Val Gln Ser Asp Ile Trp Ser Met Gly Leu Ser Leu Val Glu Met
                245                 250                 255
Ala Val Gly Arg Tyr Pro Ile Pro Pro Asp Ala Lys Glu Leu Glu
                260                 265                 270
Leu Met Phe Gly Cys Gln Val Glu Gly Asp Ala Ala Glu Thr Pro Pro
            275                 280                 285
Arg Pro Arg Thr Pro Gly Arg Pro Leu Ser Ser Tyr Gly Met Asp Ser
        290                 295                 300
Arg Pro Pro Met Ala Ile Phe Glu Leu Leu Asp Tyr Ile Val Asn Glu
305                 310                 315                 320
Pro Pro Pro Lys Leu Pro Ser Gly Val Phe Ser Leu Glu Phe Gln Asp
                325                 330                 335
Phe Val Asn Lys Cys Leu Ile Lys Asn Pro Ala Glu Arg Ala Asp Leu
```

```
                    340                 345                 350
Lys Gln Leu Met Val His Ala Phe Ile Lys Arg Ser Asp Ala Glu Glu
            355                 360                 365

Val Asp Phe Ala Gly Trp Leu Cys Ser Thr Ile Gly Leu Asn Gln Pro
    370                 375                 380

Ser Thr Pro Thr His
385

<210> SEQ ID NO 37
<211> LENGTH: 224
<212> TYPE: PRT
<213> ORGANISM: Homo sapiens
<220> FEATURE:
<221> NAME/KEY: VARIANT
<222> LOCATION: (1)..(224)
<223> OTHER INFORMATION: Wherein Xaa is any amino acid as defined in the
      specification

<400> SEQUENCE: 37

Gly Lys Val Ser Ile Ala Val Leu Arg Gly Leu Ala Tyr Leu Arg Glu
  1               5                  10                  15

Lys His Gln Ile Met His Arg Asn Val Lys Pro Ser Asn Ile Leu Val
             20                  25                  30

Asn Ser Arg Gly Glu Ile Lys Leu Cys Asp Phe Gly Val Ser Gly Gln
         35                  40                  45

Leu Ile Asp Ser Met Ala Asn Ser Phe Val Gly Thr Arg Ser Tyr Met
     50                  55                  60

Ala Pro Glu Arg Leu Gln Gly Thr His Tyr Ser Val Gln Ser Val Ile
 65                  70                  75                  80

Trp Ser Met Asp Leu Ser Leu Val Glu Leu Ala Ile Glu Arg Tyr Pro
                 85                  90                  95

Ile Pro Pro Pro Asp Ala Lys Glu Leu Glu Ala Ile Phe Gly Gln Pro
            100                 105                 110

Val Val Asp Arg Glu Glu Gly Glu Pro His Ser Ile Ser Ser Trp Pro
        115                 120                 125

Gly Ser Pro Gly Arg Pro Asn Ser Gly Tyr Gly Met Asp Ser Leu Pro
    130                 135                 140

Ala Met Ala Ile Phe Glu Leu Leu Asp Tyr Ile Val Lys Glu Pro Pro
145                 150                 155                 160

Pro Lys Leu Pro Asn Gly Val Phe Thr Pro Glu Phe Gln Glu Phe Val
                165                 170                 175

Asn Lys Cys Leu Ile Lys Asn Pro Thr Glu Arg Ala Asp Leu Lys Met
            180                 185                 190

Leu Thr Asn His Ala Phe Ile Lys Arg Ser Glu Val Lys Glu Ala Asp
        195                 200                 205

Phe Ala Cys Leu Cys Lys Thr Leu Xaa Ala Glu Pro Ser Pro Ala His
    210                 215                 220

<210> SEQ ID NO 38
<211> LENGTH: 228
<212> TYPE: PRT
<213> ORGANISM: Homo sapiens

<400> SEQUENCE: 38

Gly Glu Ile Ser Ile Cys Met Glu His Met Val Ile Lys Gly Leu Thr
  1               5                  10                  15

Tyr Leu Arg Glu Lys His Lys Ile Met His Arg Asp Val Lys Pro Ser
             20                  25                  30
```

```
Asn Ile Leu Val Asn Ser Arg Gly Glu Ile Lys Leu Cys Asp Phe Gly
            35                  40                  45
Val Ser Gly Gln Leu Ile Asp Ser Met Ala Asn Ser Phe Val Gly Thr
 50                  55                  60
Arg Ser Tyr Met Ser Pro Glu Arg Leu Gln Gly Thr His Tyr Ser Val
 65                  70                  75                  80
Gln Ser Asp Ile Trp Ser Met Gly Leu Ser Leu Val Glu Met Ala Val
                85                  90                  95
Gly Arg Tyr Pro Ile Pro Pro Asp Ala Lys Glu Leu Glu Leu Met
                100                 105                 110
Phe Gly Cys Gln Val Glu Gly Asp Ala Ala Glu Thr Pro Pro Arg Pro
            115                 120                 125
Arg Thr Thr Pro Gly Arg Pro Leu Ser Ser Tyr Gly Met Asp Ser Arg
130                 135                 140
Pro Pro Met Ala Ile Phe Gln Leu Leu Asp Tyr Ile Val Asn Glu Pro
145                 150                 155                 160
Pro Pro Lys Leu Pro Ser Gly Val Phe Ser Leu Glu Phe Gln Asp Phe
                165                 170                 175
Val Asn Lys Cys Leu Ile Lys Asn Pro Ala Glu Arg Ala Asp Leu Lys
                180                 185                 190
Gln Leu Met Val His Ala Phe Ile Lys Arg Ser Asp Ala Glu Glu Val
            195                 200                 205
Asp Phe Ala Gly Trp Leu Cys Ser Thr Ile Gly Leu Asn Gln Pro Ser
    210                 215                 220
Thr Pro Thr His
225

<210> SEQ ID NO 39
<211> LENGTH: 2096
<212> TYPE: DNA
<213> ORGANISM: Homo sapiens

<400> SEQUENCE: 39
gaaggtgcca ctatattaaa aggataaaga aaattcagat aaaatacgag caggaagcat      60
atgataatgg ctcttatata tccatacagt cccaaagaac atctgctgtc tttggcgcag    120
ggccatatat ttgtggtttc aggtgcccct aaagtgtcta taggagccta taacaaagc     180
ctataaactg tgttgtagga agacagcac atattgttac aggctcatac aaagaaaata    240
tatgtagtgt ttcagtctag ttcttacctt cctaagtaga gtccttacac atgtgtaagg   300
gagataggta ttgagaaagg gagagtggga atgtgaagtg atgcataaca tgcaacttag   360
taggaatttt gacctgtgtt gggcacagct tgacaagctt gtgtgtgtgt atcaccacat   420
accctcactt ccccttccc tacctctttc tccttactga cttcaaggga gagcatataa    480
atgacatcaa ggggtatgaa aagccactta actgcagact tgtaggcagc aactcaccct   540
caagaggaag tcttcaggct ctagaaacat ctttaacttc ggcttctgca ccataagcct   600
cagactcaat gccaccctgc agctgtgcca gatcactttg tgccctgcag gtgctgctgt   660
tgactgttct gggttcctcc accaatggac aaactaagag aaacataggg aaaaggaaat   720
gtagagatct gttccttgca cctgttgctg cttctgctat acctgtatct gggagaaaga   780
ctggcttggt gctcctgggg ctggagagtg ccattataac aacaaatcca atggagggg    840
tcacagagag ggggcacttc acatttgctg ggcattctgc tgggcacttt aataaagctt   900
tacagatcat attcacaatg gctttatgag agaggtacaa ttaccttcaa tttacaattg   960
```

```
agagaactga gaaaaatatt cacgaccact aatagatcac ttttaccccc agctgtaagt      1020
gtagacagtg acttgtacac tgaactgcgc tgcgtgtatg tgaagtcaac ctttgtactt      1080
catcccagaa acatccacaa tttggagttg gtctcagcag acccccattg cagcaaagac      1140
gaagtaatgt aagccactgc ttctgtgcta tcgcctcatc agggaagccc tctacctcca      1200
tccccatctg cattcatttc ctccagtctc acagatcctt tctgatattc aggccaggac      1260
acccacagat aattctattc tctcttgcag agccactctg taagatggga gaaaaaatct      1320
gcctggaccc agatgctccc agaatcaata aaattgtaca gaaaatgttg aaagttgatg      1380
aattcatctg gttaatttgt aactttctg ctaacgcttt tcactggaag gggaggattt       1440
tgaagtcttg actttctcag attcttattt atccaggata cttattctta ctgtattaaa      1500
attttgatct aagttctatt ctgtttcaaa aatctcattt tattctgaga atgctggata      1560
aaagataaca gaaagaaggt gaaaataagc aagccatgct tcaatatata atatatgttt      1620
tacccccaat ccttggctaa acattgtagt gcactttccc tttatttatt tgaaaatttc      1680
tattgaaaca catctttgtt gattttccca accccactct actgtaagac tagacatgct      1740
gatgataata aacagattta ataatggtta atgatattag gaatcacaca gagcccagcg      1800
caaaatactt gctcaataaa ttttgttag tatgttcagg aacttaatag ggtcttttag       1860
tgtcttagtg ctattatgtc ttgcttaaaa catcttctga agtttcttc tgatgtttgt       1920 tttagccttc aaaccctaaa aataataaag ttgtagaatg taagtcttgt gaactctgct      1980
tttttacttt aaagtgtata tatttacccc tggtagaata aaaaatagat gatggaaatg      2040
aattaatgta tcccattaaa aaacctgtga tattttttga aacaagaaag aaagaa          2096

<210> SEQ ID NO 40
<211> LENGTH: 100
<212> TYPE: PRT
<213> ORGANISM: Homo sapiens

<400> SEQUENCE: 40

Pro Pro Cys Ser Cys Ala Arg Ser Leu Cys Ala Leu Gln Val Leu Leu
 1               5                  10                  15

Leu Thr Val Leu Gly Ser Ser Thr Asn Gly Gln Thr Lys Arg Asn Ile
            20                  25                  30

Gly Lys Ser Val Asp Ser Asp Leu Tyr Thr Glu Leu Arg Cys Val Tyr
        35                  40                  45

Val Lys Ser Thr Phe Val Leu His Pro Arg Asn Ile His Asn Leu Glu
    50                  55                  60

Leu Val Ser Ala Gly Pro His Cys Ser Lys Asp Glu Glu Lys Ile Cys
65                  70                  75                  80

Leu Asp Pro Asp Ala Pro Arg Ile Asn Lys Ile Val Gln Lys Met Leu
                85                  90                  95

Lys Val Asp Glu
            100

<210> SEQ ID NO 41
<211> LENGTH: 117
<212> TYPE: PRT
<213> ORGANISM: Homo sapiens

<400> SEQUENCE: 41

Pro Ser Cys Asn Ser Ala Arg Pro Leu His Ala Leu Gln Val Leu Leu
 1               5                  10                  15
```

```
Leu Leu Ser Leu Leu Thr Ala Leu Ala Ser Ser Thr Lys Gly Gln
             20                  25                  30

Thr Lys Arg Asn Leu Ala Lys Gly Lys Glu Glu Ser Leu Asp Ser Asp
         35                  40                  45

Leu Tyr Ala Glu Leu Arg Cys Met Cys Ile Lys Thr Thr Ser Gly Ile
     50                  55                  60

His Pro Lys Asn Ile Gln Ser Leu Glu Val Ile Gly Lys Gly Thr His
 65                  70                  75                  80

Cys Asn Gln Val Glu Val Ile Ala Thr Leu Lys Asp Gly Arg Lys Ile
                 85                  90                  95

Cys Leu Asp Pro Asp Ala Pro Arg Ile Lys Lys Ile Val Gln Lys Lys
                100                 105                 110

Leu Ala Gly Asp Glu
            115

<210> SEQ ID NO 42
<211> LENGTH: 52
<212> TYPE: PRT
<213> ORGANISM: Homo sapiens

<400> SEQUENCE: 42

Lys Ser Val Asp Ser Asp Leu Tyr Thr Glu Leu Arg Cys Val Tyr Val
 1               5                  10                  15

Lys Ser Thr Phe Val Leu His Pro Arg Asn Ile His Asn Leu Glu Leu
             20                  25                  30

Val Ser Ala Gly Pro His Cys Ser Lys Asp Glu Glu Lys Ile Cys Leu
         35                  40                  45

Asp Pro Asp Ala
         50

<210> SEQ ID NO 43
<211> LENGTH: 60
<212> TYPE: PRT
<213> ORGANISM: Homo sapiens

<400> SEQUENCE: 43

Arg Ala Ala Gly Ala Ser Val Ala Thr Glu Leu Arg Cys Gln Cys Leu
 1               5                  10                  15

Gln Thr Leu Gln Gly Ile His Pro Lys Asn Ile Gln Ser Val Asn Val
             20                  25                  30

Lys Ser Pro Gly Pro His Cys Ala Gln Thr Glu Val Ile Ala Thr Leu
         35                  40                  45

Lys Asn Gly Arg Lys Ala Cys Leu Asn Pro Ala Ser
     50                  55                  60

<210> SEQ ID NO 44
<211> LENGTH: 60
<212> TYPE: PRT
<213> ORGANISM: Homo sapiens

<400> SEQUENCE: 44

Arg Ala Ala Gly Ala Pro Leu Ala Thr Glu Leu Arg Cys Gln Cys Leu
 1               5                  10                  15

Gln Thr Leu Gln Gly Ile His Leu Lys Asn Ile Gln Ser Val Lys Val
             20                  25                  30

Lys Ser Pro Gly Pro His Cys Ala Gln Thr Glu Val Ile Ala Thr Leu
         35                  40                  45

Lys Asn Gly Gln Lys Ala Cys Leu Asn Pro Ala Ser
```

<210> SEQ ID NO 45
<211> LENGTH: 53
<212> TYPE: PRT
<213> ORGANISM: Homo sapiens

<400> SEQUENCE: 45

His Val Glu Leu Arg Cys Leu Cys Leu Asn Thr Val Ser Gly Ile His
 1               5                  10                  15

Pro Ser Asn Ile Gln Ser Leu Glu Val Ile Arg Ala Gly Ala His Cys
            20                  25                  30

Ala Lys Val Glu Val Ile Ala Thr Leu Lys Asn Asp Asp Lys Ile Cys
        35                  40                  45

Leu Asp Pro Glu Ala
        50

<210> SEQ ID NO 46
<211> LENGTH: 41100
<212> TYPE: DNA
<213> ORGANISM: Homo sapiens
<220> FEATURE:
<223> OTHER INFORMATION: GENOMIC DNA

<400> SEQUENCE: 46

| | | | |
|---|---|---|---|
| taagggttgt cgttctcctt cctgatgata agggaggaga gacgcaggga gacatctact | 60 |
| tcccaagtaa atcctatagt atgggacact gaggtttcag gcaaagtgtt aaatgttctc | 120 |
| ctgatttgta tccaacttaa acctgatgtc ctgtagccct ggaagagaca ataccccttta | 180 |
| aagctagagg cacaaagagg gatccaacca ttaatagcta agtttttgca attcgggttg | 240 |
| ttaaacctct gtgagtctcg ttgtaataca ccaatcgtac cagttaaaaa accaaatgga | 300 |
| caccatagat ttggtcaaga acttcaagct ttcaatgagg ctgtcattcc catacatcct | 360 |
| atagtgccca atccctacgt gctgttagcc tgggtcccat ccctggggat gccaatttgt | 420 |
| ttacagagtt agatcttaaa gatgtctttt tgttttttt tttttttgttt ttgttttttt | 480 |
| ttggcattgc agtactccct gattcacaat tcatcttggc ttttgaatgg attgatcctg | 540 |
| acagtcattt ggtttatcaa tgaacttgga cagttcttcc ccaggtattt aggggcagcc | 600 |
| cttatctgtt tggaaatgca ttggctagag aattaaggat gttacactta ataggggca | 660 |
| ttattatcca atatgtggat gatgtgttgg ttgctagccc aaccaaaaga aacttggacg | 720 |
| aaaatacctt taagttgcta aattttctgg gagctaatgt gtatagggtc tcacagcaga | 780 |
| gggcccagat ttcaactcaa gaggctaaat acttaggata tgtcctaacc cctggcaccc | 840 |
| aggcaatagt accagaacaa aaggaagcta tcttgggcat tccaaaaccc caaactagaa | 900 |
| agcagctgcg agcttttcta gcagtgtcag gattggggca tatggtcaag cctttatatg | 960 |
| atgccctgaa aggagcgaat gtagattctt tagaatggaa tagcaattgt aaacaagctt | 1020 |
| ttaatgcttt caaggaaaaa ttgggatcag ctccagtcct acggatccct aattttgata | 1080 |
| agccattttt ctcttatgtg gctaagaaac aaggaaccac gctgggtgtc cttatccaga | 1140 |
| aactaggaga tatccccgaa ccagtgatat attttttta aacaattaga ccatgtcact | 1200 |
| tcaggatgac ctgaatgcct cagggcagtt gcagcaactg ctcttttagg agatgaagtc | 1260 |
| aataaaatgg ctttaggaca acatctggaa gttttaaccc cacatcaagt acaaggagtc | 1320 |
| ctagaagcta aaggacacca gtagatgaca ggaggtactt attgaaatat caggctttgt | 1380 |
| tgctaaacat tcctcatgca acccttaaga tacgccagac tttaaatcca gctacctatc | 1440 |

-continued

```
tgcctgaacc cactggcacc ctgtatcatt ctcgtataca agtaatgcac caagtttatt      1500
ccagctggct ggatttaaat gatgagcctc tagataatcc tgaagtagaa tgttttatag      1560
atagaagtag ctttgtgcgc cagggacaca gaaaagctgg gtatgctgtt gtcagtcaac      1620
acaaggtaat taagtctcag gcctcaccaa cttctacctc agctcaaaag gcagaatgaa      1680
tagctcttgc taatagccct gcaattatta atagctcata ttaatagccc tgcaattggg      1740
aaatgactta gtaattaaca tttgtactga ttctatgtat gccattctgg tgcttcatgc      1800
tcatggaagg aatggggaga atgaggactc ctaattgctg agggttcccc tgtgaaacat      1860
cacttaaaca ttttaaatct attagatgct gttttgctga ccaaggaagt agctataatc      1920
cattgcagag ggcatccaaa aggagactct agtgtggcta agggaaactc ctttgcagat      1980
gcaggagcta aggcagctgc attaaagcag ccagttggac ttgtaggcat gttagtgccc      2040
tctgccctgg taatgacaga accaagatat actaaagagg aataagaatg ggctaaaggt      2100
cagggtttaa ttcaagatcc ttctggctga cttatcaatg acaacaaatt attgatacca      2160
ggtgctaatc agtggaaaat agttaagcat ttgcatgact ctactcattt gggaagagat      2220
tccttctttc aattaatgtc tctctctctc ttttttttta tttttgagac agagtttcac      2280
tcttgttgcc caggctgtag tgcaatggca caatctcagc tcaccacaac ctccacctcc      2340
tgtgttcaag tgattctcct gcctcagcct cctgagtagc tgggattaca ggcatgcgcc      2400
accacgtctg gctaattttg tattttttagt agagacaggg tttctctgtg ttggtcaggc      2460
tggtctcaaa ctcctcacct caggtgatcc atgcgcctca gcctcccaaa gtgctaggat      2520
tacaggcatg aaccaccgct cccagccaat gtctcgtctt tttataggaa aaggcttact      2580
tacttagaac agtaaagcag gtaactcagt cctgtgaact ctgtgcccag aataacccaa      2640
ataaccaacc ttttccttct cctttagtaa ggcctgttca gcatagtgga atgtatgcca      2700
gtgaagattg actagtagat tatgctcaga tgtccccatg taaggatttt aaatatttat      2760
tagtattcat caatccttta ctggttggac tgaggcttttt cctacctggt ctgaaaagac      2820
aaggtttcta acctcctatg aaaggcaata attcctagat ttaggctgtc taatagcttg      2880
caaaacaata atggcccatc tttcacagtg acaattagcc aaaacataac ttcggcccta      2940
ggaattaagt acctccttca tttagtatgg atgccaccat cttcagaaaa agtggaaaga      3000
gctaatcaaa ctaaaaagta ctatgccagg aaacaccaga aaccggacta tctatattgc      3060
ctgtagcctt gttatgggtt taagctgttc ccaagagaaa tctatagtgc aacactttag      3120
aaatgatgta tggaaggcct ttcttaacta cagacttcct gattgacata gatactttca      3180
agtacaaaat tatgtaatca acttaggaca aatgcaaaag gtgctccttg aatatggaaa      3240
tcaaagactc ccttccccta ctaaggaaga gaatattgtt acaacccagc caggagaccg      3300
ggtcctatta aaaattggaa ggaaggatcc ccagcagatc aactttcacc caaaatgaaa      3360
gggatcctat caagttctcc ttagtacccc aactgcagtt aaatttctag gaataaacag      3420
ctgggttcac ttatctcgaa tgaaacctgt ctcttataaa gtcccacagg ccaacaaaac      3480
acaaaagact gatcccactt attcctgtgg gccaacccat gacctccagc tcctgttcaa      3540
aagaaacaaa aggaatgggt aacataaaga tatggattgg cattctattt ttgggtataa      3600
gctggaatca cacaaagagt aacttatttg ctaagtgggc agactgtagc ctctctacat      3660
aatccaacag tttgttggac tatgtagaga attgccattt ccttcacttt ccaggttgcc      3720
ctggcatatt caaccagcaa acctaagttt atggggattt tattatgatt ggggaaactga      3780
```

```
gcattataaa tatagtccct cttttctcat gtaccatagc cacacaggcc ttaggcccct    3840
cctcacttat ggagagacaa gaaggcacct ttttcatcta attaggaaac agctaaatgg    3900
cacctcgact ttaggttaca ctgtacacaa tagacttggg tggatgacag ttgttcaagc    3960
acaggtatca ggcaaaacac ctctatgttt tgaaagatgc attaatagtc accaccagac    4020
tgaaacccgc aatatgggat ggttgccacc tcaacaatgt aatcagaccc ttcttttaac    4080
agaccaaatg tgggtaggat ggcaacacaa tttgcaaaaa atagatgccc acccttcccc    4140
ttggggatgg ttatgggctt gtggaactca ggctggttg tatttacttt atagttggac    4200
ttgaaagttg tccttatctc ctgggactta ccctcaacaa attggactct ctcctgtcta    4260
actgggatac tgtaaaggct cgccataggg caacaaaaac aggcttcttg gtggttctat    4320
ctgatgctgt attttcccca caggcagcca taatcaatat caagttacaa gttaaagcct    4380
tagccaagca catggctgca gctttcaata atacacgcca tgcccttacc ctcctaactg    4440
aggaaacttc tcagattagg caggtggcct tacaaaacca tgtgactttg aacattttaa    4500
tagcagtcca aggggaacc tgtgctttga tcaaaactga atgttgggct aggcgcagtg    4560
gctcaggcct gtaatcccag cactttggga ggccatggta ggcggatcac ctgaggttgg    4620
actttgaggc cagcctgacc aacatagaga accccatct ctactaaaaa cacaaaatta    4680
gccaggcgtg atggtgcatg cttgtaatcc cagctactcg ggaggctgag gcaggagaat    4740
cgcttgaacc caggaggcgg agtttgtggt gagccgagat cacaccattg cattacagcc    4800
tgggcaataa gagtgaaact ccgtctcaaa caaacaaatg aacaaacaaa acacaagtgt    4860
tgtgtgtatg ctccagacta ttcccataat attacccggg ctatgaaagc tctagatact    4920
catatctttg ccactgatgc actgccagtt gaccctatat caacttggtt ccaaccacta    4980
cccagttctt ggaaagcctt ccttttagt ttacttagga tgatttact tattttgctt    5040 tgctgttgtg gaatatatac aattgtactc tttatgtggg aacgcaagac aagcttactc    5100
aatactttct taagttggat acattaattt ccagatttc gccttttgct gggactaatt    5160
tatgaacaac cctcaccata ccgaggcttt ctgactgagt tcctctctac cttgaataaa    5220
agagactcta ataattaggc aggaatatca tcgcccctgt tcagcctaag gaagttacaa    5280
aagactgatc tttgtctatc tgccacccct aggattaagg gtcctcttat aaaggaagtg    5340
gggaaatatg tcagaggtat tcaaactaga gtaactccac cttaagtgaa gggttaagaa    5400
aacataaggc tgggacttgc tgggctgcat tcccagaaag ttaggtattc ctagcctcta    5460
gaagtttaca gttaagggaa cagattgata acatgtacta aacagaccca gacttaggag    5520
tttcctggta tcccaatatc tagagaacag aagcattcct aattttgctt taagatact    5580 aatatcaatt cttgcaaaat atagtaatta agaaaattaa accttcctcg caaactcttg    5640
tagcagagcg tatctccct tgatctattt ttgtcttata cataaacaag cattgtacct    5700
agggtgaaca cgttcctcct cttactttca ggaacgtcct actctgtcta tggagtagct    5760
gttctttcac cactttactc tcttaacaaa cttactttcg ctttgcattg ttgacccacc    5820
ctgaattctt tctgttgaga tccaagaacc ctcatttagg gtctaaattg gggcacccctt    5880 ctggtaacat ttttctggtg accatgaagg gaaaatactg aggagacccc caacccaaag    5940
gaaatagact gcagtaccaa ctagctgatt gggtaagtgg ttgggtacct gggtaaagga    6000
tgggattggg ttagaggccc aacttagggg agttagagtc ccccaacag agagagttaa    6060 agacccctct tgtaaaaggc aaggacactt gactgaacct gggttccagg cccaactttg    6120
gaaggttaga gtccttccta agatttatgg gattagagga ccctttcagt aaagttcctc    6180
```

```
ttggctaaga ataggtttgg caccagggga tgttaactgc tatgctgttt gcatttatct    6240
gccttgtcct ctttgctgca tgcatcaatt ttttggtcgc tatctctgct tcactgtcat    6300
tttcaggaga tttcatttaa ttggtcttag agattttaac tttctgttcc cctgtgtgtc    6360
tcctgattta catccatttg cttgtgaaac atcgggaaga aaaacattga aggttccatc    6420
tctaaaattg ctgatggaga tttagcattt aagcaataag attacgtgga tgtgactatg    6480
ttttgtttct aataaaactt gcttttgctt tgcattgtgg acgtgctctg aactcttcct    6540
tgtgtgagat ccgaaaaccc tctcttgggt ctggatccag actttttcc ggtaacattg      6600
gtcaggaaac tgcagtcact gtggtcattg ctgtttcctg ctgatggcct ctcaaaactg    6660
tgatgtatca tgtagcattc ttccctact tccttcaccc tgtgaccacc acctcaaata      6720
ggcttgtgtc ccacttcctg ccataacacg ttctatagga gactgcgtgg tacttgcaac    6780
ttcttggcaa tttggtgtga aaagcacaat tttcacatct acttgatcta agatggagac    6840
ccagacaatg tccatggagt tggcctgagg accaatgaca aggaccatgt tccaaagcc      6900
tccataacat ttaatccctg caacacttca gaaggctcct tctgttatta tcttcatcta    6960
tagaagggga aatgaggttg agtgaagtaa agaaacttgc ccaagatcac agtgacagag    7020
ctggaattta ctccaatgtc agtgtgatcc tttgaaacct gtctttaacc accatgtgaa    7080
taaaatcatc tcttttattc ttttacatt ccctgttcca tattagcaag agttaagtag      7140
ccagtacagc aagctccaat gttataggat gaggactttg tcttaggttt atggcttggt    7200
tttattgaac ccttgggtgc cacttgtaaa cattttccag tgtcctctaa cttggggtta    7260
gggagtgaag actaccattt atggagcttc tcgaataggt tgcatttttt ttttcttttt    7320
ttgagacgga gtctcactct gtcacccagg ctggagtgca gtggcacgat ctcggctcac    7380
tgcaagctct gtctcccagg ttcacaccat tctcctgcct cagcctcgct agtagctggg    7440
actacagggg cccaccacca cgccagctaa tttttttgt atttttagta gagacggggt      7500
ttcaccatgt tagccaggat ggtcttgatc tcctgacctc gtgatccacc cacctcggcc    7560
tcccaaagtg ctgagattac aggtgtgagc caccacaccc ggctgcattt atttacttat    7620
gtatagttta caaatattct tctttctcat ctcatttata attaactaat aaccttggaa    7680
ttattaagag attgttgttt ttaacctatt tagctgtgag aaaggctcac agaggttgtt    7740
tcttgctact taaaggttgt tcccttattt acccagctac ttgggacaat ccagaacttg    7800
atctcaagta ctggggctgc cagcctcacc ttcttgcctg tgctagaggc agttacccaa    7860
ggttcagaat tcctgaatga gtcctgaatc agagacaagt agatacctca tgcatgcacc    7920
attgtccttc cttttcaggt ttggagtgtg gtttctttta gattattgag gtctttcttc    7980
ctttgacatg acaattgtgt ttctgtcctg aaaacctggt gtgctgctgt catcctgggg    8040
cagcactgaa tacaaagttc cccagagggc aaacgctata tgaggtccca tcaaaattcc    8100
actaggaagg atgcaaacta atgcagtcaa atcttagaag cattgtgttt ggtatattgc    8160
tataaaggat tgaaacaaca ttaaacttag tgctagttac ttatatttga aggttagaac    8220
attgggtcca aatttcaatc agaagtttcc acaagtgaag tattcagcca ctcacttttt    8280
atggttctgt tatgacacaa actacttgag ttttgaaaaa caaatatttt tagccaccat    8340
tttattgaca gcttcattaa attgtcaaca attatatgaa aaattattta gcaaaagcaa    8400
acaaatgcga tcccttgtta agataactac aagaatttaa ttttttttaa atgaaaacaa    8460
gtttattaag aaagtaaagc aataaagagt ggctattcca taggcaaagc agcagcctga    8520
```

```
gctgctggtt ggccattttt atggttattt cttgattata tgctaaacaa ggggtggact    8580
attcatgagt tttctaggaa aggggtgggc aatttcctag aactgagggt tcctctcttt    8640
tttagaccat acagggtaac ttcctgatgt tgccatgaca cttgtaaact gtcatggggc    8700
tggtaagagt gtcttttagc atgctaatat attataatta gtgtataatg acgagtgaga    8760
acgacagagg tcactctcgt ctccatcttg gctttggtgg gttttagctg gcttctttac    8820
tgtaacctgt tttatcagca aggtctttat gacctgtatc ttgtgccaat ctcctatctc    8880
atcctgtgac ttcgaatgcc taacctactg gaatgcagc ccagcccagt aaacctcagc    8940
cccattttgc ctagccccta ttcaagatgg agttgctctg gttaaaacgt ctctgccata    9000 tttccccccct ccatattttt aaggaggtaa atttgagtag caaggtagta aggaacttct    9060
tgtaaaaatg gcaatatgta tcagtgattc tcccatcagg ggcaagacca tagtttggta    9120
aggcacattc tttactaggt gagagccaag gggagtgaca gcaatcacca catgaaatta    9180
ggcataattc atagtttatc tgtatagcag attgaaaacc cagaaaaaaa ttgagaaata    9240
aatattgatg taaatcatca gattttcag caaatatagt ccttgttccc cccaaaataa    9300
aacaaacatt ttatatttt aaatatttta ttttcctgtt ctttgtgaaa acatcaataa    9360
atatcgaaac ctctctgctc taacacagag ggaaacactg cataattaac attaaacaag    9420
gcagtatgcc ttacaagaaa gacataaaat gtccaaggga tatttagaac attttagttc    9480
ttaaagcttc aacatgagaa atgttgacca cacactgtga aatcatttca ataaataaca    9540
actgacattc atctttacag ttacaaaata gacacacata catttccctg ccgtcacatt    9600
gatctcactg gccatttct tggattcctc agcctctatc acagtggctg acatgtgata    9660
tgtcatcacg aagaaatatt aacaaatgac tagagaaat ctgcaaacct tctatcttca    9720
aattaaatat gaatcaggat tgaactaact tgggtttgac ctaaaataaa caataaaatat    9780 aatgggagag tgtgcaagta gattcaatca taaccttatt ttacacataa aatattaaca    9840
tagaatcttc taaacaaac aaataaataa ataaataaat aaatagaaga cttctcctaa    9900
gtgatgctca aacacattag gcgcaatcca ggtggcctct gcagctgtgt ctctctttcc    9960
tcttctgttc ctgtaagggc agggcctcct tcaggaacag ccaccaataa gcttcctcct   10020
tccttctggt cagttggatt tgccactgta atgagaaaat gggtgccctg agtaggtgct   10080
caggaaagct gactgcacaa cagtcttctc ctgtcctgtt tccccaggct ctagagtttt   10140
ctgaatgcag tttccccagc ctggcaccca agtgggtact gcctgtgaca gctgtgctgt   10200
gtggcaagga cctctaggct tgggatgctc ttttaggaat ggggtgacg tggggtggag   10260 gagtggcagt ctacactgtt ttactggcta aaacagccag agcctattgc tcttttgtcat   10320 actgggcctc acttgagcct caaagcaacc tcatgatgta gctaccatta ttttccctgt   10380
tttgctgagt ctcagataaa ctaaataata ttgtctctga gtgacatggc taataggtgg   10440
tggcaaccag ttatatatccc agtgcaatat tattgtgaaa tctctgcact tcaaccctaa   10500
acttttacaa aaaccagggg ggtctgcttt tcaggtctga aagtcagtag gaactagggg   10560
aaatgaagct tgtgtttttt aacaggtgga aaacacttca gcacaactgg caaactccaa   10620
tgagacctta catgaaagca gttttaccta cattcactgg caggagggaa gaacctgggt   10680
ggtgacccct gggcactggg aatatcctct ggcaccagaa cagattaata accttaatgg   10740
caactttaat tgtgaaaata ataattttt cagtcctgca gctaacctg ggttttcctg   10800 atttactttt taggggcag acgccagtat ttctgaccaa cagctccagt cgcctgtgta   10860
catggaaatt acaactcact ttttcagcat cttttcgatg attttcttaa cccatgggcg   10920
```

-continued

```
atgcggggtt gagacaagct ttctgcccat tcttgagtgt ggctctgcag agagaaggga    10980
atctcgtgag acaggaggtc gggctgagga cagggtttgg ggcagcggga gagtcgggga    11040
ccccagcagt ggcagcggca gcgatgggcg agacttacat gacttcggtt tgggcgcagt    11100
ggggtccggg ggacttcacc ttcacacttt ggatgttctt gaggtgaatt ccctgcaggg    11160
tctgcaagca ctggcagcgc agttcagtgg ccaggggcgc tcctagggaa gaagagactc    11220
gctgattgag cggggctgtc ggcgcggggc gcccacccca gccgcgtccg gcccggggac    11280
cccagggcgc cggggacccac ctgctgcgcg ccggctggcg gccaccagga gcaggagcag    11340
cagcgccacc cgcaggagcc ggggattgct ggggcggcg gagagcgtgg cgcgggccat    11400
ggggctcagc aggcggttcg agcggctgtg cgaggaggga agctggcaag gagctgcctg    11460
tggcccgggc tctgtggctc tccgagaacg gcgaacccct tttatgcatg gttggggctg    11520
gaaagcccgg agtcccgggc cagggaaatt cccggagctc cagatcgatc ccgagttcgg    11580
aaggaaggcg atggccccgc ctctggggtg gaggggggtc ggggcactca cgagtgacgt    11640
ccgggtctga ctgtcttgcg taactcccgc caactgtggg atgttctctt tctgccccga    11700
atccctggag cgggagcgag agcccgccgc tctcagagat accgagataa ccgcctgcga    11760
ggaggcgctt cgtgaaccca gtgcagtgcg tcgtgggtca gatcccttag acccacgtag    11820
ggaccgcgct acatccttac cgggggagt tacttctctg aagacatttt cagttgttgg    11880
gattgaaagt tagggcaaga actgcagcat gtcttatcta tcctctctct ttagtttggg    11940
ttctgcaaat tcattaatg tttgaaataa acgcacgctt taacagtaca tgtgtcatct    12000
cagatgacgc ataagagctt ttgtctcctt cctggtgttt tatgatctta aaagcaaata    12060
tcacgtgtgt gtgtgtgtgt gtgtgtgtgt gtgtgtgtgt gtgtgtgtgt gtgtgtttca    12120
acgtagtgga gccaggtgtt gggtgcggga acagaccatt gcccaagggt caattcagtg    12180
tttattttag ttaacagtgt tgcaatcccc catcctttct ctctttgaaa tcttggaaca    12240
tctcgaactc tagtaattcc agtagcatca attttttgtt gtatggaagt ctgtgttttg    12300
atccatggaa gtcactggga gctgcgaggg gcctgttggg ctcaggaggt ctgccttttc    12360
tagtgctgtc cctgggcaga aaaggccata gacaccacca gaaaaggagc agggaatgag    12420
actccgcttg tttactactc taagcacaag cagacatgtc tgatatatac atactagatt    12480
gctaacataa ttgcatttcc atgccatatg tatttaccag catcctggga ttggttccct    12540
ctagagaaac agctatcgag gaaattttag ttctagagga atgtcaataa agcatttcca    12600
agcctgttta gctgatgcct tctcactgga ttactgactt tcatcatca atttcaatga    12660 ccccctctct ttaaaaatta agctgtaggc ctacaatact ctgtcttaat tcttcctggt    12720
ggatgcagac ttcagggata tggagatatt ctgccactgc tatgagaagg gctgggagtg    12780
gcacgaggat gaagaagtgg gactacctta ggaatagagt gttccctgga tgctgcagct    12840
gtagagatca cttgataagg atgtcaggc tgaagtttca gccataccac taacttgctt    12900 catgacccctt ggtaatttat gctttatttg ctcatgtttc tccctgtag aagagcttat    12960 aatagtgcct gcctcacggg gttgttagaa gtattgattg ttaatatgtg taaaccatca    13020
gtgcatgtaa agtgttatgt aaatatttgt taaataacaa aatagaagtg gtgtttcaca    13080
accttactga tataggctgg atgtttgtgt ctctttcaaa ttcagatgat gaagccctga    13140
ctcccttatg tgctaatatt agaagacagg accatgggaa gtaattaggt ttaggtgagg    13200
ttatgaaggt atggccccca tgatgggata agtgccatta cagcaagaga tcagtgagct    13260
```

-continued

```
ttcgatctct ggctctctct cccttctgc attgtgagga cacagcaaga aggccaccat    13320
ctgcaaactg agaagagggc cctcaccaag catgaaatct gccaggatct taatcttgga    13380
ctccccagcc tccagaactg tgaaataatt gttgtttaag cccctagcc tatggcattc     13440 tgttatagca gctcaaactg actaagacac ttaactaaac agaagcactc tgataaagcc    13500
ttatgaacac acacgcac aaagaaagaa atattttcaa agaaacatct tctaatttac      13560
ctttaaaatt tttcagcatc agaaattta aaggagggtg catttctatc cttatgggat     13620
cttacaataa ttttttgatc cattgttgt ttgaaatttt agtttcaatc acttccaca      13680 taaaatgaga ataagagtaa aattctaccc tatccattta ttagaaaaga tttatgaaat    13740
gactctgcct tgggcattaa cagctagctg cccaaacttc tttattttgt gctaaagaac    13800
taaagaacaa tagaaaacat cagcttataa tgattgccag actcatccca aagtattgat    13860
gtgagtaaat agaagagta aaatttctat tatctacagt aacagtccct caaaaagatg     13920
agaaatttca agaatcagcc catcatttgt aaaattatgt acgttattcc tagaatttgt    13980
ttactaaaaa ttatttgctt taggaaggga agtagaattc cttttctttt cttaatata    14040 ccactttcca tgatttaact tatgacagcc ccagaccaag cttctgaagt ttttaagggt    14100
accagtgtta tgaaacttac cataataaat tccttcttgt cttaatatga gttgagtgcc    14160
actgttacag gcacaagttg taaacccatg caattactaa ctcaaagatg ctatctctaa    14220
aatggaagta cagtttccta aattccattc tccccttaa ttttattgt atttttcaga      14280 tttgactagt acaatctaat atacctgcaa aatgtaggct tgctgctcca tgccgaccac    14340
tgacattctt gttacttggg cagcaaaatg agtggtgtgg ctctgctta ccgtgaattg      14400 ccttgaagac tttgctgata taacctccaa catatagctt gctcctctag aggaacagac    14460
tagaaaataa ataagaagt acaactgatt ttagagatag atctgatgga ggttgagata     14520
tggggctctg gaattacaga atagaagaca gataacatgg ttcatgataa gacttgttag    14580
tcctcacact gtttatgctt agtgactcct ttgctttcag gttttgctgc cacgcataca    14640
aagtggacag tggtacaacc cctttgttgt gtctgactgc atgaagaaat acataattga    14700
cttagttaca tactatgtgt atttcttgtt atttttttca ctaaagaatt aaggcagtct    14760
ctcaatgacc agagcctagg aatacttcct agtattataa acattgcaat tgacatgttc    14820 tgtgggctt ttgtgatttt ttgaaaactg tggtttatat tcattgtgct aaagttttcc     14880
ttactggctc tggcacccg gctttgggtt gtggtcctgc ggaagaaaca ttcttccttg     14940
tctgtggttc tttagtggat tgcttgttag ctcagggatt gtggccacca ctcatcgaaa    15000
catgtgctct ggagataaag cgccaaagga aagaaggga agtaatattt atttattaga     15060
ttccaattct tgattagatg cagtgcctga gttttcagt gtactgtcat tttaataatt      15120
tcaagaatgc tgggaggctg gtatcatgag tcttatttta taggtaagga aactggagta    15180
caaggtctta gaagtggaat taaattcaaa cccaagactg tctgactcag aagctcatag    15240
ccagtctttc tctagacaag aaaggaagtg acaggagaag aagaggacat gtaaaagaat    15300
cttaattaag tctatggagg atattttatt atttttcaac cctaccagaa acaatgcat     15360 ttattaaaat atttaataca gttttgatta ggaaccaaac agacatgtag aagtgatgac    15420
aactagtagc ctccagagtc ccagcagccc agagaatctc ctgcttattg tgccgtcagc    15480
ccccaaattc attccatgaa gttcccagca actcccaaca ccatatcaga atctgatatt    15540
atgattgaag gcaggctggg agtggtgtct cacacctgta attccagcac tctgggaagc    15600
caagacagta ggatcacttg aggccaggag ttcaaaacca gcctgagcaa gatagtgaga    15660
```

-continued

```
ccctgtctttt atggaaaaaa aaaaattgaa ggcagatggt agcgtaggta aaggatctag    15720
ctaagcatct tacctctagc agctcttaaa gtatcttaga aggcactaat aagaaggtag    15780
ataccactat aaactgttaa aggttggtct gtcatcaaga gactagagca atatttcaat    15840
atgtataaac tacaagtcat gatccactgg agggtcataa agtcagtttt gtgggttgta    15900
accagtattt aaaatataa  aggggcagtg gctcatgcct gtaatcccag aactttggga    15960
ggccaaggcg ggcagatcag gagaccaaga gattgagacc atcctggcca acatggtaaa    16020
accctgtctc tactaaaaat acaaaaaaaa aaattagccg ggcatagtgg caggtgcctg    16080
tagtcccagc tacttgggag gctgaggcag gagaatagct tgaacctggg aggaagaggt    16140
tgcagtgagc tgagattgca cctctgcact ccagcctggc aacagagcga gactccacct    16200
aaaaaaaata taattgtata tatacataca catatatata tgaataaaat aggatagaat    16260
tttaaaatgc atgtgccata atgcatcaca tattgttagt ttaactgtta ttttatgaca    16320
cttttgtgtc ttatatagat aggtaactgt gtaaaactaa acatttgatg cacaagatgc    16380
aaaaacagaa ctcccaggag tgaaaatatc ccttcagaga cgttattata ttgatcaagg    16440
ctgtgactat ataataagtt cccagtttgt agacattatc tcctgagaat tccaatcag    16500 gaaaaaaaag ttgaagcata ttccatttta atgtcatcac tccctaaaag tttgcacaac    16560
agggagttcc agtaaattgc tgagcttttc ccagcaggaa tgccaggttc ggatgttcct    16620
gctgataagg gtggccactt ggcagtgttc tcagcagagt tgaaagatta acatagtacc    16680
agtattggtt cgcttagcag aatttgtttc agtcccttgg tcatttgggc cacaccgacg    16740
aattattata tccagctatg aatgttgctt gtggcaggta caaagggaa ataaagaaaa    16800 tattaaacct taatacttta ccattgtcac cctacttcct ggtgtgttaa ttttcaaaa    16860 aaaatcagtg gaagtacctg ttcaatttta acattctttg tttattttg ccaaaatctt    16920 tgtcttttct aagtgtctaa ctcaacctac caaattatct atgacagtac acaaataaca    16980
atatactaat atgaaaatta taattatgaa taataactaa taataacaaa aatgctcttt    17040 tgtactttt atatctggaa gagggctgag attttgcatg catgtgcata tgtgtgtgca    17100
tgtgtgtgtg tgtgtatgtg tataatatct ccttacatgt agacacaaac tcaagagata    17160
gatactcaaa atatgcccat ttttcacatt atgaaaccaa ggtatctgcc atactaacaa    17220
aattggaact caaatatgg  gtgaaagaga actttgaat  gtttatacgt atgtgagtga    17280
catggttgta tttgtatttt agcaaaataa cttttgtggc attgaaggta aaatgcaggg    17340
gaaatattta ggttacctgg gatcattttg atatttccca aaattgtttc taagattat    17400 tattgtgggt ccacaatacc ccttagtttt ggattaattt gacccacaga aggtattgag    17460 gcaataccttt tctgaaaact ccatatttga gcctgaagca tgctttgact ttttcaagac    17520
caatatgaat tttatatgct aacaatgtaa ccacattctt tgtttctatt atagaatttt    17580 attgaatta  atacatatat tattaattta taatacataa attatttgtt ggatacaaat    17640
tgaaagtctt tggactacag aggagtttct gtaataatat atttatctgg gatgtaatcc    17700
ttttctgtta catctttact gtcattttt  tctctacttt gcgtgcatat ccatgataaa    17760
aataggtaga aaatacagtt ttgtgagata aacattgtt agctctcttg tatacctgca    17820
acaattacac ttggaacaaa acaataacgg tggctatatt ttaaatttta aggtcccaac    17880
agtcccgtat aaaagtctaa tctctacggt ccttaaactc atttccttta aatcagatta    17940
aatttgacta tatgccttca ttccaccaag gagaaaacta ttcaatctca gtcattattg    18000
```

-continued

```
tagctcccag accacactga aagtacaaaa ggtcccaagg gatttatcca agcaaaatat    18060
tcagggctgt ccatctgtac tttgacttat acttgttttc cataaaagga caaacattga    18120
tatggtcatt ttaagtgcag cactgtccag ctcttatcca ttctgtagca cagaaatctt    18180
tgctaaggtt ggtaataaca gtgcttggta atctcttaag tacaaagtac agtctttctt    18240
ccagagtcct gccacctccc tggaaggaga gagcagcaag gagaaacaaa actgttaatt    18300
ttggcagtgt gtgaaacact gtgatggccc cttttccctt cccactcctc cctccctgtg    18360
gcacacagcc aggaagcaga tgaaggatag ttcgtgagtt caaaaagaag gggagatttg    18420
agagtggtaa gaaaaataaa ataatgaatg attctcaaga gagggaaaag agaggcacat    18480
ccaagggatt tgaggttact tagctaactt tgaaagtttt gccaactggt agtccaagat    18540
tcaggaatga ggattttgaa atgagaaata aagttaaagt agctgaaaag gtggaatgga    18600
gactaggagc tacttctgtg ctccagtgcc cttctggttc tatattttct tcttgcctta    18660
ttcagatgtt tgccaaacta acattcaggc catgtaggac attgactaca ctgtctctcc    18720
tcttcctcag tgcagttcta aggctacaca tatactcaac cactggactt atttattaaa    18780
cagcaaccat atttccagga ttgagggagc cactgagatc cagaaatcaa agtgtctatt    18840
ccttccctca caagagccac actctggttg agcagacagg gatgtcaaca ggtggtaata    18900
acccagtgtt tatgctaggc attgtgtatg attacatatg taaggaactg gggataaaaa    18960
gaagggcaaa atactgaatt tgtccttaaa gtgcttaaat tctaaaatgt agaataaaca    19020 attttttaa aaaatgtat tatgttatgg tcagttccat atgggtcca ttactgctct      19080 tagactcagg aaagaaggtc ccctgtcct gagcctaagc ttcagaagat ctcactagca    19140
caaccttgca aaaaaccac aaatgtatta gagaacccg ggggcactt ctgccacctg      19200 aggaaccaga gcctagagtg ggcgccaaat gaccccttaac ctcctaaact tccttaacac   19260
tagatactta ctttcttgat taacgaagtt caagcccaag gctgagatcc cagagggaca   19320
cagtggggag cctaaagaat aatgatcatg gtggttgagc tcccttctgt tctctttggc    19380
tctggaatga ctatgaggag ctcaaagcat atttacaaac caaaattttc acagggaact    19440
tggccgaaga agcttggaaa aagtcaagag gaccatgtat ccttactgcc gactatttcc    19500
acattttcca catctttttc tgagatcagt taataagcat aaccctaagg aatcagtcca   19560
ccagatgctt tttaatttat tctgaaagct cagtgtctag gtaacttacc acagctgaca    19620
tattacaatg tgtgaatata gcatcaaatg tatgctttgt ttctgcatcc aagtagtgct    19680
ttaggaatct tattgtcatt gcattagaag agtaaaatgt ctccaaattt aaattaatta    19740
taaataaatg taagaaatga ttgaagcatc atctaaaatg gcactattgt ctatagaaca    19800
aaaattatgt gaccatttca attataaaaa tgtaattact aattttgctg aagtgaagaa    19860
aaataaattt tatataataa atatagaata atagaataaa tcttaaatta tgcatgattt    19920
tattttgtat gcatccagac attgcctaca caataacaga atacccagat atggaattac    19980
aaattcactt ttctctgata ttttgctgat tctcatcata caaattccat aactttatat    20040 attttaaaa tgttattaat atatggtcat gtgtcacatg aagatcagaa cgcattctgc     20100
aaaatctggc attaggctgt ttcctccttg tgtgaacatc ttagagtcca cttatgcaaa    20160
cccagatggt gtagcctact ccacacctat gctatatgct ctattctatt ctcccaggct    20220
acaaggctgt acatcatgtt gctgtactga atacttaggc aattgtaaca caacagtatt    20280
tgtgtatcta aacacacaaa ggatacagta aatatatata ttaatagtac tgtaatccta    20340
tgtcctcacc attgtgtatt ccaactgtag ttgtccaaaa tgtcattatg tagtgcatga    20400
```

-continued

```
ctgtatatct gtgaagacag gaagatcctc agactcattt tatttaacat tttgttagct    20460
agttaagaaa accgtaaata tttagacaga gaatcatggg cttctctgaa ctctctctca    20520
agaccccaca attgttagat atggcctcat gaagcattga agagtgcata tggaggaaaa    20580
ttatgaaaaa ttatcctaga acagatgact gaaaagatga attttggaaa aaatctaggt    20640
tattataaca tattttaatt tgtactaatt ttgacacccc ctcagaggaa ttttttatgtt    20700 tttgaaacaa gaattatttc tgtttttatc tacacacaga gttcatttta taagtgcttg    20760
gaacccaaca gagcttaatg aattgaatag gatgttcttg ggaaagagag tatagataat    20820
acgcttcaat agttaagaca tcaggtgaga aagccattaa ttttagttaa aattaccatt    20880
ttaattagtc attttatgat aacatagaca atggaagatg attaagaaaa atgaagaatc    20940
agcatttctt gattcttcaa tagacacttg aaaaactaca acacaaggaa acccactgt    21000 ttgatggtct aagatcctat cccactatgc tgacatttgt caaaacactt aaattgtttg    21060
gtttaaagaa actcctttt atccctgcta ctaatacaaa gaatatactt gtgtttgttc    21120
attgaagagt ttctaagtat tagaatttca gcaacaggaa attcatttct caacttgtat    21180
tcttcacaca aaaggcatca aattgctcat gagttaatag gttgacagct attgtcattt    21240
cctggtggga aactttcata gttagaggaa aagaaggctg aacaccagat gctgttcatc    21300
atgtattttg ggatatgttc ttgaaggtct gagatttaca ctgaatttat aaagcaatgc    21360
cattgagtca agtagagaag aatctagatt atagaacaag gctgtgaagt cagatggttg    21420
tgccaacagt gtctgctgtg cagaaccttt agctcccact tctctctcac atgcactgag    21480
tcagaaaatg ctattttgta ggctgtagct acttgtcagg tttatgactc aacaaactga    21540
aatattagcc aaatgaaata ttgttgtgca attcagggtg ctcactcata gcacatacag    21600
tgttgaatat aatcatctat agcttcaaat gtgctggtca tgagtccact aagaaatgca    21660 gaaagaagc aagaggagaa acagtctgac cttagctgca aagggcacca ggatgccagc    21720
atgctagagt catgctggtt tccccttca tggaagtgac aggcccatga caaatttacg    21780
caaatatgac atggaaaata atttcttgaa gaaaacttct ttttgccatat gtttcctggt    21840 tttcttctgg tttggcctgt gaatggtatc agtttatttt cgagtctagt atccaatatt    21900
cctggaagct agggctgagg aatgttcatt tcacaggatg gccaaggtct gatatgcaag    21960
gctgggattg agtgaggccc cagggcaggc tgagaacagg aagcggtttc actgacattc    22020
cattcctttc tctccctgac cactcccatc tcagagtggc caaggatcac tgaagaaata    22080
gtaattgtca tctaaacctc ataacagggg tgtctggcac ttgagagttg acccacttca    22140
atttattcaa gctcccactc aaaaaaactc tccttgactt acaggatatg aataccaatt    22200
ccctaaagca aagcatagtg agaatttcag taaaagaaaa gaaacgaaaa ccccagaaaa    22260
agtattcagt aattgaagag tcaccatccc gagggtccta taggagctca cccttggtcg    22320
gtgagaacta ctcagtcagc ctcacttacc tcattgctct ggccagctca tacaggctta    22380
caagagcagg ttattaaatg gtcaggaatt ttgatagcca gttattcatt gttggaagca    22440
taaatttgac cacagtggga gtgtttatgg aaatcagcaa atgctacaaa tctgatttt    22500 ttttaaattt gaaagctgtt ttaccaacac accgcggctt atagctctgc ataaacataa    22560
tctgtatcaa ctttatcctc ttttcctcc ccttactata gcctctgtcc tctgccctca    22620
ttatcctctg ctgggatctc ttgaatattt tttccccttt agctggtttt ctctttcact    22680
cattgatttg tcctgggttt catcatctag gcaactctca cgcacagaaa attcttggga    22740
```

-continued

```
gttgttctca ctagactgat agcaatacca cttttattta ttattattat tattattatt    22800
attttgaaac aagcaaaggc tctaggaatg aaatactaga agatgaagga ttttttttctt   22860 ctggatcata aatctgggca tcccatgcct acatgttctg ggactcatga ggcattctat    22920
tgatccccaa attgctatta atagatacca agtgaaaatt tggtatctct tcccatcagc    22980
cctaatctca gaatgcatta tcttttctaa gcaacaactg aagcctgtgt gcactagcag    23040
ttaaatgtgt atctgcagga ggtttaaata ttcctaagtg aatgtgggaa gtggtagtgt    23100
attttggaat tcaagggatc ttagaaataa tgtagtctaa tttgctcatt agtctggtga    23160
gtaaacagag tttcagacag attagcagtt agtggtagaa tcagtactag aattcagatc    23220
cctggcttcc tcttctgggc attttcaaat ctgcaacaat gtctatctta attaacatta    23280
taattaggac caagataatc ttcattcaac tcaacaaata ttttttgact accagatata    23340
tttctatgtg cacttatttt atactaggta ctgttccagg agttgagact accaagaagt    23400
tctctacttt ttagagcatt cttttgagaa ctaacattat ttgtattagt atgacttaac    23460
tctttgttcc aggaaattct tacatagaaa ataaaactaa gctcatggag aactttgcca    23520
tttgcttgag gaaattcttc taagtcagtt tattcaggac atcagtttgc acatctgagc    23580
cagcagatca ctcctcagac aagttcgctt tttctagcaa gaccctcacc tgttttgtcc    23640
actaactcta ttatgtcaac aactgtgccc aattccagtc cattccctac cttgtcagat    23700 cagtttaaa cattttgagt ccaattctct gaacatcctc cttctgagac actaaaatgc     23760
tgtcagagca ttgttcctcc tgttgagtaa ttctaataaa tttaacgttt cctgattgaa    23820 ggggttttt gttgttgttg ttggtagtat ttctgatgaa ttggcagttg atatgttcta     23880
ttggagacta gaacataaga atggggaagg tgatacttat aataatctat ctgggtatag    23940
ttaggatctt cacatgccac actatgtagt gacataattt gacctggaaa tagctggtca    24000
cattggctat attgatagca acaggagata gacaaattct taggcagaca ggggatgcgt    24060
ccctggtaaa acctgatctc caagccaaag acagcctgaa gactgaaaac tgagctgcca    24120
gttcggggta gagcccatga ccagagtgag aatttcctcg atgccttta gccaatataa     24180 tgatgctttt tccaggccca cccatggacc aatcagcata cactccccca ttctgaaccc    24240
ataaaaaccc caaactcagc cttacagaca gccacctgct tttgggcctc ctctcacaca    24300
gaggaccatc cacttcaagt cccctcttgt gttgagagct tttctgccac tcaggaaaat    24360
tcttctctgc tttgctcact ctccggtgtc tgtgtacgtc attcttcttg gtcacaggac    24420
aagaacccgg aacatgccaa aagggtgtaa cacatactcc tgctcactga gttacaggag    24480
tgaaaaaaac cactgggtgc cgcatgcccc tatttagcag gtacaaatga gctgtaacac    24540
aacacacccc catcctccaa gctgcaggca gcagggagag ctgtaacatg cctccatcct    24600
ccgagctgca ggctcaaaga agtgaagcag ttaggcacta ttccctcctg gccagcttgc    24660
tgaactacaa aagctgcaac atttcttggg agcttagacc tcaggattcc ccaggcgaga    24720
gctgtaacat cacctgggc tccacagttg ctggcatctc tgagttttca ggtgccactg     24780
cattcccctc atctagactc cggctcccaa tgcaaaagct gcctgtggca tgccaagttt    24840
agccacaggc aaaacacaga gtccctgttc agatgtggga tccaagcagg tagcacaagc    24900
tgagtacagc ccatcaggct gagtgggaag agtgagccca gcaggccttg gcaagactac    24960
aggcagaggt cacagcagcc acagagattt ccagctggtg aagcagcact gaaggagtcc    25020
tgtaacagta tgttagtcta caaacttggt aaattctcat tctctgtttt ctgtgacatt    25080
ttgattttaa aaattttatt ctccaataca tcgcaaggac tggatatcct gccctctatt    25140
```

```
ttgaaagtat ggtgtccaaa ttcataggag aaggcaaggg taggtgactc agaaggcaca   25200
cacacaaaaa agagtcattg gaggaacaac ccaggaagcc atagaagaat gttatcccaa   25260
actagatgga aaagttttgt ttttatgtaa tttagaaaaa cattcttatt atttatttgc   25320
ttaaagtttg tcaccatttt ttcaaatttt ttttatagaa tgccatccta tttaaactac   25380
tatccacaac atgaaatata gttaccacaa acataaaaat agccaagtgg tggaatgggg   25440
aggagggacc ctgaactgtt gaccaggagg tggcctctgg taagcctcac catacccttga  25500 tgaaagagcc ctcaaaactc tccatctcct ttgactttaa ttctgtacaa tcttctaatt   25560
tagatactga tatagtttgg atgtttgtcc actccaaatc tcatgtggaa atgtgattcc   25620
caatgttgga ggtggggtct ggtgggaggg gaatggatct tggggacaga ttccttatga   25680
atcgcttagc accattcccc ttggtgataa gtgagttctt gctcagttag ctcatgtgag   25740
atctggttgt agagtctggg accttccctc ttctctcttt tgatctctct ctcaccatgt   25800
gacaatcact gctctccctt tttcttttgc cgtgattgta agtttcctga ggccctcacc   25860
agaagcagtt gctgaagtca tgcttgcata gcctgcagaa ccatgagcca attaaacctc   25920
tttcctttat aagttaccca gtcatggtta ttcctttata gtgctttata gtcctttata   25980
gtgactcata aatggcccaa tacaggtact tagccttttg gttaaaagat accaacacat   26040
aggtgactag attgcagatc attggcattt tgaattgttt tttaagtacc catattactg   26100
tggtttacgc caaattgaat ctattatgta gaaatatgcc tataaaacta cttttcaaatt  26160 tgtacaaata tcagtttctc aaagcgtata tatatatata tatgcatgca tgtgtatgtg   26220
tctgtttaaa atacacctgc tgggattag cattgagctg aaagacaagg tcctgcccctt   26280 gccctagaag agtttgcagt gtagatggag accacctgac acctcacctg atccctgata   26340
gcaattccag gccaactttc ctaagcacta tgggaattca gactaagggc cagatcaccg   26400
ttgcctgaga ttccattgtg atgttagaat tcacattctc attcttattc aatagaactg   26460
actcgttcac cagagcacct actatgttcc aggtggtatc ataagaactt gggagacatc   26520
actaaacaaa atagaaaaat ccctgccctt atggagctga cattctagtg ggggcttggt   26580
ttttttcctt gggtactggg tttgtttttc catgatgagc atatcctatg atgcactata   26640
gcactcaagc aagatgcctg aagcaaagga ggtgagtcac catcactggg ataaaaaaac   26700
aggtcagaga agtagaagtt attttctctt ataattttaa attttgcctt aagctcttct   26760
tttgaaatgt tctaggccaa agtaatgatt catggattca gcacactttc ctttgttgaa   26820
aagcactgct tgttcccccct caaagctatg tgagaggctg tgtaggagag agtggagagc   26880
aggtagccta ccggacctac agttcaccat ttcagccctg taattgacca gctgtgggac   26940
ctcaggtaag ctggctaacc tctctcttac caatggtaga tgactatgaa agctccaaac   27000
tctctcacaa acataggaga ttattagcat acaaattaat gtctaggttt gtgggtcttg   27060
aggcttcagt ggaggtcatg ggcaaagctg caaagagcat gggaattaaa atacatgctc   27120
caggataggc agtgtgctgg cttttctat ggattaattc atttgattct cacaccaacc   27180
tcaaaaagaa ggattattag cccttgatag atgaggtaac tgggactcag agaagttgtg   27240
gagccaggat tctagatcaa agcattaagt ctttgcttct gtgctctttc accttggcca   27300
ggcagctgcc cttgcccagt aaatggtaca tcacagtaag tgttttatta aaatgccatt   27360
tccctgaaac aaagaaatga tggtattagg ggagggcaa gggagacatt ttgagaatat   27420
ttaagtatat atgatgacta tttcttcttc aaatatctat ctggtataaa actactattc   27480
```

```
tgttactcta attattttt  gaccatagga gagactgcga cagaaattcc attagtggat  27540
ttgagattga gtttagaata tttatttaag tagagctaag tgtggcaata tctgtcatat  27600
ctattagttt ggagaaatga agaagctttt ttagttatag atccagacac caatgctaat  27660
accaaatact acagccagtg ttcttctgtc gccatagttg ttacaagtat gacagcctcc  27720
caagtcattt attgattcaa ctccctttt  gttttaatgt tgacacacta gtttgtatga  27780
acaatgagca cactagctca gaagaggaca acaagaatta gcgcggatgg ttcttcccct  27840 tgaggggtg  ctctgtcagt atgaacatgc cttcatgggc agaaattagg agcccactag  27900
ctgttaatga agagtgcttt gctttccttt cagacagcag tttccaaagt tcctcttctc  27960
ctttaatggc attgcccttt agtgtgtgtt aacctgtggt ttgaaagaaa tactcgtgta  28020
tattagcaat gtaaatataa gtgattaaat taaattacat ttatcaataa aaatagctat  28080
tatcgatagc tgaatgcata agtatgcag  catcacatac ggatgaactc accgtttgtc  28140
gtgctactac aggtacatgc tctacaaaca cagaaattct gatattctat gaaacattat  28200
taaattccaa ttgaacatga tcattccaat caaataaggg gaaaaaatat aaagtatttg  28260
taatcaaaga ccctgtattg ttgagtatat tcctgaaggg gagggtttg  ttttgtctag  28320 gattgatata aagtgaatta tctgcttatg attttcact  ctgattattg gaataatatt  28380
ctccacacta gctcctggat ctgtgcattt caaccttgtc tcttccatac ctgcatcatt  28440
ttggtattgt gtatattagg acacattctg atttctgcat cagaacgctg agtgagtgtg  28500
cacagtaagc aaaggagtat acctgggagc cagtctcaca ccaggatggc tagtaaaaac  28560
agaaccattc ataacataac tgtcaaccaa taaaatacat atcactaaag ctaaactaaa  28620
ttcgagtacc ctcaactcaa cttcccccag ccacatctca aaaacatgac tagctactcc  28680
aacatcaccc aatataagga gaactgtaaa gaaataaagt cagagtgaga gaaaaaaaag  28740
cagtcctaat caacttgatt aaatatatga cttcacagca aattgcataa aactatatga  28800
ccacatgagc acattcctag gccctcccaa ggccctgaaa aaagcctgaa ctagggaggg  28860
gctctaatta gctaatgat  acacttacct atgattgtgg ttatgtcttg atttatctga  28920
ttggcattgt tttttaaatt atctaaaagt gttcatcctt attttaggt  tagcaactgt  28980 gaccctagtg actagtaaca gtaacaaatg aaagaagatg ctcttgtatg gccaaaacga  29040
tgaaacagac ctacatgatt ttatgaaaag ttttccttgg cttggttca  aagagatttt  29100 tctttccttg acactaaagt ggtagtttgc actaggcata tagataccgt tctatctttc  29160
tggttctcca cttaaatgac actcatgtct gctacattaa aattagcttg ttaggtttta  29220
tttcaccaag tttataaagt aaaccacata tcgttttctc ttttgtagat gctgaaagca  29280
aagttcatgt gggaaatgtt tggcaatagc tgatttatcc tcagggtaac aatattctat  29340
aactcctttg atcttgaggc ctctgtgatg gaaatgcttg gagaaaggga ttttaagg  g  29400 agattctgaa gtccttggga aagtccacaa gtggacgggg cttcatagcc atgacaacaa  29460
atgacattgt ctaggaaaca gtgagtcatg gcatgctgag cttagaatgg agccaacaga  29520
aggaacctgg cctcggacac agaatctttt ggctgctgac ccagaatgac tgtgaaagac  29580
taacactgtt tagcagattt ttcttgagtg tttactatgt gtgaggttcc tgggattcag  29640
attcagctac tattgttaag aggaaatcaa ccaggaagtc agttaagaaa aggtacagtg  29700
ggttttcagg ctgcagggta cagaaatgtt cccaggcctg gagaacaaac cttcagatct  29760
taatctgtac agggaggtgg agggtgaaag aatgatcttt caggaagcgt tcaagtaggg  29820
ctgctgcttg gattgaattt taagaatgc  ataggttata tgcaggatct atatatagat  29880
```

```
caatagcttc cctgagcaca tgttcaaagg ttcaaacatt tggggtcatt tctttgcaag    29940
aagagtcact cagtggcctg aaagtccatg cagcaacttc cctcatgaga gctgcttccg    30000
cagcaggccc agggtttcta aaggagagag cacacagatg taaacactct gtggttctga    30060
ggactgtcac ctcttctttt cacccatcac ttttgtctta agaactctat gctcaaccct    30120
aattctcagt ctctatatca attcccacca aacagatgca aagtcctgtc catttgcttc    30180
catgaactct gtacttatcg atgatataat actctgctga ctacatttta cttgccactt    30240
catatcctca ctagactgaa agacctataa gggaagagat atcttattta tatatctttc    30300
ttatatatct ttcccatata tcctatttac tgttgtactt acaactccta caaccgtgct    30360
tggtacatag ggtgttgaaa aagtatttat gaaattatga ataacactga ttctattaaa    30420
taacattatt aagttaatga acaaataatt aagcttagta aaatatcaaa agttaaagat    30480
atcaaaaact aaacacttat agaataaaag tttgcttttc ttgtctagtg agcacattaa    30540
tacagatttt aaccctcttt tgtcctctcc tgattcacac gaaaaaatac ataggcctca    30600
gctgttcatt ggtgccagat aaaaataaag tactttttaa ttgtaattac tgcaaaggct    30660
cttcaacagt gcacagtata ccaggaactg aaacttttct tataaaacaa aataaatatc    30720
agtagaaaca gagcaaaggc atttcattaa gtattatgga ctgaattgca ttccctgtaa    30780
atgtgttaaa gtctgaactc tcagtacacc tcagaatata actgtattta gaaatagggc    30840
ctttaaagag gtagttaaga ttaaatgaga tcatgtggat tggtcttaat ctaagatgac    30900
tggtgtcatt ataagaagag gagaagacac cagagatgca accgcacaga gaaaaggtca    30960
tgtgagcagg gatccccaaa ccctgagcca agaactgaca gtggtccatg gcttgttagg    31020
aaccatgcca cacagcagga ggtgagccaa aggcaaggga gcaaagcttc atctgtattt    31080
atagccgctc cccattgctc acattacctc ctgagctctg cctcctgtcg gatcagtggt    31140
ggcattagat tctcatagga gtgcacaccc tattgtgaac tgcgcatgag agggatctag    31200
attgcatgct ccttataaag tctaatgcct gatgatctga ggtggagctg aggtggtgat    31260
gctagctctg aggagtggtt gcaaacacag attaacatta gcagagaggt ttgactgccc    31320
agagaccata ataaatcagt tgcctgcaga cgcatatcaa aaccctgtca gtgagtggca    31380
ggtgataatt cagctgcatc tggtggctgg cttttatagt gcaagtgcgt tgatgtactt    31440
caactgtaca gctgcatctg gttgctggct ttatagtggc aagtgagttg atgtacttca    31500
actgtacagc tgcatctggt ggcaggcttt aagtcagaat ctgacactta ttttagtcca    31560
tgtgtgtcct gcccattatt ttatttgtca cttccatccg cacctctttc ctgcactgca    31620
cacttgtctc aatcagtttt ggtaagccca caagctaacc ctagccaaaa tgaataaaaa    31680
caatcatcac tggagagttt ctttgaaaag tgggaaagaa ccaatgatga gacagcagaa    31740
gactctaaga ctgccaacaa aaagaaagct gcatttaaaa gaaaatactg gccgggcgcg    31800
gtggctcatg cctgtaatcc caggactttg ggaggccgag gcgggcggat cacgaggtca    31860
ggagattgag accatcctgg ctaacaaggt gaaacccgt ctctactaaa aatacaaaaa    31920
attagccggg catggtggcg ggtgtctgta gtcccagcta ctcaggaggc tgaagcagga    31980
gaatggcgtg aacctgagag gcagagcttc agtgagccg agatcgtgcc actgcactcc    32040
agcctgggtg acagagcgag actccatctc aaaaaaaaac aaaaaaaaca aaataccatg    32100
agtcctactt aaattacagg gtcattgcac cagataattc acattctcca agccctcttt    32160
ttataatatg tggtggttgg ctatgcaatg aagccatgaa accttcagaa ctgcttcact    32220
```

```
gcatggaaac caagcaccct gtgttaaaca agactttgga gttttttcaaa agaaaaaaaa   32280 aagatgaaca agaagaacag aagcaattat tgaaggccac cattttatca aatgtgtctg   32340
tactgacagc atcatatcat tcgtagtggc taaccacatt gctaaagtta agaagcccttt   32400 tgctattggt gaagagttga ttttgcctgc tgctaagggt atatgtcatg aactttcagg   32460
agaggctgca gttcaaaagg tggcatgtgt ttctcatttg gctagcacat aactaaatga   32520
ttagatgaaa tagcagagaa tgttgaggta caattgttac agagagttaa tgagccaccg   32580
cagtacatga ttcaggttga tgagtctacc aatgttggta aggcaacaat gcttactttt   32640
gtgcaatata ttttttcagaa gatgtgcatg aggatatgtt atgtgcactt ttgttgccaa   32700
ctaataccat agctgcagaa ctattcaagt ctttgaatga ttgcatatca ggaaaactca   32760
attggtcatt ttgtgtcagt atatgcatgg acggaccgac tgccatgact ggacagcttt   32820
ctggtttcac tacttgggtc aatgaggtca cttctgaatg taactcttca cactgtgtca   32880
tccgtagaga aatgtcggct agccaaaaaa tgtcacctaa atttaacaat gttttgcaag   32940
gtgtgattaa aattattaac cacattaaag tgcatgccct taactcatat ctgttcacac   33000
agctctgcaa ggagatggac acagagcaca cagtcttctc ttatatacat aagtgagatg   33060
gctttctaaa ggtagatcac tggccagagt gtttgagtta tgagagccac tccagagact   33120
tcttttagaa aaacagacac cactggcagc acatttcagt gacacagaat gggttaaaaa   33180
acttgcttac ttgtgtgaca tattcaacct gttcagggaa ttcaatcttt cacttcagag   33240
gaaaatgaca gctgtgttca agttggcaga tagaggggct gcattcaaag ccaaagtgga   33300
attatggggg caacaagtga acagtgagat ttttgacatg ttccaaaatt agcaaagatt   33360
ttgaaaaaga ctgagccatg gccttctttc tcccagctag tgcatgatca cctgtctcag   33420 cttctcaaaag agtttaagca ttattttcta actacaaaag accctagaac tgggaaggaa   33480
tgaatctgtg acccatttgt gaataagcca agtgaactga ctttgtccat cctagaagag   33540
gatcaactgc ttgagatggc aaatgacaat gcccttaaaa gtatgtttga gacaacttca   33600
aatctccata cattctggat taaagtcaag gtggaatatc ctgagattgc cacaaaagta   33660
ctgaaaatcc tgcttccatt tccaatatcc tatctttgtg aagtagggtt ttctgcagcg   33720
acagcaacca caatgagatt atggagtaga ctggacataa gcaatatact gcaggtgtca   33780
ctgcctccca tcacctgcac atgggactat ctagttgcag gaaaacaagc ttagggctct   33840
cactgattct acattatggt gagttgtata attatttaat tatatataat taattattta   33900
attatatata attaattatt taattataca tatataatta tatataatta aatatatatt   33960
taattatata atatataaaa atatataatt atttaattat atatatggcg agttgtataa   34020
ttatatatta taaatgtaat aataatagaa ataaagtata caataaatgt aaatgcactt   34080
gaattatccc taaagcatcc ccttatccca atccacagaa aaatagtctt ctatgaaatt   34140
ggtccctggt gccaaaaagg ttgggggcca ttgcatgtga ggacacaatg agaaggcaac   34200
tatcttcaag ccaaggagag agtccctcaga aaaatatcaa acctgttgaa accttgatct   34260
tggacttcca gcctctagaa ctgtgagaaa ataaattcct gttgtgtaag ccacccagtc   34320
tgtggcattt tgttacagca gccctagcaa actaatatat tcagcaattc ttttttttttt   34380 ctaggacata aacatatttt aatgtcctac ttcctgggga gaaatccttt taattatttt   34440
tgtgtatttg gaaatagggg ttgtattcca aattgtagtc taccataaag aactacctga   34500
ggctgggtaa tttataagga aaagaggttt aattgactca caattctgca ggctgtacag   34560
gaagcatggc tggaaagcca caggaaactt ataatcatgg tagaaggtga agggggaaaca   34620
```

```
agcacatctt cacatggtga caggagagag agagagtgaa tggggaagtg ccacacactt    34680
ttacaccacc agatctcatg ataattcact gtcatgagaa gagcaagggg gaaatccatc    34740
cccatgactt aatcacctca caccaggtac ctccccaac actgggaatt acaattcaac     34800
ttgggatttg ggtggggaca cagagccaac cataacaggg atatattata ataaaacgta    34860
ctgagaggta cacaacagca ccctggaata ttgctgccaa aaatggacct aatcataagg    34920
aaacatcaga taaattcaaa ttgaggaatt gttccagaat aaacaagact aaagcaacat    34980
gacaactaaa tgcaatactt gaatctgcat tggatcctga aacagttta tctatctatc     35040 catccattta tccacccata acggtaaagg atattattgg gataattgtc ataatttgaa    35100
taaaatctat agattaggta ttagcattac atcaccatta atttcctagt tttgatagtt    35160
gtattctgct tttataagag aattttcttg ttcttaggaa atactggata atctgggcaa    35220
aaaaattctg gaattcttta gactcttctt tcaacttttc catataagtt ttaagtttat    35280
ttcaaagtat gaatgctata aaattaggaa ttcaaacaaa ataatcaaa ttgagaggtg     35340 tgtacattta acaaaacagt tatattaaat caggttaaat tttaagcatg ctgaaaattt    35400
gctgagacct gggagtgttt gtttctgcca gtgttagttt caaagtgcat agtggcatat    35460
tgaattttgt gtaatttcca gtaacatagt gcaaggatga gtagccacac acatttagtg    35520
ttgcaataat ataaaaagcc tcaggagcac tccagccagc acaacaagtc cccagggaca    35580
gctaagcact ccagtgtcta gggactgtgg gaaactggaa agaaacaatc cagtgtaaat    35640
atgacttcta agctggctgt tgctctactg ctttcttggc agttgcatgc tttctgtagc    35700
actgtgtgaa ggtaggctca tcttctaat caatagagtt ttcttttgtc taaatatgat     35760
tctccgaaag caaggctatc caaatgctt tgagatttgc ttattaaaac aaaaaaaat      35820 ccccatttgc attcatttga tgttgtcatg agtacaaaat aacttttgtg ggccttagac    35880
attttaccct ttgtgggact cttcagccat cataatatca atacttaaaa tttttttatg    35940
taacttagaa tgcttcaaca ttttttctgt tttaggtaaa atttaggga ttttatggg      36000 ccctaaaaat ttctttattt ctgttgtgag aaaaaataa cactttctta gattctaaaa    36060
cttcatgttt ttcttccgac tttaaaggca attaaaacaa tttcatgggc ttctaaaatt    36120
attgtgggcc ctaggcacta tgcctactgg ccctaatgca taagttaccc ctaatttgca    36180
ttaaatttgg aattatttag gttctatctc tatacctctc agaaaagtgt aatatttgca    36240
ttgatgtaga catttagttg ctaaaattca caacttgtcc tataacacat atatcactat    36300
atatacttat attcatttat aatttatatt atattccatt gggggcaca gttggttaat    36360 attgcctgtt aaaattgaac taggtaacca cgtattttta ctcagtgttc tgctgacaaa    36420
ggcttagaca gtaatcattt tctgcctgct ttgaagagtt ttgatgggcc ctagaccatc    36480
ttaagatcct gctatataac aaatagtgtg tttttagcat gcgttttctg tatttgcttt    36540
ttcgttttat cagcattaaa agttttttt taaaaaaat acaagtcatc tctgtaaaat      36600
agtcatgttt ctgtttattc tttctgaagg tgatatatct gttgataaga tcattgttta    36660
tctcctataa ataacattat agcatcatga agaatactgc aaaatcaaat agaagaatgg    36720
ccatatggat ataaaatatt aattttaata aatttatagt tttatgtatt tatatattta    36780
tatattagtt tttatattga cattcaaaat agtcagtgag aatcattttg aaagaaagga    36840
aattaatttc aagggttggt ctaaaactag tcttctatt tgtagcaacc tgtttcgtta     36900
agacatttct catggtccta aaaatcatca tattcaaatt taagggtat ctagcagagt     36960
```

-continued

```
tgtgccctttt gatgaaagca gtccttactt ccttgctatg ttcactgctt ccattgtgcc    37020
aagtattagt acagtaccac aatgccagtg catgaggaca cattttatac ctttgcatcc    37080
caaatttatt aaagaactca gaattattca gagtggatta tattataaaa attaagaaat    37140
catgtaagta cttcaaaag ttcttagtta ttttgcttct gtacatgtag actgtttagg    37200
tgctgagagt acaatggtaa acagaacagc aaaaaaaaaa aattctgtct ttacaaataa    37260
cttggtactg acatctggtt agttttagct attgtgtctc ccttgcttct gaattccaga    37320
gcaatacttt cattttttga tataagcaaa ttctaaaaca cattgtgggg aggtagataa    37380
tctgacattt tgcagagtta aagtaattag agaagcacaa gaaagtttcg aaaatgataa    37440
ttaaatttga aataggaatt agcatgagtg aagcaactcc aggtacatgg tgattaaccc    37500
aagtaatatg actccaggta tcctgggaat tcctttcact gtgaaagctg caatcagtgg    37560
cctttggaaa agtaagtggg gttcctgcag ctcccagaaa attgtgaaaa atcctgttg     37620 ggatcatttc catttaccac tgagccaaat gaccatgatt tccaactgca aagggatatc    37680
taaaaccaga taagtaattt acctaagtag tctttttcac tctttagtgt gaagcttatt    37740
catgaagaga cctctgcctg aacatacagc aaatttaaga aggttgtgca gatagtctga    37800
aggaggtgag ttagtttttc ccactttctc aaatttctca aatttcattt gtcatgaaac    37860
taataggaaa gattcacaaa tgtcagttta agagttttac ctaatggaat ctcactttta    37920 ttttatttttt tgcttctatt taaaagcttt tttttcaatg atagaaaaaa tgctagcgat    37980
agtaatttgc ttttttaata atggaaaatg tagagcaata tagcaaacct caagagtat    38040 tgatttctca aaacaaaagc ataacaaaat ttgtttattc tcttttaatt tatggtttta    38100 aaaatttac ttgtatttag aaataaggaa aaatgaataa gaaaaaatta aagagcattc     38160
ttccatggtt tccaagaatt tcttattaaa tatgttaaca aaactcgaag tgaataaaag    38220
ttagagctat agcctatgct attggatacc cacccatatc atctgatctg caccacttca    38280
atgctcactg ttttgtcttc caagggcttt ctctggttac cagcgtccac tatactagca    38340
aggcccaggt tggaaatatt ggaaaattaa tggccttggg cgcagtcttt aactaatgac    38400
ccactaaagc agtgtactgt aagtcctcac ttaacctcat caataaattc ttggaaactg    38460
tgactttaaa tgaaatgaat agcaaaacag attttattat aacttatttg atagaaataa    38520
tagttaagtt tctaaggcat atttctagtc acaaaacatc atcaaactgc caaataaaga    38580
tcaaaataat tctaatatta aacactgaaa tatatgtgaa ctatatatac atttcggaaa    38640
gattaataaa aagaagataa ttactcaatt tttggtgaat ctgtgagtga caaaggtcat    38700
agtagtggtg ggtgatgtgg ggagggatgt ttactcctta tcctagtgag gagtaaacat    38760
gagtcttcca atatccacac cttgctgtcc atcatcaaat ctcttaaaat atctagtttt    38820
gtttctaatg tcacactttt tctctggtgt gtgtgtgtgt ggccatagac gtaagaagag    38880
gtggatagtg caactttaaa gtttattaca acaaagttaa gtcagggaat gaatatgtaa    38940
gaagcacccc ctaccagtat ataattcaaa aacaaacata aaaaatatgg tgccctccct    39000
gagctcatac gatatctttt attgtcatgt acttgtatga ttattgtata ctttatattt    39060 tttattttt tcattaatac ataatagatg tacatatttt ggggatactt gtgataatct    39120
gatacattca tgatatggtt tggctgtttc cccatccaaa tctcatcttg aatttcagtt    39180
cccataatcc ccatgtgtcg aggaagggac ccggtgggag gtaattgaat catgggggcg    39240 atttcccca tgtcgttctc ctgatagtga atgagttatc atgaggtctg atggttttac      39300
aagaggcttc ccctttgact tggcactcat tctctgtcct gccgctccgt gaagaggtgc    39360
```

-continued

```
attctgccat gattgtaagt ttcctgaggc ctccccggcc ctgccgaact gtgagtcaat    39420
tatgcctctt ttctttataa attgcccagt ttgggggcag ttttttatag cagtgtgaga    39480
ctgaattaat acaatcaaat cagggtaatt gggatgtaca tcaccttaaa tactttctt     39540 tgtgccagga acatttgaat tattctcttc tagctatttt gaaatgtaca atagattgac    39600
ttaccctact gaactatgga acacaatgtc ttatttcttt caattaactg tatagttgtc    39660
ctcactattc aatctctgtt cttcctcctc acttccaaca attcttggcc ttggtaacca    39720
tcaatctact ctctatcttc atgatatcta cttttgtgtc tcccacatat gagtgagaat    39780
aggccatatt tgtctctctg tgcttggctt atttcactta acataatgac ctccagttcc    39840
atctatgttg ctgcaaatga caggattgca ttagttgttg tggctgaaaa atattcaatt    39900
atgtatatat accacagttt ctttatacac tcatccattg atggacactt aggttgatta    39960
catattttgt ctattgtgaa tagtgctgca ataaatatgg gattgcagat acctctttga    40020
tataccgatt ttctttcttt tggatatata cccagtagtt aattgctggg tcatgtgtag    40080
ttctattttc agttttggga ggaacctcca taccgttttt catagtggtc atttaatttt    40140
actttcccac caacatgtat gagggtttcc ctttctctcc atcctcgcca gcatctgtta    40200
ttacctgtca ttttgataaa ggccattgta agtgggtta gatgatatct cattgtggtt     40260
tggatttgca tttttctggt gactagtgat gttgagtatt ttttcatat aactgttggc     40320 catttgtatg ccttcatttg agaaatgtct gttcagatct gttgtccgtt ttaaaatcag    40380
attattttgt tttgcgctat tgaattgttg gagctcctta tatattcttg ttactaatac    40440
ttgtgaaatg gatagtttat aaaaattttc tcccattctg tctctttact ttggtgattg    40500
tttttcttgc tgtgcagaag ctttttagct ttatgtaatc tcaattgtca attttttgttc    40560 ttattgcctg tgctttgccc agcccaatgt cctagaatgt ttccccaatg ttttcttcta    40620
gtagcttcat agtttcaggt cttagattta agtctttaat tcattttgat tacattttg     40680 tatagcctga gacatagggg tctaatttca ctctatgcat atggttatcc agttttccca    40740
gcaccattta tgaaagagac tgcccttccc ccattgtcta ttcttggtgt ctttgtaaaa    40800
aatgacttgg ctataaatgt gtttattgat atctgggttc tctattctat tccattagtg    40860
tacatgtctg tttttctacc aaccatgcta atttggttac ataccttttg tagtatgttt    40920
taaagttgga tagtgtgatg cttccagctt tgtgttttt actcaggatt gctttggcta     40980
ttcagggaat tttttagtgt gtggttctat gtaaatttga gaatttttt ctatttatgg     41040 gaagaaagtc agaattttga cagggattgc attgaatctc taaattgctt gtcattcttg    41100
```

<210> SEQ ID NO 47
<211> LENGTH: 85
<212> TYPE: PRT
<213> ORGANISM: Homo sapiens

<400> SEQUENCE: 47

```
Met Thr Ser Lys Leu Ala Val Ala Leu Leu Leu Gly Ser Cys Met
  1               5                  10                  15

Leu Ser Val Ala Leu Cys Glu Val Pro Ser Ile Ser Thr Val Pro Gln
                 20                  25                  30

Cys Gln Cys Met Arg Thr His Phe Ile Pro Leu His Pro Lys Phe Ile
             35                  40                  45

Lys Glu Leu Arg Ile Ile Gln Val Leu Ser Lys Val Leu Ser Tyr Phe
         50                  55                  60
```

```
Ala Ser Val His Val Asp Cys Leu Gly Ala Glu Ser Thr Met Val Asn
 65                  70                  75                  80

Arg Thr Ala Lys Lys
                 85

<210> SEQ ID NO 48
<211> LENGTH: 91
<212> TYPE: PRT
<213> ORGANISM: Homo sapiens

<400> SEQUENCE: 48

Met Thr Ser Lys Leu Ala Val Ala Leu Leu Ala Ala Phe Leu Ile Ser
  1               5                  10                  15

Ala Ala Leu Cys Glu Gly Ala Val Leu Pro Arg Ser Ala Lys Glu Leu
                 20                  25                  30

Arg Cys Gln Cys Ile Lys Thr Tyr Ser Lys Pro Phe His Pro Lys Phe
             35                  40                  45

Ile Lys Glu Leu Arg Val Ile Glu Ser Gly Pro His Cys Ala Asn Thr
 50                  55                  60

Glu Ile Ile Val Lys Leu Ser Asp Gly Arg Glu Leu Cys Leu Asp Pro
 65                  70                  75                  80

Lys Glu Asn Trp Val Gln Arg Val Val Glu Lys
                 85                  90

<210> SEQ ID NO 49
<211> LENGTH: 85
<212> TYPE: PRT
<213> ORGANISM: Homo sapiens

<400> SEQUENCE: 49

Met Thr Ser Lys Leu Ala Val Ala Leu Leu Leu Gly Ser Cys Met
  1               5                  10                  15

Leu Ser Val Ala Leu Cys Glu Val Pro Ser Ile Ser Thr Val Pro Gln
                 20                  25                  30

Cys Gln Cys Met Arg Thr His Phe Ile Pro Leu His Pro Lys Phe Ile
             35                  40                  45

Lys Glu Leu Arg Ile Ile Gln Val Leu Ser Lys Val Leu Ser Tyr Phe
 50                  55                  60

Ala Ser Val His Val Asp Cys Leu Gly Ala Glu Ser Thr Met Val Asn
 65                  70                  75                  80

Arg Thr Ala Lys Lys
                 85

<210> SEQ ID NO 50
<211> LENGTH: 91
<212> TYPE: PRT
<213> ORGANISM: Homo sapiens

<400> SEQUENCE: 50

Met Thr Ser Lys Leu Ala Val Ala Leu Leu Ala Ala Phe Leu Ile Ser
  1               5                  10                  15

Ala Ala Leu Cys Glu Gly Ala Val Leu Pro Arg Ser Ala Lys Glu Leu
                 20                  25                  30

Arg Cys Gln Cys Ile Lys Thr Tyr Ser Lys Pro Phe His Pro Lys Phe
             35                  40                  45

Ile Lys Glu Leu Arg Val Ile Glu Ser Gly Pro His Cys Ala Asn Thr
 50                  55                  60

Glu Ile Ile Val Lys Leu Ser Asp Gly Arg Glu Leu Cys Leu Asp Pro
```

```
                65                  70                  75                  80
Lys Glu Asn Trp Val Gln Arg Val Val Glu Lys
                    85                  90
```

<210> SEQ ID NO 51
<211> LENGTH: 55
<212> TYPE: PRT
<213> ORGANISM: Homo sapiens

<400> SEQUENCE: 51

```
Met Thr Ser Lys Leu Ala Val Ala Leu Leu Leu Gly Ser Cys Met
 1               5                  10                  15
Leu Ser Val Ala Leu Cys Glu Val Pro Ser Ile Ser Thr Val Pro Gln
                20                  25                  30
Cys Gln Cys Met Arg Thr His Phe Ile Pro Leu His Pro Lys Phe Ile
                35                  40                  45
Lys Glu Leu Arg Ile Ile Gln
                50                  55
```

<210> SEQ ID NO 52
<211> LENGTH: 58
<212> TYPE: PRT
<213> ORGANISM: Homo sapiens

<400> SEQUENCE: 52

```
Met Thr Ser Lys Leu Ala Val Ala Leu Leu Ala Phe Leu Ile Ser
 1               5                  10                  15
Ala Ala Leu Cys Glu Gly Ala Val Leu Pro Arg Ser Ala Lys Glu Leu
                20                  25                  30
Arg Cys Gln Cys Ile Lys Thr Tyr Ser Lys Pro Phe His Pro Lys Phe
                35                  40                  45
Ile Lys Glu Leu Arg Val Ile Glu Ser Gly
                50                  55
```

<210> SEQ ID NO 53
<211> LENGTH: 56
<212> TYPE: PRT
<213> ORGANISM: Homo sapiens

<400> SEQUENCE: 53

```
Met Thr Ser Lys Leu Ala Val Ala Phe Leu Ala Val Phe Leu Leu Ser
 1               5                  10                  15
Ala Ala Leu Cys Glu Ala Asp Val Leu Ala Arg Val Ser Ala Glu Leu
                20                  25                  30
Arg Cys Gln Cys Ile Asn Thr His Ser Thr Pro Phe His Pro Lys Phe
                35                  40                  45
Ile Lys Glu Leu Arg Val Ile Glu
                50                  55
```

<210> SEQ ID NO 54
<211> LENGTH: 58
<212> TYPE: PRT
<213> ORGANISM: Homo sapiens

<400> SEQUENCE: 54

```
Met Thr Ser Lys Leu Ala Val Ala Leu Leu Ala Ala Phe Leu Ile Ser
 1               5                  10                  15
Ala Ala Leu Cys Glu Gly Ala Val Leu Pro Arg Ser Ala Lys Glu Leu
                20                  25                  30
```

```
Arg Cys Gln Cys Ile Lys Thr Tyr Ser Lys Pro Phe His Pro Lys Phe
            35                  40                  45

Ile Lys Glu Leu Arg Val Ile Glu Ser Gly
 50                  55

<210> SEQ ID NO 55
<211> LENGTH: 414
<212> TYPE: PRT
<213> ORGANISM: Homo sapiens

<400> SEQUENCE: 55

Met Asn Pro Thr Leu Gly Leu Ala Ile Phe Leu Ala Val Leu Leu Thr
 1               5                  10                  15

Val Lys Gly Leu Leu Lys Pro Ser Phe Ser Pro Arg Asn Tyr Lys Ala
             20                  25                  30

Leu Ser Glu Val Gln Gly Trp Lys Gln Arg Met Ala Ala Lys Glu Leu
         35                  40                  45

Ala Arg Gln Asn Met Asp Leu Gly Phe Lys Leu Leu Lys Lys Leu Ala
     50                  55                  60

Phe Tyr Asn Pro Gly Arg Asn Ile Phe Leu Ser Pro Leu Ser Ile Ser
 65                  70                  75                  80

Thr Ala Phe Ser Met Leu Cys Leu Gly Ala Gln Asp Ser Thr Leu Asp
                 85                  90                  95

Glu Ile Lys Gln Gly Phe Asn Phe Arg Lys Met Pro Glu Lys Asp Leu
            100                 105                 110

His Glu Gly Phe His Tyr Ile Ile His Glu Leu Thr Gln Lys Thr Gln
        115                 120                 125

Asp Leu Lys Leu Ser Ile Gly Asn Thr Leu Phe Ile Asp Gln Arg Leu
    130                 135                 140

Gln Pro Gln Arg Lys Phe Leu Glu Asp Ala Lys Asn Phe Tyr Ser Ala
145                 150                 155                 160

Glu Thr Ile Leu Thr Asn Phe Gln Asn Leu Glu Met Ala Gln Lys Gln
                165                 170                 175

Ile Asn Asp Phe Ile Ser Gln Lys Thr His Gly Lys Ile Asn Asn Leu
            180                 185                 190

Ile Glu Asn Ile Asp Pro Gly Thr Val Met Leu Leu Ala Asn Tyr Ile
        195                 200                 205

Phe Phe Arg Ala Arg Trp Lys His Glu Phe Asp Pro Asn Val Thr Lys
    210                 215                 220

Glu Glu Asp Phe Phe Leu Glu Lys Asn Ser Ser Val Lys Val Pro Met
225                 230                 235                 240

Met Phe Arg Ser Gly Ile Tyr Gln Val Gly Tyr Asp Asp Lys Leu Ser
                245                 250                 255

Cys Thr Ile Leu Glu Ile Pro Tyr Gln Lys Asn Ile Thr Ala Ile Phe
            260                 265                 270

Ile Leu Pro Asp Glu Gly Lys Leu Lys His Leu Glu Lys Gly Leu Gln
        275                 280                 285

Val Asp Thr Phe Ser Arg Trp Lys Thr Leu Leu Ser Arg Arg Val Val
    290                 295                 300

Asp Val Ser Val Pro Arg Leu His Met Thr Gly Thr Phe Asp Leu Lys
305                 310                 315                 320

Lys Thr Leu Ser Tyr Ile Gly Val Ser Lys Ile Phe Glu Glu His Gly
                325                 330                 335

Asp Leu Thr Lys Ile Ala Pro His Arg Ser Leu Lys Val Gly Glu Ala
            340                 345                 350
```

```
Val His Lys Ala Glu Leu Lys Met Asp Glu Arg Gly Thr Glu Gly Ala
        355                 360                 365

Ala Gly Thr Gly Ala Gln Thr Leu Pro Met Glu Thr Pro Leu Val Val
    370                 375                 380

Lys Ile Asp Lys Pro Tyr Leu Leu Ile Tyr Ser Glu Lys Ile Pro
385                 390                 395                 400

Ser Val Leu Phe Leu Gly Lys Ile Val Asn Pro Ile Gly Lys
                405                 410

<210> SEQ ID NO 56
<211> LENGTH: 414
<212> TYPE: PRT
<213> ORGANISM: Homo sapiens

<400> SEQUENCE: 56

Met Asn Pro Thr Leu Gly Leu Ala Ile Phe Leu Ala Val Leu Leu Thr
1               5                   10                  15

Val Lys Gly Leu Leu Lys Pro Ser Phe Ser Pro Arg Asn Tyr Lys Ala
                20                  25                  30

Leu Ser Glu Val Gln Gly Trp Lys Gln Arg Met Ala Ala Lys Glu Leu
            35                  40                  45

Ala Arg Gln Asn Met Asp Leu Gly Phe Lys Leu Leu Lys Lys Leu Ala
        50                  55                  60

Phe Tyr Asn Pro Gly Arg Asn Ile Phe Leu Ser Pro Leu Ser Ile Ser
65                  70                  75                  80

Thr Ala Phe Ser Met Leu Cys Leu Gly Ala Gln Asp Ser Thr Leu Asp
                85                  90                  95

Glu Ile Lys Gln Gly Phe Asn Phe Arg Lys Met Pro Glu Lys Asp Leu
            100                 105                 110

His Glu Gly Phe His Tyr Ile Ile His Glu Leu Thr Gln Lys Thr Gln
        115                 120                 125

Asp Leu Lys Leu Ser Ile Gly Asn Thr Leu Phe Ile Asp Gln Arg Leu
    130                 135                 140

Gln Pro Gln Arg Lys Phe Leu Glu Asp Ala Lys Asn Phe Tyr Ser Ala
145                 150                 155                 160

Glu Thr Ile Leu Thr Asn Phe Gln Asn Leu Glu Met Ala Gln Lys Gln
                165                 170                 175

Ile Asn Asp Phe Ile Ser Gln Lys Thr His Gly Lys Ile Asn Asn Leu
            180                 185                 190

Ile Glu Asn Ile Asp Pro Gly Thr Val Met Leu Leu Ala Asn Tyr Ile
        195                 200                 205

Phe Phe Arg Ala Arg Trp Lys His Glu Phe Asp Pro Asn Val Thr Lys
    210                 215                 220

Glu Glu Asp Phe Phe Leu Glu Lys Asn Ser Ser Val Lys Val Pro Met
225                 230                 235                 240

Met Phe Arg Ser Gly Ile Tyr Gln Val Gly Tyr Asp Asp Lys Leu Ser
                245                 250                 255

Cys Thr Ile Leu Glu Ile Pro Tyr Gln Lys Asn Ile Thr Ala Ile Phe
            260                 265                 270

Ile Leu Pro Asp Glu Gly Lys Leu Lys His Leu Glu Lys Gly Leu Gln
        275                 280                 285

Val Asp Thr Phe Ser Arg Trp Lys Thr Leu Leu Ser Arg Arg Val Val
    290                 295                 300

Asp Val Ser Val Pro Arg Leu His Met Thr Gly Thr Phe Asp Leu Lys
```

```
305                 310                 315                 320
Lys Thr Leu Ser Tyr Ile Gly Val Ser Lys Ile Phe Glu His Gly
                325                 330                 335

Asp Leu Thr Lys Ile Ala Pro His Arg Ser Leu Lys Val Gly Glu Ala
                340                 345                 350

Val His Lys Ala Glu Leu Lys Met Asp Glu Arg Gly Thr Glu Gly Ala
                355                 360                 365

Ala Gly Thr Gly Ala Gln Thr Leu Pro Met Glu Thr Pro Leu Val Val
            370                 375                 380

Lys Ile Asp Lys Pro Tyr Leu Leu Ile Tyr Ser Glu Lys Ile Pro
385                 390                 395                 400

Ser Val Leu Phe Leu Gly Lys Ile Val Asn Pro Ile Gly Lys
                405                 410
```

<210> SEQ ID NO 57
<211> LENGTH: 361
<212> TYPE: PRT
<213> ORGANISM: Homo sapiens
<220> FEATURE:
<221> NAME/KEY: VARIANT
<222> LOCATION: (1)..(361)
<223> OTHER INFORMATION: Wherein Xaa is any amino acid as defined in the specification

<400> SEQUENCE: 57

```
Asp Leu Gly Phe Lys Leu Leu Lys Lys Leu Ala Phe Tyr Asn Pro Gly
 1               5                  10                  15

Arg Asn Ile Phe Leu Ser Pro Leu Ser Ile Ser Thr Ala Phe Ser Met
                20                  25                  30

Leu Cys Leu Gly Ala Gln Asp Ser Thr Leu Asp Glu Ile Lys Gln Gly
            35                  40                  45

Phe Asn Phe Arg Lys Met Pro Glu Lys Asp Leu His Glu Gly Phe His
        50                  55                  60

Tyr Ile Ile His Glu Leu Thr Gln Lys Thr Gln Asp Leu Lys Leu Ser
 65                 70                  75                  80

Ile Gly Asn Thr Leu Phe Ile Asp Gln Arg Leu Gln Pro Gln Arg Lys
                85                  90                  95

Phe Leu Glu Asp Ala Lys Asn Phe Tyr Ser Ala Glu Thr Ile Leu Thr
            100                 105                 110

Asn Phe Gln Asn Leu Glu Met Ala Gln Lys Gln Ile Asn Asp Phe Ile
        115                 120                 125

Ser Gln Lys Thr His Gly Lys Ile Asn Asn Leu Ile Glu Asn Ile Asp
    130                 135                 140

Pro Gly Thr Val Met Leu Leu Ala Asn Tyr Ile Phe Phe Arg Ala Arg
145                 150                 155                 160

Trp Lys His Glu Phe Asp Pro Asn Val Thr Lys Glu Glu Asp Phe Phe
                165                 170                 175

Leu Glu Lys Asn Ser Ser Val Lys Val Pro Met Met Phe Arg Ser Gly
            180                 185                 190

Ile Tyr Gln Val Gly Tyr Asp Asp Lys Leu Ser Cys Thr Ile Leu Glu
        195                 200                 205

Ile Pro Tyr Gln Lys Asn Ile Thr Ala Ile Phe Ile Leu Pro Asp Glu
    210                 215                 220

Gly Lys Leu Lys His Leu Glu Lys Gly Leu Gln Val Asp Thr Phe Ser
225                 230                 235                 240

Arg Trp Lys Thr Leu Leu Ser Arg Arg Val Val Asp Val Ser Val Pro
```

```
                    245                 250                 255
Arg Leu His Met Thr Gly Thr Phe Asp Leu Lys Lys Thr Leu Ser Tyr
                260                 265                 270

Ile Gly Val Ser Lys Ile Phe Glu Glu His Gly Asp Leu Thr Lys Ile
            275                 280                 285

Ala Pro His Arg Ser Leu Lys Val Gly Glu Ala Val His Lys Ala Glu
        290                 295                 300

Leu Lys Met Asp Glu Arg Xaa Xaa Xaa Xaa Xaa Xaa Xaa Xaa
305                 310                 315                 320

Xaa Xaa Leu Pro Met Glu Thr Pro Leu Val Lys Ile Asp Lys Pro
            325                 330                 335

Tyr Leu Leu Ile Tyr Ser Glu Lys Ile Pro Ser Val Leu Phe Leu
        340                 345                 350

Gly Lys Ile Val Asn Pro Ile Gly Lys
            355                 360

<210> SEQ ID NO 58
<211> LENGTH: 363
<212> TYPE: PRT
<213> ORGANISM: Homo sapiens

<400> SEQUENCE: 58

Glu Phe Ala Phe Ser Leu Tyr Arg Gln Leu Ala His Gln Ser Asn Ser
 1               5                  10                  15

Thr Asn Ile Phe Phe Ser Pro Val Ser Ile Ala Thr Ala Phe Ala Met
             20                  25                  30

Leu Ser Leu Gly Thr Lys Ala Asp Thr Gln Ser Glu Ile Leu Glu Gly
         35                  40                  45

Leu Asn Phe Asn Leu Thr Glu Ile Pro Gln Ala Gln Val His Glu Gly
     50                  55                  60

Phe Gln Glu Leu Leu Arg Thr Leu Asn Lys Pro Asp Ser Gln Leu Gln
 65                  70                  75                  80

Leu Thr Thr Gly Asn Gly Leu Phe Leu Asn Lys Ser Leu Lys Val Val
                 85                  90                  95

Asp Lys Phe Leu Glu Asp Val Lys Asn Leu Tyr His Ser Glu Ala Phe
            100                 105                 110

Ser Val Asn Phe Gln Asp Thr Glu Glu Ala Lys Lys Gln Ile Asn Asn
        115                 120                 125

Tyr Val Glu Lys Gly Thr Gln Gly Lys Val Val Asp Leu Val Lys Glu
    130                 135                 140

Leu Asp Arg Asp Thr Val Phe Ala Leu Val Asn Tyr Ile Phe Phe Lys
145                 150                 155                 160

Gly Lys Trp Glu Arg Pro Phe Glu Val Glu Ala Thr Glu Glu Glu Asp
                165                 170                 175

Phe His Val Asp Gln Ala Thr Thr Val Lys Val Pro Met Met Arg Arg
            180                 185                 190

Leu Gly Met Phe Asn Ile Tyr His Cys Glu Lys Leu Ser Ser Trp Val
        195                 200                 205

Leu Leu Met Lys Tyr Leu Gly Asn Ala Thr Ala Ile Phe Phe Leu Pro
    210                 215                 220

Asp Gln Gly Lys Leu Gln His Leu Glu Asn Glu Leu Thr His Asp Ile
225                 230                 235                 240

Ile Thr Lys Phe Leu Glu Asn Glu Asn Arg Arg Ser Ala Asn Leu His
                245                 250                 255
```

```
Leu Pro Lys Leu Ala Ile Thr Gly Thr Tyr Asp Leu Lys Thr Val Leu
            260                 265                 270
Gly His Leu Gly Ile Thr Lys Val Phe Ser Asn Gly Ala Asp Leu Ser
            275                 280                 285
Gly Val Thr Glu Asp Ala Pro Leu Lys Leu Ser Lys Ala Val His Lys
            290                 295                 300
Ala Val Leu Thr Ile Asp Glu Lys Gly Thr Glu Ala Ala Gly Ala Met
305                 310                 315                 320
Phe Leu Glu Ala Ile Pro Met Ser Ile Pro Pro Glu Val Lys Phe Asn
                325                 330                 335
Lys Pro Phe Val Phe Leu Met Ile Glu Gln Asn Thr Lys Ser Pro Leu
            340                 345                 350
Phe Ile Gly Lys Val Val Asn Pro Thr Gln Lys
            355                 360

<210> SEQ ID NO 59
<211> LENGTH: 1090
<212> TYPE: DNA
<213> ORGANISM: Homo sapiens

<400> SEQUENCE: 59
cggatgctgg cccggaggaa gccgatgctg ccggcgctca ccatcaaccc taccatcgcc      60
gagggcccgt ccccaaccag cgagggcgcc tccgaggcaa acctggtgga cctgcagaag     120
aagctggagg agctggaact tgacgagcag cagaagcggc tggaagcctt tctcacccag     180
aaagccaagg tcggcgaact caaagacgat gacttcgaaa ggacctcaga gctggacgcg     240
ggcaacggcg gggtggtcac caaagtccag cacagaccct cgggcctcat catgccaggg     300
aagctgatcc accttgagat caagccggcc atccggaacc agatcatccg cgagcaccag     360
gtcctgcacg agtgcaactc accgtacatc gtgggcttct acggggcctt ctactgtgac     420
agggagatca gcatctgcat ggagcacatg gatgcggct cctggaccg ggggctgaaa       480
gaggccaaga ggattcccga ggacatcctg ggaaagtca gcattgcggt tctccggggc      540
ttggcgtacc tccgagagaa gcaccagatc atgcaccgaa atgtgaagcc ctccaacatc     600
ctcgtgaact ctagagggga gatcaagctg tgtgacttcg gggtgagcgg ccagctcatc     660
gactccatgg ccaactcctt cgtgggcacg cgctcctaca tggctccgga gcggttgcag     720
ggcacacatt actcggtgca gtcggtcatc tggagcatgg acctgtccct ggtggagctg     780
gccatcgaaa ggtaccccat ccccccgccc gacgccaagg agctggaggc catctttggc     840
cagcccgtgg tcgacaggga agaagagag cctcacagca tctcctcttg gccagggtcc      900
cccggcgcc caacagcgg ttacggatg gacagcctgc ccgccatggc catcttcgaa        960
ctgctggact atattgtgaa agagccgcct cctaagctgc caacggtgt gttcaccccc     1020
gacttccagg agtttgtcaa taaatgcctc atcaaaaacc aacggagcg ggcggaccta    1080
aagatgctca                                                          1090

<210> SEQ ID NO 60
<211> LENGTH: 1090
<212> TYPE: DNA
<213> ORGANISM: Homo sapiens

<400> SEQUENCE: 60
cggatgctgg cccggaggaa gccgatgctg ccggcgctca ccatcaaccc taccatcgcc      60
gagggcccgt ccccaaccag cgagggcgcc tccgaggcaa acctggtgga cctgcagaag     120
```

```
aagctggagg agctggaact tgacgagcag cagaagcggc tggaagcctt tctcacccag    180
aaagccaagg tcggcgaact caaagacgat gacttcgaaa ggacctcaga gctggacgcg    240
ggcaacggcg gggtggtcac caaagtccag cacagaccct cgggcctcat catggccagg    300
aagctgatcc accttgagat caagccggcc atccggaacc agatcatccg cgagcaccag    360
gtcctgcacg agtgcaactc accgtacatc gtgggcttct acgggccttc tactgtgac    420 agggagatca gcatctgcat ggagcacatg gatgcggct ccctggacca ggggctgaaa    480
gaggccaaga ggattcccga ggacatcctg gggaaagtca gcattgcggt tctccggggc    540
ttggcgtacc tccgagagaa gcaccagatc atgcaccgaa atgtgaagcc ctccaacatc    600
ctcgtgaact ctagagggga gatcaagctg tgtgacttcg gggtgagcgg ccagctcatc    660
gactccatgg ccaactcctt cgtgggcacg cgctcctaca tggctccgga gcggttgcag    720
ggcacacatt actcggtgca gtcggtcatc tggagcatgg acctgtccct ggtgagctg    780 gccatcgaaa ggtaccccat cccccgccc gacgccaagg agctggaggc catctttggc    840
cagcccgtgg tcgacaggga agaaggagag cctcacagca tctcctcttg gccagggtcc    900
cccgggcgcc caacagcgg ttacgggatg gacagcctgc ccgccatggc catcttcgaa    960
ctgctggact atattgtgaa agagccgcct cctaagctgc caacggtgt gttcaccccc   1020 gacttccagg agtttgtcaa taaatgcctc atcaaaaacc caacgagcg ggcggaccta   1080 aagatgctca                                                          1090

<210> SEQ ID NO 61
<211> LENGTH: 1088
<212> TYPE: DNA
<213> ORGANISM: Homo sapiens

<400> SEQUENCE: 61
gatgctggcc cggaggaagc cgatgctgcc ggcgctcacc atcaacccta ccatcgccga    60
gggcccgtcc ccaaccagcg agggcgcctc cgaggcaaac ctggtggacc tgcagaagaa   120
gctggaggag ctggaacttg acgagcagca gaagcggctg gaagcctttc tcacccagaa   180
agccaaggtc ggcgaactca agacgatga cttcgaaagg acctcagagc tggacgcggg   240
caacggcggt gtggtcacca agtccagca cagaccctcg gcctcatca tggccaggaa   300 gctgatccac cttgagatca gccggccat ccggaaccag atcatccgcg agcaccaggt   360
cctgcacgag tgcaactcac cgtacatcgt gggcttctac ggggcttct actgtgacag   420 ggagatcagc atctgcatgg agcacatgga tgcggctcc ctggaccagg gctgaaaga   480 ggccaagagg attcccgagg acatcctggg gaaagtcagc attgcggttc tccggggctt   540
ggcgtacctc cgagagaagc accagatcat gcaccgaaat gtgaagccct ccaacatcct   600
cgtgaactct agaggggaga tcaagctgtg tgacttcggg gtgagcggcc agctcatcga   660
ctccatggcc aactccttcg tgggcacgcg ctcctacatg gctccggagc ggttgcaggg   720
cacacattac tcggtgcagt cggtcatctg gagcatggac ctgtccctgg tgagctggc   780 catcgaaagg taccccatcc cccgcccga cgccaaggag ctggaggcca tctttggcca   840
gcccgtggtc gacagggaag aaggagagc tcacagcatc tcctcttggc cagggtcccc   900
cgggcgcccc aacagcggtt acgggatgga cagcctgccc gccatggcca tcttcgaact   960
gctggactat attgtgaaag agccgcctcc taagctgccc aacggtgtgt tcaccccga   1020 cttccaggag tttgtcaata atgcctcat caaaaaccca acgagcggg cggacctaaa   1080 gatgctca                                                            1088
```

<210> SEQ ID NO 62
<211> LENGTH: 1091
<212> TYPE: DNA
<213> ORGANISM: Homo sapiens

<400> SEQUENCE: 62

```
gatgctggcc cggaggaagc cggtgctgcc ggcgctcacc atcaacccta ccatcgccga      60
gggcccatcc cctaccagcg agggcgcctc cgaggcaaac ctggtggacc tgcagaagaa     120
gctggaggag ctggaacttg acgagcagca agaagcgg ctggaagcct ttctcaccca      180
gaaagccaag gttggcgaac tcaaagacga tgacttcgaa aggatctcag agctgggcgc    240
gggcaacggc ggggtggtca ccaaagtcca gcacagaccc tcgggcctca tcatggccag    300
gaagctgatc caccttgaga tcaagccggc catccggaac cagatcatcc gcgagctgca    360
ggtcctgcac gaatgcaact cgccgtacat cgtgggcttc tacggggcct tctacagtga    420
ggggagatc agcatttgca tggaacacat ggacggcggc tccctggacc aggtgctgaa     480
ggaggccaag aggattcccg aggagatcct ggggaaagtc agcatcgcgg ttctccgggg    540
gttggcgtac ctccgagaga agcaccagat catgcaccga gatgtgaagc cctccaacat    600
gctcgtgaac tctagagggg agatcaagct gtgtgacttc ggggtgagcg ccagctcat     660
ggactccatg gccaactcct tcgtgggcac gcgctcctac atggctccgg agcggttgca    720
gggcacacat tactcggtgc agtcggacat ctggagcatg ggcctgtccc tggtggagct    780
ggccgtcgga aggtacccca tcccccgcc cgacgccaaa gagctggagg ccatctttgg     840
gcggcccgtg gtcgacgggg aagaaggaga gcctcacagc atctcgcctc ggccgaggcc    900
gcccgggcgc ccgtcagcg gtcacgggat ggatagccgg cctgccatgg ccatctttga    960
gctcctggac tatattgtga acgagccacc tcctaagctg cccaacggtg tgttcacccc   1020
ggacttccag gagtttgtca ataaatgcct catcaagaac ccagcggagc gggcggacct   1080
gaagatgctc a                                                         1091
```

<210> SEQ ID NO 63
<211> LENGTH: 363
<212> TYPE: PRT
<213> ORGANISM: Homo sapiens
<220> FEATURE:
<221> NAME/KEY: VARIANT
<222> LOCATION: (1)..(363)
<223> OTHER INFORMATION: Wherein Xaa is any amino acid as defined in the specification

<400> SEQUENCE: 63

```
Met Leu Ala Arg Arg Lys Pro Met Leu Pro Ala Leu Thr Ile Asn Pro
 1               5                  10                  15

Thr Ile Ala Glu Gly Pro Ser Pro Thr Ser Glu Gly Ala Ser Glu Ala
            20                  25                  30

Asn Leu Val Xaa Xaa Xaa Xaa Xaa Xaa Xaa Xaa Xaa Xaa Xaa Xaa Xaa
        35                  40                  45

Xaa Xaa Xaa Xaa Xaa Xaa Ala Phe Leu Thr Gln Lys Ala Lys Val Gly
    50                  55                  60

Glu Leu Lys Asp Asp Asp Phe Glu Arg Thr Ser Glu Leu Asp Ala Gly
65                  70                  75                  80

Asn Gly Gly Val Val Thr Lys Val Gln His Arg Pro Ser Gly Leu Ile
                85                  90                  95

Met Ala Arg Lys Leu Ile His Leu Glu Ile Lys Pro Ala Ile Arg Asn
```

-continued

```
            100                 105                 110
Gln Ile Ile Arg Glu His Gln Val Leu His Glu Cys Asn Ser Pro Tyr
            115                 120                 125
Ile Val Gly Phe Tyr Gly Ala Phe Tyr Cys Asp Arg Glu Ile Ser Ile
            130                 135                 140
Cys Met Glu His Met Asp Gly Gly Ser Leu Asp Gln Gly Leu Lys Glu
145                 150                 155                 160
Ala Lys Arg Ile Pro Glu Asp Ile Leu Gly Lys Val Ser Ile Ala Val
                    165                 170                 175
Leu Arg Gly Leu Ala Tyr Leu Arg Glu Lys His Gln Ile Met His Arg
                    180                 185                 190
Asn Val Lys Pro Ser Asn Ile Leu Val Asn Ser Arg Gly Glu Ile Lys
                    195                 200                 205
Leu Cys Asp Phe Gly Val Ser Gly Gln Leu Ile Asp Ser Met Ala Asn
            210                 215                 220
Ser Phe Val Gly Thr Arg Ser Tyr Met Ala Pro Glu Arg Leu Gln Gly
225                 230                 235                 240
Thr His Tyr Ser Val Gln Ser Val Ile Trp Ser Met Asp Leu Ser Leu
                    245                 250                 255
Val Glu Leu Ala Ile Glu Arg Tyr Pro Ile Pro Pro Asp Ala Lys
                    260                 265                 270
Glu Leu Glu Ala Ile Phe Gly Gln Pro Val Val Asp Arg Glu Glu Gly
            275                 280                 285
Glu Pro His Ser Ile Ser Ser Trp Pro Gly Ser Pro Gly Arg Pro Asn
            290                 295                 300
Ser Gly Tyr Gly Met Asp Ser Leu Pro Ala Met Ala Ile Phe Glu Leu
305                 310                 315                 320
Leu Asp Tyr Ile Val Lys Glu Pro Pro Lys Leu Pro Asn Gly Val
                    325                 330                 335
Phe Thr Pro Asp Phe Gln Glu Phe Val Asn Lys Cys Leu Ile Lys Asn
                    340                 345                 350
Pro Thr Glu Arg Ala Asp Leu Lys Met Leu Ser
            355                 360

<210> SEQ ID NO 64
<211> LENGTH: 364
<212> TYPE: PRT
<213> ORGANISM: Homo sapiens

<400> SEQUENCE: 64

Met Leu Ala Arg Arg Lys Pro Val Leu Pro Ala Leu Thr Ile Asn Pro
1               5                   10                  15
Thr Ile Ala Glu Gly Pro Ser Pro Thr Ser Glu Gly Ala Ser Glu Ala
                20                  25                  30
Asn Leu Val Asp Leu Gln Lys Lys Leu Glu Glu Leu Glu Leu Asp Glu
            35                  40                  45
Gln Gln Lys Lys Arg Leu Glu Ala Phe Leu Thr Gln Lys Ala Lys Val
        50                  55                  60
Gly Glu Leu Lys Asp Asp Asp Phe Glu Arg Ile Ser Glu Leu Gly Ala
65                  70                  75                  80
Gly Asn Gly Gly Val Val Thr Lys Val Gln His Arg Pro Ser Gly Leu
                85                  90                  95
Ile Met Ala Arg Lys Leu Ile His Leu Glu Ile Lys Pro Ala Ile Arg
                100                 105                 110
```

```
Asn Gln Ile Ile Arg Glu Leu Gln Val Leu His Glu Cys Asn Ser Pro
        115                 120                 125
Tyr Ile Val Gly Phe Tyr Gly Ala Phe Tyr Ser Asp Gly Glu Ile Ser
    130                 135                 140
Ile Cys Met Glu His Met Asp Gly Gly Ser Leu Asp Gln Val Leu Lys
145                 150                 155                 160
Glu Ala Lys Arg Ile Pro Glu Gly Ile Leu Gly Lys Val Ser Ile Ala
                165                 170                 175
Val Leu Arg Gly Leu Ala Tyr Leu Arg Glu Lys His Gln Ile Met His
            180                 185                 190
Arg Asp Val Lys Pro Ser Asn Ile Leu Val Asn Ser Arg Gly Glu Ile
        195                 200                 205
Lys Leu Cys Asp Phe Gly Val Ser Gly Gln Leu Ile Asp Ser Met Ala
    210                 215                 220
Asn Ser Phe Val Gly Thr Arg Ser Tyr Met Ala Pro Glu Arg Leu Gln
225                 230                 235                 240
Gly Thr His Tyr Ser Val Gln Ser Asp Ile Trp Ser Met Gly Leu Ser
                245                 250                 255
Leu Val Glu Leu Ala Val Gly Arg Tyr Pro Ile Pro Pro Pro Asp Ala
            260                 265                 270
Lys Glu Leu Glu Ala Ile Phe Gly Arg Pro Val Val Asp Gly Glu Glu
        275                 280                 285
Gly Glu Pro His Ser Ile Ser Pro Arg Pro Arg Pro Pro Gly Arg Pro
    290                 295                 300
Val Ser Gly His Gly Met Asp Ser Arg Pro Ala Met Ala Ile Phe Glu
305                 310                 315                 320
Leu Leu Asp Tyr Ile Val Asn Glu Pro Pro Lys Leu Pro Asn Gly
                325                 330                 335
Val Phe Thr Pro Asp Phe Gln Glu Phe Val Asn Lys Cys Leu Ile Lys
            340                 345                 350
Asn Pro Ala Glu Arg Ala Asp Leu Lys Met Leu Thr
        355                 360

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 65
cagagcaaag aagtttcttg ga                                              22

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: PCR PROBE
      PRIMER

<400> SEQUENCE: 66
tgaaacagca ctacttaagt ccaagtcga                                       29

<210> SEQ ID NO 67
<211> LENGTH: 22
<212> TYPE: DNA
<213> ORGANISM: Artificial Sequence
<220> FEATURE:
```

<223> OTHER INFORMATION: Description of Artificial Sequence: PCR PRIMER

<400> SEQUENCE: 67
tctcatgagg acatcacatt tg                                            22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 68
agatggcatc ctctctgaag at                                            22

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: PCR PROBE
      PRIMER

<400> SEQUENCE: 69
cctgctttgc attctttgca ggct                                          24

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 70
aacgtccttg ctgtgtacaa gt                                            22

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 71
aaagtcagca ttgcggttct c                                             21

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: PCR PROBE
      PRIMER

<400> SEQUENCE: 72
cttggcgtac ctccgagaga agcacc                                        26

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 73
gcttcacatt tcggtgcatg                                               20

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 74
gctggaggag ctggaactt                                              19

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: PCR  PROBE
      PRIMER

<400> SEQUENCE: 75
aagcctttct cacccagaaa gccaag                                      26

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 76
tttcgaagtc atcgtctttg a                                           21

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 77
catgagggct tccattacat ca                                          22

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: PCR PROBE
      PRIMER

<400> SEQUENCE: 78
agctgaccca gaagacccag gacctc                                      26

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 79
gcgtgttccc aatgctcagt                                             20

<210> SEQ ID NO 80
<211> LENGTH: 20
<212> TYPE: DNA

```
<213> ORGANISM: Artificial Sequence
<220> FEATURE:
<223> OTHER INFORMATION: Description of Artificial Sequence: PCR PRIMER

<400> SEQUENCE: 80
ggaaagtcag cattgcggtt                                                     20

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: PCR PROBE
      PRIMER

<400> SEQUENCE: 81
cttggcgtac ctccgagaga agcacc                                              26

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 82
ttcacatttc ggtgcatgat c                                                   21

<210> SEQ ID NO 83
<211> LENGTH: 66
<212> TYPE: PRT
<213> ORGANISM: Homo sapiens

<400> SEQUENCE: 83

Arg Lys Pro Met Leu Pro Ala Leu Thr Ile Asn Pro Thr Ile Ala Glu
  1               5                  10                  15

Gly Pro Ser Pro Thr Ser Glu Gly Ala Ser Glu Ala Asn Leu Val Asp
                 20                  25                  30

Leu Gln Lys Lys Leu Glu Glu Leu Glu Leu Asp Glu Gln Gln Lys Arg
             35                  40                  45

Leu Glu Ala Phe Leu Thr Gln Lys Ala Lys Val Gly Glu Leu Lys Asp
         50                  55                  60

Asp Asp
 65

<210> SEQ ID NO 84
<211> LENGTH: 66
<212> TYPE: PRT
<213> ORGANISM: Cricetulus griseus

<400> SEQUENCE: 84

Pro Lys Lys Lys Pro Thr Pro Ile Gln Leu Asn Pro Thr Pro Asp Gly
  1               5                  10                  15

Ser Ala Val Asn Gly Thr Ser Ser Ala Glu Thr Asn Leu Glu Ala Leu
                 20                  25                  30

Gln Lys Lys Leu Glu Glu Leu Glu Leu Glu Glu Gln Gln Arg Asn Arg
             35                  40                  45

Leu Glu Ala Phe Leu Thr Gln Lys Gln Lys Val Gly Glu Leu Lys Asp
         50                  55                  60

Asp Asp
 65
```

```
<210> SEQ ID NO 85
<211> LENGTH: 66
<212> TYPE: PRT
<213> ORGANISM: Homo sapiens

<400> SEQUENCE: 85

Pro Lys Lys Lys Pro Thr Pro Ile Gln Leu Asn Pro Ala Pro Asp Gly
  1               5                  10                  15

Ser Ala Val Asn Gly Thr Ser Ser Ala Glu Thr Asn Leu Glu Ala Leu
             20                  25                  30

Gln Lys Lys Leu Glu Glu Leu Glu Leu Asp Glu Gln Gln Arg Lys Arg
         35                  40                  45

Leu Glu Ala Phe Leu Thr Gln Lys Gln Lys Val Gly Glu Leu Lys Asp
     50                  55                  60

Asp Asp
 65

<210> SEQ ID NO 86
<211> LENGTH: 66
<212> TYPE: PRT
<213> ORGANISM: Mus musculus

<400> SEQUENCE: 86

Pro Lys Lys Lys Pro Thr Pro Ile Gln Leu Asn Pro Ala Pro Asp Gly
  1               5                  10                  15

Ser Ala Val Asn Gly Thr Ser Ser Ala Glu Thr Asn Leu Glu Ala Leu
             20                  25                  30

Gln Lys Lys Leu Glu Glu Leu Glu Leu Asp Glu Gln Gln Arg Lys Arg
         35                  40                  45

Leu Glu Ala Phe Leu Thr Gln Lys Gln Lys Val Gly Glu Leu Lys Asp
     50                  55                  60

Asp Asp
 65

<210> SEQ ID NO 87
<211> LENGTH: 66
<212> TYPE: PRT
<213> ORGANISM: Oryctolagus cuniculus

<400> SEQUENCE: 87

Pro Lys Lys Lys Pro Thr Pro Ile Gln Leu Asn Pro Ala Pro Asp Gly
  1               5                  10                  15

Ser Ala Val Asn Gly Thr Ser Ser Ala Glu Thr Asn Leu Glu Ala Leu
             20                  25                  30

Gln Lys Lys Leu Glu Glu Leu Glu Leu Asp Glu Gln Gln Arg Lys Arg
         35                  40                  45

Leu Glu Ala Phe Leu Thr Gln Lys Gln Lys Val Gly Glu Leu Lys Asp
     50                  55                  60

Asp Asp
 65

<210> SEQ ID NO 88
<211> LENGTH: 66
<212> TYPE: PRT
<213> ORGANISM: Rattus norvegicus

<400> SEQUENCE: 88

Pro Lys Lys Lys Pro Thr Pro Ile Gln Leu Asn Pro Ala Pro Asp Gly
  1               5                  10                  15
```

Ser Ala Val Asn Gly Thr Ser Ser Ala Glu Thr Asn Leu Glu Ala Leu
            20                  25                  30

Gln Lys Lys Leu Glu Glu Leu Glu Leu Asp Glu Gln Gln Arg Lys Arg
        35                  40                  45

Leu Glu Ala Phe Leu Thr Gln Lys Gln Lys Val Gly Glu Leu Lys Asp
    50                  55                  60

Asp Asp
65

<210> SEQ ID NO 89
<211> LENGTH: 66
<212> TYPE: PRT
<213> ORGANISM: Xenopus laevis

<400> SEQUENCE: 89

Pro Lys Lys Lys Pro Thr Pro Ile Gln Leu Asn Pro Asn Pro Glu Gly
1               5                   10                  15

Thr Ala Val Asn Gly Thr Pro Thr Ala Glu Thr Asn Leu Glu Ala Leu
            20                  25                  30

Gln Lys Lys Leu Glu Glu Leu Glu Leu Asp Glu Gln Gln Arg Lys Arg
        35                  40                  45

Leu Glu Ala Phe Leu Thr Gln Lys Gln Lys Val Gly Glu Leu Lys Asp
    50                  55                  60

Asp Asp
65

<210> SEQ ID NO 90
<211> LENGTH: 66
<212> TYPE: PRT
<213> ORGANISM: Cyprinus carpio

<400> SEQUENCE: 90

Pro Lys Arg Arg Pro Val Pro Leu Ile Ile Ala Pro Thr Gly Glu Gly
1               5                   10                  15

Gln Ser Thr Asn Ile Asp Ala Ala Ser Glu Ala Asn Leu Glu Ala Leu
            20                  25                  30

Gln Arg Lys Leu Gly Glu Leu Asp Leu Asp Glu Gln Gln Arg Lys Arg
        35                  40                  45

Leu Glu Ala Phe Leu Thr Gln Lys Ala Gln Val Gly Glu Leu Lys Asp
    50                  55                  60

Glu Asp
65

<210> SEQ ID NO 91
<211> LENGTH: 69
<212> TYPE: PRT
<213> ORGANISM: Gallus gallus

<400> SEQUENCE: 91

Met Pro Ala Lys Arg Lys Pro Val Leu Pro Ala Leu Thr Ile Thr Pro
1               5                   10                  15

Ser Pro Ala Glu Gly Pro Gly Pro Gly Gly Ser Ala Glu Ala Asn Leu
            20                  25                  30

Val Asp Leu Gln Lys Lys Leu Glu Glu Leu Glu Leu Asp Glu Gln Gln
        35                  40                  45

Lys Lys Arg Leu Glu Ala Phe Leu Thr Gln Lys Ala Lys Val Gly Glu
    50                  55                  60

-continued

Leu Lys Asp Asp Asp
 65

<210> SEQ ID NO 92
<211> LENGTH: 67
<212> TYPE: PRT
<213> ORGANISM: Homo sapiens

<400> SEQUENCE: 92

Arg Lys Pro Val Leu Pro Ala Leu Thr Ile Asn Pro Thr Ile Ala Glu
 1               5                  10                  15

Gly Pro Ser Pro Thr Ser Glu Gly Ala Ser Glu Ala Asn Leu Val Asp
            20                  25                  30

Leu Gln Lys Lys Leu Glu Glu Leu Glu Leu Asp Glu Gln Gln Lys Lys
        35                  40                  45

Arg Leu Glu Ala Phe Leu Thr Gln Lys Ala Lys Val Gly Glu Leu Lys
    50                  55                  60

Asp Asp Asp
 65

<210> SEQ ID NO 93
<211> LENGTH: 67
<212> TYPE: PRT
<213> ORGANISM: Mus musculus

<400> SEQUENCE: 93

Arg Lys Pro Val Leu Pro Ala Leu Thr Ile Asn Pro Thr Ile Ala Glu
 1               5                  10                  15

Gly Pro Ser Pro Thr Ser Glu Gly Ala Ser Glu Ala Asn Leu Val Asp
            20                  25                  30

Leu Gln Lys Lys Leu Glu Glu Leu Asp Leu Asp Glu Gln Gln Arg Lys
        35                  40                  45

Arg Leu Glu Ala Phe Leu Thr Gln Lys Ala Lys Val Gly Glu Leu Lys
    50                  55                  60

Asp Asp Asp
 65

<210> SEQ ID NO 94
<211> LENGTH: 67
<212> TYPE: PRT
<213> ORGANISM: Rattus norvegicus

<400> SEQUENCE: 94

Arg Lys Pro Val Leu Pro Ala Leu Thr Ile Asn Pro Thr Ile Ala Glu
 1               5                  10                  15

Gly Pro Ser Pro Thr Ser Glu Gly Ala Ser Glu Ala His Leu Val Asp
            20                  25                  30

Leu Gln Lys Lys Leu Glu Glu Leu Asp Leu Asp Glu Gln Gln Arg Lys
        35                  40                  45

Arg Leu Glu Ala Phe Leu Thr Gln Lys Ala Lys Val Gly Glu Leu Lys
    50                  55                  60

Asp Asp Asp
 65

<210> SEQ ID NO 95
<211> LENGTH: 66
<212> TYPE: PRT
<213> ORGANISM: Homo sapiens

<400> SEQUENCE: 95

```
Arg Lys Pro Met Leu Pro Ala Leu Thr Ile Asn Pro Thr Ile Ala Glu
  1               5                  10                  15

Gly Pro Ser Pro Thr Ser Glu Gly Ala Ser Glu Ala Asn Leu Val Asp
                 20                  25                  30

Leu Gln Lys Lys Leu Glu Glu Leu Glu Leu Asp Glu Gln Gln Lys Arg
             35                  40                  45

Leu Glu Ala Phe Leu Thr Gln Lys Ala Lys Val Gly Glu Leu Lys Asp
         50                  55                  60

Asp Asp
 65
```

<210> SEQ ID NO 96
<211> LENGTH: 66
<212> TYPE: PRT
<213> ORGANISM: Cricetulus griseus

<400> SEQUENCE: 96

```
Pro Lys Lys Lys Pro Thr Pro Ile Gln Leu Asn Pro Thr Pro Asp Gly
  1               5                  10                  15

Ser Ala Val Asn Gly Thr Ser Ser Ala Glu Thr Asn Leu Glu Ala Leu
                 20                  25                  30

Gln Lys Lys Leu Glu Glu Leu Glu Leu Glu Gln Gln Arg Asn Arg
             35                  40                  45

Leu Glu Ala Phe Leu Thr Gln Lys Gln Lys Val Gly Glu Leu Lys Asp
         50                  55                  60

Asp Asp
 65
```

<210> SEQ ID NO 97
<211> LENGTH: 66
<212> TYPE: PRT
<213> ORGANISM: Homo sapiens

<400> SEQUENCE: 97

```
Pro Lys Lys Lys Pro Thr Pro Ile Gln Leu Asn Pro Ala Pro Asp Gly
  1               5                  10                  15

Ser Ala Val Asn Gly Thr Ser Ser Ala Glu Thr Asn Leu Glu Ala Leu
                 20                  25                  30

Gln Lys Lys Leu Glu Glu Leu Glu Leu Asp Glu Gln Gln Arg Lys Arg
             35                  40                  45

Leu Glu Ala Phe Leu Thr Gln Lys Gln Lys Val Gly Glu Leu Lys Asp
         50                  55                  60

Asp Asp
 65
```

<210> SEQ ID NO 98
<211> LENGTH: 66
<212> TYPE: PRT
<213> ORGANISM: Mus musculus

<400> SEQUENCE: 98

```
Pro Lys Lys Lys Pro Thr Pro Ile Gln Leu Asn Pro Ala Pro Asp Gly
  1               5                  10                  15

Ser Ala Val Asn Gly Thr Ser Ser Ala Glu Thr Asn Leu Glu Ala Leu
                 20                  25                  30

Gln Lys Lys Leu Glu Glu Leu Glu Leu Asp Glu Gln Gln Arg Lys Arg
             35                  40                  45
```

-continued

```
Leu Glu Ala Phe Leu Thr Gln Lys Gln Lys Val Gly Glu Leu Lys Asp
     50                  55                  60

Asp Asp
 65

<210> SEQ ID NO 99
<211> LENGTH: 66
<212> TYPE: PRT
<213> ORGANISM: Oryctolagus cuniculus

<400> SEQUENCE: 99

Pro Lys Lys Lys Pro Thr Pro Ile Gln Leu Asn Pro Ala Pro Asp Gly
  1               5                  10                  15

Ser Ala Val Asn Gly Thr Ser Ser Ala Glu Thr Asn Leu Glu Ala Leu
                 20                  25                  30

Gln Lys Lys Leu Glu Glu Leu Glu Leu Asp Glu Gln Gln Arg Lys Arg
             35                  40                  45

Leu Glu Ala Phe Leu Thr Gln Lys Gln Lys Val Gly Glu Leu Lys Asp
     50                  55                  60

Asp Asp
 65

<210> SEQ ID NO 100
<211> LENGTH: 66
<212> TYPE: PRT
<213> ORGANISM: Rattus norvegicus

<400> SEQUENCE: 100

Pro Lys Lys Lys Pro Thr Pro Ile Gln Leu Asn Pro Ala Pro Asp Gly
  1               5                  10                  15

Ser Ala Val Asn Gly Thr Ser Ser Ala Glu Thr Asn Leu Glu Ala Leu
                 20                  25                  30

Gln Lys Lys Leu Glu Glu Leu Glu Leu Asp Glu Gln Gln Arg Lys Arg
             35                  40                  45

Leu Glu Ala Phe Leu Thr Gln Lys Gln Lys Val Gly Glu Leu Lys Asp
     50                  55                  60

Asp Asp
 65

<210> SEQ ID NO 101
<211> LENGTH: 66
<212> TYPE: PRT
<213> ORGANISM: Xenopus laevis

<400> SEQUENCE: 101

Pro Lys Lys Lys Pro Thr Pro Ile Gln Leu Asn Pro Asn Pro Glu Gly
  1               5                  10                  15

Thr Ala Val Asn Gly Thr Pro Ala Glu Thr Asn Leu Glu Ala Leu
                 20                  25                  30

Gln Lys Lys Leu Glu Glu Leu Glu Leu Asp Glu Gln Gln Arg Lys Arg
             35                  40                  45

Leu Glu Ala Phe Leu Thr Gln Lys Gln Lys Val Gly Glu Leu Lys Asp
     50                  55                  60

Asp Asp
 65

<210> SEQ ID NO 102
<211> LENGTH: 66
<212> TYPE: PRT
```

-continued

```
<213> ORGANISM: Cyprinus carpio

<400> SEQUENCE: 102

Pro Lys Arg Arg Pro Val Pro Leu Ile Ile Ala Pro Thr Gly Glu Gly
 1               5                  10                  15

Gln Ser Thr Asn Ile Asp Ala Ala Ser Glu Ala Asn Leu Glu Ala Leu
             20                  25                  30

Gln Arg Lys Leu Gly Glu Leu Asp Leu Asp Glu Gln Gln Arg Lys Arg
         35                  40                  45

Leu Glu Ala Phe Leu Thr Gln Lys Ala Gln Val Gly Glu Leu Lys Asp
     50                  55                  60

Glu Asp
 65

<210> SEQ ID NO 103
<211> LENGTH: 67
<212> TYPE: PRT
<213> ORGANISM: Gallus gallus

<400> SEQUENCE: 103

Ala Lys Arg Lys Pro Val Leu Pro Ala Leu Thr Ile Thr Pro Ser Pro
 1               5                  10                  15

Ala Glu Gly Pro Gly Pro Gly Ser Ala Glu Ala Asn Leu Val Asp
             20                  25                  30

Leu Gln Lys Lys Leu Glu Glu Leu Glu Leu Asp Glu Gln Gln Lys Lys
         35                  40                  45

Arg Leu Glu Ala Phe Leu Thr Gln Lys Ala Lys Val Gly Glu Leu Lys
     50                  55                  60

Asp Asp Asp
 65

<210> SEQ ID NO 104
<211> LENGTH: 67
<212> TYPE: PRT
<213> ORGANISM: Homo sapiens

<400> SEQUENCE: 104

Arg Lys Pro Val Leu Pro Ala Leu Thr Ile Asn Pro Thr Ile Ala Glu
 1               5                  10                  15

Gly Pro Ser Pro Thr Ser Glu Gly Ala Ser Glu Ala Asn Leu Val Asp
             20                  25                  30

Leu Gln Lys Lys Leu Glu Glu Leu Glu Leu Asp Glu Gln Gln Lys Lys
         35                  40                  45

Arg Leu Glu Ala Phe Leu Thr Gln Lys Ala Lys Val Gly Glu Leu Lys
     50                  55                  60

Asp Asp Asp
 65

<210> SEQ ID NO 105
<211> LENGTH: 67
<212> TYPE: PRT
<213> ORGANISM: Mus musculus

<400> SEQUENCE: 105

Arg Lys Pro Val Leu Pro Ala Leu Thr Ile Asn Pro Thr Ile Ala Glu
 1               5                  10                  15

Gly Pro Ser Pro Thr Ser Glu Gly Ala Ser Glu Ala Asn Leu Val Asp
             20                  25                  30
```

```
Leu Gln Lys Lys Leu Glu Glu Leu Asp Leu Asp Glu Gln Gln Arg Lys
        35                  40                  45

Arg Leu Glu Ala Phe Leu Thr Gln Lys Ala Lys Val Gly Glu Leu Lys
    50                  55                  60

Asp Asp Asp
 65
```

<210> SEQ ID NO 106
<211> LENGTH: 67
<212> TYPE: PRT
<213> ORGANISM: Rattus norvegicus

<400> SEQUENCE: 106

```
Arg Lys Pro Val Leu Pro Ala Leu Thr Ile Asn Pro Thr Ile Ala Glu
 1               5                  10                  15

Gly Pro Ser Pro Thr Ser Glu Gly Ala Ser Glu Ala His Leu Val Asp
            20                  25                  30

Leu Gln Lys Lys Leu Glu Glu Leu Asp Leu Asp Glu Gln Gln Arg Lys
        35                  40                  45

Arg Leu Glu Ala Phe Leu Thr Gln Lys Ala Lys Val Gly Glu Leu Lys
    50                  55                  60

Asp Asp Asp
 65
```

<210> SEQ ID NO 107
<211> LENGTH: 33
<212> TYPE: DNA
<213> ORGANISM: Artificial Sequence
<220> FEATURE:
<223> OTHER INFORMATION: Description of Artificial Sequence: PCR PRIMER

<400> SEQUENCE: 107
ggatcccttc taaagccgag cttctcacca agg                33

<210> SEQ ID NO 108
<211> LENGTH: 37
<212> TYPE: DNA
<213> ORGANISM: Artificial Sequence
<220> FEATURE:
<223> OTHER INFORMATION: Description of Artificial Sequence: PCR PRIMER

<400> SEQUENCE: 108
ctcgagtttt ccaatagggt taacaatctt tcccagg            37

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: SEQUENCING
      PRIMER

<400> SEQUENCE: 109
tacatcatcc acgagctgac c                             21

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: SEQUENCING
      PRIMER

<400> SEQUENCE: 110

```
ggtcagctcg tggatgatc                                                    19

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: SEQUENCING
      PRIMER

<400> SEQUENCE: 111
agttcagtca aggtgccc                                                     18

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: SEQUENCING
      PRIMER

<400> SEQUENCE: 112
gggcaccttg actgaactg                                                    19

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: SEQUENCING
      PRIMER

<400> SEQUENCE: 113
catggtgatc tcaccaagat cg                                                22

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: SEQUENCING
      PRIMER

<400> SEQUENCE: 114
cgatcttggt gagatcacca tg                                                22

<210> SEQ ID NO 115
<211> LENGTH: 30
<212> TYPE: DNA
<213> ORGANISM: Artificial Sequence
<220> FEATURE:
<223> OTHER INFORMATION: Description of Artificial Sequence: PCR PRIMER

<400> SEQUENCE: 115
ctcgtcctcg agggtaagcc tatccctaac                                        30

<210> SEQ ID NO 116
<211> LENGTH: 31
<212> TYPE: DNA
<213> ORGANISM: Artificial Sequence
<220> FEATURE:
<223> OTHER INFORMATION: Description of Artificial Sequence: PCR PRIMER

<400> SEQUENCE: 116
ctcgtcgggc ccctgatcag cgggtttaaa c                                      31
```

```
<210> SEQ ID NO 117
<211> LENGTH: 33
<212> TYPE: DNA
<213> ORGANISM: Artificial Sequence
<220> FEATURE:
<223> OTHER INFORMATION: Description of Artificial Sequence: PCR PRIMER

<400> SEQUENCE: 117
ggatccaaag aagtttcttg gagagaattc atg                              33

<210> SEQ ID NO 118
<211> LENGTH: 28
<212> TYPE: DNA
<213> ORGANISM: Artificial Sequence
<220> FEATURE:
<223> OTHER INFORMATION: Description of Artificial Sequence: PCR PRIMER

<400> SEQUENCE: 118
ctcgaggttg ccgataggtt ctaccatc                                    28
```